US010837003B2

(12) United States Patent
Whitehead et al.

(10) Patent No.: US 10,837,003 B2
(45) Date of Patent: *Nov. 17, 2020

(54) DENGUE TETRAVALENT VACCINE CONTAINING A COMMON 30 NUCLEOTIDE DELETION IN THE 3'-UTR OF DENGUE TYPES 1, 2, 3, AND 4, OR ANTIGENIC CHIMERIC DENGUE VIRUSES 1, 2, 3, AND 4

(71) Applicant: The United States of America, as represented by the Secretary, Department of Health and Human Services, Bethesda, MD (US)

(72) Inventors: Stephen S. Whitehead, Montgomery Village, MD (US); Brian R. Murphy, Bethesda, MD (US); Lewis Markoff, Bethesda, MD (US); Barry Falgout, Rockville, MD (US); Joseph Blaney, Gettysburg, PA (US); Kathryn Hanley, Las Cruces, NM (US); Ching-Juh Lai, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 286 days.

This patent is subject to a terminal disclaimer.

(21) Appl. No.: 15/710,672

(22) Filed: Sep. 20, 2017

(65) Prior Publication Data

US 2018/0010099 A1    Jan. 11, 2018

Related U.S. Application Data

(63) Continuation of application No. 13/305,639, filed on Nov. 28, 2011, now Pat. No. 9,783,787, which is a continuation of application No. 12/398,043, filed on Mar. 4, 2009, now Pat. No. 8,075,903, which is a continuation of application No. 10/970,640, filed on Oct. 21, 2004, now Pat. No. 7,517,531, which is a continuation of application No. PCT/US03/13279, filed on Apr. 25, 2003.

(60) Provisional application No. 60/436,500, filed on Dec. 23, 2002, provisional application No. 60/377,860, filed on May 3, 2002.

(51) Int. Cl.
C12N 7/00    (2006.01)
A61K 39/12    (2006.01)
A61K 39/00    (2006.01)

(52) U.S. Cl.
CPC ............... *C12N 7/00* (2013.01); *A61K 39/12* (2013.01); *A61K 2039/5254* (2013.01); *A61K 2039/5256* (2013.01); *A61K 2039/70* (2013.01); *C12N 2770/24134* (2013.01); *C12N 2770/24161* (2013.01); *Y02A 50/386* (2018.01)

(58) Field of Classification Search
None
See application file for complete search history.

(56) References Cited

U.S. PATENT DOCUMENTS

| | | | |
|---|---|---|---|
| 7,226,602 B2 | 6/2007 | Whitehead et al. | |
| 7,517,531 B2 | 4/2009 | Whitehead et al. | |
| 7,560,118 B2 | 7/2009 | Whitehead et al. | |
| 8,039,003 B2 | 10/2011 | Whitehead et al. | |
| 8,075,903 B2 | 12/2011 | Whitehead et al. | |
| 8,632,782 B2 | 1/2014 | Whitehead et al. | |
| RE45,016 E | 7/2014 | Whitehead et al. | |
| RE45,053 E | 7/2014 | Whitehead et al. | |
| RE46,042 E * | 6/2016 | Whitehead | C07K 14/005 |
| 9,707,287 B2 * | 7/2017 | Whitehead | C12Q 1/701 |

FOREIGN PATENT DOCUMENTS

| | | |
|---|---|---|
| WO | WO-01/91790 A1 | 12/2001 |
| WO | WO-02/095075 A1 | 11/2002 |

OTHER PUBLICATIONS

Durbin et al., "Development and clinical evaluation of multiple investigational monovalent DENV vaccines to identify components for inclusion in a live attenuated tetravalent DENV vaccine," *Vaccine*, vol. 29, No. 42, pp. 7242-7250, 2011 (Author Manuscript, 18 pages).

Durbin et al., "The Live Attenuated Dengue Serotype 1 Vaccine rDEN1Δ30 is Safe and Highly Immunogenic in Healthy Adult Volunteers," *Human Vaccines*, vol. 2, No. 4, pp. 167-173, 2006.

Larsen et al., "Dengue human infection models to advance dengue vaccine development," *Vaccine*, vol. 33, No. 50, pp. 7075-7082, 2015.

An et al., "Development of a novel mouse model for dengue virus infection", *Virology*, vol. 263, pp. 70-77 (1999).

Barrett et al., "Yellow fever vaccines", *Biologicals*, vol. 25, pp. 17-25 (1997).

Bhamarapravati et al., "Live attenuated tetravalent dengue vaccine", *Vaccine*, vol. 18, pp. 44-47 (2000).

Blackwell et al., "Translation elongation factor-1 alpha interacts with the 3' stem-loop region of West Nile virus genomic RNA", *J. Virol.*, vol. 71, pp. 6433-6444 (1997).

(Continued)

*Primary Examiner* — Stacy B Chen
(74) *Attorney, Agent, or Firm* — Klarquist Sparkman, LLP

(57) ABSTRACT

The invention relates to a dengue virus tetravalent vaccine containing a common 30 nucleotide deletion (Δ30) in the 3'-untranslated region of the genome of dengue virus serotypes 1, 2, 3, and 4, or antigenic chimeric dengue viruses of serotypes 1, 2, 3, and 4.

5 Claims, 15 Drawing Sheets
Specification includes a Sequence Listing.

(56) References Cited

OTHER PUBLICATIONS

Blaney et al., "Chemical mutagenesis of dengue virus type 4 yields mutant viruses which are temperature sensitive in vero cells or human liver cells and attenuated in mice", *J. Virol.*, vol. 75, pp. 9731-9740 (2001).

Blaney, et al., "Development of a Live Attenuated Dengue Virus Vaccine Using Reverse Genetics", *Viral Immunol.*, vol. 19, pp. 10-32 (2006).

Blaney et al., "Genetic basis of attenuation of dengue virus type 4 small plaque mutants with restricted replication in suckling mice and in SCID mice transplanted with human liver cells", *Virology*, vol. 300, pp. 125-139 (2002).

Blaney et al., "Genetically modified, live attenuated dengue virus type 3 vaccine candidates", *Am. J. Trop. Med. Hyg.*, vol. 71, pp. 811-821 (2004).

Blaney et al., "Recombinant, Live-Attenuated Tetravalent Dengue Virus Vaccine Formulations Induce a Balanced, Broad, and Protective Neutralizing Antibody Response Against Each of the Four Serotypes in Rheses Monkeys", Journal of Virology, vol. 79, pp. 5516-5528 (2005).††.

Blaney et al., "Mutations which enhance the replication of dengue virus type 4 and an antigenic chimeric dengue virus type 2/4 vaccine candidate in Vero cells", *Vaccine*, vol. 21, pp. 4317-4327 (2003).

Blaney et al., "Vaccine candidates derived from a novel infectious cDNA clone of an American genotype dengue virus type 2", *BMC Infect. Dis.*, 4(39), 10 pages (2004).

Blaney, Joseph E., Neeraj S. Sathe, Christopher T. Hanson. Cai Yen Firestone, Brian R. Murphy, and Stephen S. Whitehead. "Vaccine candidates for dengue virus type 1 (DEN1) generated by replacement of the structural genes of rDEN4 and rDEN4Δ30 with those of DEN1." *Virology journal* 4, No. 1 (2007): 23.††.

Blok et al, "Comparison of a dengue-2 virus and its candidate vaccine derivative: sequence relationships with the flaviviruses and other viruses", *Virology*, vol. 187, pp. 573-590 (1992).

Bray et al., "Construction of intertypic chimeric dengue viruses by substitution of structural protein genes", *PNAS USA*, vol. 88, pp. 10342-10346 (1991).

Bray et al., "Genetic determinants responsible for acquisition of dengue type 2 virus mouse neurovirulence", *J. Virol.*, vol. 72, pp. 1647-1651 (1998).

Bray et al., "Monkeys immunized with intertypic chimeric dengue viruses are protected against wild-type virus challenge", *J. Virol.*, vol. 70, pp. 4162-4166 (1996).

Brinton et al., "The 3'-nucleotides of flavivirus genomic RNA form a conserved secondary structure", *Virology*, vol. 153, pp. 113-121 (1986).

Burke et al., "A prospective study of dengue infections in Bangkok", *Am. J. Trop. Med. Hyg.*, vol. 38, pp. 172-180 (1988).

Butrapet et al., "Attenuation markers of a candidate dengue type 2 vaccine virus, strain 16681 (PDK-53), are defined by mutations in the 5' noncoding region and nonstructural proteins 1 and 3", *J. Virol.*, vol. 74, pp. 3011-3019 (2000).

Chambers et al., "Yellow fever virus/dengue-2 virus and yellow fever virus/dengue-4 virus chimeras: biological characterization, immunogenicity, and protection against dengue encephalitis in the mouse model", *J. Virol.*, vol. 77, pp. 3655-3668 (2003).

Chen et al., "Construction of intertypic chimeric dengue viruses exhibiting type 3 antigenicity and neurovirulence for mice", *J. Virol.*, vol. 69, pp. 5186-5190 (1995).

Durbin et al., American Journal of Tropical Medicine and Hygiene, vol. 65, pp. 405-413 (2001).††.

Durbin et al., "Attenuation and immunogenicity in humans of a live dengue virus type-4 vaccine candidate with a 30 nucleotide deletion in its 3'-untranslated region", *Am. J. Trop. Med. Hyg.*, vol. 65, pp. 405-413 (2001).

Durbin et al., "rDEN2/4Δ30(ME), a live attenuated chimeric dengue serotype 2 vaccine is safe and highly immunogenic in healthy dengue-naive daults", *Human Vaccines*, 2(6), pp. 255-260 (2006).†.

Durbin et al., "The Recombinant Live Attenuated Dengue 4 Candidate Vaccine rDEN4delta30 is Safe, Immunogenic, and Highly Infectious in Healthy Adults", *Am. J. Trop. Med. Hyg.*, p. 361, Abstract 379 (2003).

European Search Report for EP Appln. No. 10 17 7735, dated May 10, 2011.†.

European Search Report for EP Appln. No. 10 17 7740, dated Mar. 25, 2011.†.

Gubler et al., "Impact of dengue/dengue hemorrhagic fever on the developing world", *Adv. Virus Res.*, vol. 53, pp. 35-70 (1999).

Guillot et al., "Natural genetic exchanges between vaccine and wild poliovirus strains in humans", *J. Virol.*, vol. 74, pp. 8434-8443 (2000).

Guirakhoo et al., "Construction, safety, and immunogenicity in nonhuman primates of a chimeric yellow fever-dengue virus tetravalent vaccine", *J. Virol.*, vol. 75, pp. 7290-7304 (2001).

Guirakhoo et al., "Viremia and immunogenicity in nonhuman primates of a tetravalent yellow fever-dengue chimeric vaccine: genetic reconstructions, dose adjustment, and antibody responses against wild-type dengue virus isolates", *Virology*, vol. 298, pp. 146-159 (2002).

Hahn et al., "Conserved elements in the 3' untranslated region of flavivirus RNAs and potential cyclization sequences", J. Mol. Biol., vol. 198, pp. 33-41 (1987).

Hanley et al., "Introduction of mutations into the non-structural genes or 3' untranslated region of an attenuated dengue virus type 4 vaccine candidate further decreases replication in rhesus monkeys while retaining protective immunity", Vaccine, vol. 22, pp. 3440-3448 (2004).

Hanley et al., "Paired Charge-to-Alanine Mutagenesis of Dengue Virus Type 4 NS5 Generates Mutants with Temperature-Sensitive, Host Range, and Mouse Attenuation Phenotypes", J. Virol., vol. 76, pp. 525-531 (2002).

Huang et al., "Chimeric dengue type 2 (vaccine strain PDK-53)/dengue type 1 virus as a potential candidate dengue type 1 virus vaccine", *J. Virol.*, vol. 74, pp. 3020-3028 (2000).

Kanesa-Thasan et al., "Safety and immunogenicity of attenuated dengue virus vaccines (Aventis pasteur) in human volunteers", *Vaccine*, vol. 19, pp. 3179-3188 (2001).

Kew et al., "Outbreak of poliomyelitis in Hispaniola associated with circulating type 1 vaccine-derived poliovirus", *Science*, vol. 296, pp. 356-359 (2002).

Khromykh et al., "RNA binding properties of core protein of the flavivirus Kunjin", *Arch. Virol.*, vol. 141, pp. 685-699 (1996).

Lai et al., *Clinical and Diagnostic Virology*, vol. 10, pp. 173-179 (1998).††.

Lai et al., "Infectious RNA transcribed from stably cloned full-length cDNA of dengue type 4 virus", *PNAS USA*, vol. 88, pp. 5139-5143 (1991).

Markoff et al., "A conserved internal hydrophobic domain mediates the stable membrane integration of the dengue virus capsid protein", *Virology*, vol. 233, pp. 105-117 (1997).

Markoff et al., "Derivation and characterization of a dengue type 1 host range-restricted mutant virus that is attenuated and highly immunogenic in monkeys", J. Virol., vol. 76, pp. 3318-3328 (2002).

Mathew et al., "Predominance of HLA-restricted cytotoxic T-lymphocyte responses to serotype-cross-reactive epitopes on nonstructural proteins following natural secondary dengue virus infection", J. Virol., vol. 72, pp. 3999-4004 (1998).

Men et al., "Dengue type 4 virus mutants containing deletions in the 3' noncoding region of the RNA genome: analysis of growth restriction in cell culture and altered viremia pattern and immunogenicity in rhesus monkeys", J. Virol., vol. 70, pp. 3930-3937 (1996).

Olsthoorn et al., RNA, vol. 7, pp. 1370-1377 (2001).

Pletnev et al., "Attenuation of the Langat tick-borne flavivirus by chimerization with mospuito-borne flavivirus dengue type 4", PNAS USA, vol. 95, pp. 1746-1751 (1998).

Pletnev et al., "Chimeric tick-borne encephalitis and dengue type 4 viruses: effects of mutations on neurovirulence in mice", *J. Virol.*, vol. 67, pp. 4956-4963 (1993).

Pletnev et al., "Construction and characterization of chimeric tick-borne encephalitis/dengue type 4 viruses", *PNAS USA*, vol. 89, pp. 10532-10536 (1992).

(56) References Cited

OTHER PUBLICATIONS

Pletnev et al., "West Nile virus/dengue type 4 virus chimeras that are reduced in neurovirulence and peripheral virulence without loss of immunogenicity or protective efficacy", *PNAS USA*, vol. 99, pp. 3036-3041 (2002).
Proutski et al., "Secondary structure of the 3' untranslated region of flaviviruses: similarities and differences", *Nucleic Acids Res.*. vol. 25, pp. 1194-1202 (1997).
Proutski et al., *Virus Research*, vol. 64, pp. 107-123 (1999).††.
Polo et al., "Infectious RNA transcripts from full-length dengue virus type 2 cDNA clones made in yeast", J. Virol., vol. 71, pp. 5366-5374 (1997).
Puri et al., "Construction of a full length infectious clone for dengue-1 virus Western Pacific, 74 strain", Virus Genes, vol. 20, pp. 57-63 (2000).
Puri et al., "Molecular analysis of dengue virus attenuation after serial passage in primary dog kidney cells", J. Gen. Virol., vol. 78, pp. 2287-2291 (1997).
Rauscher et al., "Secondary structure of the 3'-noncoding region of flavivirus genomes: comparative analysis of base pairing probabilities", RNA, vol. 3, pp. 779-791 (1997).
Rice et al., "Nucleotide sequence of yellow fever virus: implications for flavivirus gene expression and evolution", Science, vol. 229, pp. 726-733 (1985).
Rosen et al., "Comparative suceptibility of five species of Toxorhynchites mosquitoes to parenteral infection with dengue and other flaviviruses", Am. J. Trop. Med. Hyg., vol. 34, pp. 805-809 (1985).
Rosen et al., "Comparative susceptibility of mosquito species and strains to oral and parenteral infection with dengue and Japanese encephalitis viruses", *Am. J. Trop. Med. Hyg.*, vol. 34, pp. 603-615 (1985).
Ta et al., "Mov34 protein from mouse brain interacts with the 3' noncoding region of Japanese encephalitis virus", *J. Virol.*, vol. 74, pp. 5108-5115 (2000).
Thein et al., "Risk factors in dengue shock syndrome", *Am. J. Trop. Med. Hyg.*, vol. 56, pp. 566-572 (1997).
Troyer et al., "A live attenuated recombinant dengue-4 virus vaccine candidate with restricted capacity for dissemination in mosquitoes and lack of transmission from vaccine to mosquitoes", *Am. J. Trop, Med Hyg.*, vol. 65, pp. 414-419 (2001).
Whitehead et al., "A live, attenuated dengue virus type 1 vaccine candidate with a 30-nucleotide deletion in the 3' untranslated region is highly attenuated and immunogenic in monkeys", J. Virol., vol. 77, pp. 1653-1657 (2003).
Whitehead et al., "Dengue Virus Vaccine Candidates Containing a Common 30 Nucleotide Deletion in the 3'-UTR of Each Serotype or Antigenic Chimeric Viruses Representing Each Serotype Are Attenuated and Immunogenic", American Journal of Tropical Medicine & Hygiene, 69(3), pp. 530-531 (2003).†.
Whitehead et al., "Substitution of the structural genes of dengue virus type 4 with those of type 2 results in chimeric vaccine candidates which are attenuated for mosquitoes, mice, and rhesus monkeys", Vaccine, vol. 21, pp. 4307-4316 (2003).
Worobey et al., "Widespread intra-serotype recombination in natural populations of dengue virus", PNAS USA, vol. 96, pp. 7352-7357 (1999).
Zeng et al., "Identification of specific nucleotide sequences within the conserved 3'-SL in the dengue type 2 virus genome required for replication", J. Virol., vol. 72, pp. 7510-7522 (1998).

* cited by examiner

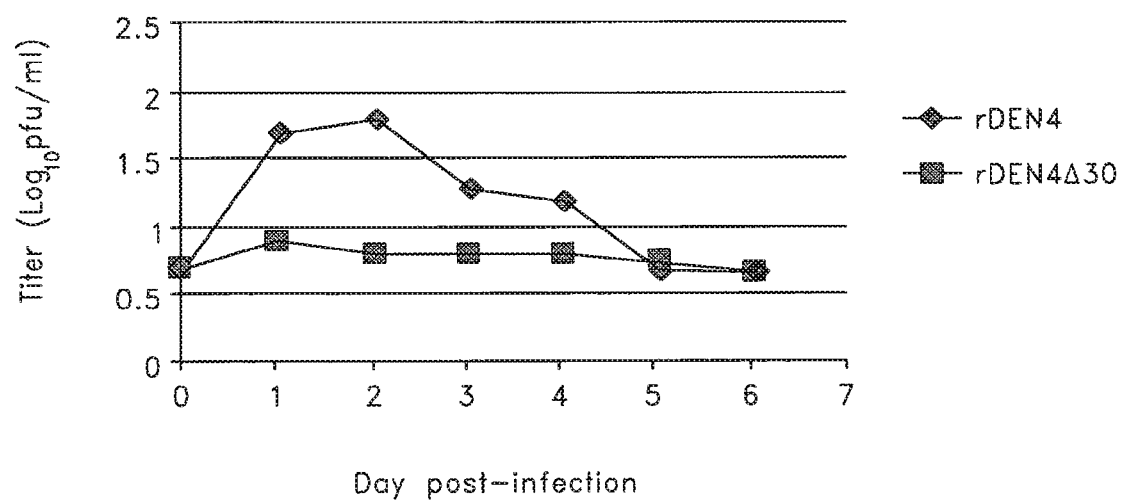
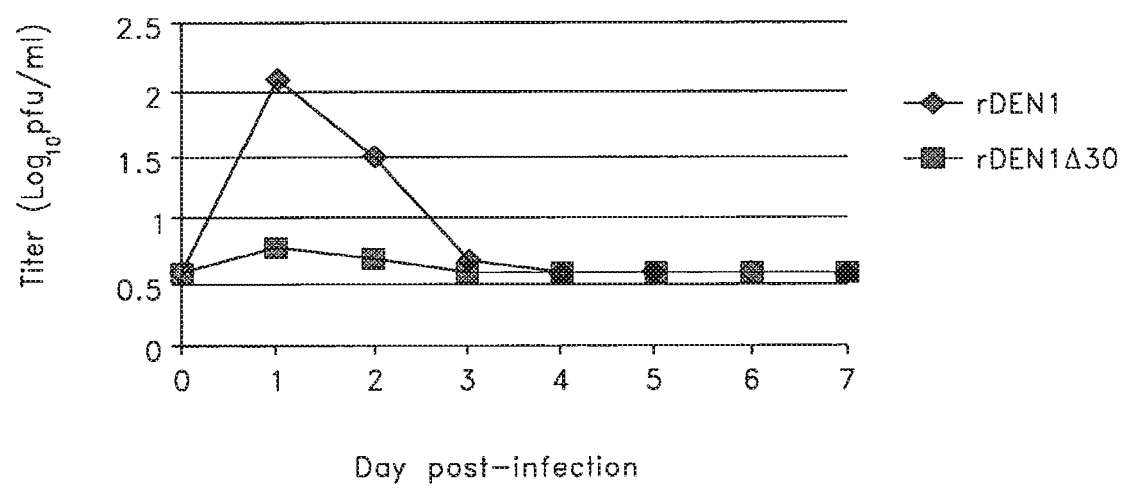
FIG. 5

FIG. 11B

Junction 1:
```
          DEN4          BglII            DEN3
-CAGTTTGTTTGAATAGAGAGCAGATCTCTGGAAAAATGAACAACCAAGG-   SEQ ID NO: 82
                                  MetAsnAsnGlnArg    SEQ ID NO: 83
```

Junction 2:
```
          DEN3          XhoI             DEN4
-CTTTTAACCTGGATAGGGTTGAACTCGAGGAACACTTCAATGGCTATGACG- SEQ ID NO: 84
 LeuLeuThrTrpIleGlyLeuAsnSerArgAsnThrS

DENGUE TETRAVALENT VACCINE CONTAINING A COMMON 30 NUCLEOTIDE DELETION IN THE 3'-UTR OF DENGUE TYPES 1, 2, 3, AND 4, OR ANTIGENIC CHIMERIC DENGUE VIRUSES 1, 2, 3, AND 4

CROSS-REFERENCE TO RELATED APPLICATIONS

This application is a continuation of U.S. application Ser. No. 13/305,639, filed Nov. 28, 2011, which is a continuation of U.S. application Ser. No. 12/398,043, filed Mar. 4, 2009, now U.S. Pat. No. 8,075,903, which is a continuation of U.S. application Ser. No. 10/970,640, filed Oct. 21, 2004, now U.S. Pat. No. 7,517,531, which is a continuation and claims the benefit of priority of International Application No. PCT/US03/13279 filed Apr. 25, 2003, designating the United States of America and published in English on Nov. 13, 2003, as WO 03/092592, which claims the benefit of priority of U.S. Provisional Application No. 60/377,860, filed May 3, 2002, and U.S. Provisional Application No. 60/436,500, filed Dec. 23, 2002, the disclosure of each of which is incorporated herein by reference in its entirety for all purposes.

FIELD OF THE INVENTION

The invention relates to a dengue virus tetravalent vaccine containing a common 30 nucleotide deletion (Δ30) in the 3'-untranslated region of the genome of dengue virus serotypes 1, 2, 3, and 4, or antigenic chimeric dengue viruses of serotypes 1, 2, 3, and 4.

BACKGROUND OF THE INVENTION

Dengue virus is a positive-sense RNA virus belonging to the *Flavivirus* genus of the family Flaviviridae. Dengue virus is widely distributed throughout the tropical and semitropical regions of the world and is transmitted to humans by mosquito vectors. Dengue virus is a leading cause of hospitalization and death in children in at least eight tropical Asian countries (WHO 1997 *Dengue Haemorrhagic Fever: Diagnosis, Treatment, Prevention, and Control* 2nd Edition, Geneva). There are four serotypes of dengue virus (DEN1, DEN2, DEN3, and DEN4) that annually cause an estimated 50-100 million cases of dengue fever and 500,000 cases of the more severe form of dengue virus infection known as dengue hemorrhagic fever/dengue shock syndrome (DHF/DSS) (Gubler, D. J. and Meltzer, M. 1999 *Adv Virus Res* 53:35-70). This latter disease is seen predominantly in children and adults experiencing a second dengue virus infection with a serotype different than that of their first dengue virus infection and in primary infection of infants who still have circulating dengue-specific maternal antibody (Burke, D. S. et al. 1988 *Am J Trop Med Hyg* 38:172-180; Halstead, S. B. et al. 1969 *Am J Trop Med Hyg* 18:997-1021; Thein, S. et al. 1997 *Am J Trop Med Hyg* 56:566-575). A dengue vaccine is needed to lessen disease burden caused by dengue virus, but none is licensed. Because of the association of more severe disease with secondary dengue virus infection, a successful vaccine must simultaneously induce immunity to all four serotypes. Immunity is primarily mediated by neutralizing antibody directed against the envelope (E) glycoprotein, a virion structural protein. Infection with one serotype induces long-lived homotypic immunity and a short-lived heterotypic immunity (Sabin, A. 1955 *Am J Trop Med Hyg* 4:198-207). Therefore, the goal of immunization is to induce a long-lived neutralizing antibody response against DEN1, DEN2, DEN3, and DEN4, which can best be achieved economically using live attenuated virus vaccines. This is a reasonable goal since a live attenuated vaccine has already been developed for the related yellow fever virus, another mosquito-borne *flavivirus* present in tropical and semitropical regions of the world (Monath, T. P. and Heinz, F. X. 1996 in: *Fields Virology*, Fields, D. M et al. eds. Philadelphia: Lippincott-Raven Publishers, pp. 961-1034).

Several live attenuated dengue vaccine candidates have been developed and evaluated in humans and non-human primates. The first live attenuated dengue vaccine candidates were host range mutants developed by serial passage of wild-type dengue viruses in the brains of mice and selection of mutants attenuated for humans (Kimura, R. and Hotta, S. 1944 *Jpn J Bacteriol* 1:96-99; Sabin, A. B. and Schlesinger, R. W. 1945 *Science* 101:640; Wisserman, C. L. et al. 1963 *Am J Trop Med Hyg* 12:620-623). Although these candidate vaccine viruses were immunogenic in humans, their poor growth in cell culture discouraged further development. Additional live attenuated DEN1, DEN2, DEN3, and DEN4 vaccine candidates have been developed by serial passage in non-human tissue culture (Angsubhakorn, S. et al. 1994 *Southeast Asian J Trop Med Public Health* 25:554-559; Bancroft, W. H. et al. 1981 *Infect Immun* 31:698-703; Bhamarapravati, N. et al. 1987 *Bull World Health Organ* 65:189-195; Eckels, K. H. et al. 1984 *Am J Trop Med Hyg* 33:684-698; Hoke, C. H. Jr. et al. 1990 *Am J Trop Med Hyg* 43:219-226; Kanesa-Thasan, N. et al. 2001 *Vaccine* 19:3179-3188) or by chemical mutagenesis (McKee, K. T. et al. 1987 *Am J Trop Med Hyg* 36:435-442). It has proven very difficult to achieve a satisfactory balance between attenuation and immunogenicity for each of the four serotypes of dengue virus using these approaches and to formulate a tetravalent vaccine that is safe and satisfactorily immunogenic against each of the four dengue viruses (Kanesa-Thasan, N. et al. 2001 *Vaccine* 19:3179-3188; Bhamarapravati, N. and Sutee, Y. 2000 *Vaccine* 18:44-47).

Two major advances using recombinant DNA technology have recently made it possible to develop additional promising live attenuated dengue virus vaccine candidates. First, methods have been developed to recover infectious dengue virus from cells transfected with RNA transcripts derived from a full-length cDNA clone of the dengue virus genome, thus making it possible to derive infectious viruses bearing attenuating mutations that have been introduced into the cDNA clone by site-directed mutagenesis (Lai, C. J. et al, 1991 *PNAS USA* 88:5139-5143). Second, it is possible to produce antigenic chimeric viruses in which the structural protein coding region of the full-length cDNA clone of dengue virus is replaced by that of a different dengue virus serotype or from a more divergent *flavivirus* (Bray, M. and Lai, C. J. 1991 *PNAS USA* 88:10342-10346; Chen, W. et al. 1995 *J Virol* 69:5186-5190; Huang, C. Y. et al. 2000 *J Virol* 74:3020-3028; Pletnev, A. G. and Men, R. 1998 *PNAS USA* 95:1746-1751). These techniques have been used to construct intertypic chimeric dengue viruses that have been shown to be effective in protecting monkeys against homologous dengue virus challenge (Bray, M. et al. 1996 *J Virol* 70:4162-4166). A similar strategy is also being used to develop attenuated antigenic chimeric dengue virus vaccines based on the attenuation of the yellow fever vaccine virus or the attenuation of the cell-culture passaged dengue viruses (Monath, T. P. et al. 1999 *Vaccine* 17:1869-1882; Huang, C. Y. et al. 2000 *J. Virol* 74:3020-3028).

Another study examined the level of attenuation for humans of a DEN4 mutant bearing a 30-nucleotide deletion (Δ30) introduced into its 3'-untranslated region by site-directed mutagenesis and that was found previously to be attenuated for rhesus monkeys (Men, R. et al. 1996 *J Virol* 70:3930-3937). Additional studies were carried out to examine whether this Δ30 mutation present in the DEN4 vaccine candidate was the major determinant of its attenuation for monkeys. It was found that the Δ30 mutation was indeed the major determinant of attenuation for monkeys, and that it specified a satisfactory balance between attenuation and immunogenicity for humans (Durbin, A. P. et al. 2001 *Am J Trop Med Hyg* 65:405-13).

SUMMARY OF THE INVENTION

The previously identified Δ30 attenuating mutation, created in dengue virus type 4 (DEN4) by the removal of 30 nucleotides from the 3'-UTR, is also capable of attenuating a wild-type strain of dengue virus type 1 (DEN1). Removal of 30 nucleotides from the DEN1 3'-UTR in a highly conserved region homologous to the DEN4 region encompassing the Δ30 mutation yielded a recombinant virus attenuated in rhesus monkeys to a level similar to recombinant virus DEN4Δ30. This establishes the transportability of the Δ30 mutation and its attenuation phenotype to a dengue virus type other than DEN4. The effective transferability of the Δ30 mutation, described by this work, establishes the usefulness of the Δ30 mutation to attenuate and improve the safety of commercializable dengue virus vaccines of any serotype. We envision a tetravalent dengue virus vaccine containing dengue virus types 1, 2, 3, and 4 each attenuated by the Δ30 mutation. We also envision a tetravalent dengue virus vaccine containing recombinant antigenic chimeric viruses in which the structural genes of dengue virus types 1, 2, and 3 replace those of DEN4Δ30; 1, 2, and 4 replace those of DEN3Δ30; 1, and 4 replace those of DEN2Δ30; and 2, 3, and 4 replace those of DEN1 Δ30. In some instances, such chimeric dengue viruses are attenuated not only by the Δ30 mutation, but also by their chimeric nature. The presence of the Δ30 attenuating mutation in each virus component precludes the reversion to a wild-type virus by intertypic recombination. In addition, because of the inherent genetic stability of deletion mutations, the Δ30 mutation represents an excellent alternative for use as a common mutation shared among each component of a tetravalent vaccine.

BRIEF DESCRIPTION OF THE DRAWINGS

FIG. 5. The Δ30 mutation attenuates both DEN1 and DEN4 for rhesus monkeys. Groups of 4 monkeys were immunized subcutaneously with 5.0 $\log_{10}$ PFU of the indicated virus. Serum was collected each day following immunization and virus titers were determined and are shown as mean $\log_{10}$ PFU/ml.

FIGS. 9A and 9B. Recombinant chimeric dengue viruses were constructed by introducing either the CME or the ME regions of DEN2 (Tonga/74) into the DEN4 genetic background. The relative location of the Δ30 mutation in the 3' UTR is indicated by an arrow and intertypic junctions 1, 2, and 3 are indicated. Nucleotide and amino acid sequence of the intertypic junction regions. Restriction enzyme recognition sites used in assembly of each chimeric cDNA are indicated.

FIGS. 11A and 11B. Recombinant chimeric dengue viruses were constructed by introducing either the CME or the ME regions of DEN3 (Sleman/78) into the DEN4 genetic background. The relative location of the Δ30 mutation in the 3' UTR is indicated by an arrow and intertypic junctions 1, 2, and 3 are indicated. Restriction enzyme recognition sites used in assembly of each chimeric cDNA are indicated. Nucleotide and amino acid sequence of the intertypic junction regions. Restriction enzyme recognition sites used in assembly of each chimeric cDNA are indicated.

BRIEF DESCRIPTION OF THE SEQUENCES

| Serotype | GenBank Accession No. or description |
|---|---|
| DEN1 | U88535 |
| DEN2 | Tonga/74 |
| DEN3 | Sleman/78 |
| DEN4 | AF326825 |

BRIEF DESCRIPTION OF THE SEQ ID NOS

Figure 2:
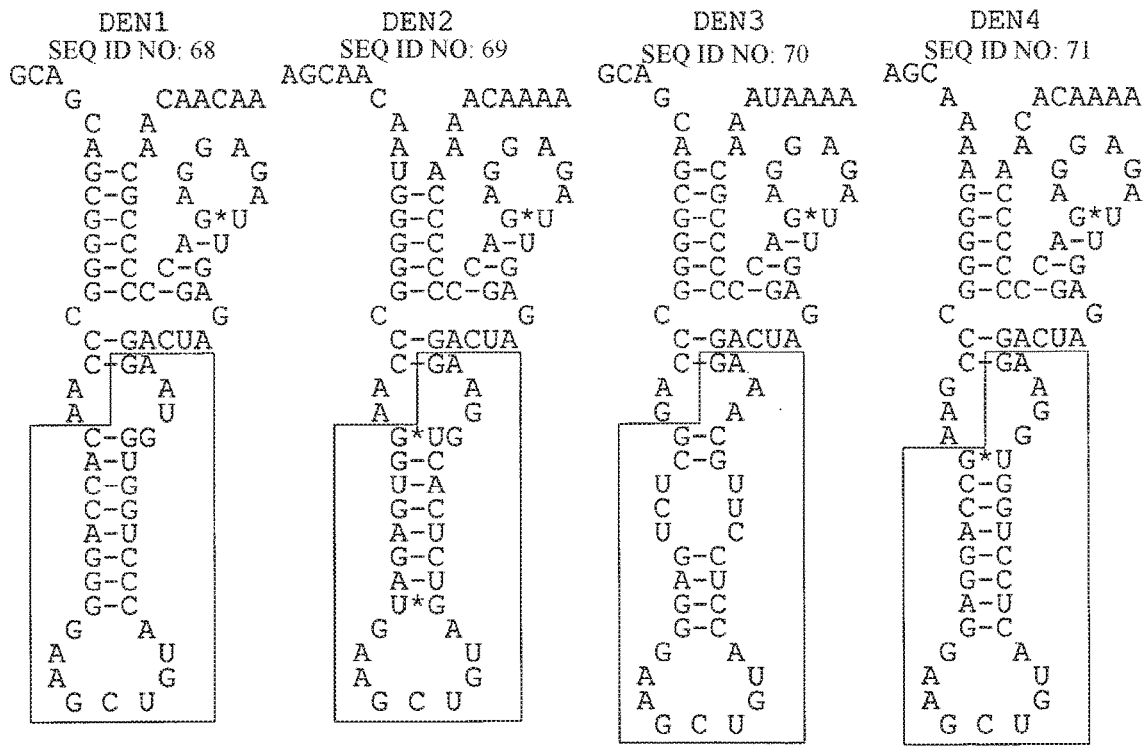
FIGS. 2A-2C. The Δ30 mutation removes 30 contiguous nucleotides (shaded) from the 3' UTR of DEN4. Nucleotides are numbered from the 3' terminus. Nucleotide sequence alignment of the TL2 region of DEN1, DEN2, DEN3, and DEN4 and their Δ30 derivatives. Also shown is the corresponding region for each of the four DEN serotypes. Upper case letters indicate sequence homology among all 4 serotypes, underlining indicates nucleotide pairing to form the stem structure. Predicted secondary structure of the TL2 region of each DEN serotype. Nucleotides that are removed by the Δ30 mutation are boxed (DEN1—between nts 10562-10591, DEN2 Tonga/74—between nts 10541-10570, DEN3 Sleman/78—between nts 10535-10565, and DEN4 between nts 10478-10507).
Figures 6A, 6B:
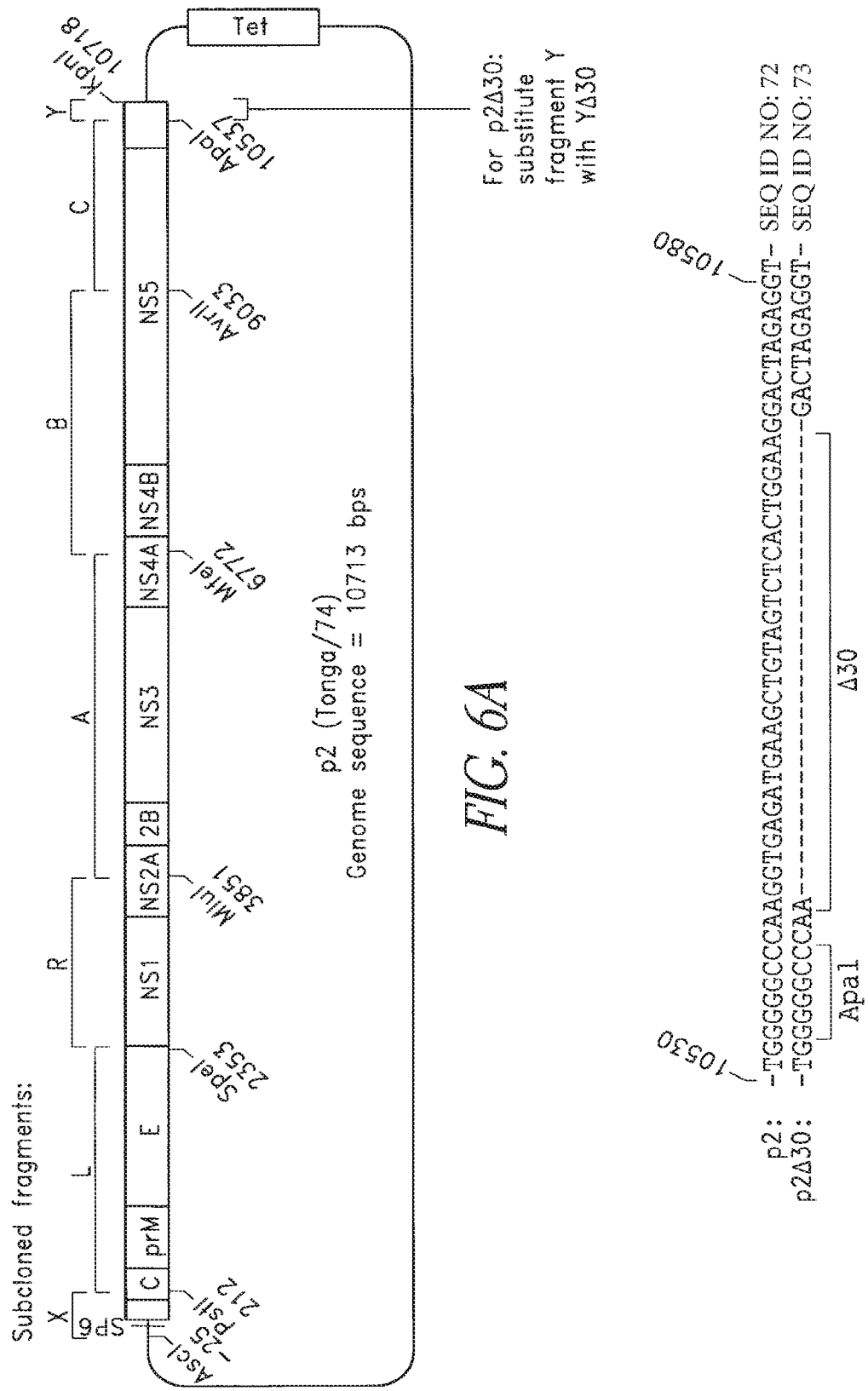
FIGS. 6A and 6B. Diagram of the p2 (Tonga/74) full-length cDNA plasmid. Regions subcloned are indicated above the plasmid. Numbering begins at the 5' end of the viral sequence. The Δ30 mutation removes the indicated 30 nucleotides from the 3' UTR sequence to create p2Δ30.
Figure 8A:
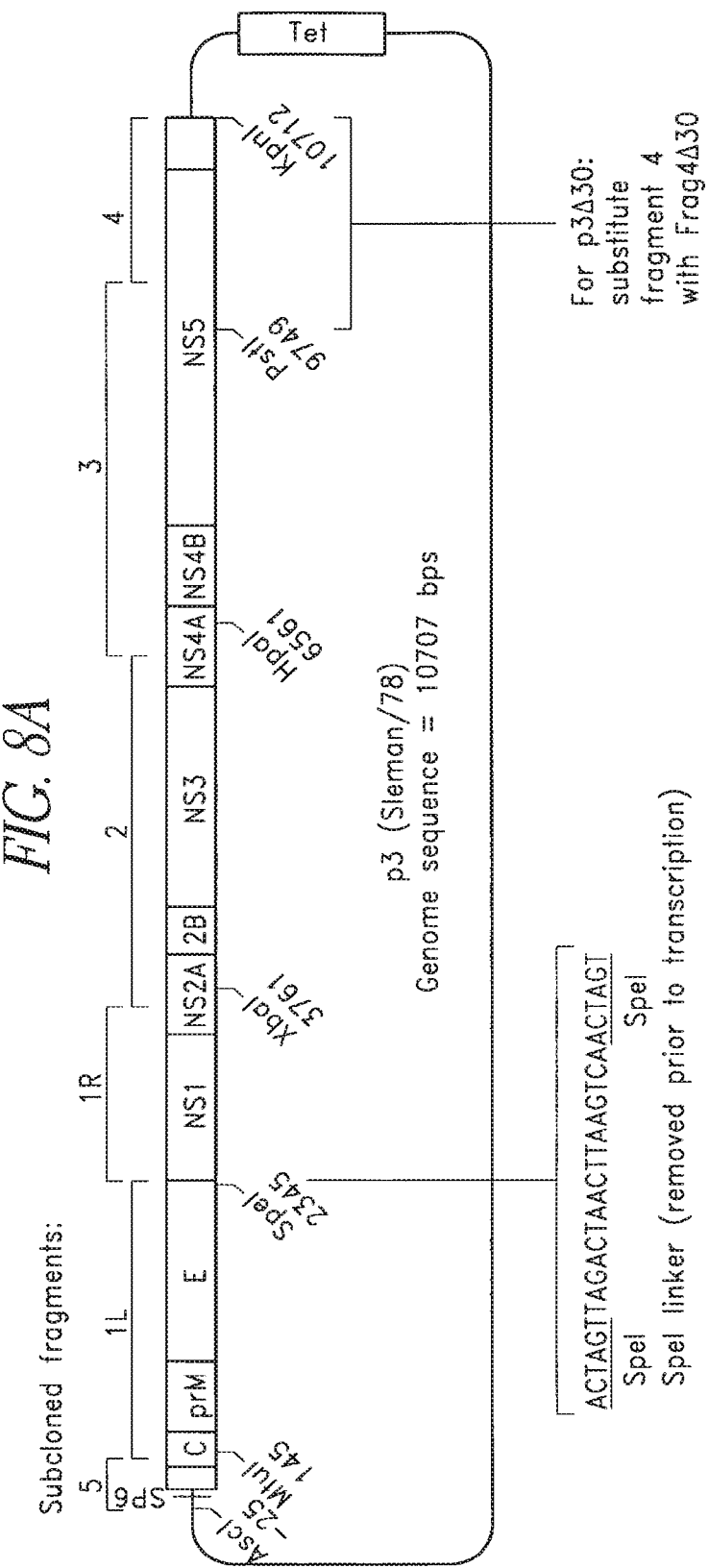
FIGS. 8A and 8B. Diagram of the p3 (Sleman/78) full-length cDNA plasmid. Regions subcloned are indicated above the plasmid. Numbering begins at the 5' end of the viral sequence. The sequence and insertion location of the SpeI linker is shown. The Δ30 mutation removes the indicated 31 nucleotides from the 3' UTR sequence to create p3Δ30.
Figure 8B:
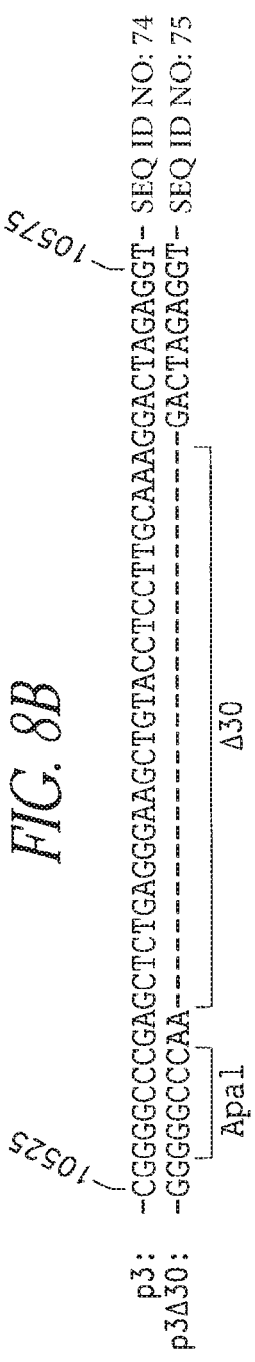
Figure 11A:
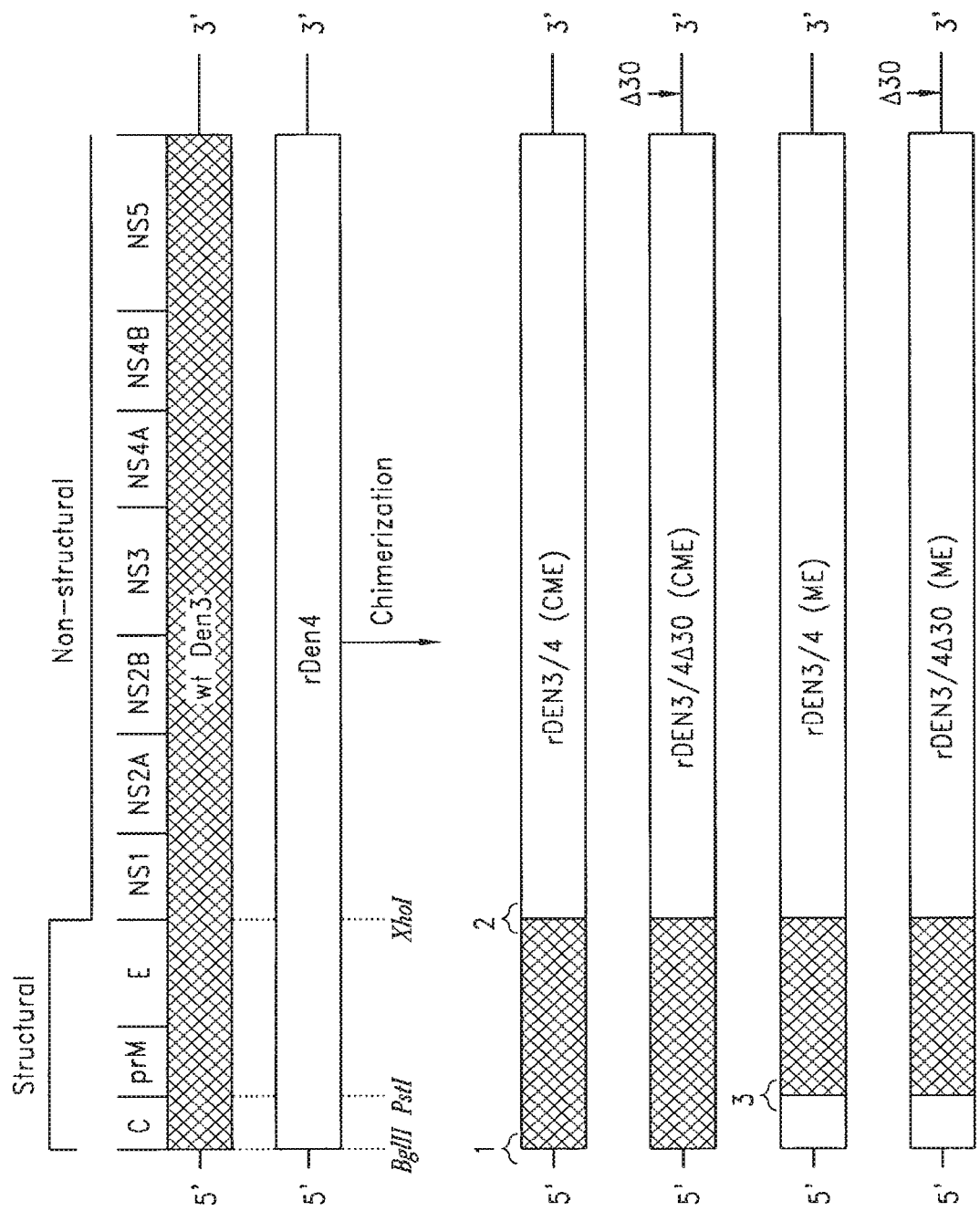
Figure 12A:
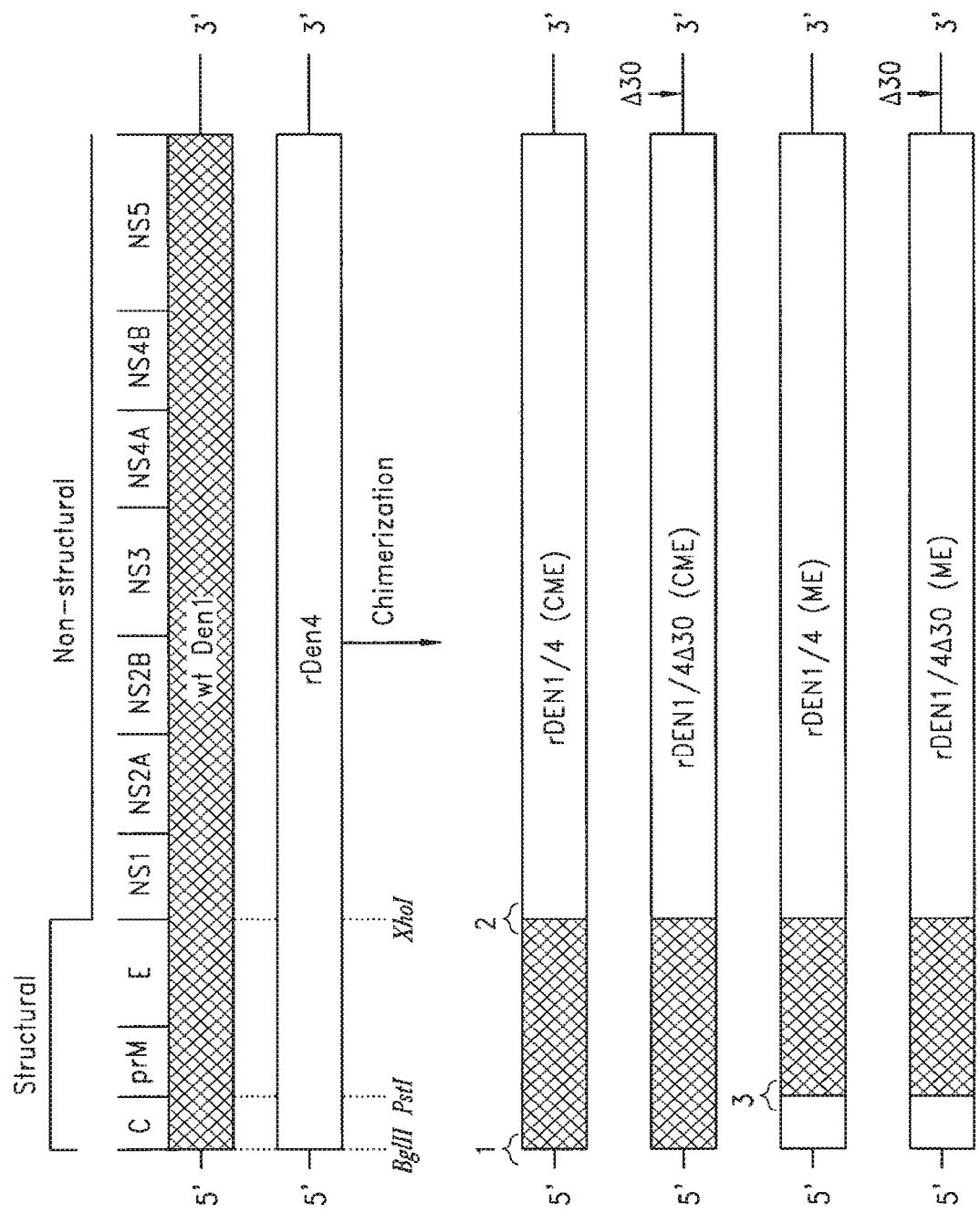
FIGS. 12A and 12B. Recombinant chimeric dengue viruses were constructed by introducing either the CME or the ME regions of DEN1 (Puerto Rico/94) into the DEN4 genetic background. The relative location of the Δ30 mutation in the 3' UTR is indicated by an arrow and intertypic junctions 1, 2, and 3 are indicated. Restriction enzyme recognition sites used in assembly of each chimeric cDNA are indicated. Nucleotide and amino acid sequence of the intertypic junction regions. Restriction enzyme recognition sites used in assembly of each chimeric cDNA are indicated.
Figure 12B:
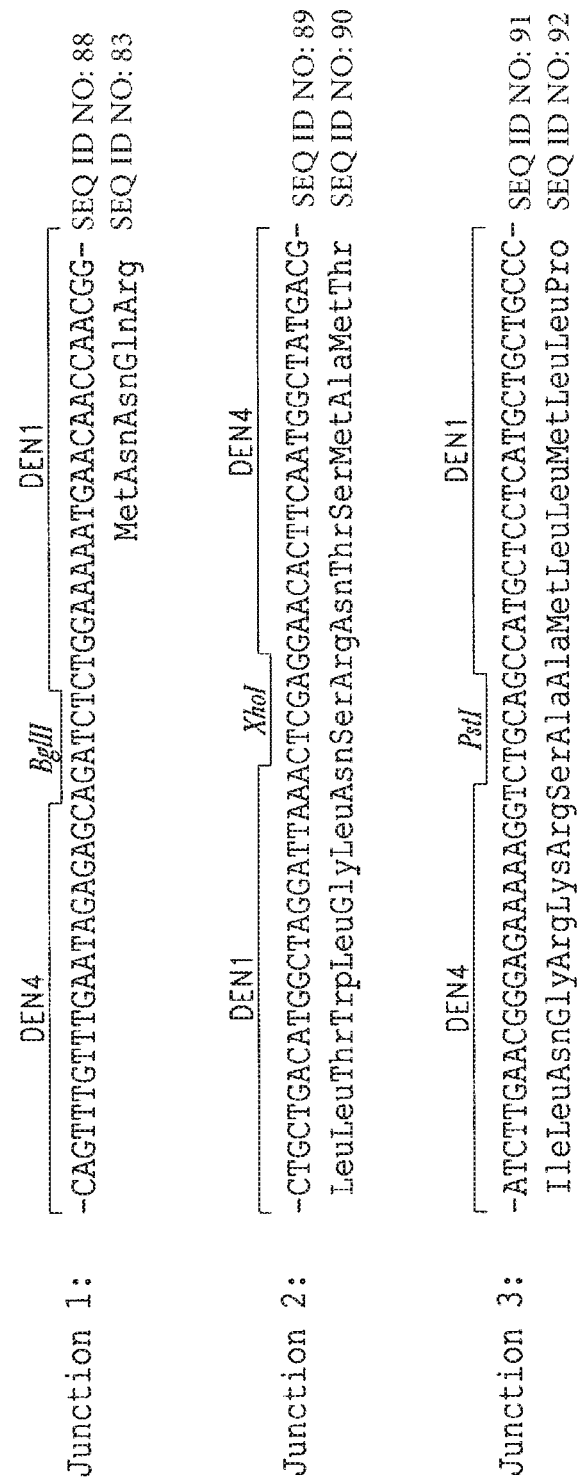

| Identification | Figure, Table, or Appendix | SEQ ID NO. |
|---|---|---|
| TL2 region of DEN1 | FIG. 2C | 1 |
| TL2 region of DEN2 | FIG. 2C | 2 |
| TL2 region of DEN3 | FIG. 2C | 3 |
| TL2 region of DEN4 | FIG. 2C | 4 |
| TL2 region of DEN1Δ30 | FIG. 2B | 5 |
| TL2 region of DEN2Δ30 | FIG. 2B | 6 |
| TL2 region of DEN3Δ30 | FIG. 2B | 7 |
| TL2 region of DEN4Δ30 | FIG. 2B | 8 |
| TL2 region of p2 | FIG. 6B | 9 |
| TL2 region of p2Δ30 | FIG. 6B | 10 |
| TL2 region of p3 | FIG. 8B | 11 |
| TL2 region of p3Δ30 | FIG. 8B | 12 |
| SpeI linker in p3 | FIG. 8A | 13 |
| rDEN2/4 junction 1 | FIG. 9B | 14-nt, 15-aa |
| rDEN2/4 junction 2 | FIG. 9B | 16-nt, 17-aa |
| rDEN2/4 junction 3 | FIG. 9B | 18-nt, 19-aa |
| rDEN3/4 junction 1 | FIG. 11B | 20-nt, 21-aa |
| rDEN3/4 junction 2 | FIG. 11B | 22-nt, 23-aa |
| rDEN3/4 junction 3 | FIG. 11B | 24-nt, 25-aa |
| rDEN1/4 junction 1 | FIG. 12B | 26-nt, 27-aa |
| rDEN1/4 junction 2 | FIG. 12B | 28-nt, 29-aa |
| rDEN1/4 junction 3 | FIG. 12B | 30-nt, 31-aa |
| D4 selected NS4B region | Table 15 | 32-nt, 33-aa |
| D1 selected NS4B region | Table 15 | 34-nt, 35-aa |
| D2 selected NS4B region | Table 15 | 36-nt, 37-aa |
| D3 selected NS4B region | Table 15 | 38-nt, 39-aa |
| CCACGGGCGCCGT | Table 26 | 40 |
| AAGGCCTGGA | Table 26 | 41 |
| TATCCCCGGGAC | Table 26 | 42 |
| AGAGCTCTCTC | Table 26 | 43 |
| GAATCTCCACCCGGA | Table 26 | 44 |
| CTGTCGAATC | Table 26 | 45 |
| DEN2 (Tonga/74) cDNA plasmid p2 | Appendix 1 | 46-nt, 47-aa |
| DEN3 (Sleman/78) cDNA plasmid p3 | Appendix 2 | 48-nt, 49-aa |
| DEN1 (Puerto Rico/94) CME chimeric region | Appendix 3 | 50-nt, 51-aa |
| DEN1 (Puerto Rico/94) ME chimeric region | Appendix 4 | 52-nt, 53-aa |

DETAILED DESCRIPTION OF THE PREFERRED EMBODIMENT

Introduction

A molecular approach is herewith used to develop a genetically stable live attenuated tetravalent dengue virus vaccine. Each component of the tetravalent vaccine, namely, DEN1, DEN2, DEN3, and DEN4, must be attenuated, genetically stable, and immunogenic. A tetravalent vaccine is needed to ensure simultaneous protection against each of the four dengue viruses, thereby precluding the possibility of developing the more serious illnesses dengue hemorrhagic fever/dengue shock syndrome (DHF/DSS), which occur in humans during secondary infection with a heterotypic wild-type dengue virus. Since dengue viruses can undergo genetic recombination in nature (Worobey, M. et al. 1999 PNAS USA 96:7352-7), the tetravalent vaccine should be genetically incapable of undergoing a recombination event between its four virus components that could lead to the generation of viruses lacking attenuating mutations. Previous approaches to develop a tetravalent dengue virus vaccine have been based on independently deriving each of the four virus components through separate mutagenic procedures, such as passage in tissue culture cells derived from a heterologous host. This strategy has yielded attenuated vaccine candidates (Bhamarapravati, N. and Sutee, Y. 2000

Vaccine 18:44-7). However, it is possible that gene exchanges among the four components of these independently derived tetravalent vaccines could occur in vaccinees, possibly creating a virulent recombinant virus. Virulent polioviruses derived from recombination have been generated in vaccinees following administration of a trivalent poliovirus vaccine (Guillot, S. et al. 2000 *J Virol* 74:8434-43).

The present invention describes: (1) improvements to the previously described rDEN4Δ30 vaccine candidate, 2) attenuated rDEN1Δ30, rDEN2Δ30, and rDEN3Δ30 recombinant viruses containing a 30 nucleotide deletion (Δ30) in a section of the 3' untranslated region (UTR) that is homologous to that in the rDEN4Δ30 recombinant virus, (3) a method to generate a tetravalent dengue virus vaccine composed of rDEN1Δ30, rDEN2Δ30, rDEN3Δ30, and rDEN4Δ30, 4) attenuated antigenic chimeric viruses, rDEN1/4Δ30, rDEN2/4Δ30, and rDEN3/4Δ30, for which the CME, ME, or E gene regions of rDEN4Δ30 have been replaced with those derived from DEN1, DEN2, or DEN3; alternatively rDEN1/3Δ30, rDEN2/3Δ30, and rDEN4/3Δ30 for which CME, ME, or E gene regions of rDEN3Δ30 have been replaced with those derived from DEN1, 2, or 4; alternatively rDEN1/2Δ30, rDEN3/2Δ30, and rDEN4/2Δ30 for which CME, ME, or E gene regions of rDEN2Δ30 have been replaced with those derived from DEN1, 3, or, 4; and alternatively rDEN2/1Δ30, rDEN3/1Δ30, and rDEN4/1Δ30 for which CME, ME, or E gene regions of rDEN1Δ30 have been replaced with those derived from DEN2, 3, or 4, and 5) a method to generate a tetravalent dengue virus vaccine composed of rDEN1/4Δ30, rDEN2/4Δ30, rDEN3/4Δ30, and rDEN4Δ30, alternatively rDEN1/3Δ30, rDEN2/3Δ30, rDEN4/3Δ30, and rDEN3Δ30, alternatively rDEN1/2Δ30, rDEN3/2Δ30, rDEN4/2Δ30, and rDEN2Δ30, and alternatively rDEN2/1Δ30, rDEN3/1Δ30, rDEN4/1Δ30, and rDEN1Δ30. These tetravalent vaccines are unique since they contain a common shared attenuating mutation which eliminates the possibility of generating a virulent wild-type virus in a vaccinee since each component of the vaccine possesses the same Δ30 attenuating deletion mutation. In addition, the rDEN1Δ30, rDEN2Δ30, rDEN3Δ30, rDEN4Δ30 tetravalent vaccine is the first to combine the stability of the Δ30 mutation with broad antigenicity. Since the Δ30 deletion mutation is in the 3' UTR of each virus, all of the proteins of the four component viruses are available to induce a protective immune response. Thus, the method provides a mechanism of attenuation that maintains each of the proteins of DEN1, DEN2, DEN3, and DEN4 viruses in a state that preserves the full capability of each of the proteins of the four viruses to induce humoral and cellular immune responses against all of the structural and non-structural proteins present in each dengue virus serotype.

Figure 1:
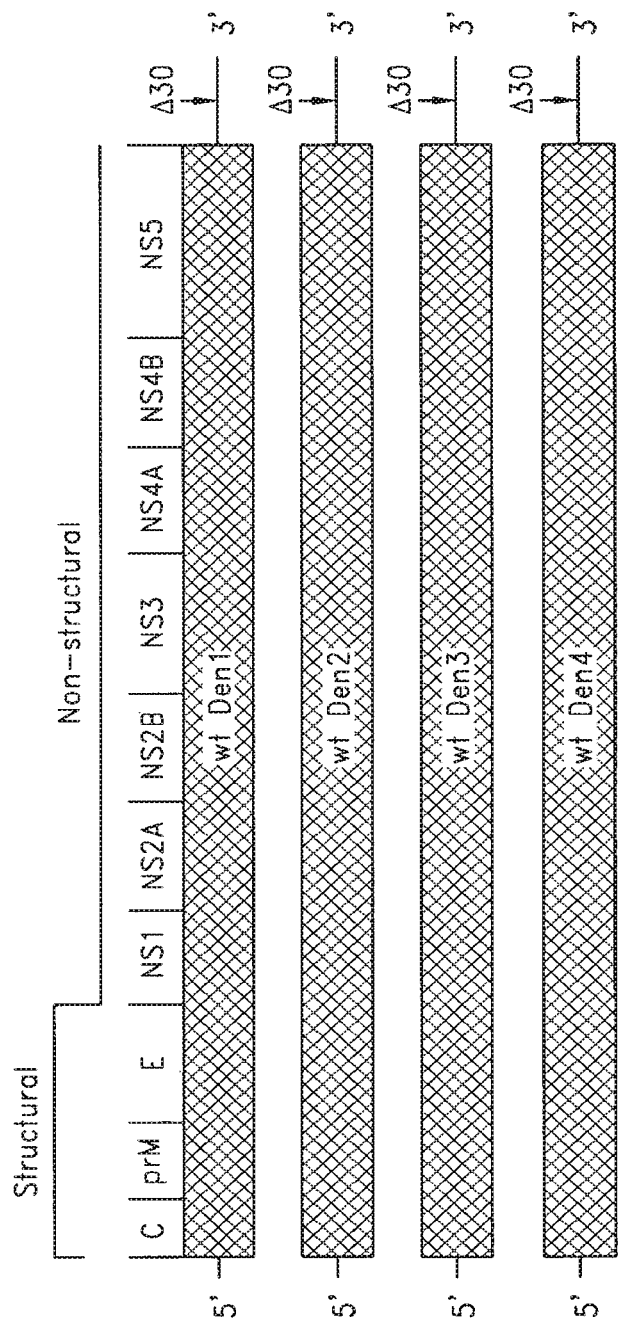
FIG. 1. The live attenuated tetravalent dengue virus vaccine contains dengue viruses representing each of the 4 serotypes, with each serotype containing its full set of unaltered wild-type structural and non-structural proteins and a shared Δ30 attenuating mutation. The relative location of the Δ30 mutation in the 3' untranslated region (UTR) of each component is indicated by an arrow.

As previously described, the DEN4 recombinant virus, rDEN4Δ30 (previously referred to as 2AΔ30), was engineered to contain a 30 nucleotide deletion in the 3' UTR of the viral genome (Durbin, A. P. et al. 2001 *Am J Trop Med Hyg* 65:405-13; Men, R. et al. 1996 *J Virol* 70:3930-7). Evaluation in rhesus monkeys showed the virus to be significantly attenuated relative to wild-type parental virus, yet highly immunogenic and completely protective. Also, a phase I clinical trial with adult human volunteers showed the rDEN4Δ30 recombinant virus to be safe and satisfactorily immunogenic (Durbin, A. P. et al. 2001 *Am J Trop Med Hyg* 65:405-13). To develop a tetravalent vaccine bearing a shared attenuating mutation in a untranslated region, we selected the Δ30 mutation to attenuate wild-type dengue viruses of serotypes 1, 2, and 3 since it attenuated wild-type DEN4 virus for rhesus monkeys and was safe in humans (FIG. 1).

The Δ30 mutation was first described and characterized in the DEN4 virus (Men, R. et al. 1996 *J Virol* 70:3930-7). In DEN4, the mutation consists of the removal of 30 contiguous nucleotides comprising nucleotides 10478-10507 of the 3' UTR (FIG. 2A) which form a putative stem-loop structure referred to as TL2 (Proutski, V. et al. 1997 *Nucleic Acids Res* 25:1194-202). Among the flaviviruses, large portions of the UTR form highly conserved secondary structures (Hahn, C. S. et al. 1987 *J Mol Biol* 198:33-41; Proutski, V. et al. 1997 *Nucleic Acids Res* 25:1194-202). Although the individual nucleotides are not necessarily conserved in these regions, appropriate base pairing preserves the stem-loop structure in each serotype, a fact that is not readily apparent when only considering the primary sequence (FIG. 2B, C).

Immunogenic Dengue Chimeras and Methods for their Preparation

Immunogenic dengue chimeras and methods for preparing the dengue chimeras are provided herein. The immunogenic dengue chimeras are useful, alone or in combination, in a pharmaceutically acceptable carrier as immunogenic compositions to minimize, inhibit, or immunize individuals and animals against infection by dengue virus.

Chimeras of the present invention comprise nucleotide sequences encoding the immunogenicity of a dengue virus of one serotype and further nucleotide sequences selected from the backbone of a dengue virus of a different serotype. These chimeras can be used to induce an immunogenic response against dengue virus.

In another embodiment, the preferred chimera is a nucleic acid chimera comprising a first nucleotide sequence encoding at least one structural protein from a dengue virus of a first serotype, and a second nucleotide sequence encoding nonstructural proteins from a dengue virus of a second serotype different from the first. In another embodiment the dengue virus of the second serotype is DEN4. In another embodiment, the structural protein can be the C protein of a dengue virus of the first serotype, the prM protein of a dengue virus of the first serotype, the E protein of a dengue virus of the first serotype, or any combination thereof.

The term "residue" is used herein to refer to an amino acid (D or L) or an amino acid mimetic that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill in the art will recognize that individual substitutions, deletions or additions in the amino acid sequence, or in the nucleotide sequence encoding for the amino acids, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art. The following six groups each contain amino acids that are conservative substitutions for one another:
1) Alanine (A), Serine (S), Threonine (T);
2) Aspartic acid (D), Glutamic acid (E);

3) Asparagine (N), Glutamine (Q);
4) Arginine (R), Lysine (K);
5) Isoleucine (D, Leucine (L), Methionine (M), Valine (V); and
6) Phenylalanine (F), Tyrosine (Y), Tryptophan (W).

As used herein, the terms "virus chimera," "chimeric virus," "dengue chimera" and "chimeric dengue virus" means an infectious construct of the invention comprising nucleotide sequences encoding the immunogenicity of a dengue virus of one serotype and further nucleotide sequences derived from the backbone of a dengue virus of a different serotype.

As used herein, "infectious construct" indicates a virus, a viral construct, a viral chimera, a nucleic acid derived from a virus or any portion thereof, which may be used to infect a cell.

As used herein, "nucleic acid chimera" means a construct of the invention comprising nucleic acid comprising nucleotide sequences encoding the immunogenicity of a dengue virus of one serotype and further nucleotide sequences derived from the backbone of a dengue virus of a different serotype. Correspondingly, any chimeric virus or virus chimera of the invention is to be recognized as an example of a nucleic acid chimera.

The structural and nonstructural proteins of the invention are to be understood to include any protein comprising or any gene encoding the sequence of the complete protein, an epitope of the protein, or any fragment comprising, for example, three or more amino acid residues thereof.

Dengue Chimeras

Dengue virus is a mosquito-borne *flavivirus* pathogen. The dengue virus genome contains a 5' untranslated region (5' UTR), followed by a capsid protein (C) encoding region, followed by a premembrane/membrane protein (prM) encoding region, followed by an envelope protein (E) encoding region, followed by the region encoding the nonstructural proteins (NS1-NS2A-NS2B-NS3-NS4A-NS4B-NS5) and finally a 3° untranslated region (3' UTR). The viral structural proteins are C, prM and E, and the nonstructural proteins are NS1-NS5. The structural and nonstructural proteins are translated as a single polyprotein and processed by cellular and viral proteases.

The dengue chimeras of the invention are constructs formed by fusing structural protein genes from a dengue virus of one serotype, e.g. DEN1, DEN2, DEN3, or DEN4, with non-structural protein genes from a dengue virus of a different serotype, e.g., DEN1, DEN2, DEN3, or DEN4.

The attenuated, immunogenic dengue chimeras provided herein contain one or more of the structural protein genes, or antigenic portions thereof, of the dengue virus of one serotype against which immunogenicity is to be conferred, and the nonstructural protein genes of a dengue virus of a different serotype.

The chimera of the invention contains a dengue virus genome of one serotype as the backbone, in which the structural protein gene(s) encoding C, prM, or E protein(s) of the dengue genome, or combinations thereof, are replaced with the corresponding structural protein gene(s) from a dengue virus of a different serotype that is to be protected against. The resulting viral chimera has the properties, by virtue of being chimerized with a dengue virus of another serotype, of attenuation and is therefore reduced in virulence, but expresses antigenic epitopes of the structural gene products and is therefore immunogenic.

The genome of any dengue virus can be used as the backbone in the attenuated chimeras described herein. The backbone can contain mutations that contribute to the attenuation phenotype of the dengue virus or that facilitate replication in the cell substrate used for manufacture, e.g., Vero cells. The mutations can be in the nucleotide sequence encoding nonstructural proteins, the 5' untranslated region or the 3' untranslated region. The backbone can also contain further mutations to maintain the stability of the attenuation phenotype and to reduce the possibility that the attenuated virus or chimera might revert back to the virulent wild-type virus. For example, a first mutation in the 3' untranslated region and a second mutation in the 5' untranslated region will provide additional attenuation phenotype stability, if desired. In particular, a mutation that is a deletion of 30 nts from the 3' untranslated region of the DEN4 genome between nts 10478-10507 results in attenuation of the DEN4 virus (Men et al. 1996 *J. Virology* 70:3930-3933; Durbin et al. 2001 *Am J Trop Med* 65:405-413, 2001). Therefore, the genome of any dengue type 4 virus containing such a mutation at this locus can be used as the backbone in the attenuated chimeras described herein. Furthermore, other dengue virus genomes containing an analogous deletion mutation in the 3' untranslated region of the genomes of other dengue virus serotypes may also be used as the backbone structure of this invention.

Such mutations may be achieved by site-directed mutagenesis using techniques known to those skilled in the art. It will be understood by those skilled in the art that the virulence screening assays, as described herein and as are well known in the art, can be used to distinguish between virulent and attenuated backbone structures.

Construction of Dengue Chimeras

The dengue virus chimeras described herein can be produced by substituting at least one of the structural protein genes of the dengue virus of one serotype against which immunity is desired into a dengue virus genome backbone of a different serotype, using recombinant engineering techniques well known to those skilled in the art, namely, removing a designated dengue virus gene of one serotype and replacing it with the desired corresponding gene of dengue virus of a different serotype. Alternatively, using the sequences provided in GenBank, the nucleic acid molecules encoding the dengue proteins may be synthesized using known nucleic acid synthesis techniques and inserted into an appropriate vector. Attenuated, immunogenic virus is therefore produced using recombinant engineering techniques known to those skilled in the art.

As mentioned above, the gene to be inserted into the backbone encodes a dengue structural protein of one serotype. Preferably the dengue gene of a different serotype to be inserted is a gene encoding a C protein, a prM protein and/or an E protein. The sequence inserted into the dengue virus backbone can encode both the prM and E structural proteins of the other serotype. The sequence inserted into the dengue virus backbone can encode the C, prM and E structural proteins of the other serotype. The dengue virus backbone is the DEN1, DEN2, DEN3, or DEN4 virus genome, or an attenuated dengue virus genome of any of these serotypes, and includes the substituted gene(s) that encode the C, prM and/or E structural protein(s) of a dengue virus of a different serotype, or the substituted gene(s) that encode the prM and/or E structural protein(s) of a dengue virus of a different serotype.

Suitable chimeric viruses or nucleic acid chimeras containing nucleotide sequences encoding structural proteins of dengue virus of any of the serotypes can be evaluated for usefulness as vaccines by screening them for phenotypic markers of attenuation that indicate reduction in virulence with retention of immunogenicity. Antigenicity and immunogenicity can be evaluated using in vitro or in vivo reactivity with dengue antibodies or immunoreactive serum using routine screening procedures known to those skilled in the art.

Dengue Vaccines

The preferred chimeric viruses and nucleic acid chimeras provide live, attenuated viruses useful as immunogens or vaccines. In a preferred embodiment, the chimeras exhibit high immunogenicity while at the same time not producing dangerous pathogenic or lethal effects.

The chimeric viruses or nucleic acid chimeras of this invention can comprise the structural genes of a dengue virus of one serotype in a wild-type or an attenuated dengue virus backbone of a different serotype. For example, the chimera may express the structural protein genes of a dengue virus of one serotype in either of a dengue virus or an attenuated dengue virus background of a different serotype.

The strategy described herein of using a genetic background that contains nonstructural regions of a dengue virus genome of one serotype, and, by chimerization, the properties of attenuation, to express the structural protein genes of a dengue virus of a different serotype has lead to the development of live, attenuated dengue vaccine candidates that express structural protein genes of desired immunogenicity. Thus, vaccine candidates for control of dengue pathogens can be designed.

Viruses used in the chimeras described herein are typically grown using techniques known in the art. Virus plaque or focus forming unit (FFU) titrations are then performed and plaques or FFU are counted in order to assess the viability, titer and phenotypic characteristics of the virus grown in cell culture. Wild type viruses are mutagenized to derive attenuated candidate starting materials.

Chimeric infectious clones are constructed from various dengue serotypes. The cloning of virus-specific cDNA fragments can also be accomplished, if desired. The cDNA fragments containing the structural protein or nonstructural protein genes are amplified by reverse transcriptase-polymerase chain reaction (RT-PCR) from dengue RNA with various primers. Amplified fragments are cloned into the cleavage sites of other intermediate clones. Intermediate, chimeric dengue clones are then sequenced to verify the sequence of the inserted dengue-specific cDNA.

Full genome-length chimeric plasmids constructed by inserting the structural or nonstructural protein gene region of dengue viruses into vectors are obtainable using recombinant techniques well known to those skilled in the art.

Methods of Administration

The viral chimeras described herein are individually or jointly combined with a pharmaceutically acceptable carrier or vehicle for administration as an immunogen or vaccine to humans or animals. The terms "pharmaceutically acceptable carrier" or "pharmaceutically acceptable vehicle" are used herein to mean any composition or compound including, but not limited to, water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The immunogenic or vaccine formulations may be conveniently presented in viral plaque forming unit (PFU) unit or focus forming unit (FFU) dosage form and prepared by using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients particularly mentioned above, the formulations of the present invention may include other agents commonly used by one of ordinary skill in the art.

The immunogenic or vaccine composition may be administered through different routes, such as oral or parenteral, including, but not limited to, buccal and sublingual, rectal, aerosol, nasal, intramuscular, subcutaneous, intradermal, and topical. The composition may be administered in different forms, including, but not limited to, solutions, emulsions and suspensions, microspheres, particles, microparticles, nanoparticles and liposomes. It is expected that from about 1 to about 5 doses may be required per immunization schedule. Initial doses may range from about 100 to about 100,000 PFU or FFU, with a preferred dosage range of about 500 to about 20,000 PFU or FFU, a more preferred dosage range of from about 1000 to about 12,000 PFU or FFU and a most preferred dosage range of about 1000 to about 4000 PFU or FFU. Booster injections may range in dosage from about 100 to about 20,000 PFU or FFU, with a preferred dosage range of about 500 to about 15,000, a more preferred dosage range of about 500 to about 10,000 PFU or FFU, and a most preferred dosage range of about 1000 to about 5000 PFU or FFU. For example, the volume of administration will vary depending on the route of administration. Intramuscular injections may range in volume from about 0.1 ml to 1.0 ml.

The composition may be stored at temperatures of from about −100° C. to about 4° C. The composition may also be stored in a lyophilized state at different temperatures including room temperature. The composition may be sterilized through conventional means known to one of ordinary skill in the art. Such means include, but are not limited to, filtration. The composition may also be combined with bacteriostatic agents to inhibit bacterial growth.

Administration Schedule

The immunogenic or vaccine composition described herein may be administered to humans, especially individuals travelling to regions where dengue virus infection is present, and also to inhabitants of those regions. The optimal time for administration of the composition is about one to three months before the initial exposure to the dengue virus. However, the composition may also be administered after initial infection to ameliorate disease progression, or after initial infection to treat the disease.

Adjuvants

A variety of adjuvants known to one of ordinary skill in the art may be administered in conjunction with the chimeric virus in the immunogen or vaccine composition of this invention. Such adjuvants include, but are not limited to, the following: polymers, co-polymers such as polyoxyethylene-polyoxypropylene copolymers, including block co-polymers, polymer p 1005, Freund's complete adjuvant (for animals), Freund's incomplete adjuvant; sorbitan monooleate, squalene, CRL-8300 adjuvant, alum, QS 21, muramyl dipeptide, CpG oligonucleotide motifs and combinations of CpG oligonucleotide motifs, trehalose, bacterial extracts, including mycobacterial extracts, detoxified endotoxins, membrane lipids, or combinations thereof.

Nucleic Acid Sequences

Nucleic acid sequences of dengue virus of one serotype and dengue virus of a different serotype are useful for designing nucleic acid probes and primers for the detection of dengue virus chimeras in a sample or specimen with high sensitivity and specificity. Probes or primers corresponding to dengue virus can be used to detect the presence of a vaccine virus. The nucleic acid and corresponding amino acid sequences are useful as laboratory tools to study the organisms and diseases and to develop therapies and treatments for the diseases.

Nucleic acid probes and primers selectively hybridize with nucleic acid molecules encoding dengue virus or complementary sequences thereof. By "selective" or "selectively" is meant a sequence which does not hybridize with other nucleic acids to prevent adequate detection of the dengue virus sequence. Therefore, in the design of hybridizing nucleic acids, selectivity will depend upon the other components present in the sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus has the same meaning as "specifically hybridizing." The selectively hybridizing nucleic acid probes and primers of this invention can have at least 70%, 80%, 85%, 90%, 95%, 97%, 98% and 99% complementarity with the segment of the sequence to which it hybridizes, preferably 85% or more.

The present invention also contemplates sequences, probes and primers that selectively hybridize to the encoding nucleic acid or the complementary, or opposite, strand of the nucleic acid. Specific hybridization with nucleic acid can occur with minor modifications or substitutions in the nucleic acid, so long as functional species-species hybridization capability is maintained. By "probe" or "primer" is meant nucleic acid sequences that can be used as probes or primers for selective hybridization with complementary nucleic acid sequences for their detection or amplification, which probes or primers can vary in length from about 5 to 100 nucleotides, or preferably from about 10 to 50 nucleotides, or most preferably about 18-24 nucleotides. Isolated nucleic acids are provided herein that selectively hybridize with the species-specific nucleic acids under stringent conditions and should have at least five nucleotides complementary to the sequence of interest as described in Molecular Cloning: A Laboratory Manual, 2nd ed., Sambrook, Fritsch and Maniatis, Cold Spring Harbor Laboratory, Cold Spring Harbor, N.Y., 1989.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of dengue virus, the degree of complementarity between the hybridizing nucleic acid (probe or primer) and the sequence to which it hybridizes is at least enough to distinguish hybridization with a nucleic acid from other organisms.

The nucleic acid sequences encoding dengue virus can be inserted into a vector, such as a plasmid, and recombinantly expressed in a living organism to produce recombinant dengue virus peptide and/or polypeptides.

The nucleic acid sequences of the invention include a diagnostic probe that serves to report the detection of a cDNA amplicon amplified from the viral genomic RNA template by using a reverse-transcription/polymerase chain reaction (RT/PCR), as well as forward and reverse amplimers that are designed to amplify the cDNA amplicon. In certain instances, one of the amplimers is designed to contain a vaccine virus-specific mutation at the 3'-terminal end of the amplimer, which effectively makes the test even more specific for the vaccine strain because extension of the primer at the target site, and consequently amplification, will occur only if the viral RNA template contains that specific mutation.

Automated PCR-based nucleic acid sequence detection systems have been recently developed. TaqMan assay (Applied Biosystems) is widely used. A more recently developed strategy for diagnostic genetic testing makes use of molecular beacons (Tyagi and Kramer, 1996 *Nature Biotechnology* 14:303-308). Molecular beacon assays employ quencher and reporter dyes that differ from those used in the TaqMan assay. These and other detection systems may used by one skilled in the art.

Example 1

Improvement of Dengue Virus Vaccine Candidate rDEN4Δ30

The safety of recombinant live-attenuated dengue-4 vaccine candidate rDEN4Δ30 was evaluated in twenty human volunteers who received a dose of 5.0 $\log_{10}$ plaque forming units (PFU) (Durbin A. P. et al. 2001 *Am J Trop Med Hyg* 65:405-413). The vaccine candidate was found to be safe, well-tolerated and immunogenic in all of the vaccinees. However, five of the vaccinees experienced a transient elevation in alanine aminotransferase levels, three experienced neutropenia and ten vaccinees developed an asymptomatic macular rash, suggesting that it may be necessary to further attenuate this vaccine candidate.

Currently, a randomized, double-blind, placebo-controlled, dose de-escalation study is being conducted to determine the human infectious dose 50 ($HID_{50}$) of rDEN4Δ30. Each dose cohort consists of approximately twenty vaccinees and four placebo recipients. To date, complete data for doses of 3.0 $\log_{10}$ PFU and 2.0 $\log_{10}$ PFU has been collected. rDEN4Δ30 infected 100% of vaccinees when 3.0 $\log_{10}$ PFU was administered and 95% of vaccinees when 2.0 $\log_{10}$ PFU was administered (Table 1). The vaccine candidate caused no symptomatic illness at either dose (Table 1). One vaccinee who received 3.0 $\log_{10}$ PFU experienced a transient elevation in alanine aminotransferase levels and approximately one fourth of the vaccinees experienced neutropenia at both doses (Table 1). Neutropenia was transient and mild. More than half of the vaccinees developed a macular rash at both doses; the occurrence of rash was not correlated with vaccination dose or with viremia (Table 1 and Table 2). Neither peak titer nor onset of viremia differed between the 3.0 $\log_{10}$ PFU and 2.0 $\log_{10}$ PFU doses, though both measures of viremia were significantly lower for these doses than for a dose of 5.0 $\log_{10}$ PFU (Table 3). The vaccine candidate was immunogenic in 95% of vaccinees at both doses and neutralizing antibody did not decline between days 28 and 42 post-vaccination (Table 4). Although the $HID_{50}$ has not been determined yet, it is clearly less than 2.0 $\log_{10}$ PFU. Interestingly, decreases in the dose of vaccine have had no consistent effect on immunogenicity, viremia, benign neutropenia or the occurrence of rash. Thus it will not necessarily be possible to further attenuate rDEN4Δ30 by decreasing the dose of virus administered, and other approaches must be developed.

TABLE 1 rDEN4Δ30 clinical summary

| No. of subjects | Dose[a] | No. infected | No. with viremia | Mean peak titer[b] | No. volunteers with: | | | |
|---|---|---|---|---|---|---|---|---|
| | | | | | Fever | Rash | Neutropenia[c] | ↑ALT |
| 20 | 5.0 | 20 | 14 | 1.2 (0.2) | 1[d] | 10 | 3 | 5 |
| 20 | 3.0 | 20 | 7 | 0.4 (0.0) | 0 | 11 | 5 | 1[e] |
| 20 | 2.0 | 19 | 11 | 0.6 (0.1) | 1[d] | 16 | 4 | 0 |
| 8 | 0 | 0 | 0 | 0 | 0 | 0 | 0 | 0 |

[a]$Log_{10}$ pfu
[b]$Log_{10}$ pfu/mL
[c]Neutropenia defined as ANC < 1500/dl
[d]T Max in volunteer = 100.4° F.
[e]ALT day 0 = 78, ALT max = 91 (day 14)

TABLE 2

Pattern of rash in vaccinees

| Dose[a] | No. with viremia | No. with rash | Viremia & rash | Viremia no rash | Mean day of onset ± SD | Mean duration (days ± SD) |
|---|---|---|---|---|---|---|
| 5 | 14/20 | 10/20 | 9/20 | 5/20 | 8.1 ± 1.3 [A][a] | 3.6 ± 2.0 [A] |
| 3 | 7/20 | 11/20 | 6/20 | 1/20 | 12.2 ± 1.4 [B] | 5.0 ± 2.1 [A] |
| 2 | 11/20 | 16/20 | 9/20 | 2/20 | 11.2 ± 1.4 [B] | 6.9 ± 1.7 [B] |

[a]$\log_{10}$ pfu
[b]Means in each column with different letters are significantly different (α = 0.05)

TABLE 3 rDEN4Δ30 viremia summary

| Dose[a] | # with viremia | Mean peak titer ($\log_{10}$ pfu/mL) | Mean onset of viremia (day ± SD) | Mean duration of viremia (day ± SD) |
|---|---|---|---|---|
| 5 | 14 | 1.2 ± 0.2 [A] | 5.8 ± 2.4 [A][b] | 4.4 ± 2.4 [A] |
| 3 | 7 | 0.4 ± 0.0 [B] | 9.1 ± 2.5 [B] | 1.6 ± 1.0 [B] |
| 2 | 11 | 0.6 ± 0.0 [B] | 8.7 ± 2.4 [B] | 2.6 ± 2.0 [A] |

[a]$\log_{10}$ pfu
[b]Means in each column with different letters are significantly different (α = 0.05)

TABLE 4

Immunogenicity of rDEN4Δ30

| No. of subjects | Dose ($\log_{10}$) | No. infected | Geometric mean serum neutralizing antibody titer (range) | | % seroconversion |
|---|---|---|---|---|---|
| | | | Day 28 | Day 42 | |
| 20 | 5.0 | 20 | 567 (72-2455) | 399 (45-1230) | 100 |
| 20 | 3.0 | 20 | 156 (5-2365) | 158 (25-1222) | 95 |
| 20 | 2.0 | 19 | 163 (5-943) | 165 (5-764) | 95 |
| 8 | 0 | 0 | 0 | 0 | 0 |

Two approaches have been taken to further attenuate rDEN4Δ30. This first is the generation and characterization of attenuating point mutations in rDEN4 using 5' fluorouracil mutagenesis (Blaney, J. E. Jr. et al. 2002 *Virology* 300: 125-139; Blaney, J. E. Jr. et al, 2001 *J. Virol.* 75: 9731-9740). This approach has identified a panel of point mutations that confer a range of temperature sensitivity (ts) and small plaque (sp) phenotypes in Vero and cells and attenuation (att) phenotypes in suckling mouse brain and SCID mice engrafted with HuH-7 cells (SCID-HuH-7 mice). In this example, a subset of these mutations has been introduced to rDEN4Δ30 and the phenotypes of the resulting viruses evaluated.

A second approach was to create a series of paired charge-to-alanine mutations in contiguous pairs of charged amino acid residues in the rDEN4 NS5 gene. As demonstrated previously, mutation of 32 individual contiguous pairs of charged amino acid residues in rDEN4 NS5 conferred a range of ts phenotypes in Vero and HuH-7 cells and a range of att phenotypes in suckling mouse brain (Hanley, K. H. et al. 2002 *J. Virol.* 76 525-531). As demonstrated below, these mutations also confer an att phenotype in SCID-HuH-7 mice. These mutations have been introduced, either as single pairs or sets of two pairs, into rDEN4Δ30 to determine whether they are compatible with the Δ30 mutation and whether they enhance the att phenotypes of rDEN4Δ30.

A panel of rDEN4 viruses bearing individual point mutations have been characterized which possess temperature sensitive and/or small plaque phenotypes in tissue culture and varying levels of attenuated replication in suckling mouse brain when compared to wild type rDEN4 virus (Blaney, J. E. et al. 2002 *Virology* 300:125-139; Blaney, J. E. et al. 2001 *J Virol.* 75:9731-9740). Three mutations have been selected to combine with the Δ30 deletion mutation to evaluate their ability to further restrict replication of rDEN4Δ30 in rhesus monkeys. First, the missense mutation in NS3 at nucleotide 4995 (Ser>Pro) which confers temperature sensitivity in Vero and HuH-7 cells and restricted replication in suckling mouse brain was previously combined with the Δ30 mutation (Blaney, J. E. et al. 2001 *J Virol.* 75:9731-9740). The resulting virus, rDEN4Δ30-4995, was found to be more restricted (1,000-fold) in mouse brain replication than rDEN4Δ30 virus (<5-fold) when compared to wild type rDEN4 virus. Second, a missense mutation at nucleotide 8092 (Glu>Gly) which also confers temperature sensitivity in Vero and HuH-7 cells and 10,000-fold restricted replication in suckling mouse brain was combined with the Δ30 mutation here. Third, a substitution in the 3' UM at nucleotide 10634 which confers temperature sensitivity in Vero and HuH-7 cells, small plaque size in HuH-7 cells, and approximately 1,000-fold restricted replication in suckling mouse brain and SCID mice transplanted with HuH-7 cells was combined with the Δ30 mutation here (Blaney, J. E. et al. 2002 *Virology* 300:125-139).

For the present investigation, subcloned fragments of p4 (Durbin, A. P. et al. 2001 *Am J Trop Med Hyg* 65:405-13) containing the above mutations were introduced into the p4Δ30 cDNA clone. For transcription and recovery of virus, cDNA was linearized with Acc65I (isoschizomer of KpnI which cleaves leaving only a single 3' nucleotide) and used as template for transcription by SP6 RNA polymerase as previously described (Blaney, J. E. et al. 2002 *Virology* 300:125-139). C6/36 mosquito cells were transfected using liposome-mediated transfection and cell culture supernatants were harvested between days five and seven. Recovered virus was terminally diluted twice in Vero cells and passaged two (rDEN4Δ30-4995) or three (rDEN4Δ30-8092 and rDEN4Δ30-10634) times in Vero cells.

The complete genomic sequences of rDEN4Δ30-4995, rDEN4Δ30-8092, and rDEN4Δ30-10634 viruses were determined as previously described (Durbin et al. 2001 *Am. J. Trop. Med. Hyg.* 65:405-413). As expected, each rDEN4Δ30 virus derivative contained the Δ30 mutation. Unexpectedly, in rDEN4Δ30-4995 virus, the nucleotide changes in the codon containing nucleotide 4995, resulted in a Ser>Leu amino acid change rather than a Ser>Pro change since the p4Δ30-4995 cDNA was designed to introduce the Ser>Pro change (Table 5). The p4Δ30-4995 cDNA clone was indeed found to encode a Ser 2>Pro change at nucleotide 4995, so it is unclear how the virus population acquired the Ser>Leu mutation. Nevertheless, this virus was evaluated to assess the phenotype specified by this missense mutation. rDEN4Δ30-4995 virus was also found to contain an incidental mutation at nucleotides 4725-6 which resulted in a single amino acid change (Ser>Asp). The rDEN4Δ30-8092 and rDEN4Δ30-10634 viruses contained the appropriate nucleotide substitutions as well as additional incidental mutations in E, NS4B and NS4B, respectively (Table 5).

TABLE 5

Missense and UTR mutations present in rDEN4Δ30 virus derivatives bearing introduced point mutations.

| Virus | Gene | Nucleotide position | Nucleotide substitution | Amino acid position[a] | Amino acid change |
|---|---|---|---|---|---|
| rDEN4Δ30-4995 | NS3 | 4725 | U > G | 1542 | Ser > Asp |
| | NS3 | 4726 | C > A | 1542 | Ser > Asp |
| | NS3 | 4995[b] | U > C | 1632 | Ser > Leu |
| rDEN4Δ30-8092 | E | 1612 | A > C | 504 | Asp > Ala |
| | NS4B | 7131 | A > G | 2344 | Thr > Ala |
| | NS5 | 8092[b] | A > G | 2664 | Glu > Gly |
| rDEN4Δ30-10634 | NS4B | 6969 | A > U | 2290 | Met > Leu |
| | NS4B | 7182 | G > C | 2361 | Gly > Arg |
| | 3' UTR | 10634[b] | U > C | none | none |

[a]Amino acid position in DEN4 polyprotein beginning with the methionine residue of the C protein (nucleotides 102-104) as position 1.

[b]Mutation restricts replication in mouse models of DEN4 infection which were introduced by Kunkel mutagenesis.

Replication of the three modified rDEN4Δ30 viruses were compared to rDEN4Δ30 and wild type rDEN4 virus in the suckling mouse brain model and SCID mice transplanted with HuH-7 cells (SCID-HuH-7 mice). Experiments were conducted as previously described (Blaney, J. E. et al. 2002 *Virology* 300:125-139; Blaney, J. E. et al. 2001 *J Virol.* 75:9731-9740). Briefly, for infection of suckling mouse brain, groups of six seven-day-old mice were inoculated intracerebrally with 4.0 $\log_{10}$ PFU of virus and the brain of each mouse was removed five days later. Clarified supernatants of 10% brain suspensions were then frozen at −70° C., and the virus titer was determined by plaque assay in Vero cells. For analysis of DEN4 virus replication in SCID-1-HuH-7 mice, four to six week-old SCID mice were injected intraperitoneally with $10^7$ HuH-7 cells. Five to six weeks after transplantation, mice were infected by direct inoculation into the tumor with 4.0 $\log_{10}$ PFU of virus, and serum for virus titration was obtained by tail-nicking on day 7. The virus titer was determined by plaque assay in Vero cells.

Wild type rDEN4 virus replicated to 6.0 $\log_{10}$ PFU/g in suckling mouse brain, and rDEN4Δ30 was restricted in replication by 0.7 $\log_{10}$ PFU/g, which is similar to previous observations (Table 6) (Blaney, J. E. et al. 2001 *J Virol.* 75:9731-9740). rDEN4Δ30-4995, rDEN4Δ30-8092, and rDEN4Δ30-10634 viruses were found to have restricted replication in suckling mouse brain when compared to rDEN4 virus of 3.3, 2.8, and 2.4 $\log_{10}$ PFU/g, respectively. These results indicate that the additional attenuating mutations serve to further restrict replication of the rDEN4Δ30 virus in mouse brain ranging from 50-fold (rDEN4Δ30-10634) to 400-fold (rDEN4Δ30-4995). In SCID-HuH-7 mice, virus titer of rDEN4Δ30 virus was 0.4 $\log_{10}$ PFU/ml lower than rDEN4 virus, which is also similar to previous studies (Blaney, J. E. et al. 2002 *Virology* 300:125-139). Each modified rDEN4Δ30 virus was found to be further restricted in replication in SOD-HuH-7 mice (Table 6). rDEN4Δ30-4995, rDEN4Δ30-8092, and rDEN4Δ30-10634 viruses had restricted replication in SCID-HuH-7 mice when compared to rDEN4 virus of 2.9, 1.1, and 2.3 $\log_{10}$ PFU/g below the level of wild type rDEN4 virus, respectively. Two important observations were made: (1) The 4995, 8092 and 10634 mutations were compatible for viability with the Δ30 mutation, and (2) These three modified rDEN4Δ30 viruses had between a 10 and 1,000-fold reduction in replication in comparison to rDEN4 wild-type virus, which allows viruses with a wide range of attenuation in this model to be further evaluated in monkeys or humans.

TABLE 6

Addition of point mutations in NS3, NS5, or the 3' UTR to rDEN4Δ30 virus further attenuates the virus for suckling mouse brain and SCID-HuH-7 mice.

| | Replication in suckling mouse brain[a] | | | Replication in SCID-HuH-7 mice[c] | | |
|---|---|---|---|---|---|---|
| Virus | No. of mice | Virus titer ± SE $\log_{10}$ PFU/g brain | Mean $\log_{10}$-unit reduction from wt[b] | No. of mice | Virus titer ± SE $\log_{10}$ PFU/ml serum | Mean $\log_{10}$-unit reduction from wt[b] |
| rDEN4 | 12 | 6.0 ± 0.1 | — | 13 | 6.4 ± 0.2 | — |
| rDEN4Δ30 | 12 | 5.3 ± 0.1 | 0.7 | 20 | 6.0 ± 0.2 | 0.4 |
| rDEN4Δ30-4995 | 6 | 2.7 ± 0.4 | 3.3 | 5 | 3.5 ± 0.3 | 2.9 |
| rDEN4Δ30-8092 | 6 | 3.2 ± 0.2 | 2.8 | 7 | 5.0 ± 0.4 | 1.1 |
| rDEN4Δ30-10634 | 12 | 3.6 ± 0.1 | 2.4 | 5 | 4.4 ± 0.3 | 2.3 |

[a]Groups of 6 suckling mice were inoculated i.c. with $10^4$ PFU of virus. Brains were removed 5 days later, homogenized, and titered in Vero cells.
[b]Comparison of mean virus titers of mice inoculated with mutant virus and concurrent rDEN4 wt control.
[c]Groups of HuH-7-SCID mice were inoculated directly into the tumor with $10^4$ PFU virus. Serum was collected on day 6 and 7 and titered in Vero cells.

Based on the findings in the two mouse models of DEN4 virus infection, each of the rDEN4Δ30-4995, rDEN4Δ30-8092, and rDEN4Δ30-10634 viruses was evaluated in the rhesus macaque model of DEN4 infection which has been previously described (Durbin et al. 2001 *Am. J. Trop. Med. Hyg.* 65:405-413). Briefly, groups of four (rDEN4Δ30-4995, rDEN4Δ30-8092, and rDEN4Δ30-10634) or two (rDEN4, rDEN4Δ30, mock) monkeys were inoculated with 5.0 $\log_{10}$ PFU virus subcutaneously. Monkeys were observed daily and serum was collected on days 0 to 6, 8, 10, and 12, and virus titers were determined by plaque assay in Vero cells for measurement of viremia. On day 28, serum was drawn and the level of neutralizing antibodies was tested by plaque reduction assay in Vero cells as previously described (Durbin et al. 2001 *Am. J. Trop. Med. Hyg.* 65:405-413).

Figure 3:
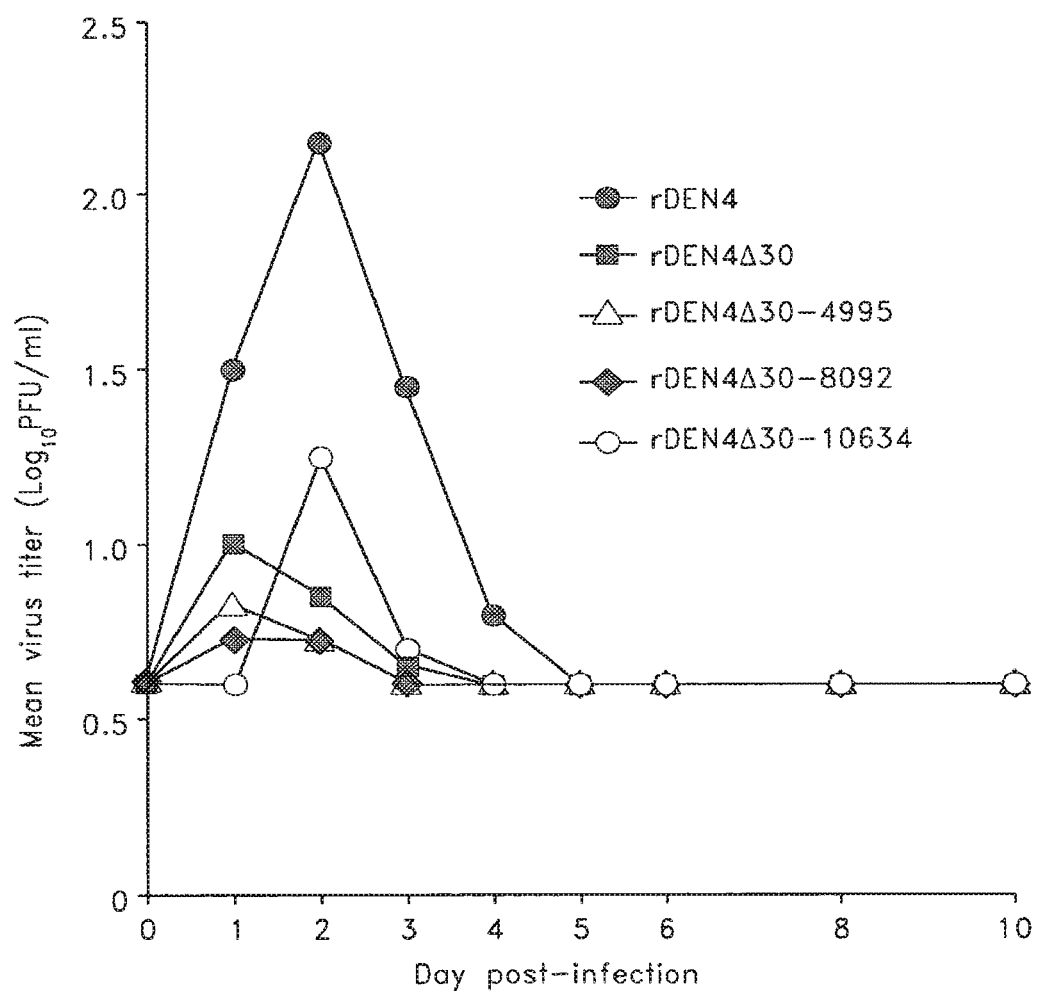
FIG. 3. Viremia levels in rhesus monkeys inoculated with rDEN4 vaccine candidates bearing 5-FU derived mutations. Groups of four or two (rDEN4 and rDEN4Δ30) monkeys were inoculated with 5.0 $\log_{10}$ PFU virus subcutaneously. Serum was collected daily and virus titers were determined by plaque assay in Vero cells. The limit of virus detection was 0.7 $\log_{10}$ PFU/ml. Mean virus titers are indicated for each group.

Viremia was detected beginning on day 1 post-infection and ended by day 4 in all monkeys (Table 7, FIG. 3). Viremia was present in each monkey infected with rDEN4, rDEN4Δ30, or rDEN4Δ30-10634 virus, but only 2 out of 4 monkeys infected with rDEN4Δ30-4995 or rDEN4Δ30-8092 virus had detectable viremia. As expected, infection with rDEN4 virus resulted in the highest mean number of viremic days per monkey (10 days) as well as mean peak virus titer (2.2 $\log_{10}$ PFU/ml). Monkeys infected with rDEN4Δ30 virus had both a lower mean number of viremic days per monkey (2.0 days) and mean peak virus titer (1.1 $\log_{10}$ PFU/ml) compared to rDEN4 virus. Groups of monkeys infected with each of the modified rDEN4Δ30 viruses had a further restricted mean number of viremic days with those inoculated with rDEN4Δ30-8092 virus having the lowest value, 0.5 days, a 4-fold reduction compared to rDEN4Δ30 virus. The mean peak virus titer of monkeys infected with rDEN4Δ30-4995 (0.9 $\log_{10}$ PFU/ml) or rDEN4Δ30-8092 (0.7 $\log_{10}$ PFU/ml) was also lower than those infected with rDEN4Δ30 virus. However, the mean peak virus titer of monkeys infected with rDEN4Δ30-10634 (1.3 $\log_{10}$ PFU/ml) was slightly higher than those infected with rDEN4Δ30 particularly on day 2 (FIG. 3).

TABLE 7

Addition of point mutations to rDEN4Δ30 further attenuates the virus for rhesus monkeys.

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) | |
|---|---|---|---|---|---|---|
| | | | | | Day 0 | Day 28 |
| mock | 2 | 0 | 0 | <0.7 | <10 | <10 |
| rDEN4 | 2 | 2 | 3.0 | 2.2 ± 0.6 | <10 | 398 |
| rDEN4Δ30 | 2 | 2 | 2.0 | 1.1 ± 0.4 | <10 | 181 |
| rDEN4Δ30-4995 | 4 | 2 | 0.8 | 0.9 ± 0.2 | <10 | 78 |
| rDEN4Δ30-8092 | 4 | 2 | 0.5 | 0.7 ± 0.1 | <10 | 61 |
| rDEN4Δ30-10634 | 4 | 4 | 1.3 | 1.3 ± 0.2 | <10 | 107 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 4.

Serum collected on day 0 and 28 was tested for the level of neutralizing antibodies against rDEN4. No detectable neutralizing antibodies were found against DEN4 on day 0, as expected, since the monkeys were pre-screened to be negative for neutralizing antibodies against flaviviruses (Table 7). On day 28, monkeys infected with rDEN4 had a mean serum neutralizing antibody titer (reciprocal dilution) of 398 which was approximately two-fold higher than monkeys infected with rDEN4Δ30 virus (1:181). This result and the two-fold higher level of viremia in rDEN4 virus-infected monkeys are similar to results obtained previously (Durbin et al. 2001 *Am. J. Trop. Med. Hyg.* 65:405-413). Monkeys infected with rDEN4Δ30-4995 (1:78), rDEN4Δ30-8092 (1:61), and rDEN4Δ30-10634 (1:107) viruses each had a reduced mean serum neutralizing antibody titer compared to monkeys infected with rDEN4Δ30 virus. The four monkeys which had no detectable viremia did have serum neutralizing antibody titers indicating that they were indeed infected. Despite the slight increase in mean peak virus titer of rDEN4Δ30-10634 virus compared with rDEN4Δ30 virus, rDEN4Δ30-10634 virus had a lower mean serum neutralizing antibody titer compared to monkeys infected with rDEN4Δ30 virus. This and the lower mean number of viremic days per monkey suggests that the 10634 mutation can attenuate the replication of rDEN4Δ30 virus in monkeys.

On day 28 after inoculation, all monkeys were challenged with 5.0 $\log_{10}$ PFU wild type rDEN4 virus subcutaneously. Monkeys were observed daily and serum was collected on days 28 to 34, 36, and 38, and virus titers were determined by plaque assay in Vero cells for measurement of viremia after challenge. Twenty eight days after rDEN4 virus challenge, serum was drawn and the level of neutralizing antibodies was tested by plaque reduction assay in Vero cells. Mock-inoculated monkeys had a mean peak virus titer of 2.3 $\log_{10}$ PFU/ml after challenge with a mean number of viremic days of 3.5 (Table 8). However, monkeys inoculated with rDEN4, rDEN4Δ30, or each of the modified rDEN4Δ30 viruses had no detectable viremia, indicating that despite the decreased replication and immunogenicity of rDEN4Δ30-4995, rDEN4Δ30-8092, and rDEN4Δ30-10634 viruses, each was sufficiently immunogenic to induce protection against wild type rDEN4, increases in mean neutralizing antibody titer were minimal (<3-fold) following challenge in all inoculation groups except mock-infected providing further evidence that the monkeys were protected from the challenge.

TABLE 8 rDEN4Δ30 containing additional point mutations protects rhesus monkeys from wt DEN4 virus challenge

| Virus[a] | No. of monkeys | Mean no. of viremic days per monkey after rDEN4 challenge | Mean peak virus titer ($\log_{10}$ PFU/ml ± SE) | Geometric mean serum neutralizing antibody titer (reciprocal dilution) Day 28 | Day 56 |
|---|---|---|---|---|---|
| Mock | 2 | 3.5 | 2.3 ± 0.1 | <10 | 358 |
| rDEN4 | 2 | 0.0 | <0.7 | 398 | 753 |
| rDEN4Δ30 | 2 | 0.0 | <0.7 | 181 | 202 |
| rDEN4Δ30-4995 | 4 | 0.0 | <0.7 | 78 | 170 |
| rDEN4Δ30-8092 | 4 | 0.0 | <0.7 | 61 | 131 |
| rDEN4Δ30-10634 | 4 | 0.0 | <0.7 | 107 | 177 |

[a]28 days after primary inoculation with the indicated viruses, rhesus monkeys were challenged subcutaneously with $10^5$ PFU rDEN4 virus in a 1 ml dose. Serum was collected on days 28 to 34, 36, 38, and 56. Virus titer was determined by plaque assay in Vero cells.

Taken together, these results indicate that the three point mutations, 4995, 8092, and 10634) described above do further attenuate the rDEN4Δ30 vaccine candidate in suckling mouse brain, SCID-HuH-7 mice, and rhesus monkeys. Because of additional incidental mutations (Table 4) present in each modified rDEN4Δ30 virus, the phenotypes cannot be directly attributed to the individual 4995, 8092, and 10634 point mutations. However, the presence of similar mouse-attenuation phenotypes in other rDEN4 viruses bearing one of these three mutations supports the contention that the 4995, 8092, and 10634 point mutations are responsible for the att phenotypes of the modified rDEN4Δ30 viruses. Since rDEN4Δ30-4995, rDEN4Δ30-8092, and rDEN4Δ30-10634 virus demonstrated decreased replication in rhesus monkeys while retaining sufficient immunogenicity to confer protective immunity, these viruses are contemplated as dengue vaccines for humans.

DEN4 viruses carrying both Δ30 and charge-to-alanine mutations were next generated. A subset of seven groups of charge-to-alanine mutations described above were identified that conferred between a 10-fold and 1,000-fold decrease in replication in SCID-HuH-7 mice and whose unmutated sequence was well-conserved across the four dengue serotypes. These mutations were introduced as single pairs and as two sets of pairs to rDEN4Δ30 using conventional cloning techniques. Transcription and recovery of virus and terminal dilution of viruses were conducted as described above. Assay of the level of temperature sensitivity of the charge-cluster-to-alanine mutant viruses in Vero and HuH-7 cells, level of replication in the brain of suckling mice and level of replication in SCID-HuH-7 mice was conducted as described above.

Introduction of one pair of charge-to-alanine mutations to rDEN4 produced recoverable virus in all cases (Table 9). Introduction of two pairs of charge-to-alanine mutations produced recoverable virus in two out of three cases (rDEN4Δ30-436-437-808-809 was not recoverable).

rDEN4Δ30 is not is in Vero or HuH-7 cells. In contrast, seven of the seven sets of charge-to-alanine mutations used in this example conferred a ts phenotype in HuH-7 cells and five also conferred a ts phenotype in Vero cells. All six viruses carrying both Δ30 and charge-to-alanine mutations showed a ts phenotype in both Vero and HuH-7 cells (Table 9). rDEN4Δ30 is not attenuated in suckling mouse brain, whereas five of the seven sets of charge-to-alanine mutations conferred an att phenotype in suckling mouse brain (Table 10). Four of the viruses carrying both Δ30 and charge-to-alanine mutations were attenuated in suckling mouse brain (Table 10). En one case (rDEN4Δ30-23-24-396-397) combination of two mutations that did not attenuate alone resulted in an attenuated virus. Generally, viruses carrying both Δ30 and charge-to-alanine mutations showed levels of replication in the suckling mouse brain more similar to their charge-to-alanine mutant parent virus than to rDEN4Δ30.

rDEN4Δ30 is attenuated in SOD-Hal-7 mice, as are six of the seven charge-to-alanine mutant viruses used in this example. Viruses carrying both Δ30 and charge-to-alanine mutations tended to show similar or slightly lower levels of replication in SCID-HuH-7 mice compared to their charge-to-alanine mutant parent virus (Table 10). In three cases, viruses carrying both Δ30 and charge-to-alanine mutations showed at least a fivefold greater reduction in SCID-HuH-7 mice than rDEN4Δ30.

The complete genomic sequence of five viruses (rDEN4-200-201, rDEN4Δ30-200-201, rDEN4-436-437 [clone 1], rDEN4Δ30-436-437, and rDEN4-23-24-200-201) that replicated to >$10^5$ PFU/ml in Vero cells at 35° C. and that showed a hundredfold or greater reduction in replication in SCID-HuH-7 mice was determined (Table 11). Each of the five contained one or more incidental mutations. In one virus, rDEN4Δ30-436-437, the one additional mutation has been previously associated with Vero cell adaptation (Blaney, J. E. Jr. et al. 2002 *Virology* 300:125-139). Each of the remaining viruses contained at least one incidental mutation whose phenotypic effect is unknown. Consequently, the phenotypes described cannot be directly attributed to the charge-to-alanine mutations. However, the fact that rDEN4 and rDEN4Δ30 viruses carrying the same charge-to-alanine mutations shared similar phenotypes provides strong support for the ability of charge-to-alanine mutations to enhance the attenuation of rDEN4Δ30. Because rDEN4-436-437 [clone 1] contained 4 incidental mutations, a second clone of this virus was prepared. rDEN4-436-437 [clone 2] contained only one incidental mutation (Table 11), and showed the same phenotypes as rDEN4-436-437 in cell culture and SCID-HuH-7 mice. rDEN4-436-437 [clone 2] was used in the rhesus monkey study described below.

TABLE 9

Addition of charge-to-alanine mutations to rDEN4Δ30 confers a ts phenotype in both Vero and HuH-7 cells.

| | | | Mean virus titer $\log_{10}$ PFU/ml) at indicated temperature (° C.)[a] | | | | | | | | | |
|---|---|---|---|---|---|---|---|---|---|---|---|---|
| | AA | No. nt | Vero | | | | | HuH-7 | | | | |
| Virus | changed[b] | changed | 35 | 37 | 38 | 39 | Δ[c] | 35 | 37 | 38 | 39 | Δ |
| rDEN4 | none | 0 | 7.4 | 7.1 | 7.7 | 7.2 | 0.2 | 7.7 | 7.5 | 7.5 | 7.4 | 0.3 |
| rDEN4Δ30 | none | 30 | 6.6 | 6.6 | 6.5 | 6.5 | 0.1 | 7.4 | 6.9 | 7.0 | 6.4 | 1.0 |
| rDEN4-23-24 | KE | 3 | 6.7 | 6.6 | 6.0 | 6.5 | 0.2 | 7.1 | 7.3 | 5.6 | ≤1.7 | >5.4 |
| rDEN4Δ30-23-24 | | | 6.1 | 5.5 | 4.9 | ≤1.7 | 4.4 | 6.5 | 5.9 | 4.7 | ≤1.7 | >4.2 |
| rDEN4-200-201 | KH | 4 | 5.3 | 4.8 | 4.8 | 4.3 | 1.0 | 5.7 | 5.4 | 2.7 | ≤1.7 | >4.0 |
| rDEN4Δ30-200-201 | | | 6.0 | 5.3 | 5.6 | ≤1.7 | >4.3 | 5.8 | 5.0 | 5.9 | ≤1.7 | >4.1 |
| rDEN4-436-437 | DK | 4 | 5.2 | 4.2 | 3.4 | 1.9 | 3.3 | 5.9 | 4.9 | 3.2 | ≤1.7 | >4.2 |
| rDEN4Δ30-436-437 [clone1] | | | 6.3 | 5.7 | 5.5 | ≤1.7 | >4.6 | 6.5 | 5.7 | 5.1 | ≤1.7 | >4.8 |
| rDEN4-808-809 | ED | 3 | 4.6 | 4.1 | ≤1.7 | ≤1.7 | >2.9 | 5.2 | ≤1.7 | ≤1.7 | ≤1.7 | >3.5 |
| rDEN4Δ30-808-809 | | | 5.6 | 4.9 | 4.9 | ≤1.7 | >3.9 | 5.9 | 4.8 | 5.1 | ≤1.7 | >4.2 |
| rDEN4-23-24-200-201 | KE, KH | 7 | 6.0 | 5.2 | 4.2 | ≤1.7 | >4.3 | 6.9 | 6.3 | ≤1.7 | ≤1.7 | >5.2 |
| rDEN4Δ30-23-24-200-201 | | | 4.5 | 4.2 | 4.8 | ≤1.7 | >2.8 | 4.9 | 4.5 | 2.9 | ≤1.7 | >3.2 |
| rDEN4-23-24-396-397 | KE, RE | 7 | 6.5 | 5.8 | 5.5 | ≤1.7 | >4.8 | 7.1 | 5.9 | 5.4 | ≤1.7 | >5.4 |
| rDEN4Δ30-23-24-396-397 | | | 6.1 | 5.2 | 4.8 | ≤1.7 | >4.4 | 6.9 | 5.4 | 4.9 | ≤1.7 | >5.2 |
| rDEN-436-437-808-809 | DK, ED | 7 | 4.9 | 4.9 | 5.1 | ≤1.7 | >3.2 | 5.5 | 3.2 | ≤1.7 | ≤1.7 | >3.8 |

[a]Underlined values indicate a 2.5 or 3.5 $\log_{10}$ PFU/ml reduction in titer in Vero or HuH-7 cells, respectively, at the indicated temperature when compared to the permissive temperature (35° C.).
[b]Amino acid pair(s) changed to pair of Ala residues.
[c]Reduction in titer ($\log_{10}$ pfu/ml) compared to the permissive temperature (35° C.).

TABLE 10

Addition of charge-to-alanine mutations attenuates rDEN4Δ30 in suckling mouse brain and enhances attenuation in SCID-HuH-7 mice.

| | Replication in suckling mice[a] | | | Replication in SCID-HuH-7 mice[c] | | |
|---|---|---|---|---|---|---|
| Virus | n | Mean virus titer ± SE ($\log_{10}$ PFU/ g brain) | Mean log reduction from wt[b] | n | Mean virus titer ± SE ($\log_{10}$ PFU/ ml serum) | Mean log reduction from wt[d] |
| rDEN4 | 18 | 6.2 ± 0.4 | — | 33 | 5.4 ± 0.3 | — |
| rDEN4Δ30 | 12 | 5.9 ± 0.8 | 0.2 | 8 | 3.4 ± 0.3 | 2.3 |
| rDEN4-23-24 | 18 | 4.7 ± 0.1 | 1.6 | 19 | 4.7 ± 0.5 | 1.3 |
| rDEN4Δ30-23-24 | 6 | 5.6 ± 0.3 | 0.7 | 7 | 4.6 ± 0.4 | 1.5 |
| rDEN4-200-201 | 12 | 5.5 ± 0.5 | 0.6 | 12 | 3.7 ± 0.2 | 2.6 |
| rDEN4Δ30-200-201 | 6 | 5.5 ± 0.6 | 0.1 | 4 | 3.3 ± 0.6 | 1.8 |
| rDEN4-436-437 | 18 | 2.7 ± 0.4 | 3.5 | 10 | 2.9 ± 0.7 | 2.5 |
| rDEN4Δ30-436-437 [clone1] | 6 | 2.9 ± 0.3 | 3.4 | 4 | 2.3 ± 0.4 | 2.8 |
| rDEN4-808-809 | 6 | 1.8 ± 0.1 | 3.1 | 8 | 3.2 ± 0.4 | 3.0 |
| rDEN4Δ30-808-809 | 12 | 3.9 ± 0.7 | 2.1 | 4 | 3.7 ± 0.6 | 2.4 |
| rDEN4-23-24-200-201 | 12 | 5.3 ± 0.5 | 0.7 | 13 | 3.4 ± 0.1 | 2.9 |
| rDEN4Δ30-23-24-200-201 | 6 | 3.0 ± 0.2 | 2.6 | 5 | 1.8 ± 0.1 | 3.3 |
| rDEN4-23-24-396-397 | 12 | 4.6 ± 0.9 | 1.5 | 8 | 3.6 ± 0.3 | 2.3 |
| rDEN4Δ30-23-24-396-397 | 6 | 3.0 ± 0.2 | 2.6 | 5 | 2.2 ± 0.3 | 2.9 |
| rDEN-436-437-808-809 | 6 | <1.7 ± 0.0 | 3.6 | 8 | 2.1 ± 0.3 | 2.4 |

[a]Groups of six suckling mice were inoculated i.c. with $10^4$ PFU virus in a 30 μl inoculum. The brain was removed 5 days later, homogenized, and virus was quantitated by titration in Vero cells.
[b]Determined by comparing the mean viral titers in mice inoculated with sample virus and concurrent wt controls (n = 6). The attenuation (att) phenotype is defined as a reduction of ≥1.5 $\log_{10}$ PFU/g compared to wt virus; reductions of ≥1.5 are listed in boldface.
[c]Groups of SCID-HuH-7 mice were inoculated directly into the tumor with $10^4$ PFU virus.
[d]Determined by comparing mean viral titers in mice inoculated with sample virus and concurrent wt controls. The attenuation phenotype is defined as a reduction of ≥1.5 $\log_{10}$ PFU/g compared to wt virus; reductions of ≥1.5 are listed in boldface.

TABLE 11

Missense and UTR mutations present in rDEN4 virus derivatives bearing charge-to-alanine and the Δ30 mutation.

| Virus | Gene[a,b] | Nucleotide position | Nucleotide substitution | Amino acid position[c] | Amino acid change[b] |
|---|---|---|---|---|---|
| rDEN4-200-201 | prM | 626 | A > T | 61 | Glu > Asp |
|  | NS4A | 6659 | C > T | 93 | Leu > Phe |
|  | NS5 | 8160-8165 | AAACA > GCAGC | 200-201 | LysHis > AlaAla |
| rDEN4Δ30-200-201 | NS3 | 4830 | G > A | 102 | Gly > Arg |
|  | NS5 | 8106 | G > A | 181 | Val > Ile |
|  | NS5 | 8160-8165 | AAACA > GCAGC | 200-201 | LysHis > AlaAla |
|  | 3' UTR | 10478-10507 | Δ30 deletion | None | None |
| rDEN4-436-437 [clone 1] | E | 2331 | T > G | 464 | Trp > Gly |
|  | NS1 | 2845 | C > T | 140 | Ser > Phe |
|  | NS3* | 4891 | T > C | 122 | Ile > Thr |
|  | NS5 | 8869-8873 | GACAA > GCAGC | 436-437 | AspLys > AlaAla |
|  | NS5 | 9659 | A > G | 699 | Lys > Arg |
| rDEN4-436-437 [clone 2] | NS4B | 7153 | T > C | 108 | Val > Ala |
|  | NS5 | 8869-8873 | GACAA > GCAGC | 436-437 | AspLys > AlaAla |
| rDEN4Δ30-436-437 | NS4B* | 7163 | A > C | 111 | Leu > Phe |
|  | NS5 | 8869-73 | GACAA > GCAGC | 436-437 | AspLys > AlaAla |
|  | 3' UTR | 10478-10507 | Δ30 deletion | None | None |
| rDEN4-23-24-200-201 | NS3 | 6751 | A > C | 124 | Lys > Thr |
|  | NS5 | 7629-7633 | AAAGA > GCAGC | 23-24 | LysGlu > AlaAla |
|  | NS5 | 8160-8165 | AAACA > GCAGC | 200-201 | LysHis > AlaAla |

[a]Asterisk indicates previously identified Vero cell adaptation mutation.
[b]Bold values indicate mutations designed to occur in the designated virus.
[c]Amino acid position in the protein product of the designated DEN4 gene; numbering starts with the amino terminus of the protein.

Figure 4:
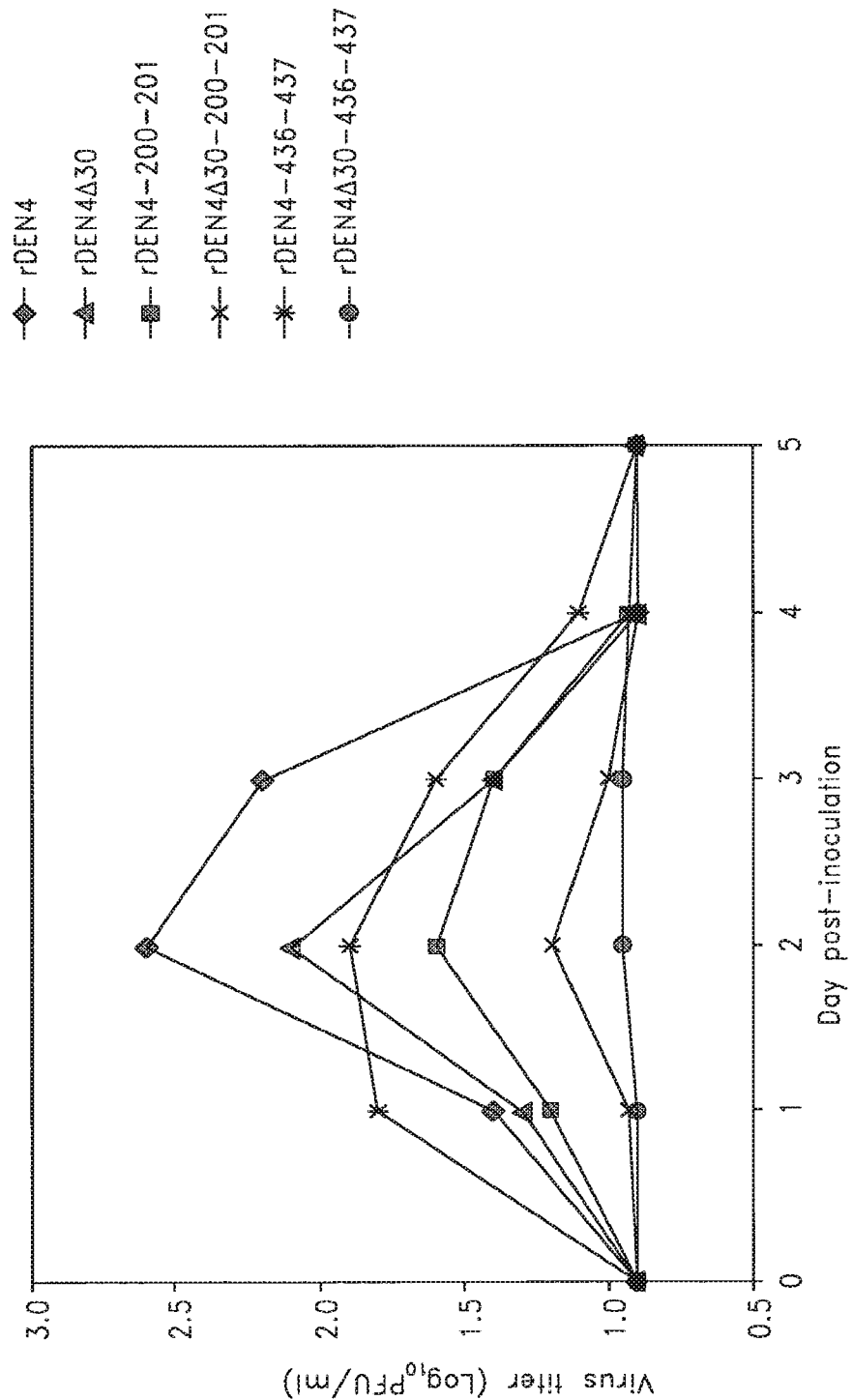
FIG. 4. Viremia levels in rhesus monkeys inoculated with rDEN4 vaccine candidates bearing pairs of charge-to-alanine mutations in NS5. Groups of four or two (rDEN4 and rDEN4Δ30) monkeys were inoculated with 5.0 $\log_{10}$ PFU virus subcutaneously. Serum was collected daily and virus titers were determined by plaque assay in Vero cells. The limit of virus detection was 1.0 $\log_{10}$ PFU/ml. Mean virus titers are indicated for each group. Viremia was not detected in any monkey after day 4.

Based on the attenuation in the SCID-HuH7 mouse model, four of the charge-to-alanine mutant viruses (rDEN4-200-201, rDEN4Δ30-200-201, rDEN4-436-437 [clone 2], rDEN4Δ30-436-437) were evaluated in rhesus macaques as described above. As with the study of viruses carrying attenuating point mutations, viremia was detected on day 1 post-infection and ended by day 4 in all monkeys (FIG. 4, Table 12). Viremia was detected in most of the monkeys infected; only one of the four monkeys infected with rDEN4Δ30-200-201 and one of the four monkeys infected with rDEN4Δ30-436-437 showed no detectable viremia. Monkeys infected with rDEN4 showed the highest mean peak virus titer; and in each case viruses carrying the Δ30 mutation showed an approximately 0.5 log decrease in mean peak virus titer relative to their parental viruses and a 0.5 to 2 day decrease in mean number of viremic days per monkey. Monkeys infected with viruses carrying both the Δ30 and charge-to-alanine mutations showed a two-fold reduction in mean peak viremia relative to those infected with rDEN4Δ30. This suggests that addition of the charge-to-alanine mutations further attenuates rDEN4Δ30 for rhesus macaques.

As expected, none of the monkeys in this study showed detectable levels of neutralizing antibody on day 0. On day 28, every monkey infected with a virus showed a detectable levels of neutralizing antibody, indicating that all of the monkeys, even those that showed no detectable viremia, had indeed been infected. As in the study of attenuating point mutations, monkeys infected with rDEN4 had a mean serum neutralizing antibody titer (reciprocal dilution) which was approximately twice that of monkeys that had been infected with rDEN4Δ30. Monkeys infected with rDEN4-200-201 and rDEN4-436-437 [clone 2] had similar mean neutralizing antibody titers to rDEN4, and those infected with rDEN4Δ30-200-201 and rDEN4Δ30-436-437 had similar mean neutralizing antibody titers to rDEN4. In each case the addition of the Δ30 mutation to a virus resulted in a two-fold decrease in neutralizing antibody. Thus, although the addition of charge-to-alanine mutations to rDEN4Δ30 decreased mean peak viremia below that of rDEN4Δ30 alone, it did not affect levels of neutralizing antibody.

TABLE 12

Addition of paired charge-to-alanine mutations to rDEN4Δ30 further attenuates the virus for rhesus monkeys.

| Virus[a] | No. of monkeys | No. of monkeys with viremia | Mean no. of viremic days per monkey[b] | Mean peak virus titer ($\log_{10}$ PFU/ml ± SE) | Geometric mean serum neutralizing antibody titer (reciprocal dilution) Day 0 | Day 28 |
|---|---|---|---|---|---|---|
| mock | 2 | 0 | 0 | <0.7 | <5 | <5 |
| rDEN4 | 2 | 2 | 2.5 | 2.6 ± 0.3 | <5 | 276 |

TABLE 12-continued

Addition of paired charge-to-alanine mutations to rDEN4Δ30
further attenuates the virus for rhesus monkeys.

| Virus[a] | No. of monkeys | No. of monkeys with viremia | Mean no. of viremic days per monkey[b] | Mean peak virus titer (log₁₀ PFU/ml ± SE) | Geometric mean serum neutralizing antibody titer (reciprocal dilution) | |
|---|---|---|---|---|---|---|
| | | | | | Day 0 | Day 28 |
| rDEN4Δ30 | 2 | 2 | 2.0 | 2.1 ± 0.1 | <5 | 131 |
| rDEN4-200, 201 | 4 | 4 | 2.3 | 1.8 ± 0.3 | <5 | 212 |
| rDEN4Δ30-200, 201 | 4 | 3 | 1.5 | 1.3 ± 0.2 | <5 | 139 |
| rDEN4-436, 437 [cl 2] | 4 | 4 | 3.3 | 1.8 ± 0.2 | <5 | 273 |
| rDEN4Δ30-436, 437 | 4 | 3 | 1.3 | 1.0 ± 0.0 | <5 | 143 |

[a]Groups of rhesus monkeys were inoculated subcutaneously with $10^5$ PFU of the indicated virus in a 1 ml dose. Serum was collected on days 0 to 6, 8, 10 and 28. Virus titer was determined by plaque assay in Vero cells.
[b]Viremia was not detected in any monkey after day 4.

After challenge with rDEN4 on day 28, mock-infected monkeys had a mean peak virus titer of 1.5 $\log_{10}$ PFU/ml and a mean number of viremic days of 3.0 (Table 13). However, none of the monkeys previously inoculated with rDEN4, rDEN4Δ30 or the charge-to-alanine mutant viruses showed detectable viremia. Additionally, none of the monkeys showed a greater than four-fold increase in serum neutralizing antibody titer. Together these data indicate that infection with any of the viruses, including those carrying both Δ30 and the charge-to-alanine mutations, protected rhesus macaques from challenge with rDEN4.

TABLE 13 rDEN4Δ30 containing charge-to-alanine mutations
protects rhesus monkeys from wt DEN4 virus challenge

| Virus[a] | No. of monkeys | Mean no. of viremic days per monkey after rDEN4 challenge | Mean peak virus titer (log₁₀ PFU/ml ± SE) | Geometric mean serum neutralizing antibody titer (reciprocal dilution) | |
|---|---|---|---|---|---|
| | | | | Day 28 | Day 56 |
| mock | 2 | 3.0 | 1.5 ± 0.7 | <5 | 284 |
| rDEN4 | 2 | 0.0 | <0.7 | 276 | 316 |
| rDEN4Δ30 | 2 | 0.0 | <0.7 | 131 | 96 |
| rDEN4-200, 201 | 4 | 0.0 | <0.7 | 212 | 356 |
| rDEN4Δ30-200, 201 | 4 | 0.0 | <0.7 | 139 | 132 |
| rDEN4-436, 437 [cl 2] | 4 | 0.0 | <0.7 | 273 | 401 |
| rDEN4Δ30-436, 437 | 4 | 0.0 | <0.7 | 143 | 182 |

[a]28 days after primary inoculation with the indicated viruses, rhesus monkeys were challenged subcutaneously with $10^5$ PFU rDEN4 virus in a 1 ml dose. Serum was collected on days 28 to 34, 36, 10, and 56. Virus titer was determined by plaque assay in Vero cells.

Addition of charge-to-alanine mutations to rDEN4Δ30 can confer a range of ts phenotypes in both Vero and HuH-7 cells and att phenotypes in suckling mouse brain and can either enhance or leave unchanged attenuation in SCID-HuH-7 mice. Most importantly, addition of these mutations can decrease the viremia produced by rDEN4Δ30 in rhesus macaques without decreasing neutralizing antibody titer or protective efficacy. Thus addition of such mutations to rDEN4Δ30 is contemplated as enhancing attenuation in humans. Also, mutations are contemplated as being added that do not change the overall level of attenuation, but stabilize the attenuation phenotype because they themselves are independently attenuating even in the absence of the Δ30 mutation. Charge-to-alanine mutations are particularly useful because they occur outside of the structural gene regions, and so can be used to attenuate structural gene chimeric viruses. Moreover, they involve at least three nucleotide changes, making them unlikely to revert to wild type sequence.

A series of point mutations that enhance the replication of rDEN4 in Vero cells tissue culture have been identified; these are primarily located in the NS4B gene (Blaney, J. E. et. al. 2002 *Virology* 300:125-139; Blaney, J. E. et al. 2001 *J Virol* 75:9731-9740). Vero cell adaptation mutations confer two desirable features upon a vaccine candidate. First, they enhance virus yield in Vero cells, the intended substrate for vaccine production, and thus render vaccine production more cost-effective. Second, although each of these Vero adaptation mutations are point mutations, they are likely to be extremely stable during vaccine manufacture, because they give a selective advantage in Vero cells. At least one Vero cell adaptation mutation, at position 7129, was also shown to decrease mosquito infectivity of rDEN4; poor mosquito infectivity is another desirable characteristic of a dengue vaccine candidate. To investigate the generality of this finding, we tested the effect of the remaining Vero cell adaptation mutations on the ability of rDEN4 to infect *Aedes aegypti* mosquitoes fed on an infectious bloodmeal. Table 14 shows the infectivity of each virus carrying a single Vero cell adaptation mutation at high titer. Of these, only one mutation, at position 7182, was associated with a large decrease in mosquito infectivity. Thus 7182 may be a particularly valuable mutation to include in an rDEN4 vaccine candidate, as it has opposite effects on replication in Vero cells and in mosquitoes.

TABLE 14

Effect of Vero cell adaptation mutations
on rDEN4 mosquito infectivity

| | *Aedes aegypti* (oral infection) | | | |
|---|---|---|---|---|
| Virus | Dose[a] (log₁₀ pfu) | No. tested | % infected[b] | |
| | | | Midgut | Head |
| rDEN4 | 4.3 | 27 | 70 | 25 |
| rDEN4-4891 | 4.4 | 23 | 74 | 13 |
| rDEN4-4995 | 4.8 | 20 | 80 | 50 |

TABLE 14-continued

Effect of Vero cell adaptation mutations on rDEN4 mosquito infectivity

| | | *Aedes aegypti* (oral infection) | | |
|---|---|---|---|---|
| Virus | Dose[a] ($\log_{10}$ pfu) | No. tested | % infected[b] Midgut | Head |
| rDEN4-7153 | 4.8 | 20 | 80 | 30 |
| rDEN4-7546 | 4.6 | 20 | 55 | 10 |
| rDEN4-7162 | 5.0 | 20 | 55 | 25 |
| rDEN4-7163 | 4.9 | 15 | 73 | 72 |
| rDEN4-7182 | 5.0 | 20 | 20 | 0 |
| rDEN4-7630 | 4.3 | 10 | 70 | 10 |

[a]Virus titer ingested, assuming a 2 μl bloodmeal.
[b]Percentage of mosquitoes with IFA detectable antigen in midgut or head tissue prepared 21 days after oral infection.

Example 2

Generation and Characterization of a Recombinant DEN1 Virus Containing the Δ30 Mutation We first sought to determine if the Δ30 mutation was able to satisfactorily attenuate a wild-type DEN virus other than the DEN4 serotype. To do this, the Δ30 mutation was introduced into the cDNA for DEN1 (Western Pacific). The pRS424DEN1WP clone (Puri, B. et al, 2000 *Virus Genes* 20:57-63) was digested with BamHI and used as template in a PCR using Pfu polymerase with forward primer 30 (DEN1 nt 10515-10561 and 10592-10607) and the M13 reverse sequencing primer (101 nt beyond the 3' end of DEN1 genome sequence). The resulting PCR product was 292 bp and contained the Δ30 mutation. The pRS424DEN1WP cDNA was partially digested with Apa I, then digested to completion with Sac II and the vector was gel isolated, mixed with PCR product, and used to transform yeast strain YPH857 to yield growth on plates lacking tryptophan (Polo, S. et al, 1997 *J Virol* 71:5366-74). Positive yeast colonies were confirmed by PCR and restriction enzyme analysis. DNA isolated from two independent yeast colonies was used to transform *E. coli* strain STBL2. Plasmid DNA suitable for generating RNA transcripts was prepared and the presence of the Δ30 mutation was verified by sequence analysis.

For transcription and generation of virus, cDNA (designated pRS424DEN1Δ30) that was linearized with Sac II was used as template in a transcription reaction using SP6 RNA polymerase as described (Polo, S. et al, 1997 *J Virol* 71:5366-74). Transcription reactions were electroporated into LLC-MK2 cells and infection was confirmed by observation of CPE and immunofluorescence and harvested on day 14. Virus stocks were amplified on C6/36 mosquito cells and titered on LLC-MK2 cells. The genome of the resulting virus, rDEN1Δ30, was sequenced to confirm the presence of the Δ30 mutation. The Δ30 mutation removes nucleotides 10562-10591 of DEN1 (FIG. 2B, C), which corresponds to the TL2 of DEN1. The virus replicates efficiently in Vero cell culture to titers of 6.5 $\log_{10}$ PFU/ml, indicating that the Δ30 mutation is compatible with efficient growth of DEN1 in cell culture, a property essential for manufacture of the vaccine. Using similar techniques, parent virus rDEN1 was generated. Incidental mutations arising from virus passage in tissue culture were identified in both rDEN1 and rDEN1Δ30 using sequence analysis and are listed in Table 15. An additional rDEN1Δ30 virus was derived by transfection and amplification in Vero cells. Although this virus was not evaluated in the studies described below, its sequence analysis is included in Table 15. The properties of rDEN1Δ30 as a vaccine in vivo were next examined.

TABLE 15

Missense mutations present among the recombinant DEN1 viruses and correlation of NS4B region mutations with those found in DEN4

| Virus | Transfection cell type | Gene | Nucleotide position | Nucleotide change | Amino acid position | Amino acid change |
|---|---|---|---|---|---|---|
| wt rDEN1 | LLC-MK2 | prM | 816 | C > U | 241 | Ala > Val |
| | | NS4B | 7165[a] | U > G | 2357 | Phe > Leu |
| | | NS4B | 7173[b] | U > C | 2360 | Val > Ala |
| rDEN1Δ30 | LLC-MK2 | E | 1748 | A > U | 552 | Thr > Ser |
| rDEN1Δ30 | Vero | E | 1545 | A > G | 484 | Lys > Arg |

[a]Same nucleotide as 7154 in rDEN4.
[b]Same nucleotide as 7162 in rDEN4

\* Nucleotide and amino acid comparison of selected NS4B region:

```
             7        7        7        7        7        7
DEN4         1        1        1        1        1        1
base         3        4        5        6        7        8
Number:   890123456789012345678901234567890123456789012345678901234567 SEQ ID
          ++     ++   + +++++   +   +   +  ++   +    ++++++++ ++ ++ ++ ++  NO:

D4 7128-  CCAACAACCUUGACAGCAUCCUUAGUCAUGCUUUUAGUCCAUUAUGCAAUAAUAGGCCCA     54
           P  T  T  L  T  A  S  L  V  M  L  L  V  H  T  A  I  I  G  P    55

D1 7139-  CCGCUGACGCUGACAGCGGCGGUAUUUAUGCUAGUGGCUCAUUAUGCCAUAAUUGGACCC     56
           P  L  T  L  T  A  A  V  P  M  L  V  A  H  T  A  I  I  G  P    57
```

-continued

```
                   7         7         7         7         7         7
DEN4               1         1         1         1         1         1
base               3         4         5         6         7         8
Number:   890123456789012345678901234567890123456789012345678901234567  SEQ ID
          ++     ++  + +++++   +    +    +   + ++   +      ++++++++ ++ ++ ++ ++    NO:

D2 7135-  CCUAUAACCCUCACAGCGGCUCUUCUUUUAUUGGUAGCACAUUAUGCCAUCAUAGGACCG   58
          P   I   T   L   T   A   A   L   L   L   L   V   A   H   T   A   I   I   G   P    59

D3 7130-  CCACUAACUCUCACAGCGGCAGUUCUCCUGCUAGUCACGCAUUAUGCUAUUAUAGGUCCA   60
          P   L   T   L   T   A   A   V   L   L   L   V   T   H   T   A   I   I   G   P    61
           +        +   +   +   +           +            +   +   +   +   +   +   +
```

D4 = rDEN4
D1 = rDEN1(WP)
D2 = rDEN2(Tonga/74)
D3 = rDEN3(Sleman/78)
+Homology among all four serotypes
Nucleotides are underlined in even multiples of 10.

Evaluation of the replication, immunogenicity, and protective efficacy of rDEN1Δ30 and wild-type parental rDEN1 virus (derived from the pRS424DEN1WP cDNA) in juvenile rhesus monkeys was performed as follows. Dengue virus-seronegative monkeys were injected subcutaneously with 5.0 $\log_{10}$ PFU of virus in a 1 ml dose divided between two injections in each side of the upper shoulder area. Monkeys were observed daily and blood was collected on days 0-10 and 28 and serum was stored at −70° C. Titer of virus in serum samples was determined by plaque assay in Vero cells as described previously (Durbin, A. P. et al. 2001 Am J Trop Med Hyg 65:405-13). Plaque reduction neutralization titers were determined for the day 28 serum samples as previously described (Durbin, A. P. et al. 2001 Am J Trop Med Hyg 65:405-13). All monkeys were challenged on day 28 with a single dose of 5.0 $\log_{10}$ PFU of wild-type rDEN1 and blood was collected for 10 days. Virus titer in post-challenge sera was determined by plaque assay in Vero cells. Monkeys inoculated with full-length wild-type rDEN1 were viremic for 2-3 days with a mean peak titer of 2.1 $\log_{10}$ PFU/ml (Table 16), and monkeys inoculated with rDEN1Δ30 were viremic for less than 1 day with a mean peak titer of 0.8 $\log_{10}$ PFU/ml, indicating that the Δ30 mutation is capable of attenuating DEN1. As expected for an attenuated virus, the immune response, as measured by neutralizing antibody titer, was lower following inoculation with rDEN1Δ30 compared to inoculation with wild-type rDEN1 (Table 16), yet sufficiently high to protect the animals against wild-type DEN1 virus challenge. Wild-type rDEN1 virus was not detected in any serum sample collected following virus challenge, indicating that monkeys were completely protected following immunization with either full-length wild-type rDEN1 or recombinant virus rDEN1Δ30. The level of attenuation specified by the Δ30 mutation was comparable in both the DEN1 and DEN4 genetic backgrounds (FIG. 5).

TABLE 16

The Δ30 mutation attenuates rDEN1 for rhesus monkeys

| Virus* | n | Mean no. days with viremia | Mean peak titer ($\log_{10}$ pfu/ml) | Mean neutralization titer | Mean peak titer of challenge virus |
|---|---|---|---|---|---|
| rDEN1 | 4 | 2.8 | 2.1 | 1230 | <0.7 |
| rDEN1Δ30 | 4 | 0.5 | 0.8 | 780 | <0.7 |

*Rhesus monkeys were inoculated subcuateously with 5.0 $\log_{10}$ PFU of virus. Serum samples were collected daily for 10 days. Serum for neutralization assay was collected on day 28. All monkeys were challenged on day 28 with 5.0 $\log_{10}$ PFU of rDEN1.

As previously reported, rDEN4 virus replicated to greater than 6.0 $\log_{10}$ PFU/ml serum in SCID-HuH-7 mice, while the replication of rDEN4 virus bearing the Δ30 mutation was reduced by about 10-fold (Blaney, J. E. Jr. et al. 2002 Virology 300:125-139). The replication of rDEN1Δ30 was compared to that of wt rDEN1 in SCID-HuH-7 mice (Table 17). rDEN1Δ30 replicated to a level approximately 100-fold less than its wt rDEN1 parent. This result further validates the use of the SCID-HuH-7 mouse model for the evaluation of attenuated strains of DEN virus, with results correlating closely with those observed in rhesus monkeys.

TABLE 17

The Δ30 mutation attenuates rDEN1 for HuH-7-SCID mice

| Virus | No. of Mice[5] | Mean peak virus titer[6] ($\log_{10}$ pfu/ml ± SE) |
|---|---|---|
| wt rDEN1 | 9 | 7.3 ± 0.2 |
| rDEN1Δ30 | 8 | 5.0 ± 0.3 |

[5]Groups of HuH-7-SCID mice were inoculated directly into the tumor with 4.0 $\log_{10}$ pfu virus. Serum was collected on day 6 and 7, and virus titer was determined by plaque assay in Vero cells.
[6]Significant difference was found between rDEN1 and rDEN1Δ30 viruses, Tukey-Kramer test ($P < 0.005$).

Finally, the infectivity of rDEN1 and rDEN1Δ30 for mosquitoes was assessed, using the methods described in detail in Example 5. Previously, the Δ30 mutation was shown to decrease the ability of rDEN4 to cross the mosquito midgut barrier and establish a salivary gland infection (Troyer, J. M. et al. 2001 Am J Trop Med Hyg 65:414-419). However neither rDEN1 nor rDEN1Δ30 was able to infect the midgut of Aedes aegypti mosquitoes efficiently via an artificial bloodmeal (Table 18), so it was not possible to determine whether Δ30 might further block salivary gland infection. A previous study also showed that the Δ30 had no effect on the infectivity of rDEN4 for Toxorhynchites splendens mosquitoes infected via intrathoracic inoculation (Troyer, J. M. et al. 2001 Am J Trop Med Hyg 65:414-419), and a similar pattern was seen for rDEN1 and rDEN1Δ30 (Table 18). The genetic basis for the inability of rDEN1 to infect the mosquito midgut has not been defined at this time. However, this important property of restricted infectivity for the mosquito midgut is highly desirable in a vaccine candidate since it would serve to greatly restrict transmission of the vaccine virus from a vaccinee to a mosquito vector.

TABLE 18

DEN1 and DEN1Δ30 viruses are both highly infectious for *Toxorhynchites splendens*, but do not infect *Aedes aegypti* efficiently.

| | *Toxorhynchites splendens* (inthrathoracic inoculation) | | | *Aedes aegypti* (oral infection) | | | |
|---|---|---|---|---|---|---|---|
| | Dose[a] | No. | % | Dose[c] | No. | % infected[d] | |
| Virus | ($log_{10}$ pfu) | tested | infected[b] | ($log_{10}$ pfu) | tested | Midgut | Head |
| rDEN1 | 3.5 | 7 | 100 | 4.0 | 26 | 11 | 0 |
| | 2.5 | 8 | 75 | | | | |
| | 1.5 | 7 | 71 | | | | |
| | 0.5 | 5 | 60 | | | | |
| | | | $MID_{50}$ < 0.5 | | | $MID_{50}$ ≥ 4.4 | |
| rDEN1 | 2.7 | 8 | 100 | 3.2 | 20 | 10 | 0 |
| Δ30 | 1.7 | 7 | 100 | | | | |
| | 0.7 | 6 | 83 | | | | |
| | | | $MID_{50}$ < 0.7 | | | $MID_{50}$ ≥ 3.6 | |

[a]Amount of virus present in 0.22 μl inoculum.
[b]Percentage of mosquitoes with IFA detectable antigen in head tissue prepared 14 days after inoculation.
[c]Virus titer ingested, assuming a 2 μl bloodmeal.
[d]Percentage of mosquitoes with IFA detectable antigen in midgut or head tissue prepared 21 days after oral infection. When virus infection was detected, but did not exceed a frequency of 50% at the highest dose of virus ingested, the $MID_{50}$ was estimated by assuming that a 10-fold more concentrated virus dose would infect 100% of the mosquitoes.

Thus, the Δ30 mutation, first described in DEN4, was successfully transferred to rDEN1. The resulting virus, rDEN1Δ30, was shown to be attenuated in monkeys and SCID-HuH-7 mice to levels similar to recombinant virus rDEN4Δ30, thereby establishing the conservation of the attenuation phenotype specified by the Δ30 mutation in a different DEN virus background. Based on the favorable results of rDEN4Δ30 in recent clinical trials (Durbin, A. P. et al. 2001 *Am J Trop Med Hyg* 65:405-13), it is predicted that rDEN1Δ30 will be suitably attenuated in humans. To complete the tetravalent vaccine, attenuated rDEN2 and rDEN3 recombinant viruses bearing the Δ30 mutation are contemplated as being prepared (See Examples 3 and 4 below). The demonstration that the Δ30 mutation specifies a phenotype that is transportable to another DEN serotype has important implications for development of the tetravalent vaccine. This indicates that the Δ30 mutation is expected to have a corresponding effect on DEN2 and DEN3 wild-type viruses.

Example 3

Generation and Characterization of a Recombinant DEN2 Virus Containing the Δ30 Mutation Evaluation of rDEN1Δ30 showed that it was satisfactorily attenuated. Based on this result, we sought to extend our technology to the creation of a DEN2 vaccine candidate. To do this, the Δ30 mutation was introduced into the cDNA of DEN2. A DEN2 virus isolate from a 1974 dengue epidemic in the Kingdom of Tonga (Tonga/74) (Gubler, D. J. et al. 1978 *Am J Trop Med Hyg* 27:581-589) was chosen to represent wt DEN2. The genome of DEN2 (Tonga/74) was sequenced in its entirety and served as consensus sequence for the construction of a full-length cDNA clone (Appendix 1). cDNA fragments of DEN2 (Tonga/74) were generated by reverse-transcription of the genome as indicated in FIG. 6A. Each fragment was subcloned into a plasmid vector and sequenced to verify that it matched the consensus sequence as determined for the virus. This yielded seven cloned cDNA fragments spanning the genome. Cloned fragments were modified as follows: Fragment X, representing the 5' end of the genome was abutted to the SP6 promoter; Fragment L was modified to contain a translationally-silent SpeI restriction site at genomic nucleotide 2353; Fragment R was modified to contain a translationally-silent SpeI restriction site also at genomic nucleotide 2353, and to stabilize the eventual full-length clone, two additional translationally-silent mutations at nucleotides 2362-2364 and 2397 were created to ensure that translation stop codons were present in all reading frames other than that used to synthesize the virus polyprotein; Fragment A was modified at nucleotide 3582 to ablate a naturally occurring SpeI restriction site and at nucleotide 4497 to ablate a naturally occurring KpnI restriction site; Fragment C was modified at nucleotide 9374 to ablate a naturally occurring KpnI restriction site; and Fragment Y, representing the 3' end of the genome was abutted to a KpnI restriction site. Each fragment was added incrementally between the AscI and KpnI restriction sites of DEN4 cDNA clone p4 (Durbin, A. P. et al. 2001 *Am J Trop Med Hyg* 65:405-13) to generate a full-length DEN2 cDNA clone (p2) with the same vector background successfully used to generate rDEN4 and rDEN4Δ30, cDNA clone p2 was sequenced to confirm that the virus genome region matched the DEN2 (Tonga/74) consensus sequence, with the exception of the translationally-silent modifications noted above. The Δ30 mutation was introduced into Fragment Y to generate Fragment YΔ30. To create p2Δ30, the Fragment Y region of p2 was replaced with Fragment YΔ30 (FIG. 6A, B).

For transcription and generation of infectious virus, cDNA (p2 and p2Δ30) was linearized with Acc65I (isoschizomer of KpnI which cleaves leaving only a single 3' nucleotide) and used as template in a transcription reaction using SP6 RNA polymerase as previously described (Blaney, J. E. et. al. 2002 *Virology* 300:125-139). Transcripts were introduced into Vero cells or C6/36 mosquito cells using liposome-mediated transfection and cell culture supernatants were harvested on day 7.

rDEN2 virus was recovered from the p2 cDNA in both Vero and C6/36 cells, while rDEN2Δ30 was recovered from the p2Δ30 cDNA clone in only C6/36 cells (Table 19). The level of infectious virus recovered in C6/36 cells was comparable for the p2 and p2Δ30 cDNA clones when assayed by plaque titration and immunostaining in Vero or C6/36 cells. As previously observed, the efficiency of transfection in C6/36 cells was higher than that in Vero cells. Two rDEN2Δ30 viruses were recovered from independent cDNA clones, #2 and #10.

TABLE 19 rDEN2 virus is recovered in Vero and C6/36 cells, but rDEN2Δ30 virus is recovered only in C6/36 cells.

| Transfection cell type | cDNA construct | Clone | Virus | Virus titer of transfection harvest (day 7) determined in the indicated cell type ($\log_{10}$ PFU/ml) | |
|---|---|---|---|---|---|
| | | | | Vero cells | C6/36 cells |
| Vero cells | p2 | #8A | rDEN2 | 3.1 | 4.3 |
| | p2Δ30 | #2 | rDEN2Δ30 | <0.7 | <0.7 |
| | p2Δ30 | #10 | rDEN2Δ30 | <0.7 | <0.7 |
| C6/36 cells | p2 | #8A | rDEN2 | 5.5 | 7.5 |
| | p2Δ30 | #2 | rDEN2Δ30 | 4.8 | 7.6 |
| | p2Δ30 | #10 | rDEN2Δ30 | 4.6 | 7.5 |

To produce working stocks of rDEN2 and rDEN2Δ30 viruses, transfection harvests were passaged and terminally diluted in Vero cells, and genomic sequences of the viruses were determined. The Vero cell transfection harvest of rDEN2 virus was terminally diluted once in Vero cells, and individual virus clones were passaged once in Vero cells. To assess whether any homologous Vero cell adaptation mutations identified in the rDEN4 NS4B 7100-7200 region were present in these virus clones, seven independent terminally diluted clones were sequenced over this region. Each of the seven rDEN2 viruses contained a single nucleotide substitution in this region at nucleotide 7169 (U>C) resulting in a Val>Ala amino acid change. This nucleotide corresponds to the 7162 mutation identified in rDEN4 (Blaney, J. E. et. al. 2002 *Virology* 300:125-139), which has a known Vero cell adaptation phenotype suggesting that this mutation may confer a replication enhancement phenotype in rDEN2 virus. One rDEN2 virus clone was completely sequenced and in addition to the 7169 mutation, a missense mutation (Glu>Ala) was found in NS5 at residue 3051 (Table 20).

TABLE 20

Missense mutations which accumulate in rDEN2 and rDEN2Δ30 viruses after transfection or passage in Vero cells.

| Virus | Gene | Nucleotide position | Nucleotide substitution | Amino acid position[a] | Amino acid change |
|---|---|---|---|---|---|
| rDEN2[b] | NS4B | 7169[c] | U > C | 2358 | Val > Ala |
| (Vero) | NS5 | 9248 | A > C | 3051 | Glu > Ala |
| rDEN2Δ30[d] | NS3 | 4946 | A > G | 1617 | Lys > Arg |
| (Vero) | NS4B | 7169[c] | U > C | 2358 | Val > Ala |

[a]Amino acid position in DEN2 polyprotein beginning with the methionine residue of the C protein (nucleotides 97-99) as position 1.
[b]Virus was recovered in Vero cells and terminally-diluted once in Vero cells. Virus stock was prepared in Vero cells.
[c]Same nucleotide position as 7162 in rDEN4.
[d]Virus was recovered in C6/36 cells and passaged three times in Vero cells. Virus was then terminally diluted and a stock was prepared in Vero cells.

Because both rDEN2 and rDEN2Δ30 viruses grown in Vero cells acquired the same mutation at nucleotide 7169, which corresponds to the Vero cell adaptation mutation previously identified in rDEN4 at nucleotide 7162, it was reasoned that this mutation is associated with growth adaptation of rDEN2 and rDEN2Δ30 in Vero cells. In anticipation that the 7169 mutation may allow rDEN2Δ30 to be recovered directly in Vero cells, the mutation was introduced into the rDEN2Δ30 cDNA plasmid to create p2Δ30-7169. Transcripts synthesized from p2Δ30-7169, as well as p2 and p2Δ30 were introduced into Vero cells or C6/36 mosquito cells using liposome-mediated transfection as described above. Virus rDEN2Δ30-7169 was recovered from the p2Δ30-7169 cDNA in both Vero and C6/36 cells, while rDEN2Δ30 was recovered from the p2Δ30 cDNA clone in only C6/36 cells (Table 21). The 7169 mutation is both necessary and sufficient for the recovery of rDEN2Δ30 in Vero cells.

TABLE 21 rDEN2Δ30-7169 virus containing the 7169 Vero cell adaptation mutation is recovered in both Vero and C6/36 cells

| Transfection cell type | cDNA construct | Clone | Virus | Virus titer of transfection harvest (day 14) determined in C6/36 cells ($\log_{10}$ PFU/ml) |
|---|---|---|---|---|
| Vero cells | p2 | #8A | rDEN2 | 6.8 |
| | p2Δ30 | #2 | rDEN2Δ30 | <0.7 |
| | p2Δ30-7169[a] | #37 | rDEN2Δ30-7169 | 5.1 |
| C6/36 cells | p2 | #8A | rDEN2 | 6.9 |
| | p2Δ30 | #2 | rDEN2Δ30 | 7.1 |
| | p2Δ30-7169 | #37 | rDEN2Δ30-7169 | 7.2 |

[a]Nucleotide 7169 in rDEN2 corresponds to nucleotide 7162 in rDEN4 which has been shown to be associated with growth adaptation in Vero cells.

To initially assess the ability of the Δ30 mutation to attenuate rDEN2 virus in an animal model, the replication of DEN2 (Tonga/74), rDEN2, and rDEN2Δ30 viruses was evaluated in SCID-HuH-7 mice. Previously, attenuation of vaccine candidates in SCID-HuH-7 mice has been demonstrated to be predictive of attenuation in the rhesus monkey model of infection (Examples 1 and 2). The recombinant viruses tested in this experiment were recovered in C6/36 cells. The DEN2 Tonga/74 virus isolate, rDEN2, and two independent rDEN2Δ30 viruses, (clones 20A and 21A) which were derived from two independent p2Δ30 cDNA clones, were terminally diluted twice in C6/36 cells prior to production of a working stock in C6/36 cells. These viruses should not contain any Vero cell adaptation mutations. DEN2 Tonga/74 virus replicated to a mean virus titer of 6.2 $\log_{10}$ PFU/ml in the serum of SCID-HuH-7 mice, and rDEN2 virus replicated to a similar level, 5.6 $\log_{10}$ PFU/ml (Table 22). Both rDEN2Δ30 viruses were greater than 100-fold restricted in replication compared to rDEN2 virus. These results indicate that the Δ30 mutation has an attenuating effect on replication of rDEN2 virus similar to that observed for rDEN4 and rDEN1 viruses.

TABLE 22

The Δ30 mutation restricts rDEN2 virus replication in SCID-HuH-7 mice.

| Virus | No. of mice | Mean virus titer ± SE ($\log_{10}$ PFU/ml serum)[a] | Mean $\log_{10}$-unit reduction from value for wt[b] |
|---|---|---|---|
| DEN2 (Tonga/74) | 8 | 6.2 ± 0.3 | — |
| rDEN2 | 9 | 5.6 ± 0.2 | — |

TABLE 22-continued

The Δ30 mutation restricts rDEN2
virus replication in SCID-HuH-7 mice.

| Virus | No. of mice | Mean virus titer ± SE ($log_{10}$ PFU/ ml serum)[a] | Mean $log_{10}$-unit reduction from value for wt[b] |
|---|---|---|---|
| rDEN2Δ30 (clone 20A) | 9 | 3.1 ± 0.2 | 2.5 |
| rDEN2Δ30 (clone 21A) | 9 | 2.9 ± 0.3 | 2.7 |

[a]Groups of SCID-HuH-7 mice were inoculated directly into the tumor with $10^4$ PFU virus grown in C6/36 cells. Serum was collected on day 7 and titered in C6/36 cells.
[b]Comparison of mean virus titers of mice inoculated with mutant virus and concurrent rDEN2 control.

DEN2 virus replication in SCID-HuH-7 mice was also determined using DEN2 (Tonga/74), rDEN2, and rDEN2Δ30 which were passaged in Vero cells (see Table 20, footnotes b and d). Both rDEN2 and rDEN2Δ30 had acquired a mutation in NS4B, nucleotide 7169, corresponding to the 7162 mutation identified in rDEN4 as Vero cell adaptation mutation. In the presence of the 7169 mutation, the Δ30 mutation reduced replication of rDEN2Δ30 by 1.0 $log_{10}$ PFU/ml (Table 23). Previously, using virus grown in C6/36 cells and lacking the 7169 mutation, the Δ30 mutation reduced replication of rDEN2Δ30 by about 2.5 $log_{10}$ PFU/ ml (Table 22). These results indicate that Vero cell growth adaptation in DEN2 may also confer a slight growth advantage in HuH-7 liver cells. Nevertheless, the attenuation conferred by the Δ30 mutation is still discernible in these Vero cell growth adapted viruses.

TABLE 23

The Δ30 mutation restricts Vero cell adapted
rDEN2 virus replication in SCID-HuH-7 mice.

| Virus | No. of mice | Mean virus titer ± SE ($log_{10}$PFU/ml serum)[a] | Mean $log_{10}$-unit reduction from value for wt[b] |
|---|---|---|---|
| DEN2 (Tonga/74) | 6 | 5.9 ± 0.3 | — |
| rDEN2 | 7 | 5.9 ± 0.2 | — |
| rDEN2Δ30 | 9 | 4.9 ± 0.3 | 1.0 |

[a]Groups of SCID-HuH-7 mice were inoculated directly into the tumor with $10^4$ PFU virus. Serum was collected on day 7 and titered in C6/36 cells.
[b]Comparison of mean virus titers of mice inoculated with rDEN2Δ30 and rDEN2 control.

Evaluation of the replication, immunogenicity, and protective efficacy of rDEN2Δ30 and wild-type parental rDEN2 virus in juvenile rhesus monkeys was performed as follows. Dengue virus-seronegative monkeys were injected subcutaneously with 5.0 $log_{10}$ PFU of virus in a 1 ml dose divided between two injections in each side of the upper shoulder area. Monkeys were observed daily and blood was collected on days 0-10 and 28 and serum was stored at −70° C. Viruses used in this experiment were passaged in Vero cells, and recombinant viruses contained the mutations shown in Table 20 (See footnotes b and d). Titer of virus in serum samples was determined by plaque assay in Vero cells as described previously (Durbin, A. P. et al. 2001 Am J Trop Med Hyg 65:405-13). Plaque reduction neutralization titers were determined for the day 28 serum samples as previously described (Durbin, A. P. et al. 2001 Am J Trop Med Hyg 65:405-13). All monkeys were challenged on day 28 with a single dose of 5.0 $log_{10}$ PFU of wt DEN2 (Tonga/74) and blood was collected for 10 days. Virus titer in post-challenge sera was determined by plaque assay in Vero cells. Monkeys inoculated with wt DEN2 (Tonga/74) or rDEN2 were viremic for 4-5 days with a mean peak titer of 2.1 or 1.9 $log_{10}$ PFU/ml, respectively.

Figure 7:
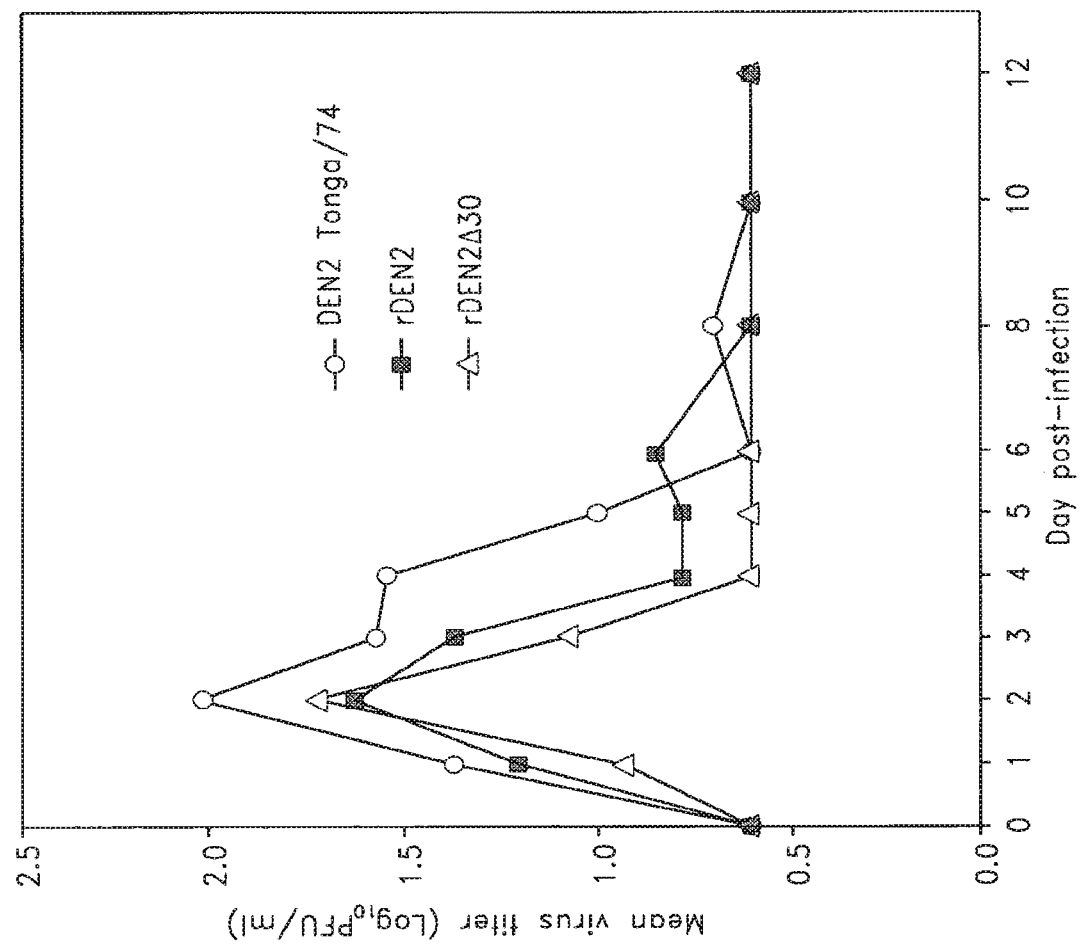
FIG. 7. Viremia levels in rhesus monkeys inoculated with DEN2 (Tonga/74), rDEN2, and rDEN2Δ30 vaccine candidate. Groups of four monkeys were inoculated with 5.0 $\log_{10}$ PFU virus subcutaneously. Serum was collected daily and virus titers were determined by plaque assay in Vero cells. The limit of virus detection was 0.7 $\log_{10}$ PFU/ml. Mean virus titers are indicated for each group. Viremia was not detected in any monkey after day 8.

Monkeys inoculated with rDEN2Δ30 were viremic for 2-3 days with a mean peak titer of 1.7 $log_{10}$ PFU/ml (Table 24, FIG. 7), indicating that the Δ30 mutation is capable of attenuating DEN2, although not to the same low level observed in rDEN1Δ30 (Table 16). As expected for an attenuated virus, the immune response, as measured by neutralizing antibody titer, was lower following inoculation with rDEN2Δ30 compared to inoculation with wt DEN2 (Tonga/74) or rDEN2 (Table 24), yet sufficiently high to protect the animals against wt DEN2 virus challenge (Table 25). Thus, the decreased number of days of viremia for rDEN2Δ30, the decreased mean peak titer, and the decreased serum antibody response indicate that the Δ30 mutation attenuates rDEN2 for rhesus monkeys.

TABLE 24 rDEN2Δ30 is slightly more attenuated for rhesus monkeys than rDEN2

| Virus[a] | No. of monkeys | No. of monkeys with viremia | Mean no. of viremic days per monkey[b] | Mean peak virus titer ($log_{10}$ PFU/ ml ± SE) | Geometric mean serum neutralizing antibody titer (reciprocal dilution) | |
|---|---|---|---|---|---|---|
| | | | | | Day 0 | Day 28 |
| mock | 2 | 0 | 0 | <0.7 | <10 | <10 |
| DEN2 (Tonga/74) | 4 | 4 | 4.5 | 2.1 ± 0.3 | <10 | 311 |
| rDEN2 (Vero) | 4 | 4 | 4.0 | 1.9 ± 0.1 | <10 | 173 |
| rDEN2Δ30 (Vero) | 4 | 4 | 2.8 | 1.7 ± 0.2 | <10 | 91 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 8.

TABLE 25 rDEN2Δ30 protects rhesus monkeys from wt DEN2 virus challenge

| Virus[a] | No. of monkeys | Mean no. of viremic days per monkey after DEN2 challenge | Mean peak vires titer ($\log_{10}$PFU/ml ± SE) | Geometric mean serum neutralizing antibody titer (reciprocal dilution) | |
|---|---|---|---|---|---|
| | | | | Day 28 | Day 56 |
| Mock | 2 | 4.0 | 2.1 ± 0.1 | <10 | 338 |
| DEN2 (Tonga/74) | 4 | 0 | <0.7 | 311 | 334 |
| rDEN2 (Vero) | 4 | 0 | <0.7 | 173 | 318 |
| rDEN2Δ30 (Vero) | 4 | 0 | <0.7 | 91 | 267 |

[a]28 days after inoculation with the indicated viruses, monkeys were challenged subcutaneously with 10[5] PFU DEN2 (Tonga/74) in a 1 ml dose. Serum was collected on days 28 to 34, 36, 38, and 56. Virus titer was determined by plaque assay in Vero cells.

The infectivity of DEN2 (Tonga/74), rDEN2 and rDEN2Δ30 for *Aedes aegypti* mosquitoes via an artificial bloodmeal was evaluated using the methods described in detail in Example 5. However at doses of 3.3 to 3.5 $\log_{10}$ pfu ingested, none of these three viruses infected any mosquitoes, indicating that DEN2 (Tonga/74) is poorly infectious for *Aedes aegypti*. As with rDEN1, the genetic basis for this lack of infectivity remains to be defined. The important property of restricted infectivity for the mosquito midgut is highly desirable in a vaccine candidate because it would serve to greatly restrict transmission of the virus from a vaccinee to a mosquito vector.

Several missense mutation identified in rDEN4 have been demonstrated to confer attenuated replication in suckling mouse brain and/or SCID-HuH-7 mice (Blaney, J. E. et al. 2002 *Virology* 300:125-139; Blaney, J. E. et al. 2001 *J Virol* 75:9731-9740). In addition, missense mutations that enhance replication of rDEN4 virus in Vero cells have been characterized. The significant sequence conservation among the DEN virus serotypes provides a strategy by which the mutations identified in rDEN4 viruses are contemplated as being used to confer similar phenotypes upon rDEN2 virus. Six mutations identified in rDEN4 virus that are at a site conserved in rDEN2 virus are being introduced into the p2 and p2Δ30 cDNA clones (Table 26). Specifically, two rDEN4 mutations, NS3 4891 and 4995, which confer Vero cell adaptation phenotypes and decreased replication in mouse brain, one mutation, NS4B 7182, which confers a Vero cell adaptation phenotype, and three mutations, NS1 2650, NS3 5097, and 3' LTR 10634 which confer decreased replication in mouse brain and SCID-HuH-7 mice are being evaluated. These mutations have been introduced into subcloned fragments of the p2 and p2Δ30 cDNA clones, and have been used to generate mutant full-length cDNA clones (Table 26), from which virus has been recovered in C6/36 cells (Table 27). The evaluation of these mutant rDEN2 viruses is contemplated as determining that such point mutations can be transported into a different DEN virus serotype and confer a similar useful phenotype, as has been demonstrated for the Δ30 deletion mutation.

TABLE 26

Introduction of conserved point mutations characterized in rDEN4 viruses into rDEN2 Tonga/74 virus.

| Phenotype in rDEN4 virus | | | Mutation in rDEN4 virus | | | | Mutation introduced into DEN2 virus | | | |
|---|---|---|---|---|---|---|---|---|---|---|
| Vero Adaptation[a] | Mouse brain att[b] | SCID-HuH-7 att[c] | Gene/ region | Nucleotide position | Amino acid position[d] | Amino acid change | Nucleotide position | Amino acid position[d] | Amino acid change | RE site/ mutagenic region[e] |
| + | + | - | NS3 | 4891 | 1597 | Ile > Thr | 4889 | 1598 | Ile > Thr | Nar I CCAcgGGcGCCGT |
| + | + | - | NS3 | 4995 | 1632 | Ser > Pro | 4993 | 1633 | Ser > Pro | Stu I AAGGccTGGA |
| + | - | - | NS4b | 7182 | 2361 | Gly > Ser | 7189 | 2365 | Gly > Ser | Xma I TAtccCCGGGAC |
| - | + | + | NS1 | 2650 | 850 | Asn > Ser | 2648 | 851 | Asn > Ser | Sac I AGAgcTctcTC |
| - | + | + | NS3 | 5097 | 1666 | Asp > Asn | 5095 | 1667 | Asp > Asn | Xma I GaATCTCCACCCgGA |
| - | + | + | 3' UTR | 10634 | n/a[f] | n/a | 10698 | n/a | n/a | none CTGTcGAATC |

[a]Presence of the indicated mutation increases plaque size in Vero cells two-fold or greater than rDEN4 virus.
[b]Presence of the indicated mutation restricts replication in 7-day-old mouse brain greater than 100-fold compared to rDEN4 virus.
[c]Presence of the indicated mutation restricts replication in SCID-HuH-7 mice greater than 100-fold compared to rDEN4 virus.
[d]Amino acid position in DEN4 or DEN2 polyprotein beginning with the methionine residue of the C protein (nucleotides 102-104 or 97-99, respectively) as position 1.
[e]Primers were engineered which introduced (underline) translationally-silent restriction enzyme (RE) sites. Lowercase letters indicate nt changes and bold letters indicate the site of the 5-FU mutation, which in some oligonucleotides differs from the original nucleotide substitution change in order to create a unique RE site. The change preserves the codon for the amino acid substitution.
[f]Nucleotide substitution in the 3' UTR is U > C in DEN4 and DEN2 virus.

TABLE 27 rDEN2 viruses containing conserved 5-FU mutations are recovered in C6/36 cells.

| Virus (nucleotide position in rDEN2) | Nucleotide position in rDEN4 | Virus titer of transfection harvest (day 7) determined in C6/36 cells (log$_{10}$PFU/ml) |
|---|---|---|
| rDEN2-4889 | 4891 | 7.6 |
| rDEN2-4993 | 4995 | 7.2 |
| rDEN2-7189 | 7182 | 3.5 |
| rDEN2-2648 | 2650 | —$^a$ |
| rDEN2-5095 | 5097 | —$^a$ |
| rDEN2-10698 | 10634 | 7.7 |

$^a$Transfection has not yet been attempted.

Example 4

Generation and Characterization of a Recombinant DEN3 Virus Containing the Δ30 Mutation Because rDEN1Δ30 was satisfactorily attenuated, we sought to extend our technology to the creation of a DEN3 vaccine candidate. To do this, the Δ30 mutation was introduced into the cDNA of DEN3, similar to the method used to create rDEN2Δ30. A DEN3 virus isolate from a 1978 dengue epidemic in rural Sleman, Central Indonesia (Sleman/78) (Gubler, D. 0.1. et al. 1981 *Am J Trop Med Hyg* 30:1094-1099) was chosen to represent wt DEN3. The genome of DEN3 (Sleman/78) was sequenced in its entirety and served as consensus sequence fir the construction of a full-length cDNA clone (Appendix 2). cDNA fragments of DEN3 (Sleman/78) were generated by reverse-transcription of the genome as indicated in FIG. 8A. Each fragment was subcloned into a plasmid vector and sequenced to verify that it matched the consensus sequence as determined for the virus. This yielded six cloned cDNA fragments spanning the genome. Cloned fragments were modified as follows: Fragment 5, representing the 5' end of the genome was abutted to the SP6 promoter preceded by an AscI restriction site; Fragment 1L was modified to contain a translationally-silent SpeI restriction site at genomic nucleotide 2345; Fragment 1R was modified to contain a translationally-silent SpeI restriction site also at genomic nucleotide 2345, and to stabilize the eventual full-length clone, three additional translationally-silent mutations at nucleotides 2354-2356, 2360-2362, and 2399 were created to ensure that translation stop codons were present in all reading frames other than that used to synthesize the virus polyprotein; Fragment 3 was modified at nucleotide 9007 to ablate a naturally occurring KpnI restriction site; and Fragment 4, representing the 3' end of the genome was abutted to a KpnI restriction site. Each fragment was added incrementally between the AscI and KpnI restriction sites of DEN4 cDNA clone p4 (Durbin, A. P. et al, 2001 *Am J Trop Med Hyg* 65:405-13) to generate a full-length DEN3 cDNA clone with the same vector background successfully used to generate rDEN4 and rDEN2. However, a stable, full-length clone could not be recovered in *E. coli* when fragments 1L and 1R were combined into the same cDNA molecule. To overcome this instability, a synthetic DNA linker (FIG. 8A) containing redundant termination codons in each of the forward and reverse open reading frames was introduced into the SpeI restriction site at the same time that fragment 1L was added to complete the full-length cDNA construct. The resulting p3 clone containing the linker sequence was stable in *E. coli*, indicating that the linker sequence was sufficient to interrupt whatever deleterious element exists in this region. cDNA clone p3 was sequenced and the virus genome was found to match the DEN3 (Sleman/78) consensus sequence, with the exception of the linker sequence and translationally-silent modifications noted above (Appendix 2—shown with the linker sequence removed). The Δ30 mutation was introduced into Fragment 4 to generate Fragment 4Δ30. To create p3Δ30, the Fragment 4 region of p3 was replaced with Fragment 4Δ30 (FIG. 8A, B).

For transcription and generation of infectious virus, cDNA plasmids p3 and p3Δ30 were digested with SpeI and re-ligated to remove the linker sequence, linearized with Acc65I (isoschizomer of KpnI which cleaves leaving only a single 3' nucleotide), and used as templates in a transcription reaction using SP6 RNA polymerase as previously described (Blaney, J. E. et. al. 2002 *Virology* 300:125-139). Transcripts were introduced into Vero cells or C6/36 mosquito cells using liposome-mediated transfection and cell culture supernatants were harvested on day 14.

rDEN3 virus was recovered from the p3 cDNA in both Vero and C6/36 cells, while rDEN3Δ30 was recovered from the p3Δ30 cDNA clone in only C6/36 cells (Table 28). The level of infectious virus recovered in C6/36 cells was comparable for the p3 and p3Δ30 cDNA clones when assayed by plaque titration in Vero or C6/36 cells. As previously observed, the efficiency of transfection in C6/36 cells was higher than that in Vero cells. Two rDEN3Δ30 viruses were recovered from independent cDNA clones, #22 and #41.

TABLE 28 rDEN3 virus is recovered in Vero and C6/36 cells, but rDEN3Δ30 virus is recovered only in C6/36 cells.

| Trans- fection cell type | cDNA construct | Clone | Virus | Virus titer of transfection harvest (day 14) determined in the indicated cell type (log$_{10}$PFU/ml) | |
|---|---|---|---|---|---|
| | | | | Vero cells | C6/36 cells |
| Vero cells | p3 | #50 | rDEN3 | 5.2 | 6.3 |
| | p3Δ30 | #22 | rDEN3Δ30 | <0.7 | <0.7 |
| | p3Δ30 | #41 | rDEN3Δ30 | <0.7 | <0.7 |
| C6/36 cells | p3 | #50 | rDEN3 | 5.2 | 6.0 |
| | p3Δ30 | #22 | rDEN3Δ30 | 5.9 | 6.9 |
| | p3Δ30 | #41 | rDEN3Δ30 | 5.1 | 7.2 |

To produce working stocks of viruses, transfection harvests will be passaged and terminally diluted in Vero cells, and genomic sequences of the viruses will be determined. To improve virus yield in Vero cells, the Vero cell adaptation mutation previously identified in rDEN4 at nucleotide 7162 was introduced into the homologous NS4B region of p3 and p3Δ30 to create p3-7164 and p3Δ30-7164. This mutation creates a Val to Ala substitution at amino acid position 2357. As demonstrated for rDEN2Δ30, this mutation allowed for the direct recovery of virus in Vero cells (Table 27) and is anticipated to have the same effect for rDEN3Δ30.

To initially assess the ability of the Δ30 mutation to attenuate rDEN3 virus in an animal model, the replication of DEN3 (Sleman/78), rDEN3, and rDEN3Δ30 viruses will be evaluated in SCID-HuH-7 mice and rhesus monkeys. Previously, attenuation of vaccine candidates in SCID-HuH-7 mice has been demonstrated to be predictive of attenuation in the rhesus monkey model of infection (Examples 1 and 2). The evaluation of these mutant rDEN3 viruses is contemplated as determining that the Δ30 deletion mutations can be transported into the DEN3 virus serotype and confer a similar useful phenotype, as has been demonstrated for DEN1, DEN2, and DEN4.

In summary, the strategy of introducing the Δ30 mutation into wild-type DEN viruses of each serotype to generate a suitably attenuated tetravalent vaccine formulation is a unique and attractive approach for several reasons. First, the mutation responsible for attenuation is a 30-nucleotide deletion in the 3' LTR, thus assuring that all of the structural and non-structural proteins expressed by each of the four components of the tetravalent vaccine are authentic wild-type proteins. Such wild-type proteins should elicit an antibody response that is broad based, rather than based solely on the M and E proteins that are present in chimeric dengue virus vaccine candidates (Guirakhoo, F. et al, 2001 *J Virol* 75:7290-304; Huang, C. Y. et al. 2000 *J Virol* 74:3020-8). The uniqueness of this approach derives from the fact that other live attenuated dengue virus vaccines have mutations in their structural or non-structural proteins (Butrapet, S. et al. 2000 *J Virol* 74:3011-9; Puri, B. et al. 1997 *J Gen Virol* 78:2287-91), therefore the immune response induced by these viruses will be to a mutant protein, rather than a wild-type protein. Second, deletion mutations are genetically more stable than point mutations, and reversion of the attenuation phenotype is unlikely. In humans, DEN4Δ30 present in serum of vaccinees retained its Δ30 mutation, confirming its genetic stability in vivo (Durbin, A. P. et al. 2001 *Am J Trop Med Hyg* 65:405-13). The attenuating mutations in other existing dengue live attenuated vaccine candidates are based on less stable point mutations (Butrapet, S. et al. 2000 *J Virol* 74:3011-9: Puri, B. et al. 1997 *J Gen Virol* 78:2287-91). Third, since the Δ30 mutation is common to each of the four viruses of the tetravalent vaccine, recombination between any of the four vaccine serotypes would not lead to loss of the attenuating mutation or reversion to a wild-type phenotype. Recombination between components of the trivalent polio vaccine has been observed (Guillot, S. et al. 2000 *J Virol* 74:8434-43), and naturally occurring recombinant dengue viruses have been described (Worobey, M. et al. 1999 *PNAS USA* 96:7352-7) indicating the ability of this *flavivirus* to exchange genetic elements between two different viruses. Clearly, gene exchange is readily achieved between different DEN virus serotypes using recombinant cDNA techniques (Bray, M. and Lai, C. J. 1991 *PNAS USA* 88:10342-6). Fourth, viruses with wild-type structural proteins appear more infectious than viruses with altered structural proteins (Huang, C. Y. et al. 2000 *J Virol* 74:3020-80). This permits the use of a low quantity of each of the four virus components in the final vaccine, contributing to the low cost of manufacture. Low-cost manufacture is an essential element in defining the ultimate utility of a dengue virus vaccine.

Example 5

Generation and Characterization of Intertypic Chimeric DEN2 Viruses Containing the Δ30 Mutation The four serotypes of dengue virus are defined by antibody responses induced by the structural proteins of the virus, primarily by a neutralizing antibody response to the envelope (E) protein. These structural proteins include the E glycoprotein, a membrane protein (M), and a capsid (C) protein. The mature virus particle consists of a well-organized outer protein shell surrounding a lipid bilayer membrane and a less-well-defined inner nucleocapsid core (Kuhn, R. J. et al. 2002 *Cell* 108:717-25). The E glycoprotein is the major protective antigen and readily induces virus neutralizing antibodies that confer protection against dengue virus infection. An effective dengue vaccine must therefore minimally contain the E protein of all four serotypes, namely DEN1, DEN2, DEN3, and DEN4, thereby inducing broad immunity and precluding the possibility of developing the more serious illnesses DHF/DSS, which occur in humans during secondary infection with a heterotypic wild-type dengue virus. Based on a previously reported strategy (Bray, M. and Lai, C. J. 1991 *PNAS USA* 88:10342-6), a recombinant cDNA technology is being used to develop a live attenuated tetravalent dengue virus vaccine composed of a set of intertypic chimeric dengue viruses bearing the structural proteins of each serotype.

Figure 9A:
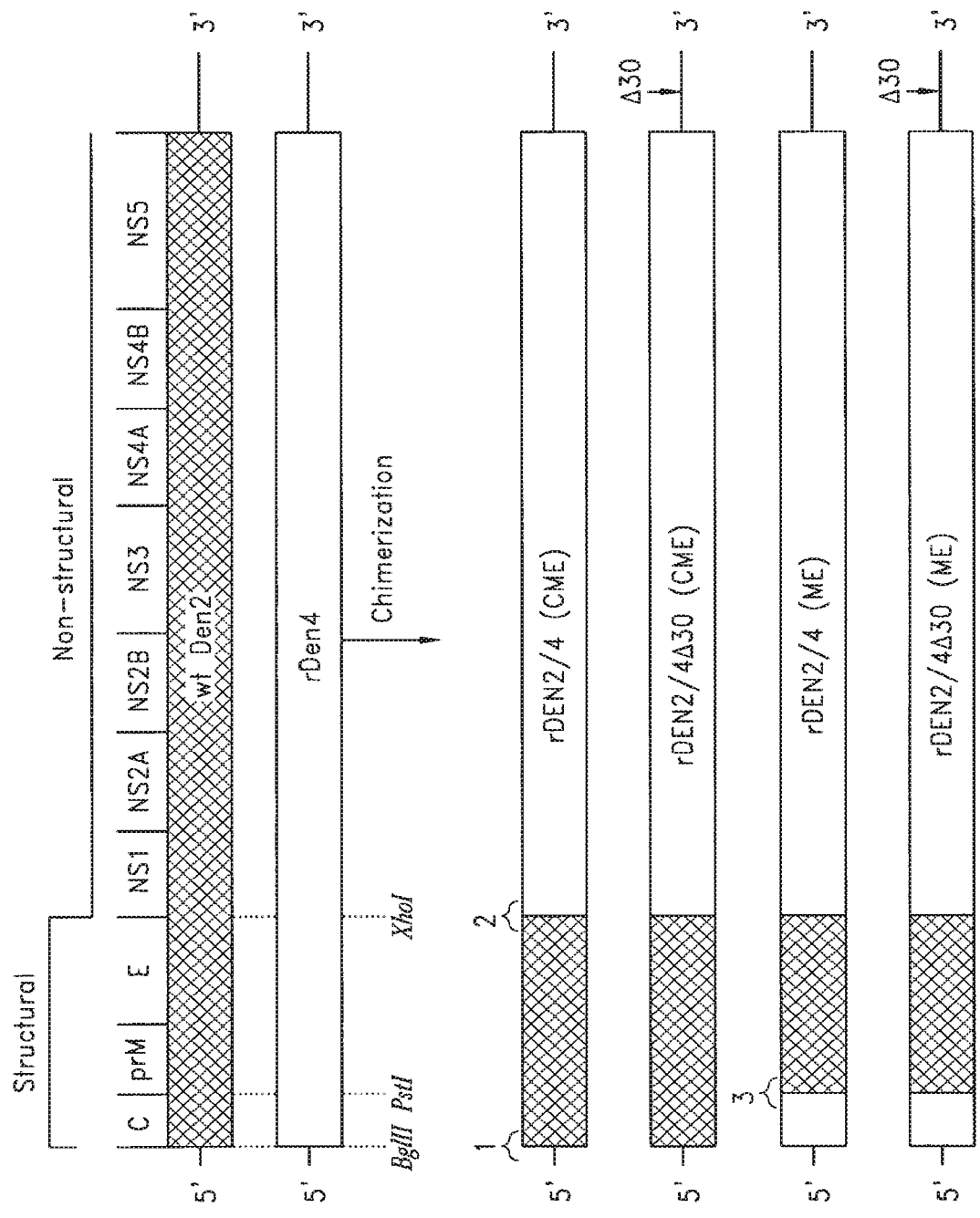

Following the identification of a suitably attenuated and immunogenic DEN4 recombinant virus, namely DEN4Δ30 (Durbin, A. P et al. 2001 *Am J Trop Med Hyg* 65:405-13), chimeric viruses based on the DEN4 cDNA have been generated in which the C-M-E (CME) or M-E (ME) genes have been replaced with the corresponding genes derived from the prototypic DEN2 New Guinea C (NGC) strain (FIG. 9A). To create the CME chimeric viruses, the BglII/XhoI region of the cDNA for either rDEN4 or rDEN4Δ30 was replaced with a similar region derived from DEN2. Likewise, to create the ME chimeric viruses, the PstI/XhoI region of the cDNA for either rDEN4 or rDEN4Δ30 was replaced with a homologous region derived from DEN2. The nucleotide and amino acid sequences of the resulting junctions are shown in FIG. 9B. The GenBank accession number for the nucleotide sequence of rDEN4Δ30 is AF326837. The GenBank accession number for DEN2 NGC is M29095, which represents the mouse neurovirulent strain of DEN2 NGC and differs from the prototypic strain used here as previously documented (Bray, M. et al. 1998 *J Virol* 72:1647-51).

For transcription and generation of virus, chimeric cDNA clones were linearized and used as template in a transcription reaction using SP6 RNA polymerase as described (Durbin, A. P et al, 2001 *Am J Trop Med Hyg* 65:405-13). Transcripts were introduced into Vero cells using liposome-mediated transfection and recombinant dengue virus was harvested on day 7. The genomes of the resulting viruses were confirmed by sequence analysis of viral RNA isolated from recovered virus as previously described (Durbin, A. P et al, 2001 *Am J Trop Med Hyg* 65:405-13). Incidental mutations arising from virus passage in tissue culture were identified in all viruses and are listed in Table 29. Notably, each virus contained a missense mutation in NS4B corresponding to a previously identified mutation from rDEN4 and associated with adaptation to replication in. Vero cells (See Table 30 for correlation of nucleotide positions between rDEN4 and chimeric viruses). All viruses replicated in Vero cells to titers in excess of 6.0 $\log_{10}$ PFU/ml, indicating that the chimeric viruses, even those containing the Δ30 mutation, replicate efficiently in cell culture, a property essential for manufacture of the vaccine.

TABLE 29

Missense mutations observed among the Vero cell-grown chimeric DEN2/4 viruses

| Virus | Gene | Nucleotide position | Nucleotide change | Amino acid position | Amino acid change |
|---|---|---|---|---|---|
| rDEN2/4(CME) | NS4B | 7161[a] | A > U | 2355 | Leu > Phe |
| rDEN2/4Δ30(CME) | M | 743 | G > A | 216 | Gly > Glu |
|  | E | 1493 | C > U | 466 | Ser > Phe |
|  | NS4B | 7544[b] | C > T | 2483 | Ala > Val |
| rDEN2/4(ME) | E | 1065 | U > C | 322 | Phe > Leu |
|  | NS4B | 7163[a] | A > U | 2354 | Leu > Phe |
| rDEN2/4Δ30(ME) | NS4B | 7163[a] | A > C | 2354 | Leu > Phe |

[a]Same nucleotide position as 7163 in rDEN4.
[b]Same nucleotide position as 7546 in rDEN4.

TABLE 30

Nucleotide (nt) length differences for DEN chimeric viruses compared to rDEN4.

| rDEN chimeric virus | nt difference from rDEN4 (following CME region) | ORF start (nt position) | Amino acid length C | M | E |
|---|---|---|---|---|---|
| 1/4 ME | 0 | 102 | 113 | 166 | 495 |
| 1/4 CME | +3 | 102 | 114 | 166 | 495 |
| 2/4 ME | 0 | 102 | 113 | 166 | 495 |
| 2/4 CME | −2 | 97 | 114 | 166 | 495 |
| 3/4 ME | −6 | 102 | 113 | 166 | 493 |
| 3/4 CME | −3 | 102 | 114 | 166 | 493 |
| rDEN4 | — | 102 | 113 | 166 | 495 |

Results of a safety, immunogenicity, and efficacy study in monkeys are presented in Table 31. Monkeys inoculated with wild-type DEN2 were viremic for approximately 5 days with a mean peak titer of 2.1 $\log_{10}$ PFU/ml, while monkeys inoculated with any of the chimeric DEN2 viruses were viremic for 1.2 days or less and had a mean peak titer of less than 1.0 $\log_{10}$ PFU/ml. This reduction in the magnitude and duration of viremia clearly indicates that the chimeric viruses containing either the CME or ME proteins of DEN2 were more attenuated than the parental DEN2 NGC virus. Neither the animals receiving the wild-type DEN2 nor the DEN2/4 chimeric viruses were ill. The decreased replication of the attenuated viruses in monkeys is accompanied by a reduction in the immune response of inoculated monkeys. This is indicated in Table 31 by approximately a 5-fold reduction in the level of neutralizing antibody following inoculation with the chimeric viruses in comparison to titers achieved in animals inoculated with wild-type virus. Addition of the Δ30 mutation to the CME chimeric virus further attenuated the virus, such that rDEN2/4Δ30(CME) did not replicate in monkeys to a detectable level and did not induce a detectable immune response. This virus appeared over-attenuated, and if similar results were seen in humans, this virus would not be suitable for use as a vaccine. However, addition of the δ30 mutation to the ME chimeric virus did not further attenuate this chimeric virus and the resulting rDEN2/4Δ30(ME) virus appears satisfactorily attenuated and immunogenic for use as a vaccine.

TABLE 31

Chimerization between dengue virus types 2 and 4 results in recombinant viruses which are attenuated for rhesus monkeys.

| Group* | Virus | n | Mean no. days with viremia | Mean peak virus titer ($\log_{10}$pfu/ml) | Geometric mean neutralizing antibody titer (reciprocal) |
|---|---|---|---|---|---|
| 1 | rDEN2/4 (CME) | 6 | 1.2 | 0.9 | 50 |
| 2 | rDEN2/4Δ30 (CME) | 8 | 0 | <0.7 | <5 |
| 3 | rDEN2/4 (ME) | 4 | 1.0 | 0.8 | 76 |
| 4 | rDEN2/4Δ30 (ME) | 4 | 0.3 | 0.7 | 62 |
| 5 | DEN2 NGC | 6 | 5.5 | 2.1 | 312 |

*Rhesus monkeys were inoculated subcutaneously with 5.0 $\log_{10}$ PFU of virus. Serum samples were collected daily for 10 days. Serum for neutralization assay was collected on day 28, Serum samples obtained before virus inoculation had a neutralizing antibody titer of <5.

As described in the previous examples, SCID mice transplanted with the HuH-7 cells are a sensitive model for the evaluation of dengue virus attenuation. Each chimeric DEN2/4 virus was inoculated into groups of SCID-HuH-7 mice and levels of virus in the serum were determined (Table 32). Chimeric viruses replicated to levels between 20- and 150-fold lower than either of the parental viruses (rDEN4 and DEN2-NGC). CME chimeric viruses were slightly more attenuated than the comparable ME chimeric viruses, with the Δ30 mutation providing a 0.5 $\log_{10}$ reduction in replication. This level of attenuation exerted by the Δ30 mutation was similar to that observed previously for rDEN4Δ30.

TABLE 32

Chimerization between dengue virus types 2 and 4 results in recombinant viruses which are attenuated for HuH-7-SCID mice.

| Virus[a] | No. of mice | Mean peak virus titer ($\log_{10}$pfu/ml ± SE) | Statistical group[b] |
|---|---|---|---|
| rDEN4 | 32 | 6.3 ± 0.2 | A |
| DEN2-NGC | 9 | 6.1 ± 0.2 | A |
| rDEN2/4 (CME) | 7 | 4.4 ± 0.3 | B |
| rDEN2/4Δ30 (CME) | 7 | 3.9 ± 0.3 | B |
| rDEN2/4 (ME) | 6 | 4.8 ± 0.5 | B |
| rDEN2/4Δ30 (ME) | 9 | 4.3 ± 0.2 | B |

[a]Groups of HuH-7-SCDD mice were inoculated into the tumor with 4.0 $\log_{10}$ PFU of the indicated virus. Serum was collected on day 7 and virus titer was determined in Vero cells.
[b]Mean peak titers were assigned to statistical groups using the Tukey post-hoc test ($P < 0.05$). Groups with the same letter designation are not significantly different.

To evaluate the replication levels of each DEN2/4 chimeric virus in mosquitoes, two different genera of mosquitoes were experimentally infected. *Aedes aegypti* were infected by ingesting a virus-containing blood meal. By evaluating the presence of virus antigen in both the midgut and head tissue, infectivity could be determined for the local tissues (midgut), and the ability of virus to disseminate and replicate in tissues beyond the midgut barrier (head) could also be measured. The presence of virus in the head is limited by the ability of the ingested virus to replicate in the midgut and then disseminate to the salivary glands in the head, as well as the innate ability of the virus to replicate in the salivary glands. Intrathoracic inoculation of virus into *Toxorhynchites splendens* bypasses the mosquito midgut barrier. Parental viruses rDEN4 and DEN2-NGC readily infect *Ae. aegypti* and *T. splendens* (Table 33), with DEN2-NGC appearing to be much more infectious in *T. splendens*.

Each of the rDEN2/4 chimeric viruses was also tested in both mosquito types. In many cases it was not possible to inoculate Ae. aegypti with an undiluted virus stock of sufficient titer to achieve a detectable infection due to the very low infectivity of several of the viruses. Nevertheless, it is clear that the rDEN2/4 chimeric viruses are less infectious for the midgut and head. Parental viruses rDEN4 and DEN2-NGC, administered at a maximum dose of approximately 4.0 $\log_{10}$ PFU, were detectable in 74% and 94% of midgut preparations, and 32% and 71% of head preparations, respectively. Among the chimeric viruses, the highest level of infectivity, as observed for rDEN2/4Δ30(CME), resulted in only 26% infected midgut samples and 6% head samples. In the more permissive T. splendens, the rDEN2/4 chimeric viruses were generally less infectious than either parental virus, with CME chimeric viruses being less infectious than ME viruses. It has previously been reported for DEN4 that the Δ30 mutation does not have a discernable effect on virus infectivity in T. splendens similar to that observed here for the rDEN2/4 chimeric viruses (Troyer, J. M. et al. 2001 Am J Trop Med Hyg 65:414-419).

rDEN2/4Δ30(CME) viruses bearing Vero cell adaptation mutations were generated as follows. DNA fragments were excised from rDEN4 cDNA constructs encompassing single or double DEN4 Vero cell adaptation mutations and introduced into the cDNA clone of rDEN2/4Δ30(CME). The presence of the Vero cell adaptation mutation was confirmed by sequence analysis, and RNA transcripts derived from the mutant cDNA clones were transfected, terminally diluted, and propagated in C6/36 cells.

For evaluation of growth kinetics, Vero cells were infected with the indicated viruses at a multiplicity of infection (MOI) of 0.01. Confluent cell monolayers in duplicate 25-cm$^2$ tissue culture flasks were washed and overlaid with a 1 ml inoculum containing the indicated virus. After a two hour incubation at 37° C., cells were washed three times in MEM and 5 ml of MEM supplemented with 2% FBS was added. A 1 ml aliquot of tissue culture medium was removed, replaced with fresh medium, and designated the day 0 time-point. At the indicated time points post-infection, 1 ml samples of tissue culture medium were removed, clarified by centrifugation, and frozen at −80° C.

TABLE 33

Dengue 2/4 chimeric viruses are less infectious compared to either parental virus strain in mosquitoes

| Virus | Toxorhynchites splendens (intrathoracic inoculation) | | | Aedes aegypti (oral infection) | | | |
|---|---|---|---|---|---|---|---|
| | Dose[a] $\log_{10}$ pfu | No. tested | % infected[b] | Dose[c] $\log_{10}$ pfu | No. tested | % infected[d] Midgut | Head |
| rDEN4 | 3.3 | 6 | 83 | 3.8 | 38 | 74 | 32 |
| | 2.3 | 7 | 57 | 2.8 | 15 | 26 | 6 |
| | 1.3 | 6 | 0 | 1.8 | 20 | 10 | 5 |
| | | | MID$_{50}$ = 2.2 | | | MID$_{50}$ = 3.4 | MID$_{50}$ ≥ 4.1 |
| DEN2-NGC | 2.5 | 5 | 100 | 4.0 | 17 | 94 | 71 |
| | 1.2 | 15 | 93 | 3.0 | 25 | 36 | 16 |
| | 0.2 | 4 | 75 | 2.0 | 30 | 0 | 0 |
| | 0.02 | 8 | 38 | | | | |
| | | | MID$_{50}$ = 0.5 | | | MID$_{50}$ = 3.2 | MID$_{50}$ = 3.6 |
| rDEN2/4 (CME) | 3.9 | 9 | 11 | 4.4 | 11 | 9 | 0 |
| | 2.9 | 5 | 0 | 3.4 | 10 | 0 | 0 |
| | | | MID$_{50}$ ≥ 4.3 | | | MID$_{50}$ ≥ 4.9 | Nc[e] |
| rDEN2/4Δ30 (CME) | 3.5 | 6 | 17 | 4.0 | 15 | 26 | 6 |
| | 2.5 | 6 | 17 | 3.0 | 10 | 0 | 0 |
| | | | MID$_{50}$ ≥ 3.9 | | | MID$_{50}$ ≥ 4.3 | MID$_{50}$ ≥ 4.5 |
| rDEN2/4 (ME) | 3.4 | 6 | 100 | 3.9 | 23 | 4 | 0 |
| | 2.4 | 5 | 20 | | | | |
| | 1.4 | 5 | 0 | | | | Nc |
| | | | MID$_{50}$ = 2.8 | | | MID$_{50}$ ≥ 4.4 | |
| rDEN2/4Δ30 (ME) | 2.6 | 11 | 9 | 3.1 | 30 | 0 | 0 |
| | | | MID$_{50}$ ≥ 3.0 | | | nc | Nc |

[a]Amount of virus present in 0.22 μl inoculum.
[b]Percentage of mosquitoes with IFA detectable antigen in head tissue prepared 14 days after inoculation.
[c]Virus titer ingested, assuming a 2 μl bloodmeal.
[d]Percentage of mosquitoes with IFA detectable antigen in midgut or head tissue prepared 21 days after oral infection. When virus infection was detected, but did not exceed a frequency of 50% at the highest dose of virus ingested, the MID$_{50}$ was estimated by assuming that a 10-fold more concentrated virus dose would infect 100% of the mosquitoes.
[e]nc = not calculated, since virus antigen was not detected.

Chimerization of the DEN2 structural genes with rDEN4Δ30 virus resulted in a virus, rDEN2/4Δ30(CME), that had decreased replication in Vero cells compared to either parent virus. To evaluate Vero cell adaptation mutations (Blaney, J. E. et al. 2002 Virology 300:125-139) as a means of increasing the virus yield of a DEN vaccine candidate in Vero cells, selected mutations were introduced into this chimeric virus. Accordingly, rDEN2/4Δ30(CME) viruses bearing adaptation mutations were recovered, terminally diluted, and propagated in C6/36 cells to determine if the virus yield in Vero cells could be increased.

The level of virus replication was assayed by plaque titration in C6/36 cells and visualized by immunoperoxidase staining. The limit of detection was <0.7 $\log_{10}$ PFU/ml.

Figure 10:
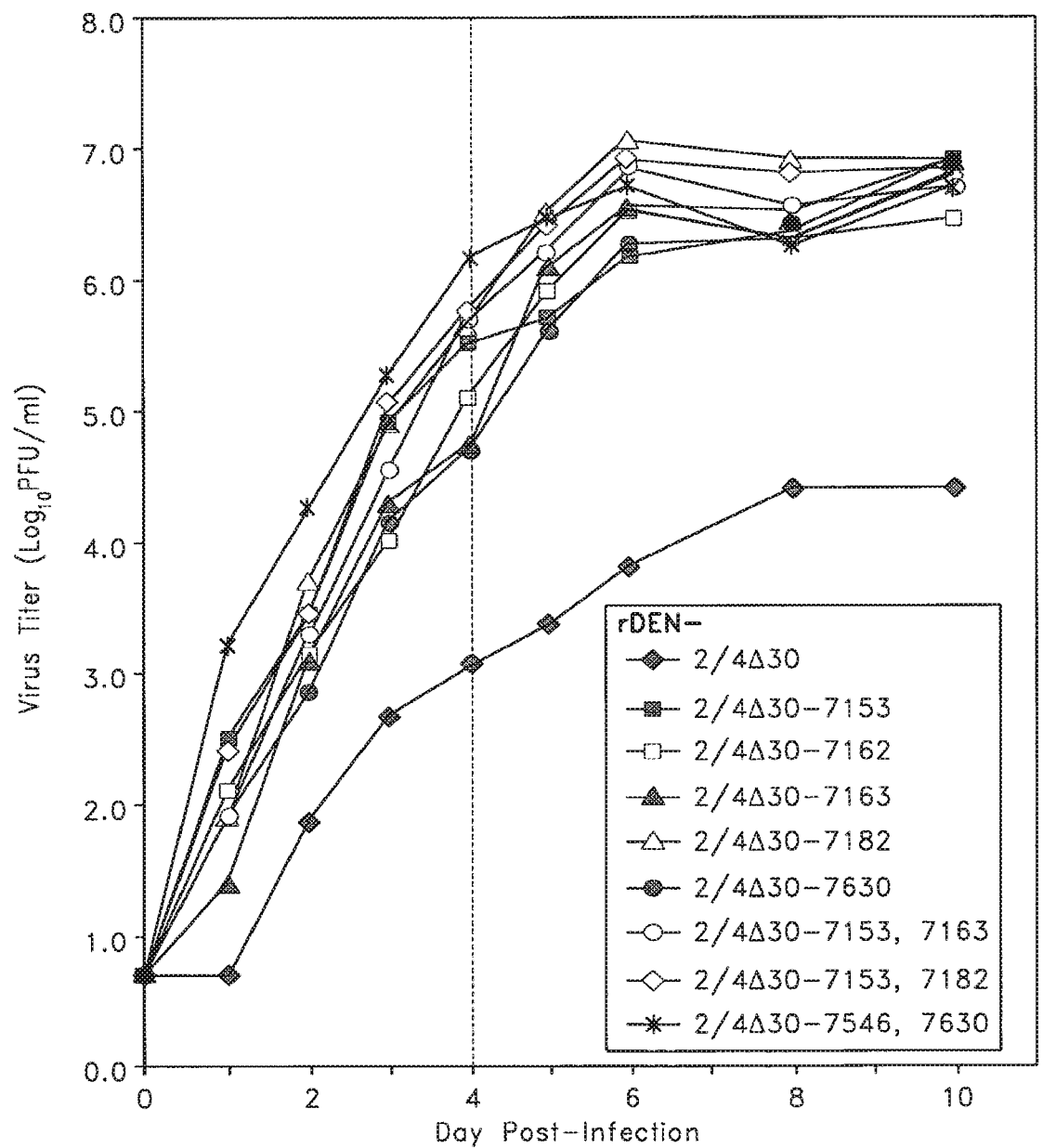
FIG. 10. Growth kinetics in Vero cells of chimeric rDEN2/4Δ30 viruses encoding single or combined Vero cell adaptation mutations. Vero cells were infected with the indicated viruses at an MOI of 0.01. At the indicated time points post-infection, 1 ml samples of tissue culture medium were removed, clarified by centrifugation, and frozen at −80° C. The level of virus replication was assayed by plaque titration in C6/36 cells. Lower limit of detection was 0.7 $\log_{10}$ PFU/ml. Replication levels on day 4 post-infection are indicated by the dashed line.

The growth properties of rDEN2/4Δ30(CME) viruses bearing single Vero cell adaptation mutations at NS4B-7153, -7162, -7163, -7182, NS5-7630 or three combinations of mutations were compared in Vero cells with rDEN2/4Δ30 (CME) virus (FIG. 10). Without an introduced Vero cell adaptation mutation, rDEN2/4Δ30(CME) virus yield peaked at 4.4 $\log_{10}$ PFU/ml. Each individual adaptation mutation and the combined mutations conferred a substantial increase in replication. Specifically, rDEN2/4Δ30(CME)-7182 grew to the highest titer of 7.1 $\log_{10}$ PFU/ml, which was a 500-fold increase in yield. rDEN2/4Δ30(CME)-7162 had the lowest yield but still was increased 125-fold over the level of replication by rDEN2/4Δ30(CME) virus. Introduction of two adaptation mutations into rDEN2/4Δ30(CME) virus did not significantly increase virus yield over that of viruses bearing single Vero cell adaptation mutations. The observed increase of up to 500-fold in virus yield by the introduction of a Vero cell adaptation mutation into this chimeric vaccine candidate demonstrates the value of identifying and characterizing specific replication-promoting sequences in DEN viruses.

These results have particular significance for the development of a live attenuated dengue virus vaccine. First, it is clear that chimerization leads to attenuation of the resulting virus, as indicated by studies in rhesus monkeys, HuH7-SCID mice and mosquitoes. Although this conclusion was not made in the previous study with DEN2/DEN4 or DEN1/DEN4 chimeric viruses (Bray, M. et al. 1996 *J Virol* 70:4162-6), careful examination of the data would suggest that the chimeric viruses are more attenuated in monkeys compared to the wild-type parent viruses. Second, the Δ30 mutation can further augment this attenuation in a chimeric-dependent manner. Specifically, in this example, chimeric viruses bearing the CME region of DEN2 were over-attenuated by the addition of Δ30, whereas the attenuation phenotype of chimeric viruses bearing just the ME region of DEN2 was unaltered by the addition of the Δ30 mutation. This unexpected finding indicates that in a tetravalent vaccine comprised of individual component viruses bearing a shared attenuating mutation, such as the Δ30 mutation, only ME chimeric viruses can be utilized since CME chimeric viruses bearing the Δ30 mutation can be over-attenuated in rhesus monkeys and might provide only limited immunogenicity in humans.

Example 6

Generation and Characterization of Intertypic Chimeric DEN3 Viruses Containing the Δ30 Mutation Chimeric viruses based on the DEN4 cDNA have been generated in which the CME or ME genes have been replaced with the corresponding genes derived from DEN3 (Sleman/78), a virus isolate from the 1978 dengue outbreak in the Sleman region of Indonesia (Gubler, D. J. et al. 1981 *Am J Trop Med Hyg* 30:1094-1099) (Appendix 2). As described in Example 5 for the DEN2 chimeric viruses, CME chimeric viruses for DEN3 were generated by replacing the BglII/XhoI region of the cDNA for either rDEN4 or rDEN4Δ30 with a similar region derived from DEN3 (Sleman/78) (FIG. 11A). Likewise, to create the ME chimeric viruses, the PstI/XhoI region of the cDNA for either rDEN4 or rDEN4Δ30 was replaced with a similar region derived from DEN3 (Sleman/78). The nucleotide and amino acid sequences of the resulting junctions are shown in FIG. 11B. The genomes of the resulting viruses were confirmed by sequence analysis of viral RNA isolated from recovered virus as previously described (Durbin, A. P et al. 2001 *Am J Trop Med Hyg* 65:405-13). Incidental mutations arising from virus passage in tissue culture were identified in all viruses and are listed in Table 34. Notably, each virus contained a missense mutation in NS4B corresponding to a previously identified mutation from rDEN4 and associated with adaptation to growth in Vero cells (See Table 30 for correlation of nucleotide positions between rDEN4 and chimeric viruses). All viruses replicated in Vero cells to titers in excess of 5.7 $\log_{10}$ PFU/ml, indicating that the chimeric viruses, even those containing the Δ30 mutation, replicate efficiently in cell culture, a property essential for manufacture of the vaccine.

TABLE 34

Missense mutations observed among Vero cell-grown chimeric DEN3/4 viruses

| Virus | Gene | Nucleotide position | Nucleotide change | Amino acid position | Amino acid change |
|---|---|---|---|---|---|
| rDEN3/4Δ30(CME) | M | 825 | T > C | 242 | Phe > Leu |
|  | E | 1641 | C > T | 514 | Leu > Phe |
|  | E | 2113 | A > G | 671 | Lys > Arg |
|  | NS4B | 7159[a] | T > C | 2353 | Leu > Ser |
| rDEN3/4(ME) | M | 460 | A > G | 120 | Asp > Gly |
|  | NS4B | 7177[b] | G > U | 2359 | Gly > Val |
|  | NS5 | 7702 | C > U | 2534 | Ser > Phe |
| rDEN3/4Δ30(ME) | E | 1432 | A > U | 444 | Gln > Leu |
|  | NS4B | 7156[a] | U > C | 2352 | Leu > Ser |
|  | NS5 | 8692 | A > C | 2864 | Asn > His |

[a]Same nucleotide position as 7162 in rDEN4.
[b]Same nucleotide position as 7183 in rDEN4.

As described in the previous examples, SCID mice transplanted with HuH-7 cells are a sensitive model for the evaluation of dengue virus attenuation. Each chimeric DEN3/4 virus was inoculated into groups of SCID-HuH-7 mice and levels of virus in the serum were determined (Table 35). While chimeric virus rDEN3/4 (CME) was not attenuated, the remaining chimeric viruses replicated to levels between 40- and 400-fold lower than either of the parental viruses (rDEN4 and DEN3-Sleman/78). In the CME chimeric virus, the Δ30 mutation providing a remarkable 2.7 $\log_{10}$ reduction in replication. This level of attenuation conferred by the Δ30 mutation in the CME chimeric virus was much greater than that observed previously for rDEN4Δ30. The rDEN3/4 (ME) virus was 100-fold reduced in replication compared to either parent virus indicating that the ME chimerization was attenuating per se. Addition of the Δ30 mutation to rDEN3/4 (ME) did not result in additional attenuation.

TABLE 35

Chimerization between dengue virus types 3 and 4 results in recombinant viruses which are attenuated for HuH-7-SCID mice.

| Virus[a] | No. of mice | Mean peak virus titer ($\log_{10}$pfu/ml ± SE) | Statistical group[b] |
|---|---|---|---|
| rDEN4 | 32 | 6.3 ± 0.2 | A |
| DEN3-Sleman/78 | 23 | 6.4 ± 0.2 | A |
| rDEN3/4 (CME) | 7 | 6.4 ± 0.6 | A |
| rDEN3/4Δ30 (CME) | 5 | 3.7 ± 0.4 | B |
| rDEN3/4 (ME) | 6 | 4.2 ± 0.7 | B |
| rDEN3/4Δ30 (ME) | 7 | 4.7 ± 0.4 | A, B |

[a]Groups of HuH-7-SCID mice were inoculated into the tumor with 4.0 $\log_{10}$ PFU of the indicated virus. Serum was collected on day 7 and virus titer was determined in Vero cells.
[b]Mean peak titers were assigned to statistical groups using the Tukey post-hoc test (P < 0.05). Groups with the same letter designation are not significantly different.

Evaluation of the replication and immunogenicity of the DEN3 chimeric recombinant viruses and wild-type DEN3 virus in monkeys was performed as described in Example 5. Results of this safety and immunogenicity study in monkeys are presented in Table 36. Monkeys inoculated with rDEN3/4(CME) and wild-type DEN (Sleman/78) were viremic for approximately 2 days with a mean peak titer of between 1.6 and 1.8 $\log_{10}$ PFU/ml, respectively, indicating that chimerization of the CME structural genes of DEN3 did not lead to attenuation of virus replication, a different pattern than that observed for DEN2 chimerization (Table 31). However, chimerization of the ME structural genes resulted in attenuated viruses with undetectable viremia in monkeys, although all monkeys seroconverted with a greater than 10-fold increase in serum antibody levels. As expected for an attenuated virus, the immune response, as measured by neutralizing antibody titer, was lower following inoculation with any of the chimeric viruses compared to inoculation with wt DEN3 (Sleman/78), yet sufficiently high to protect the animals against wt DEN3 virus challenge (Table 37). It is clear that addition of the 630 mutation to rDEN3/4(CME) was capable of further attenuating the resulting virus rDEN3/4Δ30(CME).

TABLE 36

The Δ30 mutation further attenuates rDEN3/4(CME) for rhesus monkeys

| Virus[a] | No. of monkeys | Mean no. of viremic days per monkey[b] | Mean peak virus titer ($\log_{10}$PFU/ml ± SE) | Geometric mean serum neutralizing antibody titer (reciprocal dilution) | |
|---|---|---|---|---|---|
| | | | | Day 0 | Day 28 |
| DEN3 (Sleman/78) | 4 | 2.3 | 1.8 | <5 | 707 |
| rDEN3/4 (CME) | 4 | 2.0 | 1.6 | <5 | 211 |
| rDEN3/4Δ30 (CME) | 4 | 0 | <1.0 | <5 | 53 |
| rDEN3/4 (ME) | 4 | 0 | <1.0 | <5 | 70 |
| rDEN3/4Δ30 (ME) | 4 | 0 | <1.0 | <5 | 58 |

[a]Groups of rhesus monkeys were inoculated subcutaneously with $10^5$ PFU of the indicated virus in a 1 ml dose. Serum was collected on days 0 to 6, 8, 10, 12, and 28. Virus titer was determined by plaque assay in Vero cells.
[b]Viremia was not detected in any monkey after day 4.

TABLE 37 rDEN3/4 chimeric viruses protect rhesus monkeys from wt DEN3 virus challenge

| Virus[a] | No. of monkeys | Mean no. of viremic days per monkey after rDEN3 challenge | Mean peak virus titer ($\log_{10}$PFU/ml ± SE) | Geometric mean serum neutralizing antibody titer (reciprocal dilution) | |
|---|---|---|---|---|---|
| | | | | Day 28 | Day 56 |
| Mock | 2 | 5.0 | 2.5 ± 0.4 | <5 | 372 |
| DEN3 (Sleman/78) | 4 | 0 | <1.0 | 707 | 779 |
| rDEN3/4 (CME) | 4 | 0 | <1.0 | 211 | 695 |
| rDEN3/4Δ30 (CME) | 4 | 0.8 | 1.1 ± 0.2 | 53 | 364 |
| rDEN3/4 (ME) | 4 | 0 | <1.0 | 70 | 678 |
| rDEN3/4Δ30 (ME) | 4 | 0 | <1.0 | 58 | 694 |

[a]28 days after primary inoculation with the indicated viruses, rhesus monkeys were challenged subcutaneously with $10^5$ PFU DEN3 (Sleman/78) virus in a 1 ml dose. Serum was collected on days 28 to 34, 36, 38, and 56. Virus titer was determined by plaque assay in Vero cells.

To evaluate the replication levels of each DEN3/4 chimeric virus in mosquitoes, *Aedes aegypti* were infected by ingesting a virus-containing blood meal (Table 38). Parental viruses rDEN4 and DEN3 (Sleman/78) readily infect *Ae. aegypti*. Each of the rDEN3/4 chimeric viruses was also tested. In many cases it was not possible to infect *Ae. aegypti* with an undiluted virus stock of sufficient titer to achieve a detectable infection due to the very low infectivity of several of the viruses. At a dose of approximately 2.8-2.9 $\log_{10}$ PFU, rDEN4, DEN3 (Sleman/78), and rDEN3/4(CME) were equally infectious and disseminated to the head with equal efficiency. For the remaining chimeric viruses, infection was not detectable even at a dose of 3.4 $\log_{10}$ PFU, indicating that replication of rDEN3/4(ME) and rDEN3/4Δ30(CME) is restricted in *Ae. aegypti*. By comparing infectivity of rDEN3/4(CME) and rDEN3/4Δ30(CME), it is clear that the Δ30 mutation is capable of further attenuating the chimeric virus for mosquitoes.

TABLE 38

Ability of DEN3/4 chimeric viruses to infect *Aedes aegypti* fed an infectious bloodmeal.

| Virus Tested | Dose Ingested ($\log_{10}$pfu)[a] | No. Mosquitoes Tested | No. (%) Midgut Infections[b, c, d] | No. (%) Disseminated Infections[e] |
|---|---|---|---|---|
| rDEN4 | 3.8 | 18 | 14 (77%) | 2 (14%) |
| | 2.8 | 20 | 7 (34%) | 2 (10%) |
| | 1.8 | 18 | 0 | 0 |
| | | | $MID_{50}$ = 3.4 | $MID_{50}$ ≥ 4.4 |
| DEN3 (Sleman) | 2.9 | 16 | 3 (18%) | 2 (12%) |
| | 1.9 | 10 | 1 (10%) | 0 |
| | | | $MID_{50}$ ≥ 3.5 | $MID_{50}$ ≥ 3.5 |
| rDEN3/4 (CME) | 3.9 | 20 | 6 (30%) | 2 (10%) |
| | 2.9 | 18 | 4 (22%) | 0 |
| | 1.9 | 13 | 1 (7%) | 0 |
| | | | $MID_{50}$ ≥ 4.2 | $MID_{50}$ ≥ 4.5 |
| DEN3/4Δ30 (CME) | 3.3 | 20 | 0 | 0 |
| | | | $MID_{50}$ ≥ 4.3 | $MID_{50}$ ≥ 4.3 |
| DEN3/4 (ME) | 3.4 | 15 | 0 | 0 |
| | | | $MID_{50}$ ≥ 4.4 | $MID_{50}$ ≥ 4.4 |

[a]Amount of virus ingested, assuming a 2μ bloodmeal.
[b]Number (percentage) of mosquitoes with detectable dengue virus in midgut tissue; mosquitoes were assayed 21 days post feed, and dengue virus antigen was identified by IFA.
[c]When infection was detected, but did not exceed a frequency of 50% at the highest dose of virus ingested, the $MID_{50}$ was estimated by assuming that a 10-fold more concentrated virus dose would infect 100% of the mosquitoes.
[d]When no infection was detected, the $MID_{50}$ was assumed to be greater than a 10-fold higher dose of virus than the one used.
[e]Number (percentage) of mosquitoes with detectable dengue virus antigen in both midgut and head tissue.

Example 7

Generation and Characterization of Intertypic Chimeric DEN1 Viruses Containing the Δ30 Mutation Chimeric viruses based on the DEN4 cDNA have been generated in which the CME or ME genes have been replaced with the corresponding genes derived from DEN1 (Puerto Rico/94), a virus isolate from a 1994 dengue outbreak in Puerto Rico (Appendices 3 and 4). As described in Example 4 for the DEN2 chimeric viruses, CME chimeric viruses for DEN1 were generated by replacing the BglII/XhoI region of the cDNA for either rDEN4 or rDEN4Δ30 with a similar region derived from DEN1 (Puerto Rico/94) (FIG. 12A). Likewise, to create the ME chimeric viruses, the PstI/XhoI region of the cDNA for either rDEN4 or rDEN4Δ30 was replaced with a similar region derived from DEN1 (Puerto Rico/94). The nucleotide and amino acid sequences of the resulting junctions are shown in FIG. 12B.

For transcription and generation of virus, chimeric cDNA clones were linearized and used as template in a transcription reaction using SP6 RNA polymerase as described. Transcripts were introduced into C6/36 mosquito cells using liposome-mediated transfection and recombinant dengue virus was harvested between day 7 and 14. Viruses were subsequently grown in Vero cells and biologically cloned by terminal dilution in Vero cells. All viruses replicated in Vero cells to titers in excess of 6.0 $\log_{10}$ PFU/ml, indicating that the chimeric viruses, even those containing the Δ30 mutation, replicate efficiently in cell culture. Genomic sequence analysis is currently underway to identify incidental mutations arising from virus passage in tissue culture.

To evaluate the replication levels of DEN1/4(CME) and rDEN1/4Δ30(CME) chimeric virus in mosquitoes, *Aedes aegypti* were infected by ingesting a virus-containing blood meal (Table 39). Parental virus rDEN4 infects *Ae. aegypti* with an MID50 of 4.0 $log_{10}$ PFU. However, parental virus DEN1 (Puerto Rico/94), is unable to infect *Ae. aegypti* at a dose of up to 3.4 $log_{10}$ PFU. Thus CME chimeric viruses DEN1/4 and rDEN1/4Δ30 share this inability to infect *Ae. aegypti*. Therefore, it is unnecessary in *Ae. aegypti* to evaluate the effect of the Δ30 mutation on the infectivity of the DEN1/4 chimeric viruses, in a manner similar to that used for the DEN2/4 and DEN3/4 chimeric viruses.

TABLE 39

Inability of DEN1/4 chimeric viruses to infect *Aedes aegypti* fed an infectious bloodmeal.

| Virus tested | Dose ingested ($log_{10}$pfu)[a] | No. Mosquitoes Tested | No. (%) Midgut Infections[b,c,d] | No. (%) Disseminated Infections[e] |
|---|---|---|---|---|
| rDEN4 | 4.3 | 21 | 18 (85%) | 8 (44%) |
| | 3.3 | 15 | 3 (20%) | 0 |
| | 2.3 | 20 | 0 | 0 |
| | | | $MID_{50}$ = 4.0 | $MID_{50}$ ≥ 4.3 |
| DEN1 (Puerto Rico/94) | 3.4 | 21 | 0 | 0 |
| | | | $MID_{50}$ ≥ 4.4 | $MID_{50}$ ≥ 4.4 |
| rDEN 1/4 (CME) | 3.8 | 20 | 0 | 0 |
| | | | $MID_{50}$ ≥ 4.8 | $MID_{50}$ ≥ 4.8 |
| rDEN1/4Δ30 (CME) | 2.8 | 20 | 0 | 0 |
| | | | $MID_{50}$ ≥ 3.8 | $MID_{50}$ ≥ 3.8 |

[a]Amount of virus ingested, assuming a 2μ bloodmeal.
[b]Number (percentage) of mosquitoes with detectable dengue virus in midgut tissue; mosquitoes were assayed 21 days post feed, and dengue virus antigen was identified by IFA.
[c]When infection was detected, but did not exceed a frequency of 50% at the highest dose of virus ingested, the $MID_{50}$ was estimated by assuming that a 10-fold more concentrated virus dose would infect 100% of the mosquitoes.
[d]When no infection was detected, the $MID_{50}$ was assumed to be greater than a 10-fold higher dose of virus than the one used.
[e]Number (percentage) of mosquitoes with detectable dengue virus antigen in both midgut and head tissue.

As described in the previous examples, SCID mice transplanted with the HuH-7 cells are a sensitive model for the evaluation of dengue virus attenuation. Each chimeric DEN1/4 virus was inoculated into groups of SCID-HuH-7 mice and levels of virus in the serum were determined (Table 40). Chimeric viruses replicated to levels between 15- and 250-fold lower than either of the parental viruses, rDEN4 and DEN1 (Puerto Rico/94). CME chimeric viruses were more attenuated than the comparable ME chimeric viruses, with the Δ30 Mutation providing a 0.8 $log_{10}$ reduction in replication. This level of attenuation exerted by the Δ30 mutation in the CME chimeric viruses was similar to that observed previously for rDEN4Δ30. However, the attenuating effect of the Δ30 mutation in the ME chimeric viruses is indiscernible.

TABLE 40

Chimerization between dengue virus types 1 and 4 results in recombinant viruses which are attenuated for HuH-7-SCDD mice.

| Virus[a] | No. of mice | Mean peak virus titer ($log_{10}$pfu/ml ± SE) | Statistical group[b] |
|---|---|---|---|
| rDEN4 | 32 | 6.3 ± 0.2 | A |
| DEN1 (Puerto Rico/94) | 4 | 6.4 ± 0.2 | A |
| rDEN1/4 (CME) | 8 | 4.7 ± 0.2 | B, C |
| rDEN1/4Δ30 (CME) | 6 | 3.9 ± 0.4 | C |
| rDEN1/4 (ME) | 6 | 5.0 ± 0.2 | B |
| rDEN1/4Δ30 (ME) | 6 | 5.1 ± 0.3 | B |

[a]Groups of HuH-7-SCID mice were inoculated into the tumor with 4.0 $log_{10}$ PFU of the indicated virus. Serum was collected on day 7 and virus titer was determined in Vero cells.
[b]Mean peak titers were assigned to statistical groups using the Tukey post-hoc test ($P < 0.05$). Groups with the same letter designation are not significantly different.

SEQUENCE LISTING

The Sequence Listing is submitted as an ASCII text file in the form of the file named "Sequence.txt" (~136 kb), which was created on Sep. 20, 2017, which is incorporated by reference herein.

APPENDIX 1

```
Nucleotide and amino acid sequence of DEN2 (Tonga/74) cDNA plasmid p2
(DNA: SEQ ID NO: 46; Protein: SEQ ID NO: 47)
Bases 1 to 10713: DEN2 virus genome cDNA
Bases 97 to 10269: DEN2 polyprotein ORF
Bases 97 to 438: C protein ORF
Bases 439 to 936: prM protein ORF
Bases 937 to 2421: E protein ORF
Bases 2422 to 3477: NS1 protein ORF
Bases 3478 to 4131: NS2A protein ORF
```

APPENDIX 1-continued Bases 4132 to 4521: NS2B protein ORF
Bases 4522 to 6375: NS3 protein ORF
Bases 6376 to 6756: NS4A protein ORF
Bases 6757 to 6825: 2K protein ORF
Bases 6826 to 7569: NS4B protein ORF
Bases 7570 to 10269: NS5 protein ORF

```
         10        20        30        40        50        60        70        80        90       100
AGTTGTTAGTCTACGTGGACCGACAAAGACAGATTCTTTGAGGGAGCTAAGCTCAACGTAGTTCTAACTGTTTTTTGATTAGAGAGCAGATCTCTGATGA
                                                                                                 Met>

110       120       130       140       150       160       170       180       190       200
ATAACCAACGGAAAAAGGCGAGAAACACGCCTTTCAATATGCTGAAACGCGAGAGAAACCGCGTGTCAACTGTACAACAGTTGACAAAGAGATTCTCACT
AsnAsnGlnArgLysLysAlaArgAsnThrProPheAsnMetLeuLysArgGluArgAsnArgValSerThrValGlnGlnLeuThrLysArgPheSerLeu>

210       220       230       240       250       260       270       280       290       300
TGGAATGCTGCAGGGACGAGGACCACTAAAATTGTTCATGGCCCTGGTGGCATTCCTTCGTTTCCTAACAATCCCACCAACAGCAGGGATATTAAAAAGA
GlyMetLeuGlnGlyArgGlyProLeuLysLeuPheMetAlaLeuValAlaPheLeuArgPheLeuThrIleProProThrAlaGlyIleLeuLysArg>

310       320       330       340       350       360       370       380       390       400
TGGGGAACAATTAAAAAATCAAAGGCTATTAATGTTCTGAGAGGCTTCAGGAAAGAGATTGGAAGGATGCTGAATATCTTAAACAGGAGACGTAGAACTG
TrpGlyThrIleLysLysSerLysAlaIleAsnValLeuArgGlyPheArgLysGluIleGlyArgMetLeuAsnIleLeuAsnArgArgArgArgThr>

410       420       430       440       450       460       470       480       490       500
TAGGCATGATCATCATGCTGACTCCAACAGTGATGGCGTTTCATCTGACCACACGCAACGGAGAACCACACATGATTGTCAGTAGACAAGAAAAAGGGAA
ValGlyMetIleIleMetLeuThrProThrValMetAlaIleHisLeuThrThrArgAsnGlyGluProHisMetIleValSerArgGlnGluLysGlyLys>

510       520       530       540       550       560       570       580       590       600
AAGCCTTCTGTTCAAGACAAAGGATGGCACGAACATGTGTACCCTCATGGCCATGGACCTTGGTGAGTTGTGTGAAGACACAATCACGTATAAATGTCCT
SerLeuLeuPheLysThrLysAspGlyThrAsnMetCysThrLeuMetAlaMetAspLeuGlyGluLeuCysGluAspThrIleThrTyrLysCysPro>

610       620       630       640       650       660       670       680       690       700
TTTCTCAAGCAGAACGAACCAGAAGACATAGATTGTTGGTGCAACTCCACGTCCACATGGGTAACTTATGGGACATGTACCACCACAGGAGAGCACAGAA
PheLeuLysGlnAsnGluProGluAspIleAspCysTrpCysAsnSerThrSerThrTrpValThrTyrGlyThrCysThrThrThrGlyGluHisArg>

710       720       730       740       750       760       770       780       790       800
GAGAAAAAAGATCAGTGGCGCTTGTTCCACACGTGGGAATGGGATTGGAGACACGAACTGAAACATGGATGTCATCAGAAGGGGCCTGGAAACATGCCCA
ArgGluLysArgSerValAlaLeuValProHisValGlyMetGlyLeuGluThrArgThrGluThrTrpMetSerSerGluGlyAlaTrpLysHisAlaGln>

810       820       830       840       850       860       870       880       890       900
GAGAATTGAAACTTGGATTCTGAGACATCCAGGCTTTACCATAATGGCCGCAATCCTGGCATACACCATAGGGACGACGCATTTCCAAAGAGTCCTGATA
ArgIleGluThrTrpIleLeuArgHisProGlyPheThrIleMetAlaAlaIleLeuAlaTyrThrIleGlyThrThrHisPheGlnArgValLeuIle>

910       920       930       940       950       960       970       980       990      1000
TTCATCCTACTGACAGCCATCGCTCCTTCAATGACAATGCGCTGCATAGGAATATCAAATAGGGACTTTGTGGAAGGAGTGTCAGGAGGGAGTTGGGTTG
PheIleLeuLeuThrAlaIleAlaProSerMetThrMetArgCysIleGlyIleSerAsnArgAspPheValGluGlyValSerGlyGlySerTrpVal>

1010      1020      1030      1040      1050      1060      1070      1080      1090      1100
ACATAGTTTTAGAACATGGAAGTTGTGTGACGACGATGGCAAAAAACAAACCAACACTGGACTTTGAACTGATAAAAACAGAAGCCAAACAACCTGCCAC
AspIleValLeuGluHisGlySerCysValThrThrMetAlaLysAsnLysProThrLeuAspPheGluLeuIleLysThrGluAlaLysGlnProAlaThr>

1110      1120      1130      1140      1150      1160      1170      1180      1190      1200
CTTAAGGAAGTACTGTATAGAGGCCAAACTGACCAACACGACAACAGACTCGCGCTGCCCAACACAAGGGGAACCCACCCTGAATGAAGAGCAGGACAAA
LeuArgLysTyrCysIleGluAlaLysLeuThrAsnThrThrThrAspSerArgCysProThrGlnGlyGluProThrLeuAsnGluGluGlnAspLys>

1210      1220      1230      1240      1250      1260      1270      1280      1290      1300
AGGTTTGTCTGCAAACATTCCATGGTAGACAGAGGATGGGGAAATGGATGTGGATTGTTTGGAAAAGGAGGCATCGTGACCTGTGCTATGTTCACATGCA
ArgPheValCysLysHisSerMetValAspArgGlyTrpGlyAsnGlyCysGlyLeuPheGlyLysGlyGlyIleValThrCysAlaMetPheThrCys>

1310      1320      1330      1340      1350      1360      1370      1380      1390      1400
AAAAGAACATGGAAGGAAAAATTGTGCAGCCAGAAAACCTGGAATACACTGTCGTGATAACACCTCATTCAGGGGAAGAACATGCAGTGGGAAATGACAC
LysLysAsnMetGluGlyLysIleValGlnProGluAsnLeuGluTyrThrValValIleThrProHisSerGlyGluGluHisAlaValGlyAsnAspThr>

1410      1420      1430      1440      1450      1460      1470      1480      1490      1500
AGGAAAACATGGTAAAGAAGTCAAGATAACACCACAGAGCTCCATCACAGAGGCGGAACTGACAGGCTATGGCACTGTTACGATGGAGTGCTCTCCAAGA
GlyLysHisGlyLysGluValLysIleThrProGlnSerSerIleThrGluAlaGluLeuThrGlyTyrGlyThrValThrMetGluCysSerProArg>

1510      1520      1530      1540      1550      1560      1570      1580      1590      1600
ACGGGCCTCGACTTCAATGAGATGGTGTTGCTGCAAATGGAAGACAAAGCCTGGCTGGTGCACAGACAATGGTTCCTAGACCTACCGTTGCCATGGCTGC
ThrGlyLeuAspPheAsnGluMetValLeuLeuGlnMetGluAspLysAlaTrpLeuValHisArgGlnTrpPheLeuAspLeuProLeuProTrpLeu>

1610      1620      1630      1640      1650      1660      1670      1680      1690      1700
CCGGAGCAGACACACAAGGATCAAATTGGATACAGAAAGAAACACTGGTCACCTTCAAAAATCCCCATGCGAAAAAACAGGATGTTGTTGTCTTAGGATC
ProGlyAlaAspThrGlnGlySerAsnTrpIleGlnLysGluThrLeuValThrPheLysAsnProHisAlaLysLysGlnAspValValValLeuGluSer>

1710      1720      1730      1740      1750      1760      1770      1780      1790      1800
CCAAGAGGGGGCCATGCATACAGCACTCACAGGGGCTACGGAAATCCAGATGTCATCAGGAAACCTGCTGTTCACAGGACATCTCAAGTGCAGGCTGAGA
GlnGluGlyAlaMetHisThrAlaLeuThrGlyAlaThrGluIleGlnMetSerSerGlyAsnLeuLeuPheThrGlyHisLeuLysCysArgLeuArg>

1810      1820      1830      1840      1850      1860      1870      1880      1890      1900
ATGGACAAATTACAACTTAAAGGGATGTCATACTCCATGTGCACAGGAAAGTTTAAAATTGTGAAGGAAATAGCAGAAACACAACATGGAACAATAGTCA
```

APPENDIX 1-continued

```
                                    MetAspLysLeuGlnLeuLysGlyMetSerTyrSerMetCysThrGlyLysPheLysIleValLysGluIleAlaGluThrGlnHisGlyThrIleVal>
     1910      1920      1930      1940      1950      1960      1970      1980      1990      2000
TTAGAGTACAATATGAAGGAGACGGCTCTCCATGCAAGATCCCCTTTGAGATAATGGATCTGGAAAAAAGACATGTTTTGGGCCGCCTGATCACAGTCAA
IleArgValGlnTyrGluGlyAspGlySerProCysLysIleProPheGluIleMetAspLeuGluLysArgHisValLeuGlyArgLeuIleThrValAsn>
     2010      2020      2030      2040      2050      2060      2070      2080      2090      2100
CCCAATTGTAACAGAAAAGGACAGTCCAGTCAACATAGAAGCAGAACCTCCATTCGGAGACAGCTACATCATCATAGGAGTGGAACCAGGACAATTGAAG
ProIleValThrGluLysAspSerProValAsnIleGluAlaGluProProPheGlyAspSerTyrIleIleIleGlyValGluProGlyGlnLeuLys>
     2110      2120      2130      2140      2150      2160      2170      2180      2190      2200
CTGGACTGGTTCAAGAAAGGAAGTTCCATCGGCCAAATGTTTGAGACAACAATGAGGGGAGCGAAAAGAATGGCCATTTTGGGTGACACAGCCTGGGATT
LeuAspTrpPheLysLysGlySerSerIleGlyGlnMetPheGluThrThrMetArgGlyAlaLysArgMetAlaIleLeuGlyAspThrAlaTrpAsp>
     2210      2220      2230      2240      2250      2260      2270      2280      2290      2300
TTGGATCTCTGGGAGGAGTGTTCACATCAATAGGAAAGGCTCTCCACCAGGTTTTTGGAGCAATCTACGGGGCTGCTTTCAGTGGGGTCTCATGGACTAT
PheGlySerLeuGlyGlyValPheThrSerIleGlyLysAlaLeuHisGlnValPheGlyAlaIleTyrGlyAlaAlaPheSerGlyValSerTrpThrMet>
     2310      2320      2330      2340      2350      2360      2370      2380      2390      2400
GAAGATCCTCATAGGAGTTATCATCACATGGATAGGAATGAACTCACGTAGCACTAGTCTGAGCGTGTCACTGGTGTTAGTGGGAATCGTGACACTTTAC
LysIleLeuIleGlyValIleIleThrTrpIleGlyMetAsnSerArgSerThrSerLeuSerValSerLeuValLeuValGlyIleValThrLeuTyr>
     2410      2420      2430      2440      2450      2460      2470      2480      2490      2500
TTGGGAGTTATGGTGCAGGCCGATAGTGGTTGCGTTGTGAGCTGGAAGAACAAAGAACTAAAATGTGGCAGTGGAATATTCGTCACAGATAACGTGCATA
LeuGlyValMetValGlnAlaAspSerGlyCysValValSerTrpLysAsnLysGluLeuLysCysGlySerGlyIlePheValThrAspAsnValHis>
     2510      2520      2530      2540      2550      2560      2570      2580      2590      2600
CATGGACAGAACAATACAAGTTCCAACCAGAATCCCCTTCAAAACTGGCCTCAGCCATCCAGAAAGCGCATGAAGAGGGCATCTGTGGAATCCGCTCAGT
ThrTrpThrGluGlnTyrLysIleGlnProGluSerProSerLysLeuAlaSerAlaIleGlnLysAlaHisGluGluGlyIleCysGlyIleArgSerVal>
     2610      2620      2630      2640      2650      2660      2670      2680      2690      2700
AACAAGACTGGAAAATCTTATGTGGAAACAGATAACATCAGAATTGAATCATATTCTATCAGAAAATGAAGTGAAACTGACCATCATGACAGGAGACATC
ThrArgLeuGluAsnLeuMetTrpLysGlnIleThrSerGluLeuAsnHisIleLeuSerGluAsnGluValLysLeuThrIleMetThrGlyAspIle>
     2710      2720      2730      2740      2750      2760      2770      2780      2790      2800
AAAGGAATCATGCAGGTAGGAAAACGATCTTTGCGGCCTCAACCCACTGAGTTGAGGTATTCATGGAAAACATGGGGTAAAGCGAAAATGCTCTCCACAG
LysGlyIleMetGlnValGlyLysArgSerLeuArgProGlnProThrGluLeuArgTyrSerTrpLysThrTrpGlyLysAlaLysMetLeuSerThr>
     2810      2820      2830      2840      2850      2860      2870      2880      2890      2900
AACTCCACAATCAGACCTTCCTCATTGATGGTCCCGAAACAGCAGAATGCCCCAACACAAACAGAGCTTGGAATTCACTGGAAGTTGAGGACTACGGCTT
GluLeuHisAsnGlnThrPheLeuIleAspGlyProGluThrAlaGluCysProAsnThrAsnArgAlaTrpAsnSerLeuGluValGluAspTyrGlyPhe>
     2910      2920      2930      2940      2950      2960      2970      2980      2990      3000
TGGAGTATTCACTACCAATATATCGCTAACATTGAGAGAAAAcAGGATGTATTTTGTGACTCAAAACTCATGTCAGCGGCCATAAAGGACAACAGACCC
GlyValPheThrThrAsnIleTrpLeuArgLeuArgGluLysGlnAspValPheCysAspSerLysLeuMetSerAlaAlaIleLysAspAsnArgAla>
     3010      3020      3030      3040      3050      3060      3070      3080      3090      3100
GTCCATGCTGATATGGGTTATTGGATAGAAAGCGCACTCAATGATACATGGAAGATAGAAAAGCTTCTTTCATTGAAGTCAAAAGTTGCCACTGGCCAA
ValHisAlaAspMetGlyTyrTrpIleGluSerAlaLeuAsnAspThrTrpLysIleGluLysAlaSerPheIleGluValLysSerCysHisTrpPro>
     3110      3120      3130      3140      3150      3160      3170      3180      3190      3200
AGTCACACACCCTATGGAGTAATGGAGTGCTAGAAAGCGAGATGGTCATTCCAAAGAATTTCGCTGGACCAGTGTCACAACATAATAACAGACCAGGCTA
LysSerHisThrLeuTrpSerAsnGlyValLeuGluSerGluMetValIleProLysAsnPheAlaGlyProValSerGlnHisAsnAsnArgProGlyTyr>
     3210      3220      3230      3240      3250      3260      3270      3280      3290      3300
TTACACACAAACAGCAGGACCTTGGCATCTAGGCAAGCTTGAGATGGACTTTGATTTCTGCGAAGGGACTACAGTGGTGGTAACCGAGAACTGTGGAAAC
TyrThrGlnThrAlaGlyProTrpHisLeuGlyLysLeuGluMetAspPheAspIleCysGluGlyThrThrValValValThrGluAsnCysGlyAsn>
     3310      3320      3330      3340      3350      3360      3370      3380      3390      3400
AGAGGGCCCTCTCTTTAAGAACAACCACTGCCTCAGGAAAAACTCATAACGGAATGGTGTTGTCGATCTTGCACACTACCACCACTAAGATACAGAGGTGAGG
ArgGlyProSerLeuArgThrThrThrAlaSerGlyLysLeuIleThrGluTrpCysCysArgSerCysThrLeuProProLeuArgTyrArgGlyGlu>
     3410      3420      3430      3440      3450      3460      3470      3480      3490      3500
ATGGATGTTGGTACGGGATGGAAATCAGACCATTGAAAGAGAAAGAAGAAAATCTGGTCAGTTCTCGGTTACAGCCGGACATGGGCAGATTGACAATTT
AspGlyCysTrpTyrGlyMetGluIleArgProLeuLysGluLysGluGluAsnLeuValSerSerLeuValThrAlaGlyHisGlyGlnIleAspAsnIle>
     3510      3520      3530      3540      3550      3560      3570      3580      3590      3600
CTCATTAGGAATCTTGGGAATGGCACTGTTCCTTGAAGAAATGCTGAGGACTCGAGTAGGAACAAAACATGCAATATTACTCGTCGCAGTTTCTTTCGTG
SerLeuGlyIleLeuGlyMetAlaLeuPheLeuGluGluMetLeuArgThrArgValGlyThrLysHisAlaIleLeuLeuValAlaValSerPheVal>
     3610      3620      3630      3640      3650      3660      3670      3680      3690      3700
ACGCTAATCACAGGGAACATGTCTTTTAGAGACCTGGGAAGAGTGATGGTTATGGTGGGTGCCACCATGACAGATGACATAGGCATGGGTGTGACTTATC
ThrLeuIleThrGlyAsnMetSerPheArgAspLeuGlyArgValMetValMetValGlyAlaThrMetThrAspAspIleGlyMetGlyValThrTyr>
     3710      3720      3730      3740      3750      3760      3770      3780      3790      3800
TCGCTCTACTAGCAGCTTTTAGAGTCAGACCAACCTTTGCAGCTGGACTGCTCTTGAGAAAACTGACCTCCAAGGAATTAATGATGACTACCATAGGAAT
LeuAlaLeuLeuAlaAlaPheArgValArgProThrPheAlaAlaGlyLeuLeuLeuArgLysLeuThrSerLysGluLeuMetMetThrThrIleGlyIle>
     3810      3820      3830      3840      3850      3860      3870      3880      3890      3900
CGTTCTTCTCTCCCAGAGTAGCATACCAGAGACCATTCTTGAACTGACCGACGCGTTAGCTCTAGGCATGATGGTCCTCAAGATGGTGAGAAACATGGAA
```

APPENDIX 1-continued

```
                                                                                     3910      3920      3930      3940      3950      3960      3970      3980      3990      4000
AAATATCAGCTGGCAGTGACCATCATGGCTATTTTGTGCGTCCCAAATGCTGTGATATTACAGAACGCATGCAAAGTGAGTTGCACAATATTGGCAGTGG
LysTyrGlnLeuAlaValThrIleMetAlaIleLeuCysValProAsnAlaValIleLeuGlnAsnAlaTrpLysValSerCysThrIleLeuAlaVal>

4010      4020      4030      4040      4050      4060      4070      4080      4090      4100
TGTCTGTTTCCCCCCTGCTCTTAACATCCTCACAACAGAAAGCGGACTGGATACCATTAGCGTTGACGATCAAAGGTCTTAATCCAACAGCCATTTTTCT
ValSerValSerProLeuLeuLeuThrSerSerGlnGlnLysAlaAspTrpIleProLeuAlaLeuThrIleLysGlyLeuAsnProThrAlaIlePheLeu>

4110      4120      4130      4140      4150      4160      4170      4180      4190      4200
AACAACCCTCTCAAGAACCAACAAGAAAAGGAGCTGGCCTTTAAATGAGGCCATCATGGCGGTTGGGATGGTGAGTATCTTGGCCAGCTCTCTCTTAAAG
ThrThrLeuSerArgThrAsnLysLysArgSerTrpProLeuAsnGluAlaIleMetAlaValGlyMetValSerIleLeuAlaSerSerLeuLeuLys>

4210      4220      4230      4240      4250      4260      4270      4280      4290      4300
AATGACATCCCCATGACAGGACCATTAGTGGCTGGAGGGCTCCTTACTGTGTGCTACGTGCTAACTGGGCGGTCAGCCGATCTGGAATTAGAGAGAGCTA
AsnAspIleProMetThrGlyProLeuValAlaGlyGlyLeuLeuThrValCysTyrValLeuThrGlyArgSerAlaAspLeuGluLeuGluArgAla>

4310      4320      4330      4340      4350      4360      4370      4380      4390      4400
CCGATGTCAAATGGGATGACCAGGCAGAGATATCAGGTAGCAGTCCAATCCTGTCAATAACAATATCAGAAGATGGCAGCATGTCAATAAAGAATGAAGA
ThrAspValLysTrpAspAspGlnAlaGluIleSerGlySerSerProIleLeuSerIleThrIleSerGluAspGlySerMetSerIleLysAsnGluGlu>

4410      4420      4430      4440      4450      4460      4470      4480      4490      4500
GGAAGAGCAAACACTGACTATACTCATTAGAACAGGATTGCTTGTGATCTCAGGACTCTTTCCGGTATCAATACCAATTACAGCAGCAGCATGGTATCTG
GluGluGlnThrLeuThrIleLeuIleArgThrGlyLeuLeuValIleSerGlyLeuPheProValSerIleProIleThrAlaAlaAlaTrpTyrLeu>

4510      4520      4530      4540      4550      4560      4570      4580      4590      4600
TGGGAAGTAAAGAAACAACGGGCTGGAGTGCTCTGGGATGTCCCCTCACCACCACCCGTGGGAAAAGCTGPJTTGCAAGATGGACCCTACAGAATCAAGC
TrpGluValLysLysGlnArgAlaGlyValLeuTrpAspValProSerProProProValGlyLysAlaGluLeuGluAspGlyAlaTyrArgIleLys>

4610      4620      4630      4640      4650      4660      4670      4680      4690      4700
AAAAAGGAATCCTTGGATATTCCCAGATCGGAGCTGGAGTTTACAAAGAAGGAACATTTCACACAATGTGGCACGTCACACGTGGCGCTGTCCTAATGCA
GlnLysGlyIleLeuGlyTyrSerGlnIleGlyAlaGlyValTyrLysGluGlyThrPheHisThrMetTrpHisValThrArgGlyAlaValLeuMetHis>

4710      4720      4730      4740      4750      4760      4770      4780      4790      4800
TAAGGGGAAGAGGATTGAACCATCATGGGCGGACGTCAAGAAAGACTTAATATCATATGGAGGAGGTTGGAAGCTAGAAGGAGAATGGAAAGAAGGAGAA
LysGlyLysArgIleGluProSerTrpAlaAspValLysLysAspLeuIleSerTyrGlyGlyGlyTrpLysLeuGluGlyGluTrpLysGluGlyGlu>

4810      4820      4830      4840      4850      4860      4870      4880      4890      4900
GAAGTCCAGGTCTTGGCATTGGAGCCAGGGAAAAATCCAAGAGCCGTCCAAACAAAGCCTGGCCTTTTTAGAACCAACACTGGAACCATAGGTGCCGTAT
GluValGlnValLeuAlaLeuGluProGlyLysAsnProArgAlaValGlnThrLysProGlyLeuPheArgThrAsnThrGlyThrIleGlyAlaVal>

4910      4920      4930      4940      4950      4960      4970      4980      4990      5000
CTCTGGACTTTTCCCCTGGGACGTCAGGATCTCCAATCGTCGACAAAAAAGGAAAAGTTGTAGGTCTCTATGGCAATGGTGTCGTTACAAGGAGTGGAGC
SerLeuAspPheSerProGlyThrSerGlySerProIleValAspLysLysGlyLysValValGlyLeuTyrGlyAsnGlyValValThrArgSerGlyAla>

5010      5020      5030      5040      5050      5060      5070      5080      5090      5100
ATATGTGAGTGCCATAGCTCAGACTGAAAAAAGCATTGAAGACAATCCAGAGATTGAAGATGACATCTTTCGAAAGAGAAGATTGACTATCATGGATCTC
TyrValSerAlaIleAlaGlnThrGluLysSerIleGluAspAsnProGluIleGluAspAspIlePheArgLysArgArgLeuThrIleMetAspLeu>

5110      5120      5130      5140      5150      5160      5170      5180      5190      5200
CACCCAGGAGCAGGAAAGACAAAGAGATACCTCCCGGCCATAGTCAGAGAGGCCATAAAAAGAGGCTTGAGAACACTAATCCTAGCCCCCACTAGAGTCG
HisProGlyAlaGlyLysThrLysArgTyrLeuProAlaIleValArgGluAlaIleLysArgGlyLeuArgThrLeuIleLeuAlaProThrArgVal>

5210      5220      5230      5240      5250      5260      5270      5280      5290      5300
TGGCAGCTGAAATGGAGGAAGCCCTTAGAGGACTTCCAATAAGATACCAAACTCCAGCTATCAGGGCTGAGCACACCGGGCGGGAGATTGTAGACTTAAT
ValAlaAlaGluMetGluGluAlaLeuArgGlyLeuProIleArgTyrGlnThrProAlaIleArgAlaGluHisThrGlyArgGluIleValAspLeuMet>

5310      5320      5330      5340      5350      5360      5370      5380      5390      5400
GTGTCATGCCACATTTACCATGAGGCTGCTATCACCAATCAGGGTGCCAAATTACAACCTGATCATCATGGACGAAGCCCATTTTACAGATCCAGCAAGC
CysHisAlaThrPheThrMetArgLeuLeuSerProIleArgValProAsnTyrAsnLeuIleIleMetAspGluAlaHisIleThrAspProAlaSer>

5410      5420      5430      5440      5450      5460      5470      5480      5490      5500
ATAGCAGCTAGGGGATACATCTCAACTCGAGTGGAGATGGGGGAGGCAGCTGGAATTTTTATGACAGCCACTCCTCCGGGTAGTAGAGATCCATTTCCTC
IleAlaAlaArgGlyTyrIleSerThrArgValGluMetGlyGluAlaAlaGlyIlePheMetThrAlaThrProProGlySerArgAspProPhePro>

5510      5520      5530      5540      5550      5560      5570      5580      5590      5600
AGAGCAATGCACCAATTATGGACGAAGAAAGAGAAATTCCGGAACGTTCATGGAACTCTGGGCACGAGTGGGTCACGGATTTTAAAGGAAAGACTGTCTG
GlnSerAsnAlaProIleMetAspGluGluArgGluIleProGluArgSerTrpAsnSerGlyHisGluTrpValThrAspPheLysGlyLysThrValTrp>

5610      5620      5630      5640      5650      5660      5670      5680      5690      5700
GTTTGTTCCAAGCATAAAAACCGGAAATGACATAGCAGCCTGCCTGAGAAAGAATGGAAAGAGGGTGATACAACTCAGTAGGAAGACCTTTGATTCTGAA
PheValProSerIleLysThrGlyAsnAspIleAlaAlaCysLeuArgLysAsnGlyLysArgValIleGlnLeuSerArgLysThrPheAspSerGlu>

5710      5720      5730      5740      5750      5760      5770      5780      5790      5800
TATGTCAAGACTAGAACCAATGACTGGGATTTCGTGGTTACAACTGACATCTCGGAAATGGGCGCCAACTTTAAAGCTGAGAGGGTCATAGACCCCAGAC
TyrValLysThrArgThrAsnAspTrpAspPheValValThrThrAspIleSerGluMetGlyAlaAsnIleLysAlaGluArgValIleAspProArg>

5810      5820      5830      5840      5850      5860      5870      5880      5890      5900
GCTGCATGAAACCAGTTATATTGACAGACGGCGAAGAGCGGGTGATTCTGGCAGGACCCATGCCAGTGACCCACTCTAGTGCAGCACAAAGAAGAGGGAG
```

APPENDIX 1-continued

```
ArgCysMetLysProValIleLeuThrAspGlyGluGluArgValIleLeuAlaGlyProMetProValThrHisSerSerAlaAlaGlnArgArgGlyArg>

5910      5920      5930      5940      5950      5960      5970      5980      5990      6000
AATAGGAAGGAATCCAAGGAATGAAAATGATCAATATATATATGGGGGAACCACTGGAAAATGATGAAGACTGTGCGCACTGGAAGGAAGCTAAGATG
IleGlyArgAsnProArgAsnGluAsnAspGlnTyrIleTyrMetGlyGluProLeuGluAsnAspGluAspCysAlaHisTrpLysGluAlaLysMet>

6010      6020      6030      6040      6050      6060      6070      6080      6090      6100
CTCCTAGATAATATCAACACACCTGAAGGAATCATTCCCAGCTTGTTCGAGCCAGAGCGTGAAAAGGTGGATGCCATTGACGGTGAATATCGCTTGAGAG
LeuLeuAspAsnIleAsnThrProGluGlyIleIleProSerLeuPheGluProGluArgGluLysValAspAlaIleAspGlyGluTyrArgLeuArg>

6110      6120      6130      6140      6150      6160      6170      6180      6190      6200
GAGAAGCACGGAAAACTTTTGTGGACCTAATGAGAAGAGGAGACCTACCAGTCTGGTTGGCTTATAAAGTGGCAGCTGAAGGTATCAACTACGCAGACAG
GlyGluAlaArgLysThrPheValAspLeuMetArgArgGlyAspLeuProValTrpLeuAlaTyrLysValAlaAlaGluGlyIleAsnTyrAlaAspArg>

6210      6220      6230      6240      6250      6260      6270      6280      6290      6300
AAGATGGTGTTTTGACGGAACCAGAAACAATCAAATCTTGGAAGAAAATGTGGAAGTGGAAATCTGGACAAAGGAAGGGGAAAGGAAAAAATTGAAACCT
ArgTrpCysPheAspGlyThrArgAsnAsnGlnIleLeuGluGluAsnValGluValGluIleTrpThrLysGluGlyGluArgLysLysLeuLysPro>

6310      6320      6330      6340      6350      6360      6370      6380      6390      6400
AGATGGTTAGATGCTAGGATCTACTCCGACCCACTGGCGCTAAAAGAGTTCAAGGAATTTGCAGCCGGAAGAAAGTCCCTAACCCTGAACCTAATTACAG
ArgTrpLeuAspAlaArgIleTyrSerAspProLeuAlaLeuLysGluPheLysGluPheAlaAlaGlyArgLysSerLeuThrLeuAsnLeuIleThr>

6410      6420      6430      6440      6450      6460      6470      6480      6490      6500
AGATGGGCAGACTCCCAACTTTTATGACTCAGAAGGCCAGAGATGCACTAGACAACTTGGCGGTGCTGCACACGGCTGAAGCGGGTGGAAAGGCATACAA
GluMetGlyArgLeuProThrPheMetThrGlnLysAlaArgAspAlaLeuAspAsnLeuAlaValLeuHisThrAlaGluAlaGlyGlyLysAlaTyrAsn>

6510      6520      6530      6540      6550      6560      6570      6580      6590      6600
TCATGCTCTCAGTGAATTACCGGAGACCCTGGAGACATTGCTTTTGCTGACACTGTTGGCCACAGTCACGGGAGGAATCTTCCTATTCCTGATGAGCGGA
HisAlaLeuSerGluLeuProGluThrLeuGluThrLeuLeuLeuLeuThrLeuLeuAlaThrValThrGlyGlyIleIleLeuIleLeuMetSerGly>

6610      6620      6630      6640      6650      6660      6670      6680      6690      6700
AGGGGTATGGGGAAGATGACCCTGGGAATGTGCTGCATAATCACGGCCAGCATCCTCTTATGGTATGCACAAATACAGCCACATTGGATAGCAGCCTCAA
ArgGlyMetGlyLysMetThrLeuGlyMetCysCysIleIleThrAlaSerIleLeuLeuTrpTyrAlaGlnIleGlnProHisTrpIleAlaAlaSer>

6710      6720      6730      6740      6750      6760      6770      6780      6790      6800
TAATATTGGAGTTCTTTCTCATAGTCTTGCTCATTCCAGAACCAGAAAAGCAGAGGACACCTCAGGATAATCAATTGACTTATGTCATCATAGCCATCCT
IleIleLeuGluPhePheLeuIleValLeuLeuIleProGluProGluLysGlnArgThrProGlnAspAsnGlnLeuThrTyrValIleIleAlaIleLeu>

6810      6820      6830      6840      6850      6860      6870      6880      6890      6900
CACAGTGGTGGCCGCAACCATGGCAAACGAAATGGGTTTTCTGGAAAAAACAAAGAAAGACCTCGGACTGGGAAACATTGCAACTCAGCAACCTGAGAGC
ThrValValAlaAlaThrMetAlaAsnGluMetGlyIleLeuGluLysThrLysLysAspLeuGlyLeuGlyAsnIleAlaThrGlnGlnProGluSer>

6910      6920      6930      6940      6950      6960      6970      6980      6990      7000
AACATTCTGGACATAGATCTACGTCCTGCATCAGCATGGACGTTGTATGCCGTGGCTACAACATTTATCACACCAATGTTGAGACATAGCATTGAAAATT
AsnIleLeuAspIleAspLeuArgProAlaSerAlaTrpThrLeuTyrAlaValAlaThrThrPheIleThrProMetLeuArgHisSerIleGluAsn>

7010      7020      7030      7040      7050      7060      7070      7080      7090      7100
CCTCAGTAAATGTGTCCCTAACAGCCATAGCTAACCAAGCCACAGTGCTAATGGGTCTCGGAAAAGGATGGCCATTGTCAAAGATGGACATTGGAGTTCC
SerSerValAsnValSerLeuThrAlaIleAlaAsnGlnAlaThrValLeuMetGlyLeuGlyLysGlyTrpProLeuSerLysMetAspIleGlyValPro>

7110      7120      7130      7140      7150      7160      7170      7180      7190      7200
CCTCCTTGCTATTGGGTGTTACTCACAAGTCAACCCTATAAACCCTCACAGCGGCTCTTCTTTTATTGGTAGCACATTATGCCATCATAGGACCGGGACTT
LeuLeuAlaIleGlyCysTyrSerGlnValAsnProIleThrLeuThrAlaAlaLeuLeuLeuLeuValAlaHisTyrAlaIleIleGlyProGlyLeu>

7210      7220      7230      7240      7250      7260      7270      7280      7290      7300
CAAGCCAAAGCAACTAGAGAAGCTCAGAAAAGAGCAGCAGCGGGCATCATGAAAAACCCGACTGTGGATGGAATAACAGTGATAGATCTAGATCCAATAC
GlnAlaLysAlaThrArgGluAlaGlnLysArgAlaAlaAlaGlyIleMetLysAsnProThrValAspGlyIleThrValIleAspLeuAspProIle>

7310      7320      7330      7340      7350      7360      7370      7380      7390      7400
CCTATGATCCAAAGTTTGAAAAGCAGTTGGGACAAGTAATGCTCCTAGTCCTCTGCGTGACCCAAGTGCTGATGATGAGGACTACGTGGCCTTTGTGTGA
ProTyrAspProLysPheGluLysGlnLeuGlyGlnValMetLeuLeuValLeuCysValThrGlnValLeuMetMetArgThrThrTrpAlaLeuCysGlu>

7410      7420      7430      7440      7450      7460      7470      7480      7490      7500
AGCCTTAACTCTAGCAACTGGACCCGTGTCCACATTGTGGGAAGGAAATCCAGGGAGATTCTGGAACACAACCATTGCAGTGTCAATGGCAAACATCTTT
AlaLeuThrLeuAlaThrGlyProValSerThrLeuTrpGluGlyAsnProGlyArgPheTrpAsnThrThrIleAlaValSerMetAlaAsnIlePhe>

7510      7520      7530      7540      7550      7560      7570      7580      7590      7600
AGAGGGAGTTACCTGGCTGGAGCTGGACTTCTCTTTTCTATCATGAAGAACACAACCAGCACGAGAAGAGGAACTGGCAATATAGGAGAAACGTTAGGAG
ArgGlySerTyrLeuAlaGlyAlaGlyLeuLeuPheSerIleMetLysAsnThrThrSerThrArgArgGlyThrGlyAsnIleGlyGluThrLeuGly>

7610      7620      7630      7640      7650      7660      7670      7680      7690      7700
AGAAATGGAAAAGCAGACTGAACGCATTGGGAAAAGTGAATTCCAGATCTACAAAAAAAGTGGAATTCAAGAAGTGGACAGAACCTTAGCAAAAGAAGG
GluLysTrpLysSerArgLeuAsnAlaLeuGlyLysSerGluPheGlnIleTyrLysLysSerGlyIleGlnGluValAspArgThrLeuAlaLysGluGly>

7710      7720      7730      7740      7750      7760      7770      7780      7790      7800
CATTAAAAGAGGAGAAACGGATCATCACGCTGTGTCGCGAGGCTCAGCAAAACTGAGATGGTTCGTTGAAAGGAATTTGGTCACACCAGAAGGGAAAGTA
IleLysArgGlyGluThrAspHisHisAlaValSerArgGlySerAlaLysLeuArgTrpPheValGluArgAsnLeuValThrProGluGlyLysVal>

7810      7820      7830      7840      7850      7860      7870      7880      7890      7900
GTGGACCTTGGTTGTGGCAGAGGGGGCTGGTCATACTATTGTGGAGGATTAAAGAATGTAAGAGAAGTTAAAGGCTTAACAAAAGGAGGACCAGGACACG
```

APPENDIX 1-continued

```
ValAspLeuGlyCysGlyArgGlyGlyTrpSerTyrTyrCysGlyGlyLeuLysAsnValArgGluValLysGlyLeuThrLysGlyGlyProGlyHis>

7910      7920      7930      7940      7950      7960      7970      7980      7990      8000
AAGAACCTATCCCTATGTCAACATATGGGTGGAATCTAGTACGCTTACAGAGCGGAGTTGATGTTTTTTTGTTCCACCAGAGAAGTGTGACACATTGTT
GluGluProIleProMetSerThrTyrGlyTrpAsnLeuValArgLeuGlnSerGlyValAspValPhePheValProProGluLysCysAspThrLeuLeu>

8010      8020      8030      8040      8050      8060      8070      8080      8090      8100
GTGTGACATAGGGGAATCATCACCAAATCCCACGGTAGAAGCGGGACGAACACTCAGAGTCCTCAACCTAGTGGAAAATTGGCTGAACAATAACACCCAA
CysAspIleGlyGluSerSerProAsnProThrValGluAlaGlyArgThrLeuArgValLeuAsnLeuValGluAsnTrpLeuAsnAsnAsnThrGln>

8110      8120      8130      8140      8150      8160      8170      8180      8190      8200
TTTTGCGTAAAGGTTCTTAACCCGTACATGCCCTCAGTCATTGAAAGAATGGAAACCTTACAACGGAAATACGGAGGAGCCTTGGTGAGAAATCCACTCT
PheCysValLysValLeuAsnProTyrMetProSerValIleGluArgMetGluThrLeuGlnArgLysTyrGlyGlyAlaLeuValArgAsnProLeu>

8210      8220      8230      8240      8250      8260      8270      8280      8290      8300
CACGGAATTCCACACATGAGATGTACTGGGTGTCCAATGCTTCCGGGAACATAGTGTCATCAGTGAACATGATTTCAAGAATGCTGATCAACAGATTCAC
SerArgAsnSerThrHisGluMetTyrTrpValSerAsnAlaSerGlyAsnIleValSerSerValAsnMetIleSerArgMetLeuIleAsnArgPheThr>

8310      8320      8330      8340      8350      8360      8370      8380      8390      8400
TATGAGACACAAGAAGGCCACCTATGAGCCAGATGTCGACCTCGGAAGCGGAACCCGCAATATTGGAATTGAAAGTGAGACACCGAACCTAGACATAATT
MetArgHisLysLysAlaThrTyrGluProAspValAspLeuGlySerGlyThrArgAsnIleGlyIleGluSerGluThrProAsnLeuAspIleIle>

8410      8420      8430      8440      8450      8460      8470      8480      8490      8500
GGGAAAAGAATAGAAAAAATAAAACAAGAGCATGAAACGTCATGGCACTATGATCAAGACCACCCATACAAAACATGGGCTTACCATGGCAGCTATGAAA
GlyLysArgIleGluLysIleLysGlnGluHisGluThrSerTrpHisTyrAspGlnAspHisProTyrLysThrTrpAlaTyrHisGlySerTyrGlu>

8510      8520      8530      8540      8550      8560      8570      8580      8590      8600
CAAAACAGACTGGATCAGCATCATCCATGGTGAACGGAGTAGTCAGATTGCTGACAAAACCCTGGGACGTTGTTCCAATGGTGACACAGATGGCAATGAC
ThrLysGlnThrGlySerAlaSerSerMetValAsnGlyValValArgLeuLeuThrLysProTrpAspValValProMetValThrGlnMetAlaMetThr>

8610      8620      8630      8640      8650      8660      8670      8680      8690      8700
AGACACAACTCCTTTTGGACAACAGCGCGTCTTCAAAGAGAAGGTGGATACGAGAACCCAAGAACCAAAGAAGGCACAAAAAAACTAATGAAAATCACG
AspThrThrProPheGlyGlnGlnArgValPheLysGluLysValAspThrArgThrGlnGluProLysGluGlyThrLysLysLeuMetLysIleThr>

9710      8720      8730      8740      8750      8760      8770      8780      8790      8800
GCAGAGTGGCTCTGGAAAGAACTAGGAAAGAAAAAGACACCTAGAATGTGTACCAGAGAAGAATTCACAAAAAAGGTGAGAAGCAATGCAGCCTTGGGGG
AlaGluTrpLeuTrpLysGluLeuGlyLysLysLysThrProArgMetCysThrArgGluGluPheThrLysLysValArgSerAsnAlaAlaLeuGly>

8810      8820      8830      8840      8850      8860      8870      8880      8890      8900
CCATATTCACCGATGAGAACAAGTGGAAATCGGCGCGTGAAGCCGTTGAAGATAGTAGGTTTTGGGAGCTGGTTGACAAGGAAAGGAACCTCCATCTTGA
AlaIlePheThrAspGluAsnLysTrpLysSerAlaArgGluAlaValGluAspSerArgPheTrpGluLeuValAspLysGluArgAsnLeuHisLeuGlu>

8910      8920      8930      8940      8950      8960      8970      8980      8990      9000
AGGGAAATGTGAAACATGTGTATACAACATGATGGGGAAAAGAGAGAAAAAACTAGGAGAGTTTGGTAAAGCAAAAGGCAGCAGAGCCATATGGTACATG
GlyLysCysGluThrCysValTyrAsnMetMetGlyLysArgGluLysLysLeuGlyGluPheGlyLysAlaLysGlySerArgAlaIleTrpTyrMet>

9010      9020      9030      9040      9050      9060      9070      9080      9090      9100
TGGCTCGGAGCACGCTTCTTAGAGTTTGAAGCCCTAGGATTTTTGAATGAAGACCATTGGTTCTCCAGAGAGAACTCCCTGAGTGGAGTGGAAGGAGAAG
TrpLeuGlyAlaArgPheLeuGluPheGluAlaLeuGlyPheLeuAsnGluAspHisTrpPheSerArgGluAsnSerLeuSerGlyValGluGlyGlu>

9110      9120      9130      9140      9150      9160      9170      9180      9190      9200
GGCTGCATAAGCTAGGTTACATCTTAAGAGAGGTGAGCAAGAAAGAGGAGGAGCAATGTATGCCGATGACACCGCAGGCTGGGACACAAGAATCACAAT
GlyLeuHisLysLeuGlyTyrIleLeuArgGluValSerLysLysGluGlyGlyAlaMetTyrAlaAspAspThrAlaGlyTrpAspThrArgIleThrIle>

9210      9220      9230      9240      9250      9260      9270      9280      9290      9300
AGAGGATTTGAAAAATGAAGAAATGATAACGAACCACATGGCAGGAGAACACAAGAAACTTGCCGAGGCCATTTTTAAATTGACGTACCAAAACAAGGTG
GluAspLeuLysAsnGluGluMetIleThrAsnHisMetAlaGlyGluHisLysLysLeuAlaGluAlaIlePheLysLeuThrTyrGlnAsnLysVal>

9310      9320      9330      9340      9350      9360      9370      9380      9390      9400
GTGCGTGTGCAAAGACCAACACCAAGAGGCACAGTAATGGACATCATATCGAGAAGAGACCAAAGGGGTAGTGGACAAGTTGGCACCTATGGCCTCAACA
ValArgValGlnArgProThrProArgGlyThrValMetAspIleIleSerArgArgAspGlnArgGlySerGlyGlnValGlyThrTyrGlyLeuAsn>

9410      9420      9430      9440      9450      9460      9470      9480      9490      9500
CTTTCACCAACATGGAAGCACAACTAATTAGGCAAATGGAGGGGAAGGAATCTTCAAAAGCATCCAGCACTTGACAGCCTCAGAAGAAATCGCTGTGCA
ThrPheThrAsnMetGluAlaGlnLeuIleArgGlnMetGluGlyGluGlyIlePheLysSerIleGlnHisLeuThrAlaSerGluIleAlaValGln>

9510      9520      9530      9540      9550      9560      9570      9580      9590      9600
AGATTGGCTAGTAAGAGTAGGGCGTGAAAGGTTGTCAAGAATGGCCATCAGTGGAGATGATTGTGTTGTGAAACCTTTAGATGATAGATTTGCAAGAGCT
AspTrpLeuValArgValGlyArgGluArgLeuSerArgMetAlaIleSerGlyAspAspCysValValLysProLeuAspAspArgPheAlaArgAla>

9610      9620      9630      9640      9650      9660      9670      9680      9690      9700
CTAACAGCTCTAAATGACATGGGAAAGGTTAGGAAGGACATACAGCAATGGGAGCCCTCAAGAGGATGGAACGACTGGACGCAGGTGCCCTTCTGTTCAC
LeuThrAlaLeuAsnAspMetGlyLysValArgLysAspIleGlnGlnTrpGluProSerArgGlyTrpAsnAspTrpThrGlnValProPheCysSer>

9710      9720      9730      9740      9750      9760      9770      9780      9790      9800
ACCATTTTCACGAGTTAATTATGAAAGATGGTCGCACACTCGTAGTTCCATGCAGAAACCAAGATGAATTGATCGGCAGAGCCCGAATTTCCCAGGGAGC
HisHisPheHisGluLeuIleMetLysAspGlyArgThrLeuValValProCysArgAsnGlnAspGluLeuIleGlyArgAlaArgIleSerGlnGlyAla>

9810      9820      9830      9840      9850      9860      9870      9880      9890      9900
TGGGTGGTCTTTACGGGAGACGGCCTGTTTGGGGAAGTCTTACGCCCAAATGTGGAGCTTGATGTACTTCCACAGACGTGATCTCAGGCTAGCGGCAAAT
```

APPENDIX 1-continued

```
            9910      9920      9930      9940      9950      9960      9970      9980      9990     10000
GCCATCTGCTCGGCAGTCCCATCACACTGGATTCCAACAAGCCGGACAACCTGGTCCATACACGCCAGCCATGAATGATGACGGAAGACATGTTGA
AlaIleCysSerAlaValProSerHisTrpIleProThrSerArgThrThrTrpSerIleHisAlaSerHisGluTrpMetThrThrGluAspMetLeu>

10010     10020     10030     10040     10050     10060     10070     10080     10090     10100
CAGTTTGGAACAGAGTGTGGATCCTAGAAAATCCATGGATGGAAGACAAAACTCCAGTGGAATCATGGGAGGAAATCCCATACCTGGGAAAAAGAGAAGA
ThrValTrpAsnArgValTrpIleLeuGluAsnProTrpMetGluAspLysThrProValGluSerTrpGluGluIleProTyrLeuGlyLysArgGluAsp>

10110     10120     10130     10140     10150     10160     10170     10180     10190     10200
CCAATGGTGCGGCTCGCTGATTGGGCTGACAAGCAGAGCCACCTGGGCGAAGAATATCCAGACAGCAATAAACCAAGTCAGATCCCTCATTGGCAATGAG
GlnTrpCysGlySerLeuIleGlyLeuThrSerArgAlaThrTrpAlaLysAsnIleGlnThrAlaIleAsnGlnValArgSerLeuIleGlyAsnGlu>

10210     10220     10230     10240     10250     10260     10270     10280     10290     10300
GAATACACAGATTACATGCCATCCATGAAAAGATTCAGAAGAGAAGAGGAAGAGGCAGGAGTTTTGTGGTAGAAAAACATGAAACAAAACAGAAGTCAGG
GluTyrThrAspTyrMetProSerMetLysArgPheArgArgGluGluGluGluAlaGlyValLeuTrp***>

10310     10320     10330     10340     10350     10360     10370     10380     10390     10400
TCGGATTAAGCCATAGTACGGGAAAAACTATGCTACCTGTGAGCCCCGTCCAAGGACGTTAAAAGAAGTCAGGCCATTTTGATGCCATAGCTTGAGCAAA 10410     10420     10430     10440     10450     10460     10470     10480     10490     10500
CTGTGCAGCCTGTAGCTCCACCTGAGAAGGTGTAAAAAATCCGGGAGGCCACAAACCATGGAAGCTGTACGCATGGCGTAGTGGACTAGCGGTTAGAGGA 10510     10520     10530     10540     10550     10560     10570     10580     10590     10600
GACCCCTCCCTTACAGATCGCAGCAACAATGGGGGCCCAAGGTGAGATGAAGCTGTAGTCTCACTGGAAGGACTAGAGGTTAGAGGAGACCCCCCCAAAA 10610     10620     10630     10640     10650     10660     10670     10680     10690     10700
CAAAAAACAGCATATTGACGCTGGGAAAGACCAGAGATCCTGCTGTCTCCTCAGCATCATTCCAGGCACAGGACGCCAGAAAATGGAATGGTGCTGTTGA 10710     10720     10730     10740     10750     10760     10770     10780     10790     10800
ATCAACAGGTTCTGGTACCGGTAGGCATCGTGGTGTCACGCTCGTCGTTTGGTATGGCTTCATTCAGCTCCGGTTCCCAACGATCAAGGCGAGTTACATG 10810     10820     10830     10840     10850     10860     10870     10880     10890     10900
ATCCCCCATGTTGTGCAAAAAAGCGGTTAGCTCCTTCGGTCCTCCGATCGTTGTCAGAAGTAAGTTGGCCGCAGTGTTATCACTCATGGTTATGGCAGCA 10910     10920     10930     10940     10950     10960     10970     10980     10990     11000
CTGCATAATTCTCTTACTGTCATGCCATCCGTAAGATGCTTTTCTGTGACTGGTGAGTACTCAACCAAGTCATTCTGAGAATAGTGTATGCGGCGACCGA 11010     11020     11030     11040     11050     11060     11070     11080     11090     11100
GTTGCTCTTGCCCGGCGTCAACACGGGATAATACCGCGCCACATAGCAGAACTTTAAAAGTGCTCATCATTGGAAAACGTTCTTCGGGGCGAAAACTCTC 11110     11120     11130     11140     11150     11160     11170     11180     11190     11200
AAGGATCTTACCGCTGTTGAGATCCAGTTCGATGTAACCCACTCGTGCACCCAACTGATCTTCAGCATCTTTTACTTTCACCAGCGTTTCTGGGTGAGCA 11210     11220     11230     11240     11250     11260     11270     11280     11290     11300
AAAACAGGAAGGCAAAATGCCGCAAAAAAGGGAATAAGGGCGACACGGAAATGTTGAATACTCATACTCTTCCTTTTTCAATATTATTGAAGCATTTATC 11310     11320     11330     11340     11350     11360     11370     11380     11390     11400
AGGGTTATTGTCTCATGAGCGGATACATATTTGAATGTATTTAGAAAAATAAACAAATAGGGGTTCCGCGCACATTTCCCCGAAAAGTGCCACCTGACGT 11410     11420     11430     11440     11450     11460     11470     11480     11490     11500
CTAAGAAACCATTATTATCATGACATTAACCTATAAAAATAGGCGTATCACGAGGCCCTTTCGTCTTCAAGAATTCTCATGTTTGACAGCTTATCATCGA 11510     11520     11530     11540     11550     11560     11570     11580     11590     11600
TAAGCTTTAATGCGGTAGTTTATCACAGTTAAATTGCTAACGCAGTCAGGCACCGTGTATGAAATCTAACAATGCCTCATCGTCATCCTCGGCACCGTC 11610     11620     11630     11640     11650     11660     11670     11680     11690     11700
ACCCTGGATGCTGTAGGCATAGGCTTGGTTATGCCGGTACTGCCGGGCCTCTTGCGGGATATCGTCCATTCCGACAGCATCGCCAGTCACTATGGCGTGC 11710     11720     11730     11740     11750     11760     11770     11780     11790     11800
TGCTGGCGCTATATGCGTTGATGCAATTTCTATGCGCACCCGTTCTCGGAGCACTGTCCGACCGCTTTGGCCGCCGCCCAGTCCTGCTCGCTTCGCTACT 11810     11820     11830     11840     11850     11860     11870     11880     11890     11900
TGGAGCCACTATCGACTACGCGATCATGGCGACCACACCCGTCCTGTGGATCCTCTACGCCGGACGCATCGTGGCCGGCATCACCGGCGCCACAGGTGCG 11910     11920     11930     11940     11950     11960     11970     11980     11990     12000
GTTGCTGGCGCCTATATCGCCGACATCACCGATGGGGAAGATCGGGCTCGCCACTTCGGGCTCATGAGCGCTTGTTTCGGCGTGGGTATGGTGGCAGGCC 12010     12020     12030     12040     12050     12060     12070     12080     12090     12100
CCGTGGCCGGGGGACTGTTGGGCGCCATCTCCTTGCATGCACCATTCCTTGCGGCGGCGGTGCTCAACGGCCTCAACCTACTACTGGGCTGCTTCCTAAT 12110     12120     12130     12140     12150     12160     12170     12180     12190     12200
GCAGGAGTCGCATAAGGGAGAGCGTCGACCGATGCCCTTGAGAGCCTTCAACCCAGTCAGCTCCTTCCGGTGGGCGCGGGGCATGACTATCGTCGCCGCA 12210     12220     12230     12240     12250     12260     12270     12280     12290     12300
CTTATGACTGTCTTCTTTATCATGCAACTCGTAGGACAGGTGCCGGCAGCGCTCTGGGTCATTTTCGGCGAGGACCGCTTTCGCTGGAGCGCGACGATGA 12310     12320     12330     12340     12350     12360     12370     12380     12390     12400
TCGGCCTGTCGCTTGCGGTATTCGGAATCTTGCACGCCCTCGCTCAAGCCTTCGTCACTGGTCCCGCCACCAAACGTTTCGGCGAGAAGCAGGCCATTAT
```

APPENDIX 1-continued

```
      12410     12420     12430     12440     12450     12460     12470     12480     12490     12500
CGCCGGCATGGCGGCCGACGCGCTGGGCTACGTCTTGCTGGCGTTCGCGACGCGAGGCTGGATGGCCTTCCCCATTATGATTCTTCTCGCTTCCGGCGGC 12510     12520     12530     12540     12550     12560     12570     12580     12590     12600
ATCGGGATGCCCGCGTTGCAGGCCATGCTGTCCAGGCAGGTAGATGACGACCATCAGGGACAGCTTCAAGGATCGCTCGCGGCTCTTACCAGCCTAACTT 12610     12620     12630     12640     12650     12660     12670     12680     12690     12700
CGATCACTGGACCGCTGATCGTCACGGCGATTTATGCCGCCTCGGCGAGCACATGGAACGGGTTGGCATGGATTGTAGGCGCCGCCCTATACCTTGTCTG 12710     12720     12730     12740     12750     12760     12770     12780     12790     12800
CCTCCCCGCGTTGCGTCGCGGTGCATGGAGCCGGGCCACCTCGACCTGAATGGAAGCCGGCGGCACCTCGCTAACGGATTCACCACTCCAAGAATTGGAG 12810     12820     12830     12840     12850     12860     12870     12880     12890     12900
CCAATCAATTCTTGCGGAGAACTGTGAATGCGCAAACCAACCCTTGGCAGAACATATCCATCGCGTCCGCCATCTCCAGCAGCCGCACGCGGCGCATCTC 12910     12920     12930     12940     12950     12960     12970     12980     12990     13000
GGGCAGCGTTGGGTCCTGGCCACGGGTGCGCATGATCGTGCTCCTGTCGTTGAGGACCCGGCTAGGCTGGCGGGGTTGCCTTACTGGTTAGCAGAATGAA 13010     13020     13030     13040     13050     13060     13070     13080     13090     13100
TCACCGATACGCGAGCGAACGTGAAGCGACTGCTGCTGCAAAACGTCTGCGACCTGAGCAACAACATGAATGGTCTTCGGTTTCCGTGITTCGTAAAGTC 13110     13120     13130     13140     13150     13160     13170     13180     13190     13200
TGGAAACGCGGAAGTCAGCGCCCTGCACCATTATGTTCCGGATCTGCATCGCAGGATGCTGCTGGCTACCCTGTGGAACACCTACATCTGTATTAACGAA 13210     13220     13230     13240     13250     13260     13270     13280     13290     13300
GCGCTGGCATTGACCCTGAGTGATTTTTCTCTGGTCCCGCCGCATCCATACCGCCAGTTGTTTACCCTCACAACGTTCCAGTAACCGGGCATGTTCATCA 13310     13320     13330     13340     13350     13360     13370     13380     13390     13400
TCAGTAACCCGTATCGTGAGCATCCTCTCTCGTTTCATCGGTATCATTACCCCCATGAACAGAAATCCCCCTTACACGGAGGCATCAGTGACCAAACAGG 13410     13420     13430     13440     13450     13460     13470     13480     13490     13500
AAAAAACCGCCCTTAACATGGCCCGCTTTATCAGAAGCCAGACATTAACGCTTCTGGAGAAACTCAACGAGCTGGACGCGGATGAACAGGCAGACATCTG 13510     13520     13530     13540     13550     13560     13570     13580     13590     13600
TGAATCGCTTCACGACCACGCTGATGAGCTTTACCGCAGCTGCCTCGCGCGTTTCGGTGATGACGGTGAAAACCTCTGACACATOCAGCTCCCGGAGACG 13610     13620     13630     13640     13650     13660     13670     13680     13690     13700
GTCACAGCTTGTOTGTAAGCGGATGCCGGGAGCAGACAAGCCCGTCAGGGCGCGTCAGCCGGTGTTGGCGGGTGTCGGGGCGCAGCCATGACCCAGTCAC 13710     13720     13730     13740     13750     13760     13770     13780     13790     13800
GTAGCGATAGCGGAGTGTATACTGGCTTAACTATGCGGCATCAGAGCAGATTGTACTGAGAGTGCACCATATGCGGTGTGAAATACCGCACAGATGCGTA 13810     13820     13830     13840     13850     13860     13870     13880     13890     13900
AGGAGAAAATACCGCATCAGGCGCTCTTCCGCTTCCTCGCTCACTGACTCGCTGCGCTCGGTCGTTCGGCTGCGGCGAGCGGTATCAGCTCACTCAAAGG 13910     13920     13930     13940     13950     13960     13970     13980     13990     14000
CGGTAATACGGTTATCCACAGAATCAGGGGATAACGCAGGAAAGAACATGTGAGCAAAAGGCCAGCAAAAGGCCAGGAACCGTAAAAAGGCCGCGTTGCT 14010     14020     14030     14040     14050     14060     14070     14080     14090     14100
GGCGTTTTTCCATAGGCTCCGCCCCCCTGACGAGCATCACAAAAATCGACGCTCAAGTCAGAGGTGGCGAAACCCGACAGGACTATAAAGATACCAGGCG 14110     14120     14130     14140     14150     14160     14170     14180     14190     14200
TTTCCCCCTGGAAGCTCCCTCGTGCGCTCTCCTGTTCCGACCCTGCCGCTTACCGGATACCTGTCCGCCTTTCTCCCTTCGGGAACCGTGGCGCTTTCTC 14210     14220     14230     14240     14250     14260     14270     14280     14290     14300
ATAGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATC 14310     14320     14330     14340     14350     14360     14370     14380     14390     14400
CGGTAACTATCGTCTTGAGTCCAACCCGGTAAGACACGACTTATCGCCAdTGGCAGCAGCCACTGGTAACAGGATTAGCAGAGCGAGGTATGTAGGCGGT 14410     14420     14430     14440     14450     14460     14470     14480     14490     14500
GCTACAGAGTTCTTGAAGTGGTGGCCTAACTACGGCTACACTAGAAGGACAGTATTTGGTATCTGCGCTCTGCTGAAGCCAGTTACCTTCGGAAAAAGAG 14510     14520     14530     14540     14550     14560     14570     14580     14590     14600
TTGGTACCTCTTGATCCGGCAAACAAACCACCGCTGGTAGCGGTGGTTTTTTTCTTTGCAAGCAGCAGATTACGCGCAGAAAAAAAGGATCTCAAGAAGA 14610     14620     14630     14640     14650     14660     14670     14680     14690     14700
TCCTTTGATCTTTTCTACGGGGTCTGACGCTCAGTGGAACCAAAACTCACGTTAAGGGATTTTGGTCATGAGATTATCAAAAAGGATCTTCACCTAGATC 14710     14720     14730     14740     14750     14760     14770     14780     14790     14800
CTTTTAAATTAAAAATGAAGTTTTAAATCAATCTAAAGTATATATGAGTAAACTTGGTCTGACAGTTACCAATGCTTAATCAGTGAGGCACCTATCTCAG 14810     14820     14830     14840     14850     14860     14870     14880     14890     14900
CGATCTGTCTATTTCGTTCATCCATAGTTGCCTGACTCCCCGTCGTGTAGATAACTACGATACGGGAGGGCTTACCATCTGGCCCCAGTGCTGCAATGAT 14910     14920     14930     14940     14950     14960     14970     14980     14990     15000
ACCGCGAGACCCACGCTCACCGGCTCCAGATTTATCAGCAATAAACCAGCCAGCCGGAAGGGCCGAGCGCAGAAGTGGTCCTGCAACTTTATCCGCCTCC 15010     15020     15030     15040     15050     15060     15070     15080     15090     15100
```

APPENDIX 1-continued

```
ATCCAGTCTATTAATTGTTGCCGGGAAGCTAGAGTAAGTAGTTCGCCAGTTAATAGTTTGCGCAACGTTGTTGCCATTGCTGCAAGATCTGGCTAGCGAT 15110     15120     15130     15140     15150
GACCCTGCTGATTGGTTCGCTGACCATTTCCGGGCGCGCCGATTTAGGTGACACTATAG
```

APPENDIX 2

```
Nucleotide and amino acid sequence of DEN3 (Sleman/78) cDNA plasmid p3
(DNA: SEQ ID NO: 48; Protein: SEQ ID NO: 49)
Bases 1 to 10707: DEN3 virus genome cDNA
Bases 95 to 10264: DEN3 polyprotein ORF
Bases 95 to 436: C protein ORF
Bases 437 to 934: prM protein ORF
Bases 935 to 2413: E protein ORF
Bases 2414 to 3469: NS1 protein ORF
Bases 3470 to 4123: NS2A protein ORF
Bases 4124 to 4513: NS2B protein ORF
Bases 4514 to 6370: NS3 protein ORF
Bases 6371 to 6751: NS4A protein ORF
Bases 6752 to 6820: 2K protein ORF
Bases 6821 to 7564: NS4B protein ORF
Bases 7575 to 10264: NS5 protein ORF
          10        20        30        40        50        60        70        80        90       100
AGTTGTTAGTCTACGTGGACCGACAAGAACAGTTTCGACTCGGAAGCTTGCTTAACGTAGTACTGACAGTTTTTTATTAGAGAGCAGATCTCTGATGAAC
                                                                                                 MetAsn>

110       120       130       140       150       160       170       180       190       200
AACCAACGGAAAAAGACGGGAAAACCGTCTATCAATATGCTGAAACGCGTGAGAAACCGTGTGTCAACTGGATCACAGTTGGCGAAGAGATTCTCAAGAG
AsnGlnArgLysLysThrGlyLysProSerIleAsnMetLeuLysArgValArgAsnArgValSerThrGlySerGlnLeuAlaLysArgPheSerArg>

210       220       230       240       250       260       270       280       290       300
CACTGGTGAACGGCCAAGGACCAATGAAATTGGTTATGGCGTTCATAGCTTTCCTCAGATTTCTAGCCATTCCACCGACAGCAGGAGTCTTGGCTAGATG
GlyLeuLeuAsnGlyGlnGlyProMetLysLeuValMetAlaPheIleAlaPheLeuArgPheLeuAlaIleProProThrAlaGlyValLeuAlaArgTrp>

310       320       330       340       350       360       370       380       390       400
GGGAACCTTTAAGAAGTCGGGGGCTATTAAGGTCCTGAGAGGCTTCAAGAAGGAGATCTCAAACATGCTGAGCATTATCAACAGACGGAAAAAGACATCG
GlyThrPheLysLysSerGlyAlaIleLysValLeuArgGlyPheLysLysGluIleSerAsnMetLeuSerIleIleAsnArgArgLysLysThrSer>

410       420       430       440       450       460       470       480       490       500
CTCTGTCTCATGATGATGTTACCAGCAACACTTGCTTTCCACTTGACTTCACGAGATGGAGAGCCGCGCATGATTGTGGGGAAGAATGAAAGAGGAAAT
LeuCysLeuMetMetMetLeuProAlaThrLeuAlaPheHisLeuThrSerArgAspGlyGluProArgMetIleValGlyLysAsnGluArgGlyLys>

510       520       530       540       550       560       570       580       590       600
CCCTACTTTTTAAGACAGCCTCTGGAATCAACATGTGCACACTCATAGCCATGGATTTGGGAGAGATGTGTGATGACACGGTCACCTACAAATGCCCCCT
SerLeuLeuIleLysThrAlaSerGlyIleAsnMetCysThrLeuIleAlaMetAspLeuGlyGluMetCysAspAspThrValThrTyrLysCysProLeu>

610       620       630       640       650       660       670       680       690       700
CATTACTGAAGTGGAGCCTGAAGACATTGACTGCTGGTGCAACCTTACATCGACATGGGTGACCTACGGAACGTGCAATCAAGCTGGAGAGCACAGACGG
IleThrGluValGluProGluAspIleAspCysTrpCysAsnLeuThrSerThrTrpValThrTyrGlyThrCysAsnGlnAlaGlyGluHisArgArg>

710       720       730       740       750       760       770       780       790       800
GACAAAAGATCGGTGGCGTTAGCTCCCCATGTCGGCATGGGACTGGACACACGCACCCAAACCTGGATGTCGGCTGAAGGAGCTTGGAGACAGGTCGAGA
AspLysArgSerVaaAlaLeuAlaProHisValGlyMetGlyLeuAspThrArgThrGlnThrTrpMetSerAlaGluGlyAlaTrpAraGlnValGlu>

810       820       830       840       850       860       870       880       890       900
AGGTAGAGACATGGGCCTTTAGGCACCCAGGGTTCACAATACTAGCCCTATTTCTTGCCCATTACATAGGCACTTCCTTGACCCAGAAAGTGGTTATTTT
LysValGluThrTrpAlaPheArgHisProGlyPheThrIleLeuAlaLeuPheLeuAlaHisTyrIleGlyThrSerLeuThrGlnLysValValIlePhe>

910       920       930       940       950       960       970       980       990      1000
CATACTACTAATGCTGGTCACCCCATCCATGACAATGAGATGCGTGGGAGTAGGAAACAGAGATTTTGTGGAAGGCCTATCAGGAGCTACGTGGGTTGAC
IleLeuLeuMetLeuValThrProSerMetThrMetArgCysValGlyValGlyAsnArgAspPheValGluGlyLeuSerGlyAlaThrTrpValAsp>

1010      1020      1030      1040      1050      1060      1070      1080      1090      1100
GTGGTGCTCGAGCACGGTGGGTGTGTGACTACCATGGCTAAGAACAAGCCCACGCTGGATATAGAGCTCCAGAAGACCGAGGCCACCCAACTGGCGACCC
ValValLeuGluHisGlyGlyCysValThrThrMetAlaLysAsnLysProThrLeuAspIleGluLeuGlnLysThrGluAlaThrGlnLeuAlaThr>

1110      1120      1130      1140      1150      1160      1170      1180      1190      1200
TAAGGAAACTATGTATTGAGGGGAAAATTACCAACGTAACAACCGACTCAAGGTGCCCCACCCAAGGGGAAGCGATTTTACCTGAGGAGCAGGACCAGAA
LeuArgLysLeuCysIleGluGlyLysIleThrAsnValThrThrAspSerArgCysProThrGlnGlyGluAlaIleLeuProGluGluGlnAspGlnAsn>

1210      1220      1230      1240      1250      1260      1270      1280      1290      1300
CCACGTGTGCAAGCACACATACGTGGACAGAGGCTGGGGAAACGGTTGTGGTTTGTTTGGCAAGGGAAGCCTGGTAACATGCGCGAAATTTCAATGTTTG
HisValCysLysHisThrTyrValAspArgGlyTrpGlyAsnGlyCysGlyLeuPheGlyLysGlySerLeuValThrCysAlaLysIleGlnCysLeu>

1310      1320      1330      1340      1350      1360      1370      1330      1390      1400
GAATCAATAGAGGGGAAAGTGGTGCAGCATGAGAACCTCAAATACACCGTCATCATCACAGTGCACACAGGAGATCAACACCAGGTGGGAAATGAAACGC
GluSerIleGluGlyLysValValGlnHisGluAsnLeuLysTyrThrValIleIleThrValHisThrGlyAspGlnHisGlnValGlyAsnGluThr>
```

APPENDIX 2-continued

```
      1410      1420      1430      1440      1450      1460      1470      1480      1490      1500
AGGGAGTCACGGCTGAGATAACACCCCAGGCATCAACCGTTGAAGCCATCTTACCTGAATATGGAACCCTTGGGCTAGAATGCTCACCACGGACAGGTTT
GlnGlyValThrAlaGluIleThrProGlnAlaSerThrValGluAlaIleLeuProGluTyrGlyThrLeuGlyLeuGluCysSerProArgThrGlyLeu>

1510      1520      1530      1540      1550      1560      1570      1580      1590      1600
AGATTTCAATGAAATGATTTTGTTGACAATGAAGAACAAAGCATGGATGGTACATAGACAATGGTTTTTTGACCTACCTTTACCATGGACATCAGGAGCT
AspIleAsnGluMetIleLeuLeuThrMetLysAsnLysAlaTrpMetValHisArgGlnTrpPhePheAspLeuProLeuProTrpThrSerGlyAla>

1610      1620      1630      1640      1650      1660      1670      1680      1690      1700
ACAACAGAAACACCAACCTGGAATAAGAAAGAGCTTCTTGTGACATTCAAAAACGCACATGCAAAAAACCAAGAAGTAGTAGTCCTTGGATCGCAAGAGG
ThrThrGluThrProThrTrpAsnLysLysGluLeuLeuValThrPheLysAsnAlaHisAlaLysLysGlnGluValValValLeuGlySerGlnGlu>

1710      1720      1730      1740      1750      1760      1770      1780      1790      1800
GAGCAATGCACACAGCACTGACAGGAGCTACAGAGATCCAAACCTCAGGAGGCACAAGTATTTTTGCGGGGCACTTAAAATGTAGACTCAAGATGGACAA
GlyAlaMetHisThrAlaLeuThrGlyAlaThrGluIleGlnThrSerGlyGlyThrSerIlePheAlaGlyHisLeuLysCysArgLeuLysMetAspLys>

1810      1820      1830      1840      1850      1860      1870      1880      1890      1900
ATTGGAACTCAAGGGGATGAGCTATGCAATGTGCTTGAATGCCTTTGTGTTGAAGAAAGAAGTCTCCGAAACGCAACATGGGACAATACTCATCAAGGTT
LeuGluLeuLysGlyMetSerTyrAlaMetCysLeuAsnAlaPheValLeuLysLysGluValSerGluThrGlnHisGlyThrIleLeuIleLysVal>

1910      1920      1930      1940      1950      1960      1970      1980      1990      2000
GAGTACAAAGGGGAAGATGCACCTTGCAAGATTCCTTTCTCCACGGAGGATGGACAAGGGAAAGCCCACAATGGCAGACTGATCACAGCTAACCCAGTGG
GluTyrLysGlyGluAspAlaProCysLysIleProPheSerThrGluAspGlyGlnGlyLysAlaHisAsnGlyArgLeuIleThrAlaAsnProVal>

2010      2020      2030      2040      2050      2060      2070      2080      2090      2100
TGACCAAGAAGGAGGAGCCTGTCAATATTGAGGCAGAACCTCCTTTTGGGGAAAGCAATATAGTAATTGGAATTGGAGACAAAGCCTTGAAAATCAACTG
ValThrLysLysGluGluProValAsnIleGluAlaGluProProPheGlyGluSerAsnIleValIleGlyIleGlyAspLysAlaLeuLysIleAsnTrp>

2110      2120      2130      2140      2150      2160      2170      2180      2190      2200
GTACAAGAAGGGAAGCTCGATTGGAAGATGTTCGAGGCCACTGCCAGAGGTGCAAGGCGCATGGCCATCTTGGGAGACACAGCCTGGGACTTTGGATCA
TyrLysLysGlySerSerIleGlyLysMetPheGluAlaThrAlaArgGlyAlaArgArgMetAlaIleLeuGlyAspThrAlaTrpAspPheGlySer>

2210      2220      2230      2240      2250      2260      2270      2280      2290      2300
GTAGGTGCTGTTTTAAATTCATTAGGAAAAATGGTGCACCAAATATTTGGAAGTGCTTACACAGCCCTATTTAGTGGAGTCTCCTGGATAATGAAAATTG
ValGlyGlyValLeuAsnSerLeuGlyLysMetValHisGlnIlePheGlySerAlaTyrThrAlaLeuPheSerGlyValSerTrpIleMetLysIle>

2310      2320      2330      2340      2350      2360      2370      2380      2390      2400
GAATAGGTGTCCTTTTAACCTGGATAGGGTTGAATTCAAAAAACACTAGTATGAGCTTTAGCTGCATTGTGATAGGAATCATTACACTCTATCTGGGAGC
GlyIleGlyValLeuLeuThrTrpIleGlyLeuAsnSerLysAsnThrSerMetSerPheSerCysIleValIleGlyIleIleThrLeuTyrLeuGlyAla>

2410      2420      2430      2440      2450      2460      2470      2480      2490      2500
CGTGGTGCAAGCTGACATGGGGTGTGTCATAAACTGGAAAGGCAAAGAACTCAAATGTGGAAGTGGAATTTTCGTCACTAATGAGGTCCACACCTGGACA
ValValGlnAlaAspMetGlyCysValIleAsnTrpLysGlyLysGluLeuLysCysGlySerGlyIlePheValThrAsnGluValHisThrTrpThr>

2510      2520      2530      2540      2550      2560      2570      2580      2590      2600
GAGCAATACAAATTTCAAGCAGACTCCCCCAAAAGACTGGCGACAGCCATTGCAGGCGCTTGGGAGAATGGAGTGTGCGGAATCAGGTCGACAACCAGAA
GluGlnTyrLysPheGlnAlaAspSerProLysAraLeuAlaThrAlaIleAlaGlyAlaTrpGluAsnGlyValCysGlyIleArgSerThrThrArg>

2610      2620      2630      2640      2650      2660      2670      2680      2690      2700
TGGAGAACCTCTTGTGAAGCAAATAGCCAATGAACTGAACTACATATTATGGGAAAACAACATCAAATTAACGGTAGTTGTGGGTGATATAATTGGGGT
MetGluAsnLeuLeuTrpLysGlnIleAlaAsnGluLeuAsnTyrIleLeuTrpGluAsnAsnIleLysLeuThrValValValGlyAspIleIleGlyVal>

2710      2720      2730      2740      2750      2760      2770      2780      2790      2800
CTTAGAGCAAGGGAAAGAACACTAACACCACAACCCATGGAACTAAAATATTCATGGAAAACATGGGGAAAGGCGAAGATAGTGACAGCTGAAACACAA
LeuGluGlnGlyLysArgThrLeuThrProGlnProMetGluLeuLysTyrSerTrpLysThrTrpGlyLysAlaLysIleValThrAlaGluThrGln>

2810      2820      2830      2840      2850      2860      2870      2880      2890      2900
AATTCCTCTTTCATAATAGATGGGCCAAACACACCAGAGTGTCCAAGTGCCTCAAGAGCATGGAATGTGTGGGAGGTGGAAGATTACGGGTTCGGAGTCT
AsnSerSerPheIleIleAspGlyProAsnThrProGluCysProSerAlaSerArgAlaTrpAsnValTrpGluValGluAspTyrGlyPheGlyVal>

2910      2920      2930      2940      2950      2960      2970      2980      2990      3000
TCACAACTAACATATGGCTGAAACTCCGAGAGATGTACACCCAACTATGTGACCACAGGCTAATGTCGGCAGCCGTTAAGGATGAGAGGGCCGTACACGC
PheThrThrAshIleTrpLeuLysLeuArgGluMetTyrThrGlnLeuCysAspHisArgLeuMetSerAlaAlaValLysAspGluArgAlaValHisAla>

3010      3020      3030      3040      3050      3060      3070      3080      3090      3100
CGACATGGGCTATTGGATAGAAAGCCAAAAGAATGGAAGTTGGAAGCTAGAAAAGGCATCCCTCATAGAGGTAAAAACCTGCACATGGCCAAAATCACAC
AspMetGlyTyrTrpIleGluSerGlnLysAsnGlySerTrpLysLeuGluLysAlaSerLeuIleGluValLysThrCysThrTrpProLysSerHis>

3110      3120      3130      3140      3150      3160      3170      3180      3190      3200
ACTCTTTGGAGCAATGGTGTGCTAGAGAGTGACATGATCATCCCAAAGAGTCTGGCTGGTCCCATTTCCCAACACAACTACAGGCCCGGATACCACACCC
ThrLeuTrpSerAshGlyValLeuGluSerAspMetIleIleProLysSerLeuAlaGlyProIleSerGlnHisAsnTyrArgProGlyTyrHisThr>

3210      3220      3230      3240      3250      3260      3270      3280      3290      3300
AAACGGCAGGACCCTGGCACTTAGGAAAATTGGAGCTGGACTTCAACTATTGTGAAGGAACAACAGTTGTCATCACAGAAAATTGTGGGACAAGAGGCCC
GlnThrAlaGlyProTrpHisLeuGlyLysLeuGluLeuAspPheAsnTyrCysGluGlyThrThrValValIleThrGluAsnCysGlyThrArgGlyPro>

3310      3320      3330      3340      3350      3360      3370      3380      3390      3400
ATCACTGAGAACAACAACAGTGTCAGGGAAGTTGATACACGAATGGTGTTGCCGCTCGTGTACACTTCCTCCCCTGCGATACATGGGAGAAGACGGCTGC
SerLeuArgThrThrThrValSerGlyLysLeuIleHisGluTrpCysCysArgSerCysThrLeuProProLeuArgTyrMetGlyGluAspGlyCys>
```

APPENDIX 2-continued

```
              3410      3420      3430      3440      3450      3460      3470      3480      3490      3500
TGGTATGGCATGGAAATTAGACCCATTAATGAGAAAGAAGAGAACATGGTAAAGTCTTTAGTCTCAGCAGGGAGTGGAAAGGTGGATAACTTCACAATGG
TrpTyrGlyMetGluIleArgProIleAsnGluLysGluGluAsnMetValLysSerLeuValSerAlaGlySerGlyLysValAspAsnPheThrMet>

3510      3520      3530      3540      3550      3560      3570      3580      3590      3600
GTGTCTTGTGTTTGGCAATCCTTTTTGAAGAGGTGATGAGAGGAAAATTTGGGAAAAAGCACATGATTGCAGGGGTTCTCTTCACGTTTGTACTCCTTCT
GlyValLeuCysLeuAlaIleLeuPheGluGluValMetArgGlyLysPheGlyLysLysHisMetIleAlaGlyValLeuPheThrPheValLeuLeuLeu>

3610      3620      3630      3640      3650      3660      3670      3680      3690      3700
CTCAGGGCAAATAACATGGAGAGACATGGCGCACACACTCATAATGATTGGGTCCAACGCCTCTGACAGAATGGGAATGGGCGTCACTTACCTAGCATTG
SerGlyGlnIleThrTrpArgAspMetAlaHisThrLeuIleMetIleGlySerAsnAlaSerAspArgMetGlyMetGlyValThrTyrLeuAlaLeu>

3710      3720      3730      3740      3750      3760      3770      3780      3790      3800
ATTGCAACATTTAAAATTCAGCCATTTTTGGCTTTGGGATTCTTCCTGAGGAAACTGACATCTAGAGAAAATTTATTGTTGGGAGTTGGGTTGGCCATGG
IleAlaThrPheLysIleGlnProPheLeuAlaLeuGlyPhePheLeuArgLysLeuThrSerArgGluAsnLeuLeuLeuGlyValGlyLeuAlaMet>

3810      3820      3830      3840      3850      3860      3870      3880      3890      3900
CAACAACGTTACAACTGCCAGAGGACATTGAACAAATGGCGAATGGAATAGCTTTAGGGCTCATGGCTCTTAAATTAATAACACAATTTGAAACATACCA
AlaThrThrLeuGlnLeuProGluAspIleGluGlnMetAlaAsnGlyIleAlaLeuGlyLeuMetAlaLeuLysLeuIleThrGlnPheGluThrTyrGln>

3910      3920      3930      3940      3950      3960      3970      3980      3990      4000
ACTATGGACGGCATTAGTCTCCCTAATGTGTTCAAATACAATTTTCACGTTGACTGTTGCCTGGAGAACAGCCACCCTGATTTTGGCCGGAATTTCTCTT
LeuTrpThrAlaLeuValSerLeuMetCysSerAsnThrIlePheThrLeuThrValAlaTrpArgThrAlaThrLeuIleLeuAlaGlyIleSerLeu>

4010      4020      4030      4040      4050      4060      4070      4080      4090      4100
TTGCCAGTGTGCCAGTCTTCGAGCATGAGGAAAACAGATTGGCTCCCAATGGCTGTGGCAGCTATGGGAGTTCCACCCCTACCACTTTTTATTTTCAGTT
LeuProValCysGlnSerSerSerMetArgLysThrAspTrpLeuProMetAlaValAlaAlaMetGlyValProProLeuProLeuPheIlePheSer>

4110      4120      4130      4140      4150      4160      4170      4180      4190      4200
TGAAAGATACGCTCAAAAGGAGAAGCTGGCCACTGAATGAGGGGGTGATGGCTGTTGGACTTGTGAGTATTCTAGCTAGTTCTCTCCTTAGGAATGACGT
LeuLysAspThrLeuLysArgArgSerTrpProLeuAsnGluGlyValMetAlaValGlyLeuValSerIleLeuAlaSerSerLeuLeuArgAsnAspVal>

4210      4220      4230      4240      4250      4260      4270      4280      4290      4300
GCCCATGGCTGGACCATTAGTGGCTGGGGGCTTGCTGATAGCGTGCTACGTCATAACTGGCACGTCAGCAGACCTCACTGTAGAAAAAGCAGCAGATGTG
ProMetAlaGlyProLeuValAlaGlyGlyLeuLeuIleAlaCysTyrValIleThrGlyThrSerAlaAspLeuThrValGluLysAlaAlaAspVal>

4310      4320      4330      4340      4350      4360      4370      4380      4390      4400
ACATGGGAGGAAGAGGCTGAGCAAACAGGAGTGTCCCACAATTTAATGATCACAGTTGATGACGATGGAACAATGAGAATAAAAGATGATGAGACTGAGA
ThrTrpGluGluGluAlaGluGlnThrGlyValSerHisAsnLeuMetIleThrValAspAspAspGlyThrMetArgIleLysAspAspGluThrGlu>

4410      4420      4430      4440      4450      4460      4470      4480      4490      4500
ACATCTTAACAGTGCTTTTGAAAACAGCATTACTAATAGTGTCAGGCATTTTTCCATACTCCATACCCGCAACACTGTTGGTCTGGCACACTTGGCAAAA
AsnIleLeuThrValLeuLeuLysThrAlaLeuLeuIleValSerGlyIlePheProTyrSerIleProAlaThrLeuLeuValTrpHisThrTrpGlnLys>

4510      4520      4530      4540      4550      4560      4570      4580      4590      4600
GCAAACCCCAAAGATCCGGTGTCCTATGGGACGTTCCCAGCCCCCCAGAGACACAGAAAGCAGAACTGGAAGAAGGGGTTTATAGGATCAAGCAGCAAGGA
GlnThrGlnArgSerGlyValLeuTrpAspValProSerProProGluThrGlnLysAlaGluLeuGluGluGlyValTyrArgIleLysGlnGlnGly>

4610      4620      4630      4640      4650      4660      4670      4680      4690      4700
ATTTTTGGGAAAACCCAAGTGGGGGTTGGAGTACAAAAAGAAGGAGTTTTCCACACCATGTGGCACGTCACAAGAGGAGCAGTGTTGACACACAATGGGA
IlePheGlyLysThrGlnValGlyValGlyValGlnLysGluGlyValPheHisThrMetTrpHisValThrArgGlyAlaValLeuThrHisAsnGly>

4710      4720      4730      4740      4750      4760      4770      4780      4790      4800
AAAGACTGGAACCAAACTGGGCTAGCGTGAAAAAAGATCTGATTTCATACGGAGGAGGATGGAAATTGAGTGCACAATGGCAAAAGGAGAGGAGGTGCA
LysArgLeuGluProAsnTrpAlaSerValLysLysAspLeuIleSerTyrGlyGlyGlyTrpLysLeuSerAlaGlnTrpGlnLysGlyGluGluValGln>

4810      4820      4830      4840      4850      4860      4870      4880      4890      4900
GGTTATTGCCGTAGAGCCTGGGAAGAACCCAAAGAACTTTCAAACCATGCCAGGCATTTTCCAGACAACAACAGGGGAGATAGGAGCGATTGCACTGGAC
ValIleAlaValGluProGlyLysAsnProLysAsnPheGlnThrMetProGlyIlePheGlnThrThrThrGlyGluIleGlyAlaIleAlaLeuAsp>

4910      4920      4930      4940      4950      4960      4970      4980      4990      5000
TTCAAGCCTGGAACTTCAGGATCTCCCATCATAAACAGAGAGGGAAAGGTACTGGGATTGTATGGCAATGGAGTGGTCACAAAGAATGGTGGCTATGTCA
PheLysProGlyThrSerGlySerProIleIleAsnArgGluGlyLysValLeuGlyLeuTyrGlyAsnGlyValValThrLysAsnGlyGlyTyrVal>

5010      5020      5030      5040      5050      5060      5070      5080      5090      5100
GTGGAATAGCACAAACAAATGCAGAACCAGACGGACCCGACACCAGAGTTGAAGAAGAGATGTTCAAAAAGCGAAATCTAACCATAATGGATCTCCATCC
SerGlyIleAlaGlnThrAsnAlaGluProAspGlyProThrProGluLeuGluGluGluMetIleLysLysArgAsnLeuThrIleMetAspLeuHisPro>

5110      5120      5130      5140      5150      5160      5170      5180      5190      5200
CGGGTCAGGAAAGACGCGGAAATATCTTCCAGCTATTGTTAGAGAGGCAATCAAGAGACGCTTAAGGACTCTAATTTTGGCACCAACAAGGGTAGTTGCA
GlySerGlyLysThrArgLysTyrLeuProAlaIleValArgGluAlaIleLysArgArgLeuArgThrLeuIleLeuAlaProThrArgValValAla>

5210      5220      5230      5240      5250      5260      5270      5280      5290      5300
GCTGAGATGGAAGAAGCATTGAAAGGGCTCCCAATAAGGTATCAAACAACTGCAACAAAATCTGAACACACAGGGAGAGAGATTGTTGATCTAATGTGCC
AlaGluMetGluGluAlaLeuLysGlyLeuProIleArgTyrGlnThrThrAlaThrLysSerGluHisThrGlyArgGluIleValAspLeuMetCys>

5310      5320      5330      5340      5350      5360      5370      5380      5390      5400
ACGCAACGTTCACAATGCGTTTGCTGTCACCAGTCAGGGTTCCAAACTACAACTTGATAATAATGGATGAGGCTCATTTCACAGACCCAGCCAGTATAGC
HisAlaThrPheThrMetArgLeuLeuSerProValArgValProAsnTyrAsnLeuIleIleMetAspGluAlaHisIleThrAspProAlaSerIleAla>
```

APPENDIX 2-continued

```
              5410      5420      5430      5440      5450      5460      5470      5480      5490      5500
GGCTAGAGGGTACATATCAACTCGTGTAGGAATGGGAGAGCCAGCCGCAATTTTCATGACAGCCACACCCCCTGGAACAGCTGATGCCTTTCCTCAGAGC
AlaArgGlyTyrIleSerThrArgValGlyMetGlyGluAlaAlaAlaIlePheMetThrAlaThrProProGlyThrAlaAspAlaPheProGlnSer>

5510      5520      5530      5540      5550      5560      5570      5580      5590      5600
AACGCTCCAATTCAAGATGAAGAAAGAGACATACCAGAACGCTCATGGAATTCAGGCAATGAATGGATTACCGACTTTGCCGGGAAGACGGTGTGGTTTG
AsnAlaProIleGlnAspGluGluArgAspIleProGluArgSerTrpAsnSerGlyAsnGluTrpIleThrAspPheAlaGlyLysThrValTrpPhe>

5610      5620      5630      5640      5650      5660      5670      5680      5690      5700
TCCCTAGCATCAAAGCTGGAAATGACATAGCAAACTGCTTGCGGAAAAATGGAAAAAAGGTCATTCAACTTAGTAGGAAGACTTTTGACACAGAATATCA
ValProSerIleLysAlaGlyAsnAspIleAlaAsnCysLeuArgLysAsnGlyLysLysValIleGlnLeuSerArgLysThrPheAspThrGluTyrGln>

5710      5720      5730      5740      5750      5760      5770      5780      5790      5800
AAAGACTAAACTAAATGATTGGGACTTTGTGGTGACAACAGACATTTCAGAAATGGGAGCCAATTTCAAAGCAGACAGAGTGATCGACCCAAGAAGATGT
LysThrLysLeuAsnAspTrpAspPheValValThrThrAspIleSerGluMetGlyAlaAsnPheLysAlaAspArgValIleAspProArgArgCys>

5810      5820      5830      5840      5850      5860      5870      5880      5890      5900
CTCAAGCCAGTGATTTTGACAGACGGACCCGAGCGCGTGATCCTGGCGGACCAATGCCAGTCACCGTAGCGAGCGCTGCGCAAAGGAGAGGGAGAGTTG
LeuLysProValIleLeuThrAspGlyProGluArgValIleLeuAlaGlyProMetProValThrValAlaSerAlaAlaGlnArgArgGlyArgVal>

5910      5920      5930      5940      5950      5960      5970      5980      5990      6000
GCAGGAACCCACAAAAAGAAAATGACCAATACATATTCATGGGCCAGCCCCTCAATAATGATGAAGACCATGCTCACTGGACAGAAGCAAAAATGCTGCT
GlyArgAsnProGlnLysGluAsnAspGlnTyrIlePheMetGlyGlnProLeuAsnAsnAspGluAspHisAlaHisTrpThrGluAlaLysMetLeuLeu>

6010      6020      6030      6040      6050      6060      6070      6080      6090      6100
AGACAACATCAACACACCAGAAGGGATCATACCAGCTCTCTTTGAACCAGAAAGGGAGAAGTCAGCCGCCATAGACGGCGAATACCGCCTGAAGGGTGAG
AspAsnIleAsnThrProGluGlyIleIleProAlaLeuPheGluProGluArgGluLysSerAlaAlaIleAspGlyGluTyrArgLeuLysGlyGlu>

6110      6120      6130      6140      6150      6160      6170      6180      6190      6200
TCCAGGAAGACCTTCGTGGAACTCATGAGGAGGGGTGACCTCCCAGTTTGGCTAGCCCATAAAGTAGCATCAGAAGGGATCAAATATACAGATAGAAAGT
SerArgLysThrPheValGluLeuMetArgAraGlyAspLeuProValTrpLeuAlaHisLysValAlaSerGluGlyIleLysTyrThrAspArgLys>

6210      6220      6230      6240      6250      6260      6270      6280      6290      6300
GGTGTTTTGATGGAGAACGCAACAATCAAATTTTAGAGGAGAATATGGATGTGGAAATCTGGACAAAGGAAGGAGAAAAGAAAAAATTGAGACCTAGGTG
TrpCysPheAspGlyGluArgAsnAsnGlnIleLeuGluGluAsnMetAspValGluIleTrpThrLysGluGlyGluLysLysLysLeuArgProArgTrp>

6310      6320      6330      6340      6350      6360      6370      6380      6390      6400
GCTTGATGCCCGCACTTATTCAGATCCCTTAGCGCTCAAGGAATTCAAGGACTTTGCGGCTGGTAGAAAGTCAATTGCCCTTGATCTTGTGACAGAAATA
LeuAspAlaArgThrTyrSerAspProLeuAlaLeuLysGluPheLysAspPheAlaAlaGlyArgLysSerIleAlaLeuAspLeuValThrGluIle>

6410      6420      6430      6440      6450      6460      6470      6480      6490      6500
GGAAGAGTGCCTTCACACTTAGCTCACAGAACGAGAAACGCCCTGGACAATCTGGTGATGTTGCACACGTCAGAACATGGCGGGAGGGCCTACAGGCATG
GlyArgValProSerHisLeuAlaHisArgThrArgAsnAlaLeuAspAsnLeuValMetLeuHisThrSerGluHisGlyGlyArgAlaTyrArgHis>

6510      6520      6530      6540      6550      6560      6570      6580      6590      6600
CAGTGGAGGAACTACCAGAAACAATGGAAACACTCTTACTCCTGGGACTGATGATCCTGTTAACAGGTGGAGCAATGCTTTTCTTGATATCAGGTAAAGG
AlaValGluGluLeuProGluThrMetGluThrLeuLeuLeuLeuGlyLeuMetIleLeuLeuThrGlyGlyAlaMetLeuIleLeuIleSerGlyLysGly>

6610      6620      6630      6640      6650      6660      6670      6680      6690      6700
GATTGGAAAGACTTCAATAGGACTCATTTGTGTAGCTGCTTCCAGGGGTATGTTATGGATGGCTGATGTCCCACTCCAATGGATCGCGTCTGCCATAGTC
IleGlyLysThrSerIleGlyLeuIleCysValAlaAlaSerSerGlyMetLeuTrpMetAlaAspValProLeuGlnTrpIleAlaSerAlaIleVal>

6710      6720      6730      6740      6750      6760      6770      6780      6790      6800
CTGGAGTTTTTTATGATGGTGTTACTTATACCAGAACCAGAAAAGCAGAGAACTCCCCAAGACAATCAACTCGCATATGTCGTGATAGGCATACTCACAC
LeuGluIlePheMetMetValLeuLeuIleProGluProGluLysGlnArgThrProGlnAspAsnGlnLeuAlaTyrValValIleGlyIleLeuThr>

6810      6820      6830      6840      6850      6860      6870      6880      6890      6900
TGGCTGCAATAGTAGCAGCCAATGAAATGGGACTGTTGGAAACCACAAAGAGAGATTTAGGAATGTCCAAAGAACCAGGTGTTGTTTCTCCAACCAGCTA
LeuAlaAlaIleValAlaAlaAsnGluMetGlyLeuLeuGluThrThrLysArgAspLeuGlyMetSerLysGluProGlyValValSerProThrSerTyr>

6910      6920      6930      6940      6950      6960      6970      6980      6990      7000
TTTGGATGTGGACTTGCACCCAGCATCAGCCTGGACATTGTACGCTGTGGCCACAACAGTAATAACACCAATGTTGAGACATACCATAGAGAATTCCACA
LeuAspValAspLeuHisProAlaSerAlaTrpThrLeuTyrAlaValAlaThrThrValIleThrProMetLeuArgHisThrIleGluAsnSerThr>

7010      7020      7030      7040      7050      7060      7070      7080      7090      7100
GCAAATGTGTCCCTGGCAGCTATAGCCAACCAGGCAGTGGTCCTGATGGGTTTAGAAAAGGATGGCCAATATCGAAAATGGACTTAGGCGTGCCACTAT
AlaAsnValSerLeuAlaAlaIleAlaAsnGlnAlaValValLeuMetGlyLeuAspLysGlyTrpProIleSerLysMetAspLeuGlyValProLeu>

7110      7120      7130      7140      7150      7160      7170      7180      7190      7200
TGGCACTGGGTTGTTATTCACAAGTGAACCCACTAACTCTCACAGCGGCAGTTCTCCTGCTAGTCACGCATTATGCTATTATAGGTCCAGGATTGCAGGC
LeuAlaLeuGlyCysTyrSerGlnValAsnProLeuThrLeuThrAlaAlaValLeuLeuLeuValThrHisTyrAlaIleIleGlyProGlyLeuGlnAla>

7210      7220      7230      7240      7250      7260      7270      7280      7290      7300
AAAAGCCACTCGTGAAGCTCAAAAAAGGACAGCTGCTGGAATAATGAAGAATCCAACGGTGGATGGATAATGACAATAGACCTAGATCCTGTAATATAC
LysAlaThrArgGluAlaGlnLysArgThrAlaAlaGlyIleMetLysAsnProThrValAspGlyIleMetThrIleAspLeuAspProValIleTyr>

7310      7320      7330      7340      7350      7360      7370      7380      7390      7400
GATTCAAAATTTGAAAAGCAACTAGGACAGGTTATGCTCCTGGTTCTGTGTGCAGTTCAACTTTTGTTAATGAGAACATCATGGGCTTTTTGTGAAGCTC
AspSerLysIleGluLysGlnLeuGlyGlnValMetLeuLeuValLeuCysAlaValGlnLeuLeuLeuMetArgThrSerTrpAlaPheCysGluAla>
```

APPENDIX 2-continued

```
         7410      7420      7430      7440      7450      7460      7470      7480      7490      7500
TAACCCTAGCCACAGGACCAATAACAACACTCTGGGAAGGATCACCTGGGAAGTTCTGGAACACCACGATAGCTGTTTCCATGGCGAACATCTTTAGAGG
LeuThrLeuAlaThrGlyProIleThrThrLeuTrpGluGlySerProGlyLysPheTrpAsnThrThrIleAlaValSerMetAlaAsnIlePheArgGly>

7510      7520      7530      7540      7550      7560      7570      7580      7590      7600
GAGCTATTTAGCAGGAGCTGGGCTTGCTTTTTCTATCATGAAATCAGTTGGAACAGGAAAGAGAGGGACAGGGTCACAGGGTGAAACCTTGGGAGAAAAG
SerTyrLeuAlaGlyAlaGlyLeuAlaPheSerIleMetLysSerValGlyThrGlyLysArgGlyThrGlySerGlnGlyGluThrLeuGlyGluLys>

7610      7620      7630      7640      7650      7660      7670      7680      7690      7700
TGGAAAAAGAAATTGAATCAATTACCCCGGAAAGAGTTTGACCTTTACAAGAAATCCGGAATCACTGAAGTGGATAGAACAGAAGCCAAAGAAGGGTTGA
TrpLysLysLysLeuAsnGlnLeuProArgLysGluPheAspLeuTyrLysLysSerGlyIleThrGluValAspArgThrGluAlaLysGluGlyLeu>

7710      7720      7730      7740      7750      7760      7770      7780      7790      7800
AAAGAGGAGAAATAACACACCATGCCGTGTCCAGAGGCAGCGCAAAACTTCAATGGTTCGTGGAGAGAAACATGGTCATCCCCGAAGGAAGAGTCATAGA
LysArgGlyGluIleThrHisHisAlaValSerArgGlySerAlaLysLeuGlnTrpPheValGluArgAsnMetValIleProGluGlyArgValIleAsp>

7810      7820      7830      7840      7850      7860      7870      7880      7890      7900
CTTAGGCTGTGGAAGAGGAGGCTGGTCATATTATTGTGCAGGACTGAAAAAAGTTACAGAAGTGCGAGGATACACAAAAGGCGGCCCAGGACATGAAGAA
LeuGlyCysGlyArgGlyGlyTrpSerTyrTyrCysAlaGlyLeuLysLysValThrGluValAraGlyTyrThrLysGlyGlyProGlyHisGluGlu>

7910      7920      7930      7940      7950      7960      7970      7980      7990      8000
CCAGTACCTATGTCTACATACGGATGGAACATAGTCAAGTTAATGAGTGGAAAGGATGTGTTTTATCTTCCACCTGAAAAGTGTGATACTCTATTGTGTG
ProValProMetSerThrTyrGlyTrpAsnIleValLysLeuMetSerGlyLysAspValIleTyrLeuProProGluLysCysAspThrLeuLeuCys>

8010      8020      8030      8040      8050      8060      8070      8080      8090      8100
ACATTGGAGAATCTTCACCAAGCCCAACAGTGGAAGAAAGCAGAACCATAAGAGTCTTGAAGATGGTTGAACCATGGCTAAAAAATAACCAGTTTTGCAT
AspIleGlyGluSerSerProSerProThrValGluGluSerArgThrIleArgValLeuLysMetValGluProTrpLeuLysAsnAsnGlnPheCysIle>

8110      8120      8130      8140      8150      8160      8170      8180      8190      8200
TAAAGTATTGAACCCTTACATGCCAACTGTGATTGAGCACCTAGAAAGACTACAAAGGAAACATGGAGGAATGCTTGTGAGAAATCCACTCTCACGAAAC
LysValLeuAsnProTyrMetProThrValIleGluHisLeuGluArgLeuGlnArgLysHisGlyGlyMetLeuValArgAsnProLeuSerArgAsn>

8210      8220      8230      8240      8250      8260      8270      8280      8290      8300
TCCACGCACGAAATGTACTGGATATCTAATGGCACAGGCAATATCGTTTCTTCAGTCAACATGGTATCCAGATTGCTACTTAACAGATTCACAATGACAC
SerThrHisGluMetTyrTrpIleSerAsnGlyThrGlyAsnIleValSerSerValAsnMetValSerArgLeuLeuLeuAsnArgPheThrMetThr>

8310      8320      8330      8340      8350      8360      8370      8380      8390      8400
ATAGGAGACCCACCATAGAGAAAGATGTGGATTTAGGAGCGGGGACCCGACATGTCAATGCGGAACCAGAAACACCCAACATGGATGTCATTGGGGAAAG
HisArgArgProThrIleGluLysAspValAspLeuGlyAlaGlyThrArgHisValAsnAlaGluProGluThrProAsnMetAspValIleGlyGluArg>

8410      8420      8430      8440      8450      8460      8470      8480      8490      8500
AATAAGAAGGATCAAGGAGGAGCATAGTTCAACATGGCACTATGATGATGAAAATCCTTATAAAACGTGGGCTTACCATGGATCCTATGAAGTTAAGGCC
IleArgArgIleLysGluGluHisSerSerThrTrpHisTyrAspAspGluAsnProTyrLysThrTrpAlaTyrHisGlySerTyrGluValLysAla>

8510      8520      8530      8540      8550      8560      8570      8580      8590      8600
ACAGGCTCAGCCTCCTCCATGATAAATGGAGTCGTGAAACTCCTCACGAAACCATGGGATGTGGTGCCCATGGTGACACAGATGGCAATGACGGATACAA
ThrGlySerAlaSerSerMetIleAsnGlyValValLysLeuLeuThrLysProTrpAspValValProMetValThrGlnMetAlaMetThrAspThr>

8610      8620      8630      8640      8650      8660      8670      2680      8690      8700
CCCCATTCGGCCAGCAAAGGGTTTTTAAAGAGAAAGTGGACACCAGGACACCCAGACCTATGCCAGGAACAAGAAAGGTTATGGAGATCACAGCGGAATG
ThrProPheGlyGlnGlnArgValPheLysGluLysValAspThrAraThrProArgProMetProGlyThrArgLysValMetGluIleThrAlaGluTrp>

8710      8720      8730      8740      8750      8760      8770      8780      8790      8800
GCTTTGGAGAACCCTGGGAAGGAACAAAAGACCCAGATTATGTACGAGAGAGGAGTTCACAAAAAAGGTCAGAACCAACGCAGCTATGGGCGCCGTTTTT
LeuTrpArgThrLeuGlyArgAsnLysAraProArgLeuCysThrAraGluGluPheThrLysLysValArgThrAsnAlaAlaMetGlyAlaValPhe>

8810      8820      8830      8840      8850      8860      8870      8880      8890      8900
ACAGAGGAGAACCAATGGGACAGTGCTAGAGCTGCTGTTGAGGATGAAGAATTCTGGAAACTCGTGGACAGAGAACGTGAACTCCACAAATTGGGCAAGT
ThrGluGluAsnGlnTrpAspSerAlaArgAlaAlaValGluAspGluGluPheTrpLysLeuValAspArgGluArgGluLeuHisLysLeuGlyLys>

8910      8920      8930      8940      8950      8960      8970      8980      8990      9000
GTGGAAGCTGCGTTTACAACATGATGGGCAAGAGAGAGAAGAAACTTGGAGAGTTTGGCAAAGCAAAAGGCAGTAGAGCCATATGGTACATGTGGTTGGG
CysGlySerCysValTyrAsnMetMetGlyLysArgGluLysLysLeuGlyGluPheGlyLysAlaLysGlySerArgAlaIleTrpTyrMetTrpLeuGly>

9010      9020      9030      9040      9050      9060      9070      9080      9090      9100
AGCCAGATACCTTGAGTTCGAAGCACTCGGATTCTTAAATGAAGACCATTGGTTCTCGCGTGAAAACTCTTACAGTGGAGTAGAAGGAGAAGGACTGCAC
AlaArgTyrLeuGluPheGluAlaLeuGlyPheLeuAsnGluAspHisTrpPheSerArgGluAsnSerTyrSerGlyValGluGlyGluGlyLeuHis>

9110      9120      9130      9140      9150      9160      9170      9180      9190      9200
AAGCTGGGATACATCTTAAGAGACATTTCCAAGATACCCGGAGGAGCTATGTATGCTGATGACACAGCTGGTTGGGACACAAGAATAACAGAAGATGACC
LysLeuGlyTyrIleLeuArgAspIleSerLysIleProGlyGlyAlaMetTyrAlaAspAspThrAlaGlyTrpAspThrArgIleThrGluAspAsp>

9210      9220      9230      9240      9250      9260      9270      9280      9290      9300
TGCACAATGAGGAGAAAAATCACACAGCAAATGGACCCTGAACACAGGCAGTTAGCAAACGCTATATTCAAGCTCACATACCAAAACAAAGTGGTCAAAGT
LeuHisAsnGluGluLysIleThrGlnGlnMetAspProGluHisArgGlnLeuAlaAsnAlaIlePheLysLeuThrTyrGlnAsnLysValValLysVal>

9310      9320      9330      9340      9350      9360      9370      9380      9390      9400
TCAACGACCAACTCCAAAGGGCACGGTAATGGACATCATATCTAGGAAAGACCAAAGAGGCAGTGGACAGGTGGAACTTATGGTCTGAATACATTCACC
GlnArgProThrProLysGlyThrValMetAspIleIleSerArgLysAspGlnArgGlySerGlyGlnValGlyThrTyrGlyLeuAsnThrPheThr>
```

APPENDIX 2-continued

```
           9410      9420      9430      9440      9450      9460      9470      9480      9490      9500
AACATGGAAGCCCAGTTAATCAGACAAATGGAAGGAGAAGGTGTGTTGTCGAAGGCAGACCTCGAGAACCCTCATCTGCTAGAGAAGAAAGTTACACAAT
AsnMetGluAlaGlnLeuIleArgGlnMetGluGlyGluGlyValLeuSerLysAlaAspLeuGluAsnProHisLeuLeuGluLysLysValThrGln>

9510      9520      9530      9540      9550      9560      9570      9580      9590      9600
GGTTGGAAACAAAAGGAGTGGAGAGGTTAAAAAGAATGGCCATCAGCGGGGATGATTGCGTGGTGAAACCAATTGATGACAGGTTCGCCAATGCCCTGCT
TrpLeuGluThrLysGlyValGluArgLeuLysArgMetAlaIleSerGlyAspAspCysValValLysProIleAspAspArgPheAlaAsnAlaLeuLeu>

9610      9620      9630      9640      9650      9660      9670      9680      9690      9700
TGCCCTGAATGACATGGGAAAAGTTAGGAAGGACATACCTCAATGGCAGCCATCAAAGGGATGGCATGATTGGCAACAGGTCCCTTTCTGCTCCCACCAC
AlaLeuAsnAspMetGlyLysValArgLysAspIleProGlnTrpGlnProSerLysGlyTrpHisAspTrpGlnGlnValProPheCysSerHisHis>

9710      9720      9730      9740      9750      9760      9770      9780      9790      9800
TTTCATGAATTGATCATGAAAGATGGAAGAAAGTTGGTAGTTCCCTGCAGACCTCAGGATGAATTAATCGGGAGAGCGAGAATCTCTCAAGGAGCAGGAT
PheHisGluLeuIleMetLysAspGlyArgLysLeuValValProCysArgProGlnAspGluLeuIleGlyArgAlaArgIleSerGlnGlyAlaGly>

9810      9820      9830      9340      9850      9860      9870      9330      9890      9900
GGAGCCTTAGAGAAACTGCATGCCTAGGGAAAGCCTACGCCCAAATGTGGACTCTCATGTACTTTCACAGAAGAGATCTTAGACTAGCATCCAACGCCAT
TrpSerLeuArgGluThrAlaCysLeuGlyLysAlaTyrAlaGlnMetTrpThrLeuMetTyrPheHisArgArgAspLeuArgLeuAlaSerAsnAlaIle>

9910      9920      9930      9940      9950      9960      9970      9980      9990     10000
ATGTTCAGCAGTACCAGTCCATTGGGTCCCCACAAGCAGAACGACGTGGTCTATTCATGCTCACCATCAGTGGATGACTACAGAAGACATGCTTACTGTT
CysSerAlaValProValHisTrpValProThrSerArgThrThrTrpSerIleHisAlaHisHisGlnTrpMetThrThrGluAspMetLeuThrVal>

10010     10020     10030     10040     10050     10060     10070     10080     10090     10100
TGGAACAGGGTGTGGATAGAGGATAATCCATGGATGGAAGACAAAACTCCAGTCAAAACCTGGGAAGATGTTCCATATCTAGGGAAGAGAGAAGACCAAT
TrpAsnArgValTrpIleGluAspAsnProTrpMetGluAspLysThrProValLysThrTrpGluAspValProTyrLeuGlyLysArgGluAspGln>

10110     10120     10130     10140     10150     10160     10170     10180     10190     10200
GGTGCGGATCACTCATTGGTCTCACTTCCAGAGCAACCTGGGCCCAGAACATACTTACGGCAATCCAACAGGTGAGAAGCCTTATAGGCAATGAAGAGTT
TrpCysGlySerLeuIleGlyLeuThrSerArgAlaThrTrpAlaGlnAsnIleLeuThrAlaIleGlnGlnValArgSerLeuIleGlyAsnGluGluPhe>

10210     10220     10230     10240     10250     10260     10270     10280     10290     10300
TCTGGACTACATGCCTTCGATGAAGAGATTCAGGAAGGAGGAGGAGTCAGAGGGAGCCATTTGGTAAACGTAGGAAGTGAAAAAGAGGCAAACTGTCAGG
LeuAspTyrMetProSerMetLysArgPheArgLysGluGluGluSerGluGlyAlaIleTrp***>

10310     10320     10330     10340     10350     10360     10370     10380     10390     10400
CCACCTTAAGCCACAGTACGGAAGAAGCTGTGCAGCCTGTGAGCCCCGTCCAAGGACGTTAAAAGAAGAAGTCAGGCCCAAAAGCCACGGTTTGAGCAAA 10410     10420     10430     10440     10450     10460     10470     10480     10490     10500
CCGTGCTGCCTGTGGCTCCGTCGTGGGGACGTAAAACCTGGGAGGCTGCAAACTGTGGAAGCTGTACGCACGGTGTAGCAGACTAGCGGTTAGAGGAGAC 10510     10520     10530     10540     10550     10560     10570     10580     10590     10600
CCCTCCCATGACACAACGCAGCAGCGGGGCCCGAGCTCTGAGGGAAGCTGTACCTCCTTGCAAAGGACTAGAGGTTAGAGGAGACCCCCCGCAAATAAAA 10610     10620     10630     10640     10650     10660     10670     10680     10690     10700
ACAGCATATTGACGCTGGGAGAGACCAGAGATCCTGCTGTCTCCTCAGCATCATTCCAGGCACAGAACGCCAGAAAATGGAATGGTGCTGTTGAATCAAC 10710     10720     10730     10740     10750     10760     10770     10780     10790     10800
AGGTTCTGGTACCGGTAGGCATCGTGGTGTCACGCTCGTCGTTTGGTATGGCTTCATTCAGCTCCGGTTCCCAACGATCAAGGCGAGTTACATGATCCCC 10810     10820     10830     10840     10850     10860     10870     10880     10890     10900
CATGTTGTGCAAAAAACCGGTTAGCTCCTTCGGTCCTCCGATCGTTGTCAGAAGTAACTTGGCCGCAGTGTTATCACTCATGGTTATGGCAGCACTGCAT 10910     10920     10930     10940     10950     10960     10970     10980     10990     11000
AATTCTCTTACTGTCATGCCATCCGTAAGATGCTTTTCTGTGACTGGTGAGTACTCAACCAAGTCATTCTGAGAATAGTGTATGCGGCGACCGAGTTGCT 11010     11020     11030     11040     11050     11060     11070     11080     11090     11100
CTTGCCCGGCGTCAACACGGGATAATACCGCGCCACATAGCAGAACTTTAAAAGTGCTCATCATTGGAAAACGTTCTTCGGGGCGAAAACTCTCAAGGAT 11110     11120     11130     11140     11150     11160     11170     11180     11190     11200
CTTACCGCTGTTGAGATCCAGTTCGATGTAACCCACTCGTGCACCCAACTGATCTTCAGCATCTTTTACTTTCACCAGCGTTTCTGGGTGAGCAAAAACA 11210     11220     11230     11240     11250     11260     11270     11280     11290     11300
GGAAGGCAAAATGCCGCAAAAAAGGGAATAAGGGCGACACGGAAATGTTGAATACTCATACTCTTCCTTTTTCAATATTATTGAACCATTTATCAGGGTT 11310     11320     11330     11340     11350     11360     11370     11380     11390     11400
ATTGTCTCATGAGCGGATACATATTTGAATGTATTTAGAAAAATAAACAAATAGGGGTTCCGCGCACATTTCCCCGAAAAGTGCCACCTGACGTCTAAGA 11410     11420     11430     11440     11450     11460     11470     11480     11490     11500
AACCATTATTATCATGACATTAACCTATAAAAATAGGCGTATCACGAGGCCCTTTCGTCTTCAACAATTCTCATGTTTGACAGCTTATCATCCATAAGCT 11510     11520     11530     11540     11550     11560     11570     11580     11590     11600
TTAATGCGGTAGTTTATCACAGTTAAATTGCTAACGCAGTCAGGCACCGTGTATGAAATCTAACAATGCGCTCATCGTCATCCTCGGCACCGTCACCCTG 11610     11620     11630     11640     11650     11660     11670     11680     11690     11700
GATGCTGTAGGCATAGGCTTGGTTATGCCGGTACTGCCGGGCCTCTTGCGGGATATCGTCCATTCCGACAGCATCGCCAGTCACTATGGCGTGCTGCTGG 11710     11720     11730     11740     11750     11760     11770     11780     11790     11800
```

APPENDIX 2-continued

```
CGCTATATGCGTTGATGCAATTTCTATGCGCACCCGTTCTCGGAGCACTGTCCGACCGCTTTGGCCGCCGCCCAGTCCTGCTCGCTTCGCTACTTGGAGC
         11810     11820     11830     11840     11850     11860     11870     11880     11890     11900
CACTATCCACTACGCGATCATGGCGACCACACCCGTCCTGTGGATCCTCTACGCCGGACGCATCGTGGCCGGCATCACCGGCGCCACAGGTGCGGTTGCT
         11910     11920     11930     11940     11950     11960     11970     11980     11990     12000
GGCGCCTATATCGCCGACATCACCGATGGGGAAGATCGGGCTCGCCACTTCGGGCTCATGAGCGCTTGTTTCGGCGTGGGTATGGTGGCAGGCCCCGTGG
         12010     12020     12030     12040     12050     12060     12070     12080     12090     12100
CCGGGGGACTGTTGGGCGCCATCTCCTTGCATGCACCATTCCTTGCCGCGGCGGTGCTCAACGGCCTCAACCTACTACTGGGCTGCTTCCTAATGCAGGA
         12110     12120     12130     12140     12150     12160     12170     12180     12190     12200
GTCGCATAAGGGAGAGCGTCGACCGATGCCCTTGAGAGCCTTCAACCCAGTCAGCTCCTTCCGGTGGGCGCGGGGCATGACTATCGTCGCCGCACTTATG
         12210     12220     12230     12240     12250     12260     12270     12280     12290     12300
ACTGTCTTCTTTATCATGCAACTCGTAGGACAGGTGCCGGCAGCGCTCTGGGTCATTTTCGGCGAGGACCGCTTTCGCTGGAGCGCGACGATGATCGGCC
         12310     12320     12330     12340     12350     12360     12370     12380     12390     12400
TGTCGCTTGCGGTATTCGGAATCTTGCACGCCCTCGCTCAAGCCTTCGTCACTGGTCCCGCCACCAAACGTTTCGGCGAGAAGCAGGCCATTATCGCCGG
         12410     12420     12430     12440     12450     12460     12470     12480     12490     12500
CATGGCGGCCGACGCGCTGGGCTACGTCTTGCTGGCGTTCGCGACGCGAGGCTGGATGGCCTTCCCCATTATGATTCTTCTCGCTTCCGGCGGCATCGGG
         12510     12520     12530     12540     12550     12560     12570     12580     12590     12600
ATGCCCGCGTTGCAGGCCATGCTGTCCAGGCAGGTAGATGACGACCATCAGGGACAGCTTCAAGGATCGCTCGCGGCTCTTACCAGCCTAACTTCGATCA
         12610     12620     12630     12640     12650     12660     12670     12680     12690     12700
CTGGACCGCTGATCGTCACGGCGATTTATGCCGCCTCGGCGAGCACATGGAACGGGTTGGCATGGATTGTAGGCGCCGCCCTATACCTTGTCTGCCTCCC
         12710     12720     12730     12740     12750     12760     12770     12780     12790     12800
CGCGTTGCGTCGCGGTGCATGGAGCCGGGCCACCTCGACCTGAATGGAAGCCGGCGCACCTCGCTAACGGATTCACCACTCCAAGAATTGGAGCCAATC
         12810     12820     12830     12840     12850     12860     12870     12880     12890     12900
AATTCTTGCGGAGAACTGTGAATGCGCAAACCAACCCTTGGCAGAACATATCCATCGCGTCCGCCATCTCCAGCAGCCGCACGCGGCGCATCTCGGGCAG
         12910     12920     12930     12940     12950     12960     12970     12980     12990     13000
CGTTGGGTCCTGGCCACGGGTGCGCATGATCGTGCTCCTGTCGTTGAGGACCGGCTAGGCTGGCGGGGTTGCCTTACTGGTTAGCAGAATGAATCACCG
         13010     13020     13030     13040     13050     13060     13070     13080     13090     13100
ATACGCGAGCGAACGTGAAGCGACTGCTGCTGCAAAACGTCTGCGACCTGAGCAACAACATGAATGGTCTTCGGTTTCCGTGTTTCGTAAAGTCTGGAAA
         13110     13120     13130     13140     13150     13160     13170     13180     13190     13200
CGCGGAAGTCAGCGCCCTGCACCATTATGTTCCGGATCTGCATCGCAGGATGCTGCTGGCTACCCTGTGGAACACCTACATCTGTATTAACGAAGCGCTG
         13210     13220     13230     13240     13250     13260     13270     13280     13290     13300
GCATTGACCCTGAGTGATTTTTCTCTGGTCCCGCCGCATCCATACCGCCAGTTGTTTACCCTCACAACGTTCCAGTAACCGGGCATGTTCATCATCAGTA
         13310     13320     13330     13340     13350     13360     13370     13380     13390     13400
ACCCGTATCGTGAGCATCCTCTCTCGTTTCATCGGTATCATTACCCCCATGAACAGAAATCCCCCTTACACGGAGGCATCAGTGACCAAACAGGAAAAAA
         13410     13420     13430     13440     13450     13460     13470     13480     13490     13500
CCGCCCTTAACATGGCCCGCTTTATCAGAAGCCAGACATTAACGCTTCTGGAGAAACTCAACGAGCTGGACGCGGATGAACAGGCAGACATCTGTGAATC
         13510     13520     13530     13540     13550     13560     13570     13580     13590     13600
GCTTCACGACCACGCTGATGAGCTTTACCGCAGCTGCCTCGCGCGTTTCGGTGATGACGGTGAAAACCTCTGACACATGCAGCTCCCGGAGACGGTCACA
         13610     13620     13630     13640     13650     13660     13670     13680     13690     13700
GCTTGTCTGTAAGCGGATGCCGGGAGCAGACAAGCCCGTCAGGGCGCGTCAGCGGGTGTTGGCGGGTGTCGGGGCGCAGCCATGACCCAGTCACGTAGCG
         13710     13720     13730     13740     13750     13760     13770     13780     13790     13800
ATAGCGGAGTGTATACTGGCTTAACTATGCGGCATCAGAGCAGATTGTACTGAGAGTGCACCATATGCGGTGTGAAATACCGCACAGATGCGTAAGGAGA
         13810     13820     13830     13840     13850     13860     13870     13880     13890     13900
AAATACCGCATCAGGCGCTCTTCCGCTTCCTCGCTCACTGACTCGCTGCGCTCGGTCGTTCGGCTGCGGCGAGCGGTATCAGCTCACTCAAAGGCGGTAA
         13910     13920     13930     13940     13950     13960     13970     13980     13990     14000
TACGGTTATCCACAGAATCAGGGGATAACGCAGGAAAGAACATGTGAGCAAAAGGCCAGCAAAAGGCCAGGAACCGTAAAAAGGCCGCGTTGCTGGCGTT
         14010     14020     14030     14040     14050     14060     14070     14080     14090     14100
TTTCCATAGGCTCCGCCCCCTGACGAGCATCACAAAAATCGACGCTCAAGTCAGAGGTGGCGAAACCCGACAGGACTATAAAGATACCAGGCGTTTCCC
         14110     14120     14130     14140     14150     14160     14170     14180     14190     14200
CCTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCT
         14210     14220     14230     14240     14250     14260     14270     14260     14290     14300
CACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAA
         14310     14320     14330     14340     14350     14360     14370     14380     14390     14400
CTATCGTCTTGAGTCCAACCCGGTAAGACACGACTTATCGCCACTGGCAGCAGCCACTGGTAACAGGATTAGCAGAGCGAGGTATGTAGGCGGTGCTACA
```

APPENDIX 2-continued

```
        14410      14420      14430      14440      14450      14460      14470      14480      14490      14500
GAGTTCTTGAAGTGGTGGCCTAACTACGGCTACACTAGAAGGACAGTATTTGGTATCTGCGCTCTGCTGAAGCCAGTTACCTTCGGAAAAAGAGTTGGTA 14510      14520      14530      14540      14550      14560      14570      14580      14590      14600
GCTCTTGATCCGGCAAACAAACCACCGCTGGTAGCGGTGGTTTTTTTGTTTGCAAGCAGCAGATTACGCGCAGAAAAAAAGGATCTCAAGAAGATCCTTT 14610      14620      14630      14640      14650      14660      14670      14680      14690      14700
GATCTTTTCTACGGGGTCTGACGCTCAGTGGAACGAAAACTCACGTTAAGGGATTTTGGTCATGAGATTATCAAAAAGGATCTTCACCTAGATCCTTTTA 14710      14720      14730      14740      14750      14760      14770      14780      14790      14800
AATTAAAAATGAAGTTTTAAATCAATCTAAAGTATATATGAGTAAACTTGGTCTGACAGTTACCAATGCTTAATCAGTGAGGCACCTATCTCAGCGATCT 14810      14820      14830      14840      14850      14860      14870      14880      14890      14900
GTCTATTTCGTTCATCCATAGTTGCCTGACTCCCCGTCGTGTAGATAACTACGATACGGGAGGGCTTACCATCTGCCCCCAGTGCTGCAATGATACCGCG 14910      14920      14930      14940      14950      14960      14970      14980      14990      15000
AGACCCACGCTCACCGGCTCCAGATTTATCAGCAATAAACCAGCCAGCCGGAAGGGCCGAGCGCAGAAGTGGTCCTGCAACTTTATCCGCCTCCATCCAG 15010      15020      15030      15040      15050      15060      15070      15080      15090      15100
TCTATTAATTGTTGCCGGGAAGCTAGAGTAAGTAGTTCGCCAGTTAATAGTTTGCGCAACGTTGTTGCCATTGCTGCAAGATCTGGCTAGCGATGACCCT 15110      15120      15130      15140      15150
GCTGATTGGTTCGCTGACCATTTCCGGGCGCGCCGATTTAGGTGACACTATAG
```

APPENDIX 3

```
Nucleotide and amino acid sequence of DEN1 (Puerto Rico/94) CME chimeric region
(DNA: SEQ ID NO: 50; Protein: SEQ ID NO: 51)
Bases 1 to 88 (BglII): DEN4
Bases 89 (BglII) to 2348 (XhoI): DEN1
Bases 2349 (XhoI) to 2426: DEN4
Bases 102 to 443: C protein ORF
Bases 444 to 941: prM protein ORF
Bases 942 to 2426: E protein ORF
        10         20         30         40         50         60         70         80         90        100
AGTTGTTAGTCTGTGTGGACCGACAAGGACAGTTCCAAATCGGAAGCTTGCTTAACACAGTTCTAACAGTTTGTTTGAATAGAGAGCAGATCTCTGGAAA 110        120        130        140        150        160        170        180        190        200
AATGAACAACCAACGGAAAAAGACGGGTCGACCGTCTTTCAATATGCTGAAACGCGCGAGAAACCGCGTGTCAACTGGTTCACAGTTGGCGAAGAGATTC
MetAsnAsnGlnArgLysLysThrGlyArgProSerPheAsnMetLeuLysArgAlaArgAsnArgValSerThrGlySerGlnLeuAlaLysArgPhe>

210        220        230        240        250        260        270        280        290        300
TCAAAAGGATTGCTTTCAGGCCAAGGACCCATGAAATTGGTGATGGCTTTCATAGCATTTCTAAGATTTCTAGCCATACCCCCAACAGCAGGAATTTTGG
SerLysGlyLeuLeuSerGlyGlnGlyProMetLysLeuValMetAlaPheIleAlaPheLeuArgPheLeuAlaIleProProThrAlaGlyIleLeu>

310        320        330        340        350        360        370        380        390        400
CTAGATGGAGCTCATTCAAGAAGAATGGAGCGATCAAAGTGTTACGGGGTTTCAAAAAAGAGATCTCAAGCATGTTGAACATTATGAACAGGAGGAAAAA
AlaArgTrpSerSerPheLysLysAsnGlyAlaIleLysValLeuArgGlyPheLysLysGluIleSerSerMetLeuAsnIleMetAsnArgArgLysLys>

410        420        430        440        450        460        470        480        490        500
ATCTGTGACCATGCTCCTCATGCTGCTGCCCACAGCCCTGGCGTTCCATTTGACCACACGAGGGGGAGAGCCACACATGATAGTTAGTAAGCAGGAAAGA
SerValThrMetLeuLeuMetLeuIleProThrAlaLeuAlaPheHisLeuThrThrArgGlyGlyGluProHisMetIleValSerLysGlnGluArg>

510        520        530        540        550        560        570        580        590        600
GGAAAGTCACTGTTGTTTAAGACCTCTGCAGGCATCAATATGTGGACTCTCATTGCGATGGATTTGGGAGAGTTATGCGAGGACACAATGACCTACAAAT
GlyLysSerLeuLeuPheLysThrSerAlaGlyIleAsnMetCysThrLeuIleAlaMetAspLeuGlyGluLeuCysGluAspThrMetThrTyrLys>

610        620        630        640        650        660        670        680        690        700
GCCCCCGGATCACTGAGGCGGAACCAGATGACGTTGACTGCTGGTGCAATGCCACAGACACATGGGTGACCTATGGGACGTGTTCTCAAACCGGCGAACA
CysProArgIleThrGluAlaGluProAspAspValAspLysTrpCysAsnAlaThrAspThrTrpValThrTyrGlyThrCysSerGlnThrGlyGluHis>

710        720        730        740        750        760        770        780        790        800
CCGACGAGACAAACGTTCCGTGGCACTGGCCCCACACGTGGGACTTGGTCTAGAAACAAGAACCGAAACATGGATGTCCTCTGAAGGTGCCTGGAAACAA
ArgArgAspLysArgSerValAlaLeuAlaProHisValGlyLeuGlyLeuGluThrArgThrGluThrTrpMetSerSerGluGlyAlaTrpLysGln>

810        820        830        840        850        860        870        880        890        900
GTACAAAAAGTGGAGACTTGGGCTTTGAGACACCCAGGATTCACGGTGACAGCCCTTTTTTTAGCACATGCCATAGGAAGATCCATTACTCAGAAAGGGA
ValGlnLysValGluThrTrpAlaLeuArgHisProGlyPheThrValThrAlaLeuIleLeuAlaHisAlaIleGlyThrSerIleThrGlnLysGly>

910        920        930        940        950        960        970        980        990       1000
TCATTTTCATTCTGCTGATGCTAGTAACACCATCAATGGCCATGCGATGTGTGGGAATAGGCAACAGAGACTTCGTTGAAGGACTGTCAGGAGCAACGTG
IleIlePheIleLeuLeuMetLeuValThrProSerMetAlaMetArgCysValGlyIleGlyAsnAraAspPheValGluGlyLeuSerGlyAlaThrTrp>

1010       1020       1030       1040       1050       1060       1070       1080       1090       1100
GGTGGACGTGGTATTGGAGCATGGAAGCTGCGTCACCACCATGGCAAAAGATAAACCAACATTGGACATTGAACTCTTGAAGACGGAGGTCACAAACCCT
ValAspValValLeuGluHisGlySerCysValThrThrMetAlaLysAspLysProThrLeuAspIleGluLeuLeuLysThrGluValThrAsnPro>
```

APPENDIX 3-continued

```
         1110      1120      1130      1140      1150      1160      1170      1180      1190      1200
GCCGTCTTGCGCAAACTGTGCATTGAAGCTAAAATATCAAACACCACCACCGATTCAAGGTGTCCAACACAAGGAGAGGCTACACTGGTGGAAGAACAGG
AlaValLeuArgLysLeuCysIleGluAlaLysIleSerAsnThrThrThrAspSerAryCysProThrGlnGlyGluAlaThrLeuValGluGluGln>

1210      1220      1230      1240      1250      1260      1270      1280      1290      1300
ACTCGAACTTTGTGTGTCGACGAACGTTTGTGGACAGAGGCTGGGGTAATGGCTGCGGACTATTTGGAAAAGGAAGCCTACTGACGTGTGCTAAGTTCAA
AspSerAsnPheValCysArgArgThrPheValAspArgGlyTrpGlyAsnGlyCysGlyLeuPheGlyLysGlySerLeuLeuThrCysAlaLysPheLys>

1310      1320      1330      1340      1350      1360      1370      1380      1390      1400
GTGTGTGACAAAACTAGAAGGAAAGATAGTTCAATATGAAAACTTAAAATATTCAGTGATAGTCACTGTCCACACTGGGGACCAGCACCAGGTGGGAAAC
CysValThrLysLeuGluGlyLysIleValGlnTyrGluAsnLeuLysTyrSerValIleValThrValHisThrGlyAspGlnHisGlnValGlyAsn>

1410      1420      1430      1440      1450      1460      1470      1480      1490      1500
GAGACTACAGAACATGGAACAATTGCAACCATAACACCTCAAGCTCCTACGTCGGAAATACAGCTGACTGACTACGGAGCCCTCACATTGGACTGCTCGC
GluThrThrGluHisGlyThrIleAlaThrIleThrProGlnAlaProThrSerGluIleGlnLeuThrAspTyrGlyAlaLeuThrLeuAspCysSer>

1510      1520      1530      1540      1550      1560      1570      1580      1590      1600
CTAGAACAGGGCTGGACTTTAATGAGATGGTTCTATTGACAATGAAAGAAAAATCATGGCTTGTCCACAAACAATGGTTTCTAGACTTACCACTGCCTTG
ProArgThrGlyLeuAspPheAsnGluMetValLeuLeuThrMetLysGluLysSerTrpLeuValHisLysGlnTrpIleLeuAspLeuProLeuProTrp>

1610      1620      1630      1640      1650      1660      1670      1680      1690      1700
GACTTCAGGAGCTTCAACATCTCAAGAGACTTGGAACAGACAAGATTTGCTGGTCACATTCAAGACAGCTCATGCAAAGAAACAGGAAGTAGTCGTACTG
ThrSerGlyAlaSerThrSerGlnGluThrTrpAsnArgGlnAspLeuLeuValThrPheLysThrAlaHisAlaLysLysGlnGluValValValLeu>

1710      1720      1730      1740      1750      1760      1770      1780      1790      1800
GGATCACAGGAAGGAGCAATGCACACTGCGTTGACTGGGGCGACAGAAATCCAGACGTCAGGAACGACAACAATCTTTGCAGGACACCTGAAATGCAGAC
GlySerGlnGluGlyAlaMetHisThrAlaLeuThrGlyAlaThrGluIleGlnThrSerGlyThrThrThrIlePheAlaGlyHisLeuLysCysArg>

1810      1820      1830      1840      1850      1860      1870      1880      1890      1900
TAAAAATGGATAAACTGACTTTAAAAGGGATGTCATATGTAATGTGCACAGGCTCATTTAAGCTAGAGAAGGAAGTGGCTGAGACCCAGCATGGAACTGT
LeuLysMetAspLysLeuThrLeuLysGlyMetSerValMetCysThrGlySerPheLysLeuGluLysGluValAlaGluThrGlnHisGlyThrVal>

1910      1920      1930      1940      1950      1960      1970      1980      1990      2000
TTTAGTGCAGGTTAAATACGAAGGAACAGATGCGCCATGCAAGATCCCTTTTTCGGCCCAAGATGAGAAAGGAGTGACCCAGAATGGGAGATTGATAACA
LeuValGlnValLysTyrGluGlyThrAspAlaProCysLysIleProPheSerAlaGlnAspGluLysGlyValThrGlnAsnGlyArgLeuIleThr>

2010      2020      2030      2040      2050      2060      2070      2080      2090      2100
GCCAACCCCATAGTCACTGACAAAGAAAAACCAGTCAACATTGAGACAGAACCACCTTTTGGTGAGAGCTACATCGTGGTAGGGGCAGGTGAAAAAGCTT
AlaAsnProIleValThrAspLysGluLysProValAsnIleGluThrGluProProPheGlyGluSerTyrIleValValGlyAlaGlyGluLysAla>

2110      2120      2130      2140      2150      2160      2170      2180      2190      2200
TGAAACTGAGCTGGTTCAAGAAAGGGAGCAGCATAGGGAAAATGTTCGAAGCAACTGCCCGAGGAGCGCGAAGGATGGCTATCCTGGGAGACACCGCATG
LeuLysLeuSerTrpPheLysLysGlySerSerIleGlyLysMetPheGluAlaThrAlaArgGlyAlaArgArgMetAlaIleLeuGlyAspThrAlaTrp>

2210      2220      2230      2240      2250      2260      2270      2280      2290      2300
GGACTTTGGCTCTATAGGAGGAGTGTTCACATCAGTGGGAAAATTGGTACACCAGGTTTTTGGAGCCGCATATGGGGTTCTGTTCAGCGGTGTTTCTTGG
AspPheGlySerIleGlyGlyValPheThrSerValGlyLysLeuValHisGlnValPheGlyAlaAlaTyrGlyValLeuPheSerGlyValSerTsp>

2310      2320      2330      2340      2350      2360      2370      2380      2390      2400
ACCATGAAAATAGGAATAGGGATTCTGCTGACATGGCTAGGATTAAACTCGAGGAACACTTCAATGGCTATGACGTGCATAGCTGTTGGAGGAATCACTC
ThrMetLysIleGlyIleGlyIleLeuLeuThrTrpLeuGlyLeuAsnSerArgAsnThrSerMetAlaMetThrCysIleAlaValGlyGlyI1eThr>

2410      2420
TGTTTCTGGGCTTCACAGTTCAAGCA
LeuPheLeuGlyPheThrValGlnAla>
```

APPENDIX 4

Nucleotide and amino acid sequence of DEN1 (Puerto Rico/94) ME chimeric region
(DNA: SEQ ID NO: 52; Protein: SEQ ID NO: 53)
Bases 1 to 404 (PstI): DEN4
Bases 405 (PstI) to 2345 (XhoI): DEN1
Bases 2346 (XhoI) to 2423: DEN4
Bases 102 to 440: C protein ORF
Bases 441 to 938: prM protein ORF
Bases 939 to 2423: E protein ORF

```
         10        20        30        40        50        60        70        80        90        100
AGTTGTTAGTCTGTGTGGACCGACAAGGACAGTTCCAAATCGGAAGCTTGCTTAACACAGTTCTAACAGTTTGTTTGAATAGAGAGCAGATCTCTGGAAA 110       120       130       140       150       160       170       180       190       200
AATGAACCAACGAAAAAAGGTGGTTAGACCACCTTTCAATATGCTGAAACGCGAGAGAAACCGCGTATCAACCCCTCAAGGGTTGGTGAAGAGATTCTCA
MetAsnGlnArgLysLysValValArgProProPheAsnMetLeuLysArgGluArgAsnArgValSerThrProGlnGlyLeuValLysArgPheSer>

210       220       230       240       250       260       270       280       290       300
ACCGGACTTTTTTCTGGGAAAGGACCCTTACGGATGGTGCTAGCATTCATCACGTTTTTGCGAGTCCTTTCCATCCCACCAACAGCAGGGATTCTGAAGA
ThrGlyLeuPheSerGlyLysGlyProLeuArgMetValLeuAlaPheIleThrPheLeuArgValLeuSerIleProProThrAlaGlyIleLeuLys>
```

APPENDIX 4-continued

```
         310       320       330       340       350       360       370       380       390       400
GATGGGGACAGTTGAAGAAAAATAAGGCCATCAAGATACTGATTGGATTCAGGAAGGAGATAGGCCGCATGCTGAACATCTTGAACGGGAGAAAAGGTC
ArgTrpGlyGlnLeuLysLysAsnLysAlaIleLysIleLeuIleGlyIleArgLysGluIleGlyArgMetLeuAsnIleLeuAsnGlyArgLysArgSer>

410       420       430       440       450       460       470       480       490       500
TGCAGCCATGCTCCTCATGCTGCTGCCCACAGCCCTGGCGTTCCATTTGACCACACGAGGGGGAGAGCCACACATGATAGTTAGTAAGCAGGAAAGAGGA
AlaAlaMetLeuLeuMetLeuLeuProThrAlaLeuAlaPheHisLeuThrThrArgGlyGlyGluProHisMetIleValSerLysGlnGluArgGly>

510       520       530       540       550       560       570       580       590       600
AAGTCACTGTTGTTTAAGACCTCTGCAGGCATCAATATGTGCACTCTCATTGCGATGGATTTGGGAGAGTTATGCGAGGACACAATGACCTACAAATGCC
LysSerLeuLeuPheLysThrSerAlaGlyIleAsnMetCysThrLeuIleAlaMetAspLeuGlyGluLeuCysGluAspThrMetThrTyrLysCys>

610       620       630       640       650       660       670       680       690       700
CCCGGATCACTGAGGCGGAACCAGATGACGTTGACTGCTGGTGCAATGCCACAGACACATGGGTGACCTATGGGACGTGTTCTCAAACCGGCGAACACCG
ProArgIleThrGluAlaGluProAspAspValAspCysTrpCysAsnAlaThrAspThrTrpValThrTyrGlyThrCysSerGlnThrGlyGluHisArg>

710       720       730       740       750       760       770       780       790       800
ACGAGACAAACGTTCCGTGGCACTGGCCCCACACGTGGGACTTGGTCTAGAAACAAGAACCGAAACATGGATGTCCTCTGAAGGTGCCTGGAAACAAGTA
ArgAspLysArgSerValAlaLeuAlaProHisValGlyLeuGlyLeuGluThrArgThrGluThrTrpMetSerSerGluGlyAlaTrpLysGlnVal>

810       820       830       840       850       860       870       880       890       900
CAAAAAGTGGAGACTTGGGCTTTGAGACACCCAGGATTCACGGTGACAGCCCTTTTTTTAGCACATGCCATAGGAACATCCATTACTCAGAAAGGGATCA
GlnLysValGluThrTrpAlaLeuArgHisProGlyPheThrValThrAlaLeuPheLeuAlaHisAlaIleGlyThrSerIleThrGlnLysGlyIle>

910       920       930       940       950       960       970       980       990      1000
TTTTTCATTCTGCTGATGCTAGTAACACCATCAATGGCCATGCGATGTGTGGGAATAGGCAACAGAGACTTCGTTGAAGGACTGTCAGGAGCAACGTGGGT
IlePheIleLeuLeuMetLeuValThrProSerMetAlaMetArgCysValGlyIleGlyAsnArgAspPheValGluGlyLeuSerGlyAlaThrTrpVal>

1010      1020      1030      1040      1050      1060      1070      1080      1090      1100
GGACGTGGTATTGGAGCATGGAAGCTGCGTCACCACCATGGCAAAAGATAAACCAACATTGGACATTGAACTCTTGAAGACGGAGGTCACAAACCCTGCC
AspValValLeuGluHisGlySerCysValThrThrMetAlaLysAspLysProThrLeuAspIleGluLeuLeuLysThrGluValThrAsnProAla>

1110      1120      1130      1140      1150      1160      1170      1180      1190      1200
GTCTTGCGCAAACTGTGCATTGAAGCTAAAATATCAAACACCACCACCGATTCAAGGTGTCCAACACAAGGAGAGGCTACACTGGTGGAAGAACAGGACT
ValLeuArgLysLeuCysIleGluAlaLysIleSerAsnThrThrThrAspSerArgCysProThrGlnGlyGluAlaThrLeuValGluGluGlnAsp>

1210      1220      1230      1240      1250      1260      1270      1280      1290      1300
CGAACTTTGTGTCGACGAACGTTTGTGGACAGAGGCTGGGGTAATGGCTGGGACTATTTGGAAAAGGAAGCCTACTGACGTGTGCTAAGTTCAGTG
SerAsnPheValCysArgArgThrPheValAspArgGlyTrpGlyAsnGlyCysGlyLeuPheGlyLysGlySerLeuLeuThrCysAlaLysIleLysCys>

1310      1320      1330      1340      1350      1360      1370      1380      1390      1400
TGTGACAAAACTAGAAGGAAAGATAGTTCAATATGAAAACTTAAAATATTCAGTGATAGTCACTGTCCACACTGGGGACCAGCACCAGGTGGGAAACGAG
ValThrLysLeuGluGlyLysIleValGlnTyrGluAsnLeuLysTyrSerValIleValHisThrGlyAspGlnHisGlnValGlyAsnGlu>

1410      1420      1430      1440      1450      1460      1470      1480      1490      1500
ACTACAGAACATGGAACAATTGCAACCATAACCCTCAAGCTCCTACGTCGGAAATACAGCTGACTGACTACGGAGCCCTCACATTGGACTGCTCGCCTA
ThrThrGluHisGlyThrIleAlaThrIleThrProGlnAlaProThrSerGluIleGlnLeuThrAspTyrGlyAlaLeuThrLeuAspCysSerPro>

1510      1520      1530      1540      1550      1560      1570      1580      1590      1600
GAACAGGGCTGGACTTTAATGAGATGGTTCTATTGACAATGAAAGAAAAATCATGGCTTGTCCACAAACAATGGTTTCTAGACTTACCACTGCCTTGGAC
ArgThrGlyLeuAspPheAsnGluMetValLeuLeuThrMetLysGluLysSerTrpLeuValHisLysGlnTrpPheLeuAspLeuProLeuProTrpThr>

1610      1620      1630      1640      1650      1660      1670      1680      1690      1700
TTCAGGAGCTTCAACATCTCAAGAGACTTGGAACAGACAAGATTTGCTGGTCACATTCAAGACAGCTCATGCAAAGAAACAGGAAGTAGTCGTACTGGGA
SerGlyAlaSerThrSerGlnGluThrTrpAsnArgGlnAspLeuLeuValThrPheLysThrAlaHisAlaLysLysGlnGluValValValLeuGly>

1710      1720      1730      1740      1750      1760      1770      1780      1790      1800
TCACAGGAAGGAGCAATGCACACTGCGTTGACTGGGGCGACAGAAATCCAGACGTCAGGAACGACAACAATCTTTGCAGGACACCTGAAATGCAGACTAA
SerGlnGluGlyAlaMetHisThrAlaLeuThrGlyAlaThrGluIleGlnThrSerGlyThrThrThrIlePheAlaGlyHisLeuLysCysArgLeu>

1810      1820      1830      1840      1850      1860      1870      1880      1890      1900
AAATGGATAAACTGACTTTAAAAGGGATGTCATATGTAATGTGCACAGGCTCATTTAAGCTAGAGAAGGAAGTGGCTGAGACCCAGCATGGAACTGTTTT
LysMetAspLysLeuThrLeuLysGlyMetSerTyrValMetCysThrGlySerPheLysLeuGluLysGluValAlaGluThrGlnHisGlyThrValLeu>

1910      1920      1930      1940      1950      1960      1970      1980      1990      2000
AGTGCAGGTTAAATACGAAGGAACAGATGCGCCATGCAAGATCCCTTTTTCGGCCCAAGATGAGAAAGGAGTGACCCAGAATGGGAGATTGATAACAGCC
ValGluValLysTyrGluGlyThrAspAlaProCysLysIleProPheSerAlaGlnAspGluLysGlyValThrGlnAsnGlyArgLeuIleThrAla>

2010      2020      2030      2040      2050      2060      2070      2080      2090      2100
AACCCCATAGTCACTGACAAAGAAAAACCAGTCAACATTGAGACAGAACCACCTTTTGGTGAGAGCTACATCGTGGTAGGGGCAGGTGAAAAAGCTTTGA
AsnProIleValThrAspLysGluLysProValAsnIleGluThrGluProProPheGlyGluSerTyrIleValValGlyAlaGlyGluLysAlaLeu>

2110      2120      2130      2140      2150      2160      2170      2180      2190      2200
AACTGAGCTGGTTCAAGAAAGGGAGCAGCATAGGGAAAATGTTCGAAGCAACTGCCCGAGGAGCGCGAAGGATGGCTATCCTGGGAGACACCGCATGGGA
LysLeuSerTrpPheLysLysGlySerSerIleGlyLysMetPheGluAlaThrAlaArgGlyAlaArgArgMetAlaIleLeuGlyAspThrAlaTrpAsp>

2210      2220      2230      2240      2250      2260      2270      2280      2290      2300
CTTTGGCTCTATAGGAGGAGTGTTCACATCAGTGGGAAAATTGGTACACCAGGTTTTTGGAGCCGCATATGGGGTTCTGTTCAGCGGTGTTTCTTGGACC
PheGlySerIleGlyGlyValPheThrSerValGlyLysLeuValHisGlnValPheGlyAlaAlaTyrGlyValLeuPheSerGlyValSerTrpThr>
```

APPENDIX 4-continued

```
           2310        2320        2330        2340        2350        2360        2370        2380        2390        2400
ATGAAAATAGGAATAGGGATTCTGCTGACATGGCTAGGATTAAACTCGAGGAACACTTCAATGGCTATGACGTGCATAGCTGTTGGAGGAATCACTCTGT
MetLysIleGlyIleGlyIleLeuLeuThrTrpLeuGlyLeuAsnSerArgAsnThrSerMetAlaMetThrCysIleAlaValGlyGlyIleThrLeu>

2410        2420
TTCTGGGCTTCACAGTTCAAGCA
PheLeuGlyPheThrVaiGlnAla
```

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

SEQUENCE LISTING

```
<160> NUMBER OF SEQ ID NOS: 92

<210> SEQ ID NO 1
<211> LENGTH: 82
<212> TYPE: RNA
<213> ORGANISM: Dengue 1 virus

<400> SEQUENCE: 1
gcagcagcgg ggcccaacac caggggaagc uguacccugg ugguaaggac uagagguuag    60
aggagacccc ccgcaacaac aa                                             82

<210> SEQ ID NO 2
<211> LENGTH: 84
<212> TYPE: RNA
<213> ORGANISM: Dengue 2 virus

<400> SEQUENCE: 2
agcaacaaug ggggcccaag gugagaugaa gcuguagucu cacuggaagg acuagagguu    60
agaggagacc cccccaaaac aaaa                                           84

<210> SEQ ID NO 3
<211> LENGTH: 83
<212> TYPE: RNA
<213> ORGANISM: Dengue 3 virus

<400> SEQUENCE: 3
gcagcagcgg ggcccgagcu cugagggaag cuguaccucc uugcaaagga cuagagguua    60
gaggagaccc cccgcaaaua aaa                                            83

<210> SEQ ID NO 4
<211> LENGTH: 83
<212> TYPE: RNA
<213> ORGANISM: Dengue 4 virus

<400> SEQUENCE: 4
agcaaaaggg ggcccgaagc caggaggaag cuguacuccu ggugggaagga cuagagguua    60 gaggagaccc ccccaacaca aaa                                            83

<210> SEQ ID NO 5
<211> LENGTH: 16
<212> TYPE: RNA
<213> ORGANISM: Artificial Sequence
<220> FEATURE:
<223> OTHER INFORMATION: Dengue 1 delta 30
```

-continued

```
<400> SEQUENCE: 5
ggggcccaag acuaga                                                      16

<210> SEQ ID NO 6
<211> LENGTH: 16
<212> TYPE: RNA
<213> ORGANISM: Artificial Sequence
<220> FEATURE:
<223> OTHER INFORMATION: Dengue 2 delta 30

<400> SEQUENCE: 6
ggggcccaag acuaga                                                      16

<210> SEQ ID NO 7
<211> LENGTH: 16
<212> TYPE: RNA
<213> ORGANISM: Artificial Sequence
<220> FEATURE:
<223> OTHER INFORMATION: Dengue 3 delta 30

<400> SEQUENCE: 7
ggggcccaag acuaga                                                      16

<210> SEQ ID NO 8
<211> LENGTH: 16
<212> TYPE: RNA
<213> ORGANISM: Artificial Sequence
<220> FEATURE:
<223> OTHER INFORMATION: Dengue 4 delta 30

<400> SEQUENCE: 8
ggggcccaag acuaga                                                      16

<210> SEQ ID NO 9
<211> LENGTH: 51
<212> TYPE: DNA
<213> ORGANISM: Artificial Sequence
<220> FEATURE:
<223> OTHER INFORMATION: TL2 region of p2 plasmid

<400> SEQUENCE: 9
tgggggccca aggtgagatg aagctgtagt ctcactggaa ggactagagg t               51

<210> SEQ ID NO 10
<211> LENGTH: 21
<212> TYPE: DNA
<213> ORGANISM: Artificial Sequence
<220> FEATURE:
<223> OTHER INFORMATION: TL2 region of p2 delta 30

<400> SEQUENCE: 10
tgggggccca agactagagg t                                                21

<210> SEQ ID NO 11
<211> LENGTH: 51
<212> TYPE: DNA
<213> ORGANISM: Artificial Sequence
<220> FEATURE:
<223> OTHER INFORMATION: TL2 region of p3 plasmid

<400> SEQUENCE: 11
cggggcccga gctctgaggg aagctgtacc tccttgcaaa ggactagagg t               51

<210> SEQ ID NO 12
```

```
<211> LENGTH: 20
<212> TYPE: DNA
<213> ORGANISM: Artificial Sequence
<220> FEATURE:
<223> OTHER INFORMATION: TL2 region of p3 delta 30

<400> SEQUENCE: 12
gggggcccaa gactagaggt                                          20

<210> SEQ ID NO 13
<211> LENGTH: 29
<212> TYPE: DNA
<213> ORGANISM: Artificial Sequence
<220> FEATURE:
<223> OTHER INFORMATION: Spe1 linker in p3

<400> SEQUENCE: 13
actagttaga ctaacttaag tcaactagt                                29

<210> SEQ ID NO 14
<211> LENGTH: 51
<212> TYPE: DNA
<213> ORGANISM: Artificial Sequence
<220> FEATURE:
<223> OTHER INFORMATION: rDEN2/4 junction 1

<400> SEQUENCE: 14
cagtttgttt gaatagagag cagatctctg atgaataacc aacgaaaaaa g       51

<210> SEQ ID NO 15
<211> LENGTH: 7
<212> TYPE: PRT
<213> ORGANISM: Artificial Sequence
<220> FEATURE:
<223> OTHER INFORMATION: rDEN2/4 junction 1

<400> SEQUENCE: 15

Met Asn Asn Gln Arg Lys Lys
1               5

<210> SEQ ID NO 16
<211> LENGTH: 51
<212> TYPE: DNA
<213> ORGANISM: Artificial Sequence
<220> FEATURE:
<223> OTHER INFORMATION: rDEN2/4 junction 2

<400> SEQUENCE: 16
attatcacat ggataggaat gaactcgagg aacacttcaa tggctatgac g       51

<210> SEQ ID NO 17
<211> LENGTH: 17
<212> TYPE: PRT
<213> ORGANISM: Artificial Sequence
<220> FEATURE:
<223> OTHER INFORMATION: rDEN2/4 junction 2

<400> SEQUENCE: 17

Ile Ile Thr Trp Ile Gly Met Asn Ser Arg Asn Thr Ser Met Ala Met
1               5                   10                  15

Thr

<210> SEQ ID NO 18
<211> LENGTH: 51
<212> TYPE: DNA
<213> ORGANISM: Artificial Sequence
```

```
<220> FEATURE:
<223> OTHER INFORMATION: rDEN2/4 junction 3

<400> SEQUENCE: 18
atcttgaacg ggagaaaaag gtctgcaggc atgatcatta tgctgattcc a          51

<210> SEQ ID NO 19
<211> LENGTH: 17
<212> TYPE: PRT
<213> ORGANISM: Artificial Sequence
<220> FEATURE:
<223> OTHER INFORMATION: rDEN2/4 junction 3

<400> SEQUENCE: 19

Ile Leu Asn Gly Arg Lys Arg Ser Ala Gly Met Ile Ile Met Leu Ile
1               5                   10                  15

Pro

<210> SEQ ID NO 20
<211> LENGTH: 50
<212> TYPE: DNA
<213> ORGANISM: Artificial Sequence
<220> FEATURE:
<223> OTHER INFORMATION: rDEN3/4 junction 1

<400> SEQUENCE: 20
cagtttgttt gaatagagag cagatctctg gaaaaatgaa caaccaacgg             50

<210> SEQ ID NO 21
<211> LENGTH: 5
<212> TYPE: PRT
<213> ORGANISM: Artificial Sequence
<220> FEATURE:
<223> OTHER INFORMATION: rDEN3/4 junction 1

<400> SEQUENCE: 21

Met Asn Asn Gln Arg
1               5

<210> SEQ ID NO 22
<211> LENGTH: 51
<212> TYPE: DNA
<213> ORGANISM: Artificial Sequence
<220> FEATURE:
<223> OTHER INFORMATION: rDEN3/4 junction 2

<400> SEQUENCE: 22
cttttaacct ggatagggtt gaactcgagg aacacttcaa tggctatgac g          51

<210> SEQ ID NO 23
<211> LENGTH: 17
<212> TYPE: PRT
<213> ORGANISM: Artificial Sequence
<220> FEATURE:
<223> OTHER INFORMATION: rDEN3/4 junction 2

<400> SEQUENCE: 23

Leu Leu Thr Trp Ile Gly Leu Asn Ser Arg Asn Thr Ser Met Ala Met
1               5                   10                  15

Thr

<210> SEQ ID NO 24
<211> LENGTH: 51
<212> TYPE: DNA
<213> ORGANISM: Artificial Sequence
```

<220> FEATURE:
<223> OTHER INFORMATION: rDEN3/4 junction 3

<400> SEQUENCE: 24
atcttgaacg ggagaaaaag gtctgcagtc tgtctcatga tgatgttacc a          51

<210> SEQ ID NO 25
<211> LENGTH: 17
<212> TYPE: PRT
<213> ORGANISM: Artificial Sequence
<220> FEATURE:
<223> OTHER INFORMATION: rDEN3/4 junction 3

<400> SEQUENCE: 25

Ile Leu Asn Gly Arg Lys Arg Ser Ala Val Cys Leu Met Met Met Leu
1               5                   10                  15

Pro

<210> SEQ ID NO 26
<211> LENGTH: 50
<212> TYPE: DNA
<213> ORGANISM: Artificial Sequence
<220> FEATURE:
<223> OTHER INFORMATION: rDEN1/4 junction 1

<400> SEQUENCE: 26
cagtttgttt gaatagagag cagatctctg gaaaaatgaa caaccaacgg            50

<210> SEQ ID NO 27
<211> LENGTH: 5
<212> TYPE: PRT
<213> ORGANISM: Artificial Sequence
<220> FEATURE:
<223> OTHER INFORMATION: rDEN1/4 junction 1

<400> SEQUENCE: 27

Met Asn Asn Gln Arg
1               5

<210> SEQ ID NO 28
<211> LENGTH: 51
<212> TYPE: DNA
<213> ORGANISM: Artificial Sequence
<220> FEATURE:
<223> OTHER INFORMATION: rDEN1/4 junction 2

<400> SEQUENCE: 28
ctgctgacat ggctaggatt aaactcgagg aacacttcaa tggctatgac g          51

<210> SEQ ID NO 29
<211> LENGTH: 17
<212> TYPE: PRT
<213> ORGANISM: Artificial Sequence
<220> FEATURE:
<223> OTHER INFORMATION: rDEN1/4 junction 2

<400> SEQUENCE: 29

Leu Leu Thr Trp Leu Gly Leu Asn Ser Arg Asn Thr Ser Met Ala Met
1               5                   10                  15

Thr

<210> SEQ ID NO 30
<211> LENGTH: 51
<212> TYPE: DNA
<213> ORGANISM: Artificial Sequence

```
<220> FEATURE:
<223> OTHER INFORMATION: rDEN1/4 junction 3

<400> SEQUENCE: 30
atcttgaacg ggagaaaaag gtctgcagcc atgctcctca tgctgctgcc c          51

<210> SEQ ID NO 31
<211> LENGTH: 17
<212> TYPE: PRT
<213> ORGANISM: Artificial Sequence
<220> FEATURE:
<223> OTHER INFORMATION: rDEN1/4 junction 3

<400> SEQUENCE: 31

Ile Leu Asn Gly Arg Lys Arg Ser Ala Ala Met Leu Leu Met Leu Leu
1               5                   10                  15

Pro

<210> SEQ ID NO 32
<211> LENGTH: 60
<212> TYPE: RNA
<213> ORGANISM: Dengue 4 virus

<400> SEQUENCE: 32
ccaacaaccu ugacagcauc cuuagucaug cuuuuagucc auuaugcaau aauaggccca    60

<210> SEQ ID NO 33
<211> LENGTH: 20
<212> TYPE: PRT
<213> ORGANISM: Dengue 4 virus

<400> SEQUENCE: 33

Pro Thr Thr Leu Thr Ala Ser Leu Val Met Leu Leu Val His Thr Ala
1               5                   10                  15

Ile Ile Gly Pro
            20

<210> SEQ ID NO 34
<211> LENGTH: 60
<212> TYPE: RNA
<213> ORGANISM: Dengue 1 virus

<400> SEQUENCE: 34
ccgcugacgc ugacagcggc gguauuuaug cuaguggcuc auuaugccau aauuggaccc    60

<210> SEQ ID NO 35
<211> LENGTH: 20
<212> TYPE: PRT
<213> ORGANISM: Dengue 1 virus

<400> SEQUENCE: 35

Pro Leu Thr Leu Thr Ala Ala Val Pro Met Leu Val Ala His Thr Ala
1               5                   10                  15

Ile Ile Gly Pro
            20

<210> SEQ ID NO 36
<211> LENGTH: 60
<212> TYPE: RNA
<213> ORGANISM: Dengue 2 virus

<400> SEQUENCE: 36
ccuauaaccc ucacagcggc ucuucuuuua uugguagcac auuaugccau cauaggaccg    60
```

<210> SEQ ID NO 37
<211> LENGTH: 20
<212> TYPE: PRT
<213> ORGANISM: Dengue 2 virus

<400> SEQUENCE: 37

Pro Ile Thr Leu Thr Ala Ala Leu Leu Leu Val Ala His Thr Ala
1               5                   10                  15

Ile Ile Gly Pro
            20

<210> SEQ ID NO 38
<211> LENGTH: 60
<212> TYPE: RNA
<213> ORGANISM: Dengue 3 virus

<400> SEQUENCE: 38
ccacuaacuc ucacagcggc aguucuccug cuagucacgc auuaugcuau uauaggucca    60

<210> SEQ ID NO 39
<211> LENGTH: 20
<212> TYPE: PRT
<213> ORGANISM: Dengue 3 virus

<400> SEQUENCE: 39

Pro Leu Thr Leu Thr Ala Ala Val Leu Leu Val Thr His Thr Ala
1               5                   10                  15

Ile Ile Gly Pro
            20

<210> SEQ ID NO 40
<211> LENGTH: 13
<212> TYPE: DNA
<213> ORGANISM: Artificial Sequence
<220> FEATURE:
<223> OTHER INFORMATION: primer

<400> SEQUENCE: 40
ccacgggcgc cgt                                                      13

<210> SEQ ID NO 41
<211> LENGTH: 10
<212> TYPE: DNA
<213> ORGANISM: Artificial Sequence
<220> FEATURE:
<223> OTHER INFORMATION: primer

<400> SEQUENCE: 41
aaggcctgga                                                          10

<210> SEQ ID NO 42
<211> LENGTH: 12
<212> TYPE: DNA
<213> ORGANISM: Artificial Sequence
<220> FEATURE:
<223> OTHER INFORMATION: primer

<400> SEQUENCE: 42
tatccccggg ac                                                       12

<210> SEQ ID NO 43
<211> LENGTH: 11
<212> TYPE: DNA

<213> ORGANISM: Artificial Sequence
<220> FEATURE:
<223> OTHER INFORMATION: primer

<400> SEQUENCE: 43
agagctctct c                                                         11

<210> SEQ ID NO 44
<211> LENGTH: 15
<212> TYPE: DNA
<213> ORGANISM: Artificial Sequence
<220> FEATURE:
<223> OTHER INFORMATION: primer

<400> SEQUENCE: 44
gaatctccac ccgga                                                     15

<210> SEQ ID NO 45
<211> LENGTH: 10
<212> TYPE: DNA
<213> ORGANISM: Artificial Sequence
<220> FEATURE:
<223> OTHER INFORMATION: primer

<400> SEQUENCE: 45
ctgtcgaatc                                                           10

<210> SEQ ID NO 46
<211> LENGTH: 15159
<212> TYPE: DNA
<213> ORGANISM: Artificial Sequence
<220> FEATURE:
<223> OTHER INFORMATION: Dengue 2 plasmid p2

<400> SEQUENCE: 46
agttgttagt ctacgtggac cgacaaagac agattctttg agggagctaa gctcaacgta      60
gttctaactg tttttttgatt agagagcaga tctctgatga ataaccaacg aaaaaggcg     120 agaaacacgc ctttcaatat gctgaaacgc gagagaaacc gcgtgtcaac tgtacaacag    180
ttgacaaaga gattctcact tggaatgctg cagggacgag gaccactaaa attgttcatg    240
gccctggtgg cattccttcg tttcctaaca atcccaccaa cagcagggat attaaaaga     300 tggggaacaa ttaaaaaatc aaaggctatt aatgttctga gaggcttcag aaagagatt     360 ggaaggatgc tgaatatctt aaacaggaga cgtagaactg taggcatgat catcatgctg    420
actccaacag tgatggcgtt tcatctgacc acacgcaacg gagaaccaca catgattgtc    480
agtagacaag aaaaagggaa agccttctg ttcaagacaa aggatggcac gaacatgtgt     540
accctcatgg ccatggacct tggtgagttg tgtgaagaca caatcacgta taatgtcct     600 tttctcaagc agaacgaacc agaagacata gattgttggt gcaactccac gtccacatgg    660
gtaacttatg gacatgtac caccacagga gagcacagaa gagaaaaaag atcagtggcg    720
cttgttccac acgtgggaat gggattggag acacgaactg aaacatggat gtcatcagaa    780
ggggcctgga acatgccca gagaattgaa acttggattc tgagacatcc aggctttacc    840
ataatggccg caatcctggc atacaccata gggacgacgc atttccaaag agtcctgata    900
ttcatcctac tgacagccat cgctccttca atgacaatgc gctgcatagg aatatcaaat    960
agggactttg tggaaggagt gtcaggaggg agttgggttg acatagtttt agaacatgga   1020
agttgtgtga cgacgatggc aaaaaacaaa ccaacactgg actttgaact gataaaaaca   1080
gaagccaaac aacctgccac cttaaggaag tactgtatag aggccaaact gaccaacacg   1140

```
acaacagact cgcgctgccc aacacaaggg gaacccaccc tgaatgaaga gcaggacaaa    1200
aggtttgtct gcaaacattc catggtagac agaggatggg gaaatggatg tggattgttt    1260
ggaaaaggag gcatcgtgac ctgtgctatg ttcacatgca aaaagaacat ggaaggaaaa    1320
attgtgcagc cagaaaacct ggaatacact gtcgtgataa cacctcattc aggggaagaa    1380
catgcagtgg gaaatgacac aggaaaacat ggtaaagaag tcaagataac accacagagc    1440
tccatcacag aggcggaact gacaggctat ggcactgtta cgatggagtg ctctccaaga    1500
acgggcctcg acttcaatga gatggtgttg ctgcaaatgg aagacaaagc ctggctggtg    1560
cacagacaat ggttcctaga cctaccgttg ccatggctgc ccggagcaga cacacaagga    1620
tcaaattgga tacagaaaga aacactggtc accttcaaaa atccccatgc gaaaaaacag    1680
gatgttgttg tcttaggatc ccaagagggg gccatgcata cagcactcac aggggctacg    1740
gaaatccaga tgtcatcagg aaacctgctg ttcacaggac atctcaagtg caggctgaga    1800
atggacaaat acaacttaaa agggatgtca tactccatgt gcacaggaaa gtttaaaatt    1860
gtgaaggaaa tagcagaaac acaacatgga acaatagtca ttagagtaca atatgaagga    1920
gacggctctc catgcaagat ccccttttgag ataatggatc tggaaaaaag acatgttttg    1980
ggccgcctga tcacagtcaa cccaattgta acagaaaagg acagtccagt caacatagaa    2040
gcagaacctc cattcggaga cagctacatc atcataggag tggaaccagg acaattgaag    2100
ctggactggt tcaagaaagg aagttccatc ggccaaatgt ttgagacaac aatgaggggga    2160 gcgaaaagaa tggccatttt gggtgacaca gcctgggatt ttggatctct gggaggagtg    2220
ttcacatcaa taggaaaggc tctccaccag gttttttggag caatctacgg ggctgctttc    2280
agtggggtct catggactat gaagatcctc ataggagtta tcatcacatg gataggaatg    2340
aactcacgta gcactagtct gagcgtgtca ctggtgttag tgggaatcgt gacactttac    2400
ttgggagtta tggtgcaggc cgatagtggt tgcgttgtga ctggaagaa caaagaacta    2460 aaatgtggca gtggaatatt cgtcacagat aacgtgcata catggacaga acaatacaag    2520
ttccaaccag aatccccttc aaaactggcc tcagccatcc agaaagcgca tgaagagggc    2580
atctgtggaa tccgctcagt aacaagactg gaaaatctta tgtggaaaca gataacatca    2640
gaattgaatc atattctatc agaaaatgaa gtgaaactga ccatcatgac aggagacatc    2700
aaaggaatca tgcaggtagg aaaacgatct ttgcggcctc aacccactga gttgaggtat    2760
tcatggaaaa catggggtaa agcgaaaatg ctctccacag aactccacaa tcagaccttc    2820
ctcattgatg gtccccgaaac agcagaatgc cccaacacaa acagagcttg gaattcactg    2880
gaagttgagg actacggctt tggagtattc actaccaata tatggctaag attgagagaa    2940
aagcaggatg tattttgtga ctcaaaactc atgtcagcgg ccataaagga caacagagcc    3000
gtccatgctg atatgggtta ttggatagaa agcgcactca atgatacatg gaagatagag    3060
aaagcttctt tcattgaagt caaaagttgc cactggccaa agtcacacac cctatggagt    3120
aatggagtgc tagaaagcga gatggtcatt ccaaagaatt tcgctggacc agtgtcacaa    3180
cataataaca gaccaggcta ttacacacaa acagcaggac cttggcatct aggcaagctt    3240
gagatggact ttgatttctg cgaagggact acagtggtgg taaccgagaa ctgtggaaac    3300 agagggcct ctttaagaac aaccactgcc tcaggaaaac tcataacgga atggtgttgt    3360
cgatcttgca cactaccacc actaagatac agaggtgagg atggatgttg gtacgggatg    3420
gaaatcagac cattgaaaga gaaagaagaa aatctggtca gttctctggt tacagccgga    3480
```

```
catgggcaga ttgacaattt ctcattagga atcttgggaa tggcactgtt ccttgaagaa   3540
atgctcagga ctcgagtagg aacaaaacat gcaatattac tcgtcgcagt ttctttcgtg   3600
acgctaatca cagggaacat gtcttttaga gacctgggaa gagtgatggt tatggtgggt   3660
gccaccatga cagatgacat aggcatgggt gtgacttatc tcgctctact agcagctttt   3720
agagtcagac caacctttgc agctggactg ctcttgagaa aactgacctc caaggaatta   3780
atgatgacta ccataggaat cgttcttctc tcccagagta gcataccaga gaccattctt   3840
gaactgaccg acgcgttagc tctaggcatg atggtcctca agatggtgag aaacatggaa   3900
aaatatcagc tggcagtgac catcatggct attttgtgcg tcccaaatgc tgtgatatta   3960
cagaacgcat ggaaagtgag ttgcacaata ttggcagtgg tgtctgtttc cccctgctc    4020 ttaacatcct cacaacagaa agcggactgg ataccattag cgttgacgat caaaggtctt   4080
aatccaacag ccattttct aacaaccctc tcaagaacca caagaaaag gagctggcct    4140 ttaaatgagg ccatcatggc ggttgggatg gtgagtatct tggccagctc tctcttaaag   4200
aatgacatcc ccatgacagg accattagtg gctggagggc tccttactgt gtgctacgtg   4260
ctaactgggc ggtcagccga tctggaatta gagagagcta ccgatgtcaa atgggatgac   4320
caggcagaga tatcaggtag cagtccaatc ctgtcaataa caatatcaga gatggcagc    4380 atgtcaataa agaatgaaga ggaagagcaa acactgacta tactcattag aacaggattg   4440
cttgtgatct caggactctt tccggtatca ataccaatta cagcagcagc atggtatctg   4500
tgggaagtaa agaaacaacg ggctggagtg ctgtgggatg tccccctcacc accaccccgtg 4560 ggaaaagctg aattggaaga tggagcctac agaatcaagc aaaaaggaat ccttggatat   4620
tcccagatcg gagctggagt ttacaaagaa ggaacatttc acacaatgtg gcacgtcaca   4680
cgtggcgctg tcctaatgca taaggggaag aggattgaac catcatgggc ggacgtcaag   4740
aaagacttaa tatcatatgg aggaggttgg aagctagaag gagaatggaa agaaggagaa   4800
gaagtccagg tcttggcatt ggagccaggg aaaaatccaa gagccgtcca aacaaagcct   4860
ggccttttta gaaccaacac tggaaccata ggtgccgtat ctctggactt ttcccctggg   4920
acgtcaggat ctccaatcgt cgacaaaaaa ggaaaagttg taggtctcta tggcaatggt   4980
gtcgttacaa ggagtggagc atatgtgagt gccatagctc agactgaaaa aagcattgaa   5040
gacaatccag agattgaaga tgacatcttt cgaaagagaa gattgactat catggatctc   5100
cacccaggag caggaaagac aaagagatac ctcccggcca tagtcagaga ggccataaaa   5160
agaggcttga acactaat cctagcccc actagagtcg tggcagctga atgaggaa     5220 gcccttagag gacttccaat aagataccaa actccagcta tcagggctga gcacaccggg   5280
cgggagattg tagacttaat gtgtcatgcc acatttacca tgaggctgct atcaccaatc   5340
agggtgccaa attcaacct gatcatcatg gacgaagccc atttacaga tccagcaagc   5400 atagcagcta ggggatacat ctcaactcga gtggagatgg gggaggcagc tggaattttt   5460
atgacagcca ctcctccggg tagtagagat ccatttcctc agagcaatgc accaattatg   5520
gacgaagaaa gagaaattcc ggaacgttca tggaactctg gcacgagtg ggtcacggat    5580 tttaaaggaa agactgtctg gtttgttcca agcataaaaa ccggaaatga catagcagcc   5640
tgcctgagaa agaatggaaa agggtgata caactcagta ggaagacctt tgattctgaa    5700
tatgtcaaga ctagaaccaa tgactgggat ttcgtggtta caactgacat ctcggaaatg   5760
ggcgccaact ttaaagctga gagggtcata gaccccagac gctgcatgaa accagttata   5820
ttgacagacg gcgaagagcg ggtgattctg gcaggaccca tgccagtgac ccactctagt   5880
```

```
gcagcacaaa gaagagggag aataggaagg aatccaagga atgaaaatga tcaatatata   5940
tatatggggg aaccactgga aaatgatgaa gactgtgcgc actggaagga agctaagatg   6000
ctcctagata atatcaacac acctgaagga atcattccca gcttgttcga gccagagcgt   6060
gaaaaggtgg atgccattga cggtaatatc gcttgagag  gagaagcacg gaaaactttt   6120
gtggacctaa tgagaagagg agacctacca gtctggttgg cttataaagt ggcagctgaa   6180
ggtatcaact acgcagacag aagatggtgt tttgacggaa ccagaaacaa tcaaatcttg   6240
gaagaaaatg tggaagtgga aatctggaca aaggaagggg aaaggaaaaa attgaaacct   6300
agatggttag atgctaggat ctactccgac ccactggcgc taaagagtt  caaggaattt   6360
gcagccggaa gaaagtccct aaccctgaac ctaattacag agatgggcag actcccaact   6420
tttatgactc agaaggccag agatgcacta gacaacttgg cggtgctgca cacggctgaa   6480
gcgggtggaa aggcatacaa tcatgctctc agtgaattac cggagaccct ggagacattg   6540
cttttgctga cactgttggc cacagtcacg ggaggaatct tcctattcct gatgagcgga   6600
aggggtatgg ggaagatgac cctgggaatg tgctgcataa tcacggccag catcctctta   6660
tggtatgcac aaatacagcc acattggata gcagcctcaa taatattgga gttctttctc   6720
atagtcttgc tcattccaga accagaaaag cagaggacac ctcaggataa tcaattgact   6780
tatgtcatca tagccatcct cacagtggtg gccgcaacca tggcaaacga aatgggtttt   6840
ctggaaaaaa caaagaaaga cctcggactg ggaaacattg caactcagca acctgagagc   6900
aacattctgg acatagatct acgtcctgca tcagcatgga cgttgtatgc cgtggctaca   6960
acatttatca caccaatgtt gagacatagc attgaaaatt cctcagtaaa tgtgtcccta   7020
acagccatag ctaaccaagc cacagtgcta atgggtctcg gaaaaggatg gccattgtca   7080
aagatggaca ttggagttcc cctccttgct attgggtgtt actcacaagt caaccctata   7140
accctcacag cggctcttct tttattggta gcacattatg ccatcatagg accgggactt   7200
caagccaaag caactagaga agctcagaaa agagcagcag cgggcatcat gaaaaaccca   7260
actgtggatg gaataacagt gatagatcta gatccaatac cctatgatcc aaagtttgaa   7320
aagcagttgg gacaagtaat gctcctagtc ctctgcgtga cccaagtgct gatgatgagg   7380
actacgtggg ctttgtgtga agccttaact ctagcaactg gacccgtgtc cacattgtgg   7440
gaaggaaatc cagggagatt ctggaacaca accattgcag tgtcaatggc aaacatcttt   7500
agagggagtt acctggctgg agctggactt ctctttttcta tcatgaagaa cacaaccagc   7560
acgagaagag gaactggcaa tataggagaa acgttaggag agaaatggaa aagcagactg   7620
aacgcattgg ggaaaagtga attccagatc tacaaaaaaa gtggaattca gaagtggac   7680
agaaccttag caaagaagg  cattaaaaga ggagaaacgg atcatcacgc tgtgtcgcga   7740
ggctcagcaa aactgagatg gttcgttgaa aggaatttgg tcacaccaga agggaaagta   7800
gtggaccttg gttgtggcag aggggctgg  tcatactatt gtgaggatt  aaagaatgta   7860
agagaagtta aaggcttaac aaaaggagga ccaggacacg aagaacctat ccctatgtca   7920
acatatgggt ggaatctagt acgcttacag agcggagttg atgtttttt  tgttccacca   7980
gagaagtgtg acacattgtt gtgtgacata ggggaatcat caccaaatcc cacggtagaa   8040
gcgggacgaa cactcagagt cctcaaccta gtggaaaatt ggctgaacaa taacacccaa   8100
ttttgcgtaa aggttcttaa cccgtacatg ccctcagtca ttgaaagaat ggaaccttta   8160
caacggaaat acggaggagc cttggtgaga aatccactct cacggaattc cacacatgag   8220
```

```
atgtactggg tgtccaatgc ttccgggaac atagtgtcat cagtgaacat gatttcaaga    8280
atgctgatca acagattcac tatgagacac aagaaggcca cctatgagcc agatgtcgac    8340
ctcggaagcg aacccgcaa tattggaatt gaaagtgaga caccgaacct agacataatt    8400
gggaaaagaa tagaaaaaat aaaacaagag catgaaacgt catggcacta tgatcaagac    8460
cacccataca aacatgggc ttaccatggc agctatgaaa caaaacagac tggatcagca    8520
tcatccatgg tgaacggagt agtcagattg ctgacaaaac cctggacgt tgttccaatg    8580
gtgacacaga tggcaatgac agacacaact ccttttggac aacagcgcgt cttcaaagag    8640
aaggtggata cgagaaccca agaaccaaaa gaaggcacaa aaaactaat gaaaatcacg    8700
gcagagtggc tctggaaaga actaggaaag aaaaagacac ctagaatgtg taccagagaa    8760
gaattcacaa aaaaggtgag aagcaatgca gccttggggg ccatattcac cgatgagaac    8820
aagtggaaat cggcgcgtga agccgttgaa gatagtaggt tttgggagct ggttgacaag    8880
gaaaggaacc tccatcttga agggaaatgt gaaacatgtg tatacaacat gatggggaaa    8940
agagagaaaa aactaggaga gtttggtaaa gcaaaaggca gcagagccat atggtacatg    9000
tggctcggag cacgcttctt agagtttgaa gccctaggat tttgaatga agaccattgg    9060
ttctccagag agaactccct gagtggagtg aaggagaag ggctgcataa gctaggttac    9120
atcttaagag aggtgagcaa gaaagaagga ggagcaatgt atgccgatga caccgcaggc    9180
tgggacacaa gaatcacaat agaggatttg aaaaatgaag aaatgataac gaaccacatg    9240
gcaggagaac acaagaaact tgccgaggcc atttttaaat tgacgtacca aaacaaggtg    9300
gtgcgtgtgc aaagaccaac accaagaggc acagtaatgg acatcatatc gagaagagac    9360
caaaggggta gtggacaagt tggcacctat ggcctcaaca ctttcaccaa catggaagca    9420
caactaatta ggcaaatgga gggggaagga atcttcaaaa gcatccagca cttgacagcc    9480
tcagaagaaa tcgctgtgca agattggcta gtaagagtag ggcgtgaaag gttgtcaaga    9540
atggccatca gtggagatga ttgtgttgtg aaacctttag atgatagatt tgcaagagct    9600
ctaacagctc taatgacat gggaaaggtt aggaaggaca tacagcaatg ggagccctca    9660
agaggatgga acgactggac gcaggtgccc ttctgttcac accattttca cgagttaatt    9720
atgaaagatg gtcgcacact cgtagttcca tgcagaaacc aagatgaatt gatcggcaga    9780
gcccgaattt cccagggagc tgggtggtct ttacgggaga cggcctgttt ggggaagtct    9840
tacgcccaaa tgtggagctt gatgtacttc cacagacgtg atctcaggct agcggcaaat    9900
gccatctgct cggcagtccc atcacactgg attccaacaa gccggacaac ctggtccata    9960
cacgccagcc atgaatggat gacgacggaa gacatgttga cagtttggaa cagagtgtgg    10020
atcctagaaa atccatggat ggaagacaaa actccagtgg aatcatggga ggaaatccca    10080
tacctgggaa aaagagaaga ccaatggtgc ggctcgctga ttgggctgac aagcagagcc    10140
acctgggcga gaatatcca acagcaata aaccaagtca gatccctcat ggcaatgag    10200
gaatacacag attacatgcc atccatgaaa agattcagaa gagaagagga gaggcagga    10260
gttttgtggt agaaaaacat gaaacaaaac agaagtcagg tcggattaag ccatagtacg    10320
ggaaaaacta tgctacctgt gagccccgtc caaggacgtt aaaagaagtc aggccatttt    10380
gatgccatag cttgagcaaa ctgtgcagcc tgtagctcca cctgagaagg tgtaaaaaat    10440
ccgggaggcc acaaaccatg gaagctgtac gcatggcgta gtggactagc ggttagagga    10500
gacccctccc ttacagatcg cagcaacaat ggggcccaa ggtgagatga agctgtagtc    10560
tcactggaag gactagaggt tagaggagac ccccccaaaa caaaaaacag catattgacg    10620
```

```
ctgggaaaga ccagagatcc tgctgtctcc tcagcatcat tccaggcaca ggacgccaga    10680
aaatggaatg gtgctgttga atcaacaggt tctggtaccg gtaggcatcg tggtgtcacg    10740
ctcgtcgttt ggtatggctt cattcagctc cggttcccaa cgatcaaggc gagttacatg    10800
atcccccatg ttgtgcaaaa aagcggttag ctccttcggt cctccgatcg ttgtcagaag    10860
taagttggcc gcagtgttat cactcatggt tatggcagca ctgcataatt ctcttactgt    10920
catgccatcc gtaagatgct tttctgtgac tggtgagtac tcaaccaagt cattctgaga    10980
atagtgtatg cggcgaccga gttgctcttg cccggcgtca acacgggata ataccgcgcc    11040
acatagcaga actttaaaag tgctcatcat tggaaaacgt tcttcgggc gaaaactctc      11100 aaggatctta ccgctgttga atccagttc gatgtaaccc actcgtgcac ccaactgatc      11160
ttcagcatct tttactttca ccagcgtttc tgggtgagca aaaacaggaa ggcaaaatgc    11220
cgcaaaaaag ggaataaggg cgacacggaa atgttgaata ctcatactct cctttttca    11280 atattattga agcatttatc agggttattg tctcatgagc ggatacatat ttgaatgtat    11340
ttagaaaaat aaacaaatag gggttccgcg cacatttccc cgaaaagtgc cacctgacgt    11400
ctaagaaacc attattatca tgacattaac ctataaaaat aggcgtatca cgaggccctt    11460
tcgtcttcaa gaattctcat gtttgacagc ttatcatcga taagctttaa tgcggtagtt    11520
tatcacagtt aaattgctaa cgcagtcagg caccgtgtat gaaatctaac aatgcgctca    11580
tcgtcatcct cggcaccgtc acctggatg ctgtaggcat aggcttggtt atgccggtac      11640
tgccgggcct cttgcgggat atcgtccatt ccgacagcat cgccagtcac tatggcgtgc    11700
tgctggcgct atatgcgttg atgcaatttc tatgcgcacc cgttctcgga gcactgtccg    11760
accgctttgg ccgccgccca gtcctgctcg cttcgctact tggagccact atcgactacg    11820
cgatcatggc gaccacaccc gtcctgtgga tcctctacgc cggacgcatc gtggccggca    11880
tcaccggcgc cacaggtgcg gttgctggcg cctatatcgc cgacatcacc gatggggaag    11940
atcgggctcg ccacttcggg ctcatgagcg cttgtttcgg cgtgggtatg gtggcaggcc    12000
ccgtggccgg gggactgttg ggcgccatct ccttgcatgc accattcctt gcggcggcgg    12060
tgctcaacgg cctcaaccta ctactgggct gcttcctaat gcaggagtcg cataagggag    12120
agcgtcgacc gatgcccttg agagccttca acccagtcag ctccttccgg tgggcgcggg    12180
gcatgactat cgtcgccgca cttatgactg tcttctttat catgcaactc gtaggacagg    12240
tgccggcagc gctctgggtc attttcggcg aggaccgctt tcgctggagc gcgacgatga    12300
tcggcctgtc gcttgcggta ttcggaatct tgcacgccct cgctcaagcc ttcgtcactg    12360
gtcccgccac caaacgtttc ggcgagaagc aggccattat cgccggcatg gcggccgacg    12420
cgctgggcta cgtcttgctg gcgttcgcga cgcgaggctg gatggccttc cccattatga    12480
ttcttctcgc ttccggcggc atcgggatgc ccgcgttgca ggccatgctg tccaggcagg    12540
tagatgacga ccatcaggga cagcttcaag gatcgctcgc ggctcttacc agcctaactt    12600
cgatcactgg accgctgatc gtcacggcga tttatgccgc ctcggcgagc acatggaacg    12660
ggttggcatg gattgtaggc gccgccctat accttgtctg cctccccgcg ttgcgtcgcg    12720
gtgcatggag ccgggccacc tcgacctgaa tggaagccgg cggcacctcg ctaacggatt    12780
caccactcca agaattggag ccaatcaatt cttgcggaga actgtgaatg cgcaaaccaa    12840
cccttggcag aacatatcca tcgcgtccgc catctccagc agccgcacgc ggcgcatctc    12900
gggcagcgtt gggtcctggc cacgggtgcg catgatcgtg ctcctgtcgt tgaggacccg    12960
```

```
gctaggctgg cggggttgcc ttactggtta gcagaatgaa tcaccgatac gcgagcgaac    13020
gtgaagcgac tgctgctgca aaacgtctgc gacctgagca caacatgaa tggtcttcgg     13080 tttccgtgtt tcgtaaagtc tggaaacgcg gaagtcagcg ccctgcacca ttatgttccg    13140
gatctgcatc gcaggatgct gctggctacc ctgtggaaca cctacatctg tattaacgaa    13200
gcgctggcat tgaccctgag tgattttttct ctggtcccgc cgcatccata ccgccagttg   13260
tttaccctca caacgttcca gtaaccgggc atgttcatca tcagtaaccc gtatcgtgag    13320
catcctctct cgtttcatcg gtatcattac ccccatgaac agaaatcccc cttacacgga    13380
ggcatcagtg accaaacagg aaaaaaccgc ccttaacatg gcccgcttta tcagaagcca    13440
gacattaacg cttctggaga aactcaacga gctggacgcg gatgaacagg cagacatctg    13500
tgaatcgctt cacgaccacg ctgatgagct ttaccgcagc tgcctcgcgc gtttcggtga    13560
tgacggtgaa aacctctgac acatgcagct cccggagacg gtcacagctt gtctgtaagc    13620
ggatgccggg agcagacaag cccgtcaggg cgcgtcagcg ggtgttggcg ggtgtcgggg    13680
cgcagccatg acccagtcac gtagcgatag cggagtgtat actggcttaa ctatgcggca    13740
tcagagcaga ttgtactgag agtgcaccat atgcggtgtg aaataccgca cagatgcgta    13800
aggagaaaat accgcatcag gcgctcttcc gcttcctcgc tcactgactc gctgcgctcg    13860
gtcgttcggc tgcggcgagc ggtatcagct cactcaaagg cggtaatacg gttatccaca    13920
gaatcagggg ataacgcagg aaagaacatg tgagcaaaag gccagcaaaa ggccaggaac    13980
cgtaaaaagg ccgcgttgct ggcgtttttc cataggctcc gcccccctga cgagcatcac    14040
aaaaatcgac gctcaagtca gaggtggcga acccgacag gactataaag ataccaggcg    14100
tttccccctg gaagctccct cgtgcgctct cctgttccga ccctgccgct taccggatac    14160
ctgtccgcct ttctcccttc gggaagcgtg gcgctttctc atagctcacg ctgtaggtat    14220
ctcagttcgg tgtaggtcgt tcgctccaag ctgggctgtg tgcacgaacc ccccgttcag    14280
cccgaccgct gcgccttatc cggtaactat cgtcttgagt ccaacccggt aagacacgac    14340
ttatcgccac tggcagcagc cactggtaac aggattagca gagcgaggta tgtaggcggt    14400
gctacagagt tcttgaagtg gtggcctaac tacggctaca ctagaaggac agtatttggt    14460
atctgcgctc tgctgaagcc agttaccttc ggaaaaagag ttggtagctc ttgatccggc    14520
aaacaaacca ccgctggtag cggtggtttt tttgtttgca agcagcagat tacgcgcaga    14580
aaaaaaggat ctcaagaaga tccttttgatc ttttctacgg ggtctgacgc tcagtggaac    14640
gaaaactcac gttaagggat tttggtcatg agattatcaa aaaggatctt cacctagatc    14700
cttttaaatt aaaaatgaag ttttaaatca atctaaagta tatatgagta aacttggtct    14760
gacagttacc aatgcttaat cagtgaggca cctatctcag cgatctgtct atttcgttca    14820
tccatagttg cctgactccc cgtcgtgtag ataactacga tacgggaggg cttaccatct    14880
ggccccagtg ctgcaatgat accgcgagac ccacgctcac cggctccaga tttatcagca    14940 ataaccagc cagccggaag ggccgagcgc agaagtggtc ctgcaacttt atccgcctcc    15000
atccagtcta ttaattgttg ccgggaagct agagtaagta gttcgccagt taatagtttg    15060
cgcaacgttt tgccattgc tgcaagatct ggctagcgat gaccctgctg attggttcgc     15120
tgaccatttc cgggcgcgcc gatttaggtg acactatag                           15159
```

<210> SEQ ID NO 47
<211> LENGTH: 3391
<212> TYPE: PRT
<213> ORGANISM: Dengue 2 virus (Tonga/74)

<400> SEQUENCE: 47

Met Asn Asn Gln Arg Lys Lys Ala Arg Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Val Gly Met Ile Ile Met Leu Thr Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Lys Asp Gly
    130                 135                 140

Thr Asn Met Cys Thr Leu Met Ala Met Asp Leu Gly Glu Leu Cys Glu
145                 150                 155                 160

Asp Thr Ile Thr Tyr Lys Cys Pro Phe Leu Lys Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Val Leu Ile Phe Ile Leu Leu
            260                 265                 270

Thr Ala Ile Ala Pro Ser Met Thr Met Arg Cys Ile Gly Ile Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Asp Ser
            340                 345                 350

Arg Cys Pro Thr Gln Gly Glu Pro Thr Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Ile Val Thr Cys Ala Met Phe Thr
385                 390                 395                 400

Cys Lys Lys Asn Met Glu Gly Lys Ile Val Gln Pro Glu Asn Leu Glu

```
            405                 410                 415
Tyr Thr Val Val Ile Thr Pro His Ser Gly Glu Glu His Ala Val Gly
            420                 425                 430

Asn Asp Thr Gly Lys His Gly Lys Glu Val Lys Ile Thr Pro Gln Ser
            435                 440                 445

Ser Ile Thr Glu Ala Glu Leu Thr Gly Tyr Gly Thr Val Thr Met Glu
            450                 455                 460

Cys Ser Pro Arg Thr Gly Leu Asp Phe Asn Glu Met Val Leu Leu Gln
465                 470                 475                 480

Met Glu Asp Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
                500                 505                 510

Gln Lys Glu Thr Leu Val Thr Phe Lys Asn Pro His Ala Lys Lys Gln
                515                 520                 525

Asp Val Val Leu Gly Ser Gln Glu Gly Ala Met His Thr Ala Leu
            530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Ile Val Lys Glu Ile
                580                 585                 590

Ala Glu Thr Gln His Gly Thr Ile Val Ile Arg Val Gln Tyr Glu Gly
                595                 600                 605

Asp Gly Ser Pro Cys Lys Ile Pro Phe Glu Ile Met Asp Leu Glu Lys
            610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asp Trp Phe
                660                 665                 670

Lys Lys Gly Ser Ser Ile Gly Gln Met Phe Glu Thr Thr Met Arg Gly
            675                 680                 685

Ala Lys Arg Met Ala Ile Leu Gly Asp Thr Ala Trp Asp Phe Gly Ser
            690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Ser Leu Val Leu Val Gly Ile Val Thr Leu Tyr
            755                 760                 765

Leu Gly Val Met Val Gln Ala Asp Ser Gly Cys Val Val Ser Trp Lys
            770                 775                 780

Asn Lys Glu Leu Lys Cys Gly Ser Gly Ile Phe Val Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Gly Ile Cys Gly Ile
            820                 825                 830
```

-continued

Arg Ser Val Thr Arg Leu Glu Asn Leu Met Trp Lys Gln Ile Thr Ser
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Val Gly Lys Arg Ser Leu Arg
865                 870                 875                 880

Pro Gln Pro Thr Glu Leu Arg Tyr Ser Trp Lys Thr Trp Gly Lys Ala
                885                 890                 895

Lys Met Leu Ser Thr Glu Leu His Asn Gln Thr Phe Leu Ile Asp Gly
                900                 905                 910

Pro Glu Thr Ala Glu Cys Pro Asn Thr Asn Arg Ala Trp Asn Ser Leu
            915                 920                 925

Glu Val Glu Asp Tyr Gly Phe Gly Val Phe Thr Thr Asn Ile Trp Leu
        930                 935                 940

Arg Leu Arg Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
                980                 985                 990

Ile Glu Val Lys Ser Cys His Trp Pro Lys Ser His Thr Leu Trp Ser
            995                 1000                1005

Asn Gly Val Leu Glu Ser Glu Met Val Ile Pro Lys Asn Phe Ala
    1010                1015                1020

Gly Pro Val Ser Gln His Asn Asn Arg Pro Gly Tyr Tyr Thr Gln
    1025                1030                1035

Thr Ala Gly Pro Trp His Leu Gly Lys Leu Glu Met Asp Phe Asp
    1040                1045                1050

Phe Cys Glu Gly Thr Thr Val Val Val Thr Glu Asn Cys Gly Asn
    1055                1060                1065

Arg Gly Pro Ser Leu Arg Thr Thr Thr Ala Ser Gly Lys Leu Ile
    1070                1075                1080

Thr Glu Trp Cys Cys Arg Ser Cys Thr Leu Pro Pro Leu Arg Tyr
    1085                1090                1095

Arg Gly Glu Asp Gly Cys Trp Tyr Gly Met Glu Ile Arg Pro Leu
    1100                1105                1110

Lys Glu Lys Glu Glu Asn Leu Val Ser Ser Leu Val Thr Ala Gly
    1115                1120                1125

His Gly Gln Ile Asp Asn Phe Ser Leu Gly Ile Leu Gly Met Ala
    1130                1135                1140

Leu Phe Leu Glu Glu Met Leu Arg Thr Arg Val Gly Thr Lys His
    1145                1150                1155

Ala Ile Leu Leu Val Ala Val Ser Phe Val Thr Leu Ile Thr Gly
    1160                1165                1170

Asn Met Ser Phe Arg Asp Leu Gly Arg Val Met Val Met Val Gly
    1175                1180                1185

Ala Thr Met Thr Asp Asp Ile Gly Met Gly Val Thr Tyr Leu Ala
    1190                1195                1200

Leu Leu Ala Ala Phe Arg Val Arg Pro Thr Phe Ala Ala Gly Leu
    1205                1210                1215

Leu Leu Arg Lys Leu Thr Ser Lys Glu Leu Met Met Thr Thr Ile
    1220                1225                1230

Gly Ile Val Leu Leu Ser Gln Ser Ser Ile Pro Glu Thr Ile Leu
1235                1240                1245

Glu Leu Thr Asp Ala Leu Ala Leu Gly Met Met Val Leu Lys Met
1250                1255                1260

Val Arg Asn Met Glu Lys Tyr Gln Leu Ala Val Thr Ile Met Ala
1265                1270                1275

Ile Leu Cys Val Pro Asn Ala Val Ile Leu Gln Asn Ala Trp Lys
1280                1285                1290

Val Ser Cys Thr Ile Leu Ala Val Val Ser Val Ser Pro Leu Leu
1295                1300                1305

Leu Thr Ser Ser Gln Gln Lys Ala Asp Trp Ile Pro Leu Ala Leu
1310                1315                1320

Thr Ile Lys Gly Leu Asn Pro Thr Ala Ile Phe Leu Thr Thr Leu
1325                1330                1335

Ser Arg Thr Asn Lys Lys Arg Ser Trp Pro Leu Asn Glu Ala Ile
1340                1345                1350

Met Ala Val Gly Met Val Ser Ile Leu Ala Ser Ser Leu Leu Lys
1355                1360                1365

Asn Asp Ile Pro Met Thr Gly Pro Leu Val Ala Gly Gly Leu Leu
1370                1375                1380

Thr Val Cys Tyr Val Leu Thr Gly Arg Ser Ala Asp Leu Glu Leu
1385                1390                1395

Glu Arg Ala Thr Asp Val Lys Trp Asp Asp Gln Ala Glu Ile Ser
1400                1405                1410

Gly Ser Ser Pro Ile Leu Ser Ile Thr Ile Ser Glu Asp Gly Ser
1415                1420                1425

Met Ser Ile Lys Asn Glu Glu Glu Gln Thr Leu Thr Ile Leu
1430                1435                1440

Ile Arg Thr Gly Leu Leu Val Ile Ser Gly Leu Phe Pro Val Ser
1445                1450                1455

Ile Pro Ile Thr Ala Ala Ala Trp Tyr Leu Trp Glu Val Lys Lys
1460                1465                1470

Gln Arg Ala Gly Val Leu Trp Asp Val Pro Ser Pro Pro Pro Val
1475                1480                1485

Gly Lys Ala Glu Leu Glu Asp Gly Ala Tyr Arg Ile Lys Gln Lys
1490                1495                1500

Gly Ile Leu Gly Tyr Ser Gln Ile Gly Ala Gly Val Tyr Lys Glu
1505                1510                1515

Gly Thr Phe His Thr Met Trp His Val Thr Arg Gly Ala Val Leu
1520                1525                1530

Met His Lys Gly Lys Arg Ile Glu Pro Ser Trp Ala Asp Val Lys
1535                1540                1545

Lys Asp Leu Ile Ser Tyr Gly Gly Gly Trp Lys Leu Glu Gly Glu
1550                1555                1560

Trp Lys Glu Gly Glu Glu Val Gln Val Leu Ala Leu Glu Pro Gly
1565                1570                1575

Lys Asn Pro Arg Ala Val Gln Thr Lys Pro Gly Leu Phe Arg Thr
1580                1585                1590

Asn Thr Gly Thr Ile Gly Ala Val Ser Leu Asp Phe Ser Pro Gly
1595                1600                1605

Thr Ser Gly Ser Pro Ile Val Asp Lys Lys Gly Lys Val Val Gly
1610                1615                1620

Leu Tyr Gly Asn Gly Val Val Thr Arg Ser Gly Ala Tyr Val Ser

```
            1625                1630                1635

Ala Ile Ala Gln Thr Glu Lys Ser Ile Glu Asp Asn Pro Glu Ile
            1640                1645                1650

Glu Asp Asp Ile Phe Arg Lys Arg Arg Leu Thr Ile Met Asp Leu
            1655                1660                1665

His Pro Gly Ala Gly Lys Thr Lys Arg Tyr Leu Pro Ala Ile Val
            1670                1675                1680

Arg Glu Ala Ile Lys Arg Gly Leu Arg Thr Leu Ile Leu Ala Pro
            1685                1690                1695

Thr Arg Val Val Ala Ala Glu Met Glu Glu Ala Leu Arg Gly Leu
            1700                1705                1710

Pro Ile Arg Tyr Gln Thr Pro Ala Ile Arg Ala Glu His Thr Gly
            1715                1720                1725

Arg Glu Ile Val Asp Leu Met Cys His Ala Thr Phe Thr Met Arg
            1730                1735                1740

Leu Leu Ser Pro Ile Arg Val Pro Asn Tyr Asn Leu Ile Ile Met
            1745                1750                1755

Asp Glu Ala His Phe Thr Asp Pro Ala Ser Ile Ala Ala Arg Gly
            1760                1765                1770

Tyr Ile Ser Thr Arg Val Glu Met Gly Glu Ala Ala Gly Ile Phe
            1775                1780                1785

Met Thr Ala Thr Pro Pro Gly Ser Arg Asp Pro Phe Pro Gln Ser
            1790                1795                1800

Asn Ala Pro Ile Met Asp Glu Glu Arg Glu Ile Pro Glu Arg Ser
            1805                1810                1815

Trp Asn Ser Gly His Glu Trp Val Thr Asp Phe Lys Gly Lys Thr
            1820                1825                1830

Val Trp Phe Val Pro Ser Ile Lys Thr Gly Asn Asp Ile Ala Ala
            1835                1840                1845

Cys Leu Arg Lys Asn Gly Lys Arg Val Ile Gln Leu Ser Arg Lys
            1850                1855                1860

Thr Phe Asp Ser Glu Tyr Val Lys Thr Arg Thr Asn Asp Trp Asp
            1865                1870                1875

Phe Val Val Thr Thr Asp Ile Ser Glu Met Gly Ala Asn Phe Lys
            1880                1885                1890

Ala Glu Arg Val Ile Asp Pro Arg Arg Cys Met Lys Pro Val Ile
            1895                1900                1905

Leu Thr Asp Gly Glu Glu Arg Val Ile Leu Ala Gly Pro Met Pro
            1910                1915                1920

Val Thr His Ser Ser Ala Ala Gln Arg Arg Gly Arg Ile Gly Arg
            1925                1930                1935

Asn Pro Arg Asn Glu Asn Asp Gln Tyr Ile Tyr Met Gly Glu Pro
            1940                1945                1950

Leu Glu Asn Asp Glu Asp Cys Ala His Trp Lys Glu Ala Lys Met
            1955                1960                1965

Leu Leu Asp Asn Ile Asn Thr Pro Glu Gly Ile Ile Pro Ser Leu
            1970                1975                1980

Phe Glu Pro Glu Arg Glu Lys Val Asp Ala Ile Asp Gly Glu Tyr
            1985                1990                1995

Arg Leu Arg Gly Glu Ala Arg Lys Thr Phe Val Asp Leu Met Arg
            2000                2005                2010

Arg Gly Asp Leu Pro Val Trp Leu Ala Tyr Lys Val Ala Ala Glu
            2015                2020                2025
```

-continued

Gly Ile Asn Tyr Ala Asp Arg Arg Trp Cys Phe Asp Gly Thr Arg
    2030            2035                2040

Asn Asn Gln Ile Leu Glu Glu Asn Val Glu Val Glu Ile Trp Thr
    2045            2050                2055

Lys Glu Gly Glu Arg Lys Lys Leu Lys Pro Arg Trp Leu Asp Ala
    2060            2065                2070

Arg Ile Tyr Ser Asp Pro Leu Ala Leu Lys Glu Phe Lys Glu Phe
    2075            2080                2085

Ala Ala Gly Arg Lys Ser Leu Thr Leu Asn Leu Ile Thr Glu Met
    2090            2095                2100

Gly Arg Leu Pro Thr Phe Met Thr Gln Lys Ala Arg Asp Ala Leu
    2105            2110                2115

Asp Asn Leu Ala Val Leu His Thr Ala Glu Ala Gly Gly Lys Ala
    2120            2125                2130

Tyr Asn His Ala Leu Ser Glu Leu Pro Glu Thr Leu Glu Thr Leu
    2135            2140                2145

Leu Leu Leu Thr Leu Leu Ala Thr Val Thr Gly Gly Ile Phe Leu
    2150            2155                2160

Phe Leu Met Ser Gly Arg Gly Met Gly Lys Met Thr Leu Gly Met
    2165            2170                2175

Cys Cys Ile Ile Thr Ala Ser Ile Leu Leu Trp Tyr Ala Gln Ile
    2180            2185                2190

Gln Pro His Trp Ile Ala Ala Ser Ile Ile Leu Glu Phe Phe Leu
    2195            2200                2205

Ile Val Leu Leu Ile Pro Glu Pro Lys Gln Arg Thr Pro Gln
    2210            2215                2220

Asp Asn Gln Leu Thr Tyr Val Ile Ile Ala Ile Leu Thr Val Val
    2225            2230                2235

Ala Ala Thr Met Ala Asn Glu Met Gly Phe Leu Glu Lys Thr Lys
    2240            2245                2250

Lys Asp Leu Gly Leu Gly Asn Ile Ala Thr Gln Gln Pro Glu Ser
    2255            2260                2265

Asn Ile Leu Asp Ile Asp Leu Arg Pro Ala Ser Ala Trp Thr Leu
    2270            2275                2280

Tyr Ala Val Ala Thr Thr Phe Ile Thr Pro Met Leu Arg His Ser
    2285            2290                2295

Ile Glu Asn Ser Ser Val Asn Val Ser Leu Thr Ala Ile Ala Asn
    2300            2305                2310

Gln Ala Thr Val Leu Met Gly Leu Gly Lys Gly Trp Pro Leu Ser
    2315            2320                2325

Lys Met Asp Ile Gly Val Pro Leu Leu Ala Ile Gly Cys Tyr Ser
    2330            2335                2340

Gln Val Asn Pro Ile Thr Leu Thr Ala Ala Leu Leu Leu Leu Val
    2345            2350                2355

Ala His Tyr Ala Ile Ile Gly Pro Gly Leu Gln Ala Lys Ala Thr
    2360            2365                2370

Arg Glu Ala Gln Lys Arg Ala Ala Ala Gly Ile Met Lys Asn Pro
    2375            2380                2385

Thr Val Asp Gly Ile Thr Val Ile Asp Leu Asp Pro Ile Pro Tyr
    2390            2395                2400

Asp Pro Lys Phe Glu Lys Gln Leu Gly Gln Val Met Leu Leu Val
    2405            2410                2415

```
Leu Cys Val Thr Gln Val Leu Met Met Arg Thr Thr Trp Ala Leu
    2420            2425            2430

Cys Glu Ala Leu Thr Leu Ala Thr Gly Pro Val Ser Thr Leu Trp
    2435            2440            2445

Glu Gly Asn Pro Gly Arg Phe Trp Asn Thr Thr Ile Ala Val Ser
    2450            2455            2460

Met Ala Asn Ile Phe Arg Gly Ser Tyr Leu Ala Gly Ala Gly Leu
    2465            2470            2475

Leu Phe Ser Ile Met Lys Asn Thr Thr Ser Thr Arg Arg Gly Thr
    2480            2485            2490

Gly Asn Ile Gly Glu Thr Leu Gly Glu Lys Trp Lys Ser Arg Leu
    2495            2500            2505

Asn Ala Leu Gly Lys Ser Glu Phe Gln Ile Tyr Lys Lys Ser Gly
    2510            2515            2520

Ile Gln Glu Val Asp Arg Thr Leu Ala Lys Glu Gly Ile Lys Arg
    2525            2530            2535

Gly Glu Thr Asp His His Ala Val Ser Arg Gly Ser Ala Lys Leu
    2540            2545            2550

Arg Trp Phe Val Glu Arg Asn Leu Val Thr Pro Glu Gly Lys Val
    2555            2560            2565

Val Asp Leu Gly Cys Gly Arg Gly Gly Trp Ser Tyr Tyr Cys Gly
    2570            2575            2580

Gly Leu Lys Asn Val Arg Glu Val Lys Gly Leu Thr Lys Gly Gly
    2585            2590            2595

Pro Gly His Glu Glu Pro Ile Pro Met Ser Thr Tyr Gly Trp Asn
    2600            2605            2610

Leu Val Arg Leu Gln Ser Gly Val Asp Val Phe Phe Val Pro Pro
    2615            2620            2625

Glu Lys Cys Asp Thr Leu Leu Cys Asp Ile Gly Glu Ser Ser Pro
    2630            2635            2640

Asn Pro Thr Val Glu Ala Gly Arg Thr Leu Arg Val Leu Asn Leu
    2645            2650            2655

Val Glu Asn Trp Leu Asn Asn Asn Thr Gln Phe Cys Val Lys Val
    2660            2665            2670

Leu Asn Pro Tyr Met Pro Ser Val Ile Glu Arg Met Glu Thr Leu
    2675            2680            2685

Gln Arg Lys Tyr Gly Gly Ala Leu Val Arg Asn Pro Leu Ser Arg
    2690            2695            2700

Asn Ser Thr His Glu Met Tyr Trp Val Ser Asn Ala Ser Gly Asn
    2705            2710            2715

Ile Val Ser Ser Val Asn Met Ile Ser Arg Met Leu Ile Asn Arg
    2720            2725            2730

Phe Thr Met Arg His Lys Lys Ala Thr Tyr Glu Pro Asp Val Asp
    2735            2740            2745

Leu Gly Ser Gly Thr Arg Asn Ile Gly Ile Glu Ser Glu Thr Pro
    2750            2755            2760

Asn Leu Asp Ile Ile Gly Lys Arg Ile Glu Lys Ile Lys Gln Glu
    2765            2770            2775

His Glu Thr Ser Trp His Tyr Asp Gln Asp His Pro Tyr Lys Thr
    2780            2785            2790

Trp Ala Tyr His Gly Ser Tyr Glu Thr Lys Gln Thr Gly Ser Ala
    2795            2800            2805

Ser Ser Met Val Asn Gly Val Val Arg Leu Leu Thr Lys Pro Trp
```

```
                2810                2815                2820
Asp Val Val Pro Met Val Thr Gln Met Ala Met Thr Asp Thr Thr
        2825                2830                2835
Pro Phe Gly Gln Gln Arg Val Phe Lys Glu Lys Val Asp Thr Arg
        2840                2845                2850
Thr Gln Glu Pro Lys Glu Gly Thr Lys Lys Leu Met Lys Ile Thr
        2855                2860                2865
Ala Glu Trp Leu Trp Lys Glu Leu Gly Lys Lys Thr Pro Arg
        2870                2875                2880
Met Cys Thr Arg Glu Glu Phe Thr Lys Lys Val Arg Ser Asn Ala
        2885                2890                2895
Ala Leu Gly Ala Ile Phe Thr Asp Glu Asn Lys Trp Lys Ser Ala
        2900                2905                2910
Arg Glu Ala Val Glu Asp Ser Arg Phe Trp Glu Leu Val Asp Lys
        2915                2920                2925
Glu Arg Asn Leu His Leu Glu Gly Lys Cys Glu Thr Cys Val Tyr
        2930                2935                2940
Asn Met Met Gly Lys Arg Glu Lys Lys Leu Gly Glu Phe Gly Lys
        2945                2950                2955
Ala Lys Gly Ser Arg Ala Ile Trp Tyr Met Trp Leu Gly Ala Arg
        2960                2965                2970
Phe Leu Glu Phe Glu Ala Leu Gly Phe Leu Asn Glu Asp His Trp
        2975                2980                2985
Phe Ser Arg Glu Asn Ser Leu Ser Gly Val Glu Gly Glu Gly Leu
        2990                2995                3000
His Lys Leu Gly Tyr Ile Leu Arg Glu Val Ser Lys Lys Glu Gly
        3005                3010                3015
Gly Ala Met Tyr Ala Asp Asp Thr Ala Gly Trp Asp Thr Arg Ile
        3020                3025                3030
Thr Ile Glu Asp Leu Lys Asn Glu Glu Met Ile Thr Asn His Met
        3035                3040                3045
Ala Gly Glu His Lys Lys Leu Ala Glu Ala Ile Phe Lys Leu Thr
        3050                3055                3060
Tyr Gln Asn Lys Val Val Arg Val Gln Arg Pro Thr Pro Arg Gly
        3065                3070                3075
Thr Val Met Asp Ile Ile Ser Arg Arg Asp Gln Arg Gly Ser Gly
        3080                3085                3090
Gln Val Gly Thr Tyr Gly Leu Asn Thr Phe Thr Asn Met Glu Ala
        3095                3100                3105
Gln Leu Ile Arg Gln Met Glu Gly Glu Gly Ile Phe Lys Ser Ile
        3110                3115                3120
Gln His Leu Thr Ala Ser Glu Glu Ile Ala Val Gln Asp Trp Leu
        3125                3130                3135
Val Arg Val Gly Arg Glu Arg Leu Ser Arg Met Ala Ile Ser Gly
        3140                3145                3150
Asp Asp Cys Val Val Lys Pro Leu Asp Asp Arg Phe Ala Arg Ala
        3155                3160                3165
Leu Thr Ala Leu Asn Asp Met Gly Lys Val Arg Lys Asp Ile Gln
        3170                3175                3180
Gln Trp Glu Pro Ser Arg Gly Trp Asn Asp Trp Thr Gln Val Pro
        3185                3190                3195
Phe Cys Ser His His Phe His Glu Leu Ile Met Lys Asp Gly Arg
        3200                3205                3210
```

Thr Leu Val Val Pro Cys Arg Asn Gln Asp Glu Leu Ile Gly Arg
3215                3220                3225

Ala Arg Ile Ser Gln Gly Ala Gly Trp Ser Leu Arg Glu Thr Ala
3230                3235                3240

Cys Leu Gly Lys Ser Tyr Ala Gln Met Trp Ser Leu Met Tyr Phe
3245                3250                3255

His Arg Arg Asp Leu Arg Leu Ala Ala Asn Ala Ile Cys Ser Ala
3260                3265                3270

Val Pro Ser His Trp Ile Pro Thr Ser Arg Thr Thr Trp Ser Ile
3275                3280                3285

His Ala Ser His Glu Trp Met Thr Thr Glu Asp Met Leu Thr Val
3290                3295                3300

Trp Asn Arg Val Trp Ile Leu Glu Asn Pro Trp Met Glu Asp Lys
3305                3310                3315

Thr Pro Val Glu Ser Trp Glu Glu Ile Pro Tyr Leu Gly Lys Arg
3320                3325                3330

Glu Asp Gln Trp Cys Gly Ser Leu Ile Gly Leu Thr Ser Arg Ala
3335                3340                3345

Thr Trp Ala Lys Asn Ile Gln Thr Ala Ile Asn Gln Val Arg Ser
3350                3355                3360

Leu Ile Gly Asn Glu Glu Tyr Thr Asp Tyr Met Pro Ser Met Lys
3365                3370                3375

Arg Phe Arg Arg Glu Glu Glu Ala Gly Val Leu Trp
3380                3385                3390

<210> SEQ ID NO 48
<211> LENGTH: 15153
<212> TYPE: DNA
<213> ORGANISM: Artificial Sequence
<220> FEATURE:
<223> OTHER INFORMATION: Dengue 3 plasmid p3

<400> SEQUENCE: 48
agttgttagt ctacgtggac cgacaagaac agtttcgact cggaagcttg cttaacgtag      60
tactgacagt ttttattag agagcagatc tctgatgaac aaccaacgga aaagacggg      120 aaaccgtct atcaatatgc tgaaacgcgt gagaaaccgt gtgtcaactg gatcacagtt      180
ggcgaagaga ttctcaagag gactgctgaa cggccaagga ccaatgaaat tggttatggc      240
gttcatagct ttcctcagat ttctagccat tccaccgaca gcaggagtct tggctagatg      300
gggaaccttt aagaagtcgg gggctattaa ggtcctgaga ggcttcaaga aggagatctc      360
aaacatgctg agcattatca acagacggaa aaagacatcg ctctgtctca tgatgatgtt      420
accagcaaca cttgctttcc acttgacttc acgagatgga gagccgcgca tgattgtggg      480
gaagaatgaa agaggaaaat ccctactttt aagacagcc tctggaatca acatgtgcac      540
actcatagcc atggatttgg gagagatgtg tgatgacacg tcacctaca aatgccccct      600 cattactgaa gtggagcctg aagacattga ctgctggtgc aaccttacat cgacatgggt      660
gacctacgga acgtgcaatc aagctggaga gcacagacgc gacaaaagat cggtggcgtt      720
agctccccat gtcggcatgg gactggacac acgcacccaa acctggatgt cggctgaagg      780
agcttggaga caggtcgaga aggtagagac atgggcctt aggcacccag ggttcacaat      840
actagcccta tttcttgccc attacatagg cacttccttg acccagaaag tggttatttt      900
catactacta atgctggtca ccccatccat gacaatgaga tgcgtgggag taggaaacag      960

```
agattttgtg gaaggcctat caggagctac gtgggttgac gtggtgctcg agcacggtgg    1020
gtgtgtgact accatggcta agaacaagcc cacgctggat atagagctcc agaagaccga    1080
ggccacccaa ctggcgaccc taaggaaact atgtattgag ggaaaaatta ccaacgtaac    1140
aaccgactca aggtgcccca cccaaggga agcgatttta cctgaggagc aggaccagaa     1200
ccacgtgtgc aagcacacat acgtggacag aggctggga aacggttgtg gtttgtttgg     1260
caagggaagc ctggtaacat gcgcgaaatt tcaatgtttg gaatcaatag agggaaaagt    1320
ggtgcagcat gagaacctca aatacaccgt catcatcaca gtgcacacag agatcaaca    1380 ccaggtggga aatgaaacgc agggagtcac ggctgagata acacccag catcaaccgt      1440 tgaagccatc ttacctgaat atggaaccct tgggctagaa tgctcaccac ggacaggttt    1500
agatttcaat gaaatgattt tgttgacaat gaagaacaaa gcatggatgg tacatagaca    1560
atggtttttt gacctacctt taccatggac atcaggagct acaacagaaa caccaacctg    1620
gaataagaaa gagcttcttg tgacattcaa aaacgcacat gcaaaaagc aagaagtagt     1680 agtccttgga tcgcaagagg gagcaatgca cacagcactg acaggagcta cagagatcca    1740
aacctcagga ggcacaagta tttttgcggg gcacttaaaa tgtagactca agatggacaa    1800
attggaactc aaggggatga gctatgcaat gtgcttgaat gcctttgtgt tgaagaaga     1860 agtctccgaa acgcaacatg ggacaatact catcaaggtt gagtacaaag gggaagatgc    1920
accttgcaag attccttct ccacggagga tggacaaggg aaagcccaca atggcagact     1980
gatcacagct aacccagtgg tgaccaagaa ggaggagcct gtcaatattg aggcagaacc    2040 tcctttggg gaaagcaata tagtaattgg aattggagac aaagccttga aaatcaactg     2100
gtacaagaag ggaagctcga ttgggaagat gttcgaggcc actgccagag gtgcaaggcg    2160
catggccatc ttgggagaca cagcctggga ctttggatca gtaggtggtg ttttaaattc    2220
attaggaaaa atggtgcacc aaatatttgg aagtgcttac acagccctat ttagtggagt    2280
ctcctggata atgaaaattg gaataggtgt ccttttaacc tggataggg tgaattcaaa     2340 aaacactagt atgagcttta gctgcattgt gataggaatc attacactct atctgggagc    2400
cgtggtgcaa gctgacatgg ggtgtgtcat aaactggaaa ggcaaagaac tcaaatgtgg    2460
aagtggaatt ttcgtcacta atgaggtcca cacctggaca gagcaataca aatttcaagc    2520
agactccccc aaaagactgg cgacagccat tgcaggcgct tgggagaatg gagtgtgcgg    2580
aatcaggtcg acaaccagaa tggagaacct cttgtggaag caaatagcca atgaactgaa    2640
ctacatatta tgggaaaaca acatcaaatt aacggtagtt gtgggtgata taattggggt    2700
cttagagcaa gggaaaagaa cactaacacc acaacccatg gaactaaaat attcatggaa    2760
aacatgggga aaggcgaaga tagtgacagc tgaaacacaa aattcctctt tcataataga    2820
tgggccaaac acaccagagt gtccaagtgc ctcaagagca tggaatgtgt gggaggtgga    2880
agattacggg ttcggagtct tcacaactaa catatggctg aaactccgag atgtgtacac    2940
ccaactatgt gaccacaggc taatgtcggc agccgttaag gatgagaggg ccgtacacgc    3000
cgacatgggc tattggatag aaagccaaaa gaatggaagt tggaagctag aaaaggcatc    3060
cctcatagag gtaaaaacct gcacatggcc aaaatcacac actctttgga gcaatggtgt    3120
gctagagagt gacatgatca tcccaaagag tctggctggt cccatttcgc aacacaacta    3180
caggcccgga taccacaccc aaacggcagg accctggcac ttaggaaaat tggagctgga    3240
cttcaactat tgtgaaggaa caacagttgt catcacagaa aattgtggga caagaggccc    3300
atcactgaga acaacaacag tgtcagggaa gttgatacac gaatggtgtt gccgctcgtg    3360
```

```
tacacttcct cccctgcgat acatgggaga agacggctgc tggtatggca tggaaattag   3420
acccattaat gagaaagaag agaacatggt aaagtcttta gtctcagcag ggagtggaaa   3480
ggtggataac ttcacaatgg gtgtcttgtg tttggcaatc cttttttgaag aggtgatgag   3540
aggaaaattt gggaaaaagc acatgattgc aggggttctc ttcacgtttg tactccttct   3600
ctcagggcaa ataacatgga gagacatggc gcacacactc ataatgattg ggtccaacgc   3660
ctctgacaga atgggaatgg gcgtcactta cctagcattg attgcaacat ttaaaattca   3720
gccattttg gctttgggat tcttcctgag gaaactgaca tctagagaaa atttattgtt   3780
gggagttggg ttggccatgg caacaacgtt acaactgcca gaggacattg aacaaatggc   3840
gaatggaata gctttagggc tcatggctct taaattaata acacaatttg aaacatacca   3900
actatggacg gcattagtct ccctaatgtg ttcaaataca attttcacgt tgactgttgc   3960
ctggagaaca gccaccctga ttttggccgg aatttctctt ttgccagtgt gccagtcttc   4020
gagcatgagg aaaacagatt ggctcccaat ggctgtggca gctatgggag ttccacccct   4080
accacttttt attttcagtt tgaaagatac gctcaaaagg agaagctggc cactgaatga   4140
gggggtgatg gctgttggac ttgtgagtat tctagctagt tctctcctta ggaatgacgt   4200
gcccatggct ggaccattag tggctggggg cttgctgata gcgtgctacg tcataactgg   4260
cacgtcagca gacctcactg tagaaaaagc agcagatgtg acatgggagg aagaggctga   4320
gcaaacagga gtgtcccaca atttaatgat cacagttgat gacgatggaa caatgagaat   4380
aaaagatgat gagactgaga acatcttaac agtgctttg aaaacagcat tactaatagt   4440
gtcaggcatt tttccatact ccatacccgc aacactgttg gtctggcaca cttggcaaaa   4500
gcaaacccaa agatccggtg tcctatggga cgttcccagc ccccagaga cacagaaagc   4560
agaactggaa gaaggggttt ataggatcaa gcagcaagga attttttggga aacccaagt   4620
gggggttgga gtacaaaaag aaggagtttt ccacaccatg tggcacgtca aagaggagc   4680
agtgttgaca cacaatggga aaagactgga accaaactgg gctagcgtga aaaagatct   4740
gatttcatac ggaggaggat ggaaattgag tgcacaatgg caaaaggag aggaggtgca   4800
ggttattgcc gtagagcctg ggaagaaccc aaagaacttt caaaccatgc caggcatttt   4860
ccagacaaca acaggggaga taggagcgat tgcactggac ttcaagcctg gaacttcagg   4920
atctcccatc ataaacagag agggaaaggt actgggattg tatggcaatg gagtggtcac   4980
aaagaatggt ggctatgtca gtggaatagc acaaacaaat gcagaaccag acggaccgac   5040
accagagttg gaagaagaga tgttcaaaaa gcgaaatcta accataatgg atctccatcc   5100
cgggtcagga aagacgcgga aatatcttcc agctattgtt agagaggcaa tcaagagacg   5160
cttaaggact ctaattttgg caccaacaag ggtagttgca gctgagatgg aagaagcatt   5220
gaaagggctc ccaataaggt atcaaacaac tgcaacaaaa tctgaacaca gggagaga   5280
gattgttgat ctaatgtgcc acgcaacgtt cacaatgcgt ttgctgtcac cagtcagggt   5340
tccaaactac aacttgataa taatggatga ggctcatttc acagacccag ccagtatagc   5400
ggctagaggg tacatatcaa ctcgtgtagg aatgggagag gcagccgcaa ttttcatgac   5460
agccacaccc cctggaacag ctgatgcctt tcctcagagc aacgctccaa ttcaagatga   5520
agaaagagac ataccagaac gctcatggaa ttcaggcaat gaatggatta ccgactttgc   5580
cgggaagacg gtgtggtttg tccctagcat caaagctgga aatgacatag caactgcttt   5640
gcggaaaaat ggaaaaaagg tcattcaact tagtaggaag acttttgaca cagaatatca   5700
```

```
aaagactaaa ctaaatgatt gggactttgt ggtgacaaca gacatttcag aaatgggagc    5760
caatttcaaa gcagacagag tgatcgaccc aagaagatgt ctcaagccag tgattttgac    5820
agacggaccc gagcgcgtga tcctggcggg accaatgcca gtcaccgtag cgagcgctgc    5880
gcaaaggaga gggagagttg gcaggaaccc acaaaaagaa aatgaccaat acatattcat    5940
gggccagccc ctcaataatg atgaagacca tgctcactgg acagaagcaa aaatgctgct    6000
agacaacatc aacacaccag aagggatcat accagctctc tttgaaccag aaagggagaa    6060
gtcagccgcc atagacggcg aataccgcct gaagggtgag tccaggaaga ccttcgtgga    6120
actcatgagg aggggtgacc tcccagtttg gctagcccat aaagtagcat cagaagggat    6180
caaatataca gatagaaagt ggtgtttttga tggagaacgc aacaatcaaa ttttagagga    6240
gaatatggat gtggaaatct ggacaaagga aggagaaaag aaaaaattga gacctaggtg    6300
gcttgatgcc cgcacttatt cagatccctt agcgctcaag gaattcaagg actttgcggc    6360
tggtagaaag tcaattgccc ttgatcttgt gacagaaata ggaagagtgc cttcacactt    6420
agctcacaga acgagaaacg ccctggacaa tctggtgatg ttgcacacgt cagaacatgg    6480
cgggagggcc tacaggcatg cagtggagga actaccagaa acaatggaaa cactcttact    6540
cctgggactc atgatcctgt aacaggtgg agcaatgctt ttcttgatat caggtaaagg    6600
gattggaaag acttcaatag gactcatttg tgtagctgct tccagcggta tgttatggat    6660
ggctgatgtc ccactccaat ggatcgcgtc tgccatagtc ctggagtttt ttatgatggt    6720
gttacttata ccagaaccag aaaagcagag aactcccccaa gacaatcaac tcgcatatgt    6780
cgtgataggc atactcacac tggctgcaat agtagcagcc aatgaaatgg gactgttgga    6840
aaccacaaag agagatttag gaatgtccaa agaaccaggt gttgtttctc caaccagcta    6900
tttggatgtg gacttgcacc cagcatcagc ctggacattg tacgctgtgg ccacaacagt    6960
aataacacca atgttgagac ataccataga gaattccaca gcaaatgtgt ccctggcagc    7020
tatagccaac caggcagtgg tcctgatggg tttagacaaa ggatggccga tatcgaaaat    7080
ggacttaggc gtgccactat tggcactggg ttgttattca caagtgaacc cactaactct    7140
cacagcggca gttctcctgc tagtcacgca ttatgctatt ataggtccag gattgcaggc    7200
aaaagccact cgtgaagctc aaaaaaggac agctgctgga ataatgaaga atccaacggt    7260
ggatgggata atgacaatag acctagatcc tgtaatatac gattcaaaat ttgaaaagca    7320
actaggacag gttatgctcc tggttctgtg tgcagttcaa cttttgttaa tgagaacatc    7380
atgggctttt tgtgaagctc taaccctagc cacaggacca ataacaacac tctgggaagg    7440
atcacctggg aagttctgga acaccacgat agctgtttcc atggcgaaca tctttagagg    7500 gagctatttta gcaggagctg gcttgctttt ttctatcatg aaatcagttg gaacaggaaa    7560
gagagggaca gggtcacagg gtgaaacctt gggagaaaag tggaaaaaga aattgaatca    7620
attaccccgg aaagagtttg acctttacaa gaaatccgga atcactgaag tggatagaac    7680
agaagccaaa gaagggttga aaagaggaga aataacacac catgccgtgt ccagaggcag    7740
cgcaaaactt caatggttcg tggagagaaa catggtcatc cccgaaggaa gagtcataga    7800
cttaggctgt ggaagaggag ctggtcata ttattgtgca ggactgaaaa aagttacaga    7860
agtgcgagga tacacaaaag cggcccagg acatgaagaa ccagtaccta tgtctacata    7920
cggatggaac atagtcaagt taatgagtgg aaaggatgtg ttttatcttc cacctgaaaa    7980
gtgtgatact ctattgtgtg acattggaga atccttcacca agcccaacag tggaagaaag    8040
cagaaccata agagtcttga gatggttga accatggcta aaaaataacc agttttgcat    8100
```

```
taaagtattg aacccttaca tgccaactgt gattgagcac ctagaaagac tacaaaggaa    8160
acatggagga atgcttgtga gaaatccact ctcacgaaac tccacgcacg aaatgtactg    8220
gatatctaat ggcacaggca atatcgtttc ttcagtcaac atggtatcca gattgctact    8280
taacagattc acaatgacac ataggagacc caccatagaa aaagatgtgg atttaggagc    8340
ggggacccga catgtcaatg cggaaccaga acacccaac atggatgtca ttggggaaag     8400
aataagaagg atcaaggagg agcatagttc aacatggcac tatgatgatg aaaatcctta    8460
taaaacgtgg gcttaccatg gatcctatga agttaaggcc acaggctcag cctcctccat    8520
gataaatgga gtcgtgaaac tcctcacgaa accatgggat gtggtgccca tggtgacaca    8580
gatggcaatg acggatacaa ccccattcgg ccagcaaagg ttttttaaag agaaagtgga    8640
caccaggaca cccagaccta tgccaggaac aagaaaggtt atggagatca cagcggaatg    8700
gctttggaga accctgggaa ggaacaaaag acccagatta tgtacgagag aggagttcac    8760
aaaaaaggtc agaaccaacg cagctatggg cgccgttttt acagaggaga accaatggga    8820
cagtgctaga gctgctgttg aggatgaaga attctggaaa ctcgtggaca gagaacgtga    8880
actccacaaa ttgggcaagt gtggaagctg cgtttacaac atgatgggca agagagagaa    8940
gaaacttgga gagtttggca aagcaaaagg cagtagagcc atatggtaca tgtggttggg    9000
agccagatac cttgagttcg aagcactcgg attcttaaat gaagaccatt ggttctcgcg    9060
tgaaaactct tacagtggag tagaaggaga aggactgcac aagctgggat acatcttaag    9120
agacatttcc aagatacccg gaggagctat gtatgctgat gacacagctg gttgggacac    9180
aagaataaca gaagatgacc tgcacaatga ggaaaaaatc acacagcaaa tggacccdga    9240
acacaggcag ttagcaaacg ctatattcaa gctcacatac caaaacaaag tggtcaaagt    9300
tcaacgacca actccaaagg gcacggtaat ggacatcata tctaggaaag accaaagagg    9360
cagtggacag gtgggaactt atggtctgaa tacattcacc aacatggaag cccagttaat    9420
cagacaaatg gaaggagaag gtgtgttgtc gaaggcagac ctcgagaacc ctcatctgct    9480
agagaagaaa gttacacaat ggttggaaac aaaaggagtg agaggttaa aaagaatggc    9540 catcagcggg gatgattgcg tggtgaaacc aattgatgac aggttcgcca atgccctgct    9600
tgccctgaat gacatgggaa aagttaggaa ggacatacct caatggcagc catcaaaggg    9660
atggcatgat tggcaacagg tcccttctg ctcccaccac tttcatgaat tgatcatgaa     9720
agatggaaga agttggtag ttccctgcag acctcaggat gaattaatcg ggagagcgag      9780
aatctctcaa ggagcaggat ggagccttag agaaactgca tgcctaggga aagcctacgc    9840
ccaaatgtgg actctcatgt actttcacag aagagatctt agactagcat ccaacgccat    9900
atgttcagca gtaccagtcc attgggtccc cacaagcaga acgacgtggt ctattcatgc    9960
tcaccatcag tggatgacta cagaagacat gcttactgtt tggaacaggg tgtggataga   10020
ggataatcca tggatggaag acaaaactcc agtcaaaacc tgggaagatg ttccatatct   10080
agggaagaga gaagaccaat ggtgcggatc actcattggt ctcacttcca gagcaacctg   10140
ggcccagaac atacttacgg caatccaaca ggtgagaagc cttataggca atgaagagtt   10200
tctggactac atgccttcga tgaagagatt caggaaggag gaggagtcag agggagccat   10260
ttggtaaacg taggaagtga aaaagaggca aactgtcagg ccaccttaag ccacagtacg   10320
gaagaagctg tgcagcctgt gagccccgtc caaggacgtt aaaagaagaa gtcaggccca   10380
aaagccacgg tttgagcaaa ccgtgctgcc tgtggctccg tcgtgggac gtaaaacctg     10440
```

```
ggaggctgca aactgtggaa gctgtacgca cggtgtagca gactagcggt tagaggagac    10500
ccctcccatg acacaacgca gcagcggggc ccgagctctg agggaagctg tacctccttg    10560
caaaggacta gaggttagag gagacccccc gcaaataaaa acagcatatt gacgctggga    10620
gagaccagag atcctgctgt ctcctcagca tcattccagg cacagaacgc cagaaaatgg    10680
aatggtgctg ttgaatcaac aggttctggt accggtaggc atcgtggtgt cacgctcgtc    10740
gtttggtatg gcttcattca gctccggttc ccaacgatca aggcgagtta catgatcccc    10800
catgttgtgc aaaaaagcgg ttagctcctt cggtcctccg atcgttgtca gaagtaagtt    10860
ggccgcagtg ttatcactca tggttatggc agcactgcat aattctctta ctgtcatgcc    10920
atccgtaaga tgcttttctg tgactggtga gtactcaacc aagtcattct gagaatagtg    10980
tatgcggcga ccgagttgct cttgcccggc gtcaacacgg gataataccg cgccacatag    11040
cagaacttta aaagtgctca tcattggaaa acgttcttcg gggcgaaaac tctcaaggat    11100
cttaccgctg ttgagatcca gttcgatgta acccactcgt gcacccaact gatcttcagc    11160
atcttttact ttcaccagcg tttctgggtg agcaaaaaca ggaaggcaaa atgccgcaaa    11220
aaagggaata agggcgacac ggaaatgttg aatactcata ctcttccttt tcaatatta    11280 ttgaagcatt tatcagggtt attgtctcat gagcggatac atatttgaat gtatttagaa    11340
aaataaacaa ataggggttc cgcgcacatt tccccgaaaa gtgccacctg acgtctaaga    11400
aaccattatt atcatgacat taacctataa aaataggcgt atcacgaggc cctttcgtct    11460
tcaagaattc tcatgtttga cagcttatca tcgataagct ttaatgcggt agtttatcac    11520
agttaaattg ctaacgcagt caggcaccgt gtatgaaatc taacaatgcg ctcatcgtca    11580
tcctcggcac cgtcaccctg gatgctgtag gcataggctt ggttatgccg gtactgccgg    11640
gcctcttgcg ggatatcgtc cattccgaca gcatcgccag tcactatggc gtgctgctgg    11700
cgctatatgc gttgatgcaa tttctatgcg cacccgttct cggagcactg tccgaccgct    11760
ttggccgccg cccagtcctg ctcgcttcgc tacttggagc cactatcgac tacgcgatca    11820
tggcgaccac acccgtcctg tggatcctct acgccggacg catcgtggcc ggcatcaccg    11880
gcgccacagg tgcggttgct ggcgcctata tcgccgacat caccgatggg gaagatcggg    11940
ctcgccactt cgggctcatg agcgcttgtt tcggcgtggg tatggtggca ggccccgtgg    12000
ccgggggact gttgggcgcc atctccttgc atgcaccatt ccttgcggcg gcggtgctca    12060
acggcctcaa cctactactg ggctgcttcc taatgcagga gtcgcataag ggagagcgtc    12120
gaccgatgcc cttgagagcc ttcaacccag tcagctcctt ccgtgggcg cggggcatga    12180 ctatcgtcgc cgcacttatg actgtcttct ttatcatgca actcgtagga caggtgccgg    12240
cagcgctctg ggtcattttc ggcgaggacc gctttgctg gagcgcgacg atgatcggcc    12300
tgtcgcttgc ggtattcgga atcttgcacg ccctcgctca agccttcgtc actggtcccg    12360
ccaccaaacg tttcggcgag aagcaggcca ttatcgccgg catggcggcc gacgcgctgg    12420
gctacgtctt gctggcgttc gcgacgcgag gctggatggc cttccccatt atgattcttc    12480
tcgcttccgg cggcatcggg atgcccgcgt tgcaggccat gctgtccagg caggtagatg    12540
acgaccatca gggacagctt caaggatcgc tcgcggctct taccagccta acttcgatca    12600
ctggaccgct gatcgtcacg gcgatttatg ccgcctcggc gagcacatgg aacgggttgg    12660
catggattgt aggcgccgcc ctataccttg tctgcctccc cgcgttgcgt cgcggtgcat    12720
ggagccgggc cacctcgacc tgaatggaag ccggcggcac ctcgctaacg gattcaccac    12780
tccaagaatt ggagccaatc aattcttgcg gagaactgtg aatgcgcaaa ccaacccttg    12840
```

```
gcagaacata tccatcgcgt ccgccatctc cagcagccgc acgcggcgca tctcgggcag   12900
cgttgggtcc tggccacggg tgcgcatgat cgtgctcctg tcgttgagga cccggctagg   12960
ctggcggggt tgccttactg gttagcagaa tgaatcaccg atacgcgagc gaacgtgaag   13020
cgactgctgc tgcaaaacgt ctgcgacctg agcaacaaca tgaatggtct tcggtttccg   13080
tgtttcgtaa agtctggaaa cgcggaagtc agcgccctgc accattatgt tccggatctg   13140
catcgcagga tgctgctggc taccctgtgg aacacctaca tctgtattaa cgaagcgctg   13200
gcattgaccc tgagtgattt ttctctggtc ccgccgcatc cataccgcca gttgtttacc   13260
ctcacaacgt tccagtaacc gggcatgttc atcatcagta acccgtatcg tgagcatcct   13320
ctctcgtttc atcggtatca ttaccccat gaacagaaat ccccttaca cggaggcatc   13380 agtgaccaaa caggaaaaaa ccgcccttaa catggcccgc tttatcagaa ccagacatt   13440 aacgcttctg gagaaactca acgagctgga cgcggatgaa caggcagaca tctgtgaatc   13500
gcttcacgac cacgctgatg agctttaccg cagctgcctc gcgcgtttcg gtgatgacgg   13560
tgaaaacctc tgacacatgc agctcccgga cggtcaca gcttgtctgt aagcggatgc   13620
cgggagcaga caagcccgtc agggcgcgtc agcgggtgtt ggcgggtgtc ggggcgcagc   13680
catgacccag tcacgtagcg atagcggagt gtatactggc ttaactatgc ggcatcagag   13740
cagattgtac tgagagtgca ccatatgcgg tgtgaaatac cgcacagatg cgtaaggaga   13800
aaataccgca tcaggcgctc ttccgcttcc tcgctcactg actcgctgcg ctcggtcgtt   13860
cggctgcggc gagcggtatc agctcactca aaggcggtaa tacggttatc cacagaatca   13920
ggggataacg caggaaagaa catgtgagca aaaggccagc aaaaggccag gaaccgtaaa   13980
aaggccgcgt tgctggcgtt tttccatagg ctccgccccc ctgacgagca tcacaaaaat   14040
cgacgctcaa gtcagaggtg gcgaaacccg acaggactat aaagatacca ggcgtttccc   14100
cctggaagct ccctcgtgcg ctctcctgtt ccgaccctgc cgcttaccgg atacctgtcc   14160
gcctttctcc cttcgggaag cgtggcgctt tctcatagct cacgctgtag gtatctcagt   14220
tcggtgtagg tcgttcgctc caagctgggc tgtgtgcacg aacccccgt tcagcccgac   14280 cgctgcgcct tatccggtaa ctatcgtctt gagtccaacc cggtaagaca cgacttatcg   14340
ccactggcag cagccactgg taacaggatt agcagagcga gtatgtagg cggtgctaca   14400 gagttcttga agtggtggcc taactacggc tacactagaa ggacagtatt tggtatctgc   14460
gctctgctga agccagttac cttcggaaaa agagttggta gctcttgatc cggcaaacaa   14520
accaccgctg gtagcggtgg tttttttgtt tgcaagcagc agattacgcg cagaaaaaaa   14580
ggatctcaag aagatccttt gatcttttct acggggtctg acgctcagtg gaacgaaaac   14640
tcacgttaag ggattttggt catgagatta tcaaaaagga tcttcaccta gatcctttta   14700
aattaaaaat gaagttttaa atcaatctaa agtatatatg agtaaacttg gtctgacagt   14760
taccaatgct taatcagtga ggcacctatc tcagcgatct gtctatttcg ttcatccata   14820
gttgcctgac tccccgtcgt gtagataact acgatacggg agggcttacc atctggcccc   14880
agtgctgcaa tgataccgcg agacccacgc tcaccggctc cagatttatc agcaataaac   14940
cagccagccg gaagggccga gcgcagaagt ggtcctgcaa ctttatccgc ctccatccag   15000
tctattaatt gttgccggga agctagagta agtagttcgc cagttaatag tttgcgcaac   15060
gttgttgcca ttgctgcaag atctggctag cgatgaccct gctgattggt tcgctgacca   15120
tttccgggcg cgccgattta ggtgacacta tag                                15153
```

<210> SEQ ID NO 49
<211> LENGTH: 3390
<212> TYPE: PRT
<213> ORGANISM: Dengue 3 (Sleman/78) virus

<400> SEQUENCE: 49

Met Asn Asn Gln Arg Lys Lys Thr Gly Lys Pro Ser Ile Asn Met Leu
1 5 10 15

Lys Arg Val Arg Asn Arg Val Ser Thr Gly Ser Gln Leu Ala Lys Arg
20 25 30

Phe Ser Arg Gly Leu Leu Asn Gly Gln Gly Pro Met Lys Leu Val Met
35 40 45

Ala Phe Ile Ala Phe Leu Arg Phe Leu Ala Ile Pro Pro Thr Ala Gly
50 55 60

Val Leu Ala Arg Trp Gly Thr Phe Lys Lys Ser Gly Ala Ile Lys Val
65 70 75 80

Leu Arg Gly Phe Lys Lys Glu Ile Ser Asn Met Leu Ser Ile Ile Asn
85 90 95

Arg Arg Lys Lys Thr Ser Leu Cys Leu Met Met Met Leu Pro Ala Thr
100 105 110

Leu Ala Phe His Leu Thr Ser Arg Asp Gly Glu Pro Arg Met Ile Val
115 120 125

Gly Lys Asn Glu Arg Gly Lys Ser Leu Leu Phe Lys Thr Ala Ser Gly
130 135 140

Ile Asn Met Cys Thr Leu Ile Ala Met Asp Leu Gly Glu Met Cys Asp
145 150 155 160

Asp Thr Val Thr Tyr Lys Cys Pro Leu Ile Thr Glu Val Glu Pro Glu
165 170 175

Asp Ile Asp Cys Trp Cys Asn Leu Thr Ser Thr Trp Val Thr Tyr Gly
180 185 190

Thr Cys Asn Gln Ala Gly Glu His Arg Arg Asp Lys Arg Ser Val Ala
195 200 205

Leu Ala Pro His Val Gly Met Gly Leu Asp Thr Arg Thr Gln Thr Trp
210 215 220

Met Ser Ala Glu Gly Ala Trp Arg Gln Val Glu Lys Val Glu Thr Trp
225 230 235 240

Ala Phe Arg His Pro Gly Phe Thr Ile Leu Ala Leu Phe Leu Ala His
245 250 255

Tyr Ile Gly Thr Ser Leu Thr Gln Lys Val Val Ile Phe Ile Leu Leu
260 265 270

Met Leu Val Thr Pro Ser Met Thr Met Arg Cys Val Gly Val Gly Asn
275 280 285

Arg Asp Phe Val Glu Gly Leu Ser Gly Ala Thr Trp Val Asp Val Val
290 295 300

Leu Glu His Gly Gly Cys Val Thr Thr Met Ala Lys Asn Lys Pro Thr
305 310 315 320

Leu Asp Ile Glu Leu Gln Lys Thr Glu Ala Thr Gln Leu Ala Thr Leu
325 330 335

Arg Lys Leu Cys Ile Glu Gly Lys Ile Thr Asn Val Thr Thr Asp Ser
340 345 350

Arg Cys Pro Thr Gln Gly Glu Ala Ile Leu Pro Glu Glu Gln Asp Gln
355 360 365

Asn His Val Cys Lys His Thr Tyr Val Asp Arg Gly Trp Gly Asn Gly
370 375 380

```
Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
            405                 410                 415

Tyr Thr Val Ile Ile Thr Val His Thr Gly Asp Gln His Gln Val Gly
                420                 425                 430

Asn Glu Thr Gln Gly Val Thr Ala Glu Ile Thr Pro Gln Ala Ser Thr
        435                 440                 445

Val Glu Ala Ile Leu Pro Glu Tyr Gly Thr Leu Gly Leu Glu Cys Ser
    450                 455                 460

Pro Arg Thr Gly Leu Asp Phe Asn Glu Met Ile Leu Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Thr Thr Glu Thr Pro Thr Trp Asn Lys Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Asn Ala Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Ser Gly Val Ser Trp Ile Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Val Ile Gly Ile Ile Thr Leu Tyr Leu Gly
        755                 760                 765

Ala Val Val Gln Ala Asp Met Gly Cys Val Ile Asn Trp Lys Gly Lys
    770                 775                 780

Glu Leu Lys Cys Gly Ser Gly Ile Phe Val Thr Asn Glu Val His Thr
785                 790                 795                 800
```

```
Trp Thr Glu Gln Tyr Lys Phe Gln Ala Asp Ser Pro Lys Arg Leu Ala
            805                 810                 815

Thr Ala Ile Ala Gly Ala Trp Glu Asn Gly Val Cys Gly Ile Arg Ser
        820                 825                 830

Thr Thr Arg Met Glu Asn Leu Leu Trp Lys Gln Ile Ala Asn Glu Leu
        835                 840                 845

Asn Tyr Ile Leu Trp Glu Asn Asn Ile Lys Leu Thr Val Val Val Gly
    850                 855                 860

Asp Ile Ile Gly Val Leu Glu Gln Gly Lys Arg Thr Leu Thr Pro Gln
865                 870                 875                 880

Pro Met Glu Leu Lys Tyr Ser Trp Lys Thr Trp Gly Lys Ala Lys Ile
            885                 890                 895

Val Thr Ala Glu Thr Gln Asn Ser Ser Phe Ile Ile Asp Gly Pro Asn
        900                 905                 910

Thr Pro Glu Cys Pro Ser Ala Ser Arg Ala Trp Asn Val Trp Glu Val
        915                 920                 925

Glu Asp Tyr Gly Phe Gly Val Phe Thr Thr Asn Ile Trp Leu Lys Leu
    930                 935                 940

Arg Glu Met Tyr Thr Gln Leu Cys Asp His Arg Leu Met Ser Ala Ala
945                 950                 955                 960

Val Lys Asp Glu Arg Ala Val His Ala Asp Met Gly Tyr Trp Ile Glu
            965                 970                 975

Ser Gln Lys Asn Gly Ser Trp Lys Leu Glu Lys Ala Ser Leu Ile Glu
        980                 985                 990

Val Lys Thr Cys Thr Trp Pro Lys Ser His Thr Leu Trp Ser Asn Gly
        995                 1000                1005

Val Leu Glu Ser Asp Met Ile Ile Pro Lys Ser Leu Ala Gly Pro
    1010                1015                1020

Ile Ser Gln His Asn Tyr Arg Pro Gly Tyr His Thr Gln Thr Ala
    1025                1030                1035

Gly Pro Trp His Leu Gly Lys Leu Glu Leu Asp Phe Asn Tyr Cys
    1040                1045                1050

Glu Gly Thr Thr Val Val Ile Thr Glu Asn Cys Gly Thr Arg Gly
    1055                1060                1065

Pro Ser Leu Arg Thr Thr Thr Val Ser Gly Lys Leu Ile His Glu
    1070                1075                1080

Trp Cys Cys Arg Ser Cys Thr Leu Pro Pro Leu Arg Tyr Met Gly
    1085                1090                1095

Glu Asp Gly Cys Trp Tyr Gly Met Glu Ile Arg Pro Ile Asn Glu
    1100                1105                1110

Lys Glu Glu Asn Met Val Lys Ser Leu Val Ser Ala Gly Ser Gly
    1115                1120                1125

Lys Val Asp Asn Phe Thr Met Gly Val Leu Cys Leu Ala Ile Leu
    1130                1135                1140

Phe Glu Glu Val Met Arg Gly Lys Phe Gly Lys Lys His Met Ile
    1145                1150                1155

Ala Gly Val Leu Phe Thr Phe Val Leu Leu Leu Ser Gly Gln Ile
    1160                1165                1170

Thr Trp Arg Asp Met Ala His Thr Leu Ile Met Ile Gly Ser Asn
    1175                1180                1185

Ala Ser Asp Arg Met Gly Met Gly Val Thr Tyr Leu Ala Leu Ile
    1190                1195                1200

Ala Thr Phe Lys Ile Gln Pro Phe Leu Ala Leu Gly Phe Phe Leu
```

-continued

```
            1205                1210                1215

Arg Lys Leu Thr Ser Arg Glu Asn Leu Leu Gly Val Gly Leu
            1220                1225                1230

Ala Met Ala Thr Thr Leu Gln Leu Pro Glu Asp Ile Glu Gln Met
            1235                1240                1245

Ala Asn Gly Ile Ala Leu Gly Leu Met Ala Leu Lys Leu Ile Thr
            1250                1255                1260

Gln Phe Glu Thr Tyr Gln Leu Trp Thr Ala Leu Val Ser Leu Met
            1265                1270                1275

Cys Ser Asn Thr Ile Phe Thr Leu Thr Val Ala Trp Arg Thr Ala
            1280                1285                1290

Thr Leu Ile Leu Ala Gly Ile Ser Leu Leu Pro Val Cys Gln Ser
            1295                1300                1305

Ser Ser Met Arg Lys Thr Asp Trp Leu Pro Met Ala Val Ala Ala
            1310                1315                1320

Met Gly Val Pro Pro Leu Pro Leu Phe Ile Phe Ser Leu Lys Asp
            1325                1330                1335

Thr Leu Lys Arg Arg Ser Trp Pro Leu Asn Glu Gly Val Met Ala
            1340                1345                1350

Val Gly Leu Val Ser Ile Leu Ala Ser Ser Leu Leu Arg Asn Asp
            1355                1360                1365

Val Pro Met Ala Gly Pro Leu Val Ala Gly Gly Leu Leu Ile Ala
            1370                1375                1380

Cys Tyr Val Ile Thr Gly Thr Ser Ala Asp Leu Thr Val Glu Lys
            1385                1390                1395

Ala Ala Asp Val Thr Trp Glu Glu Ala Glu Gln Thr Gly Val
            1400                1405                1410

Ser His Asn Leu Met Ile Thr Val Asp Asp Gly Thr Met Arg
            1415                1420                1425

Ile Lys Asp Asp Glu Thr Glu Asn Ile Leu Thr Val Leu Leu Lys
            1430                1435                1440

Thr Ala Leu Leu Ile Val Ser Gly Ile Phe Pro Tyr Ser Ile Pro
            1445                1450                1455

Ala Thr Leu Leu Val Trp His Thr Trp Gln Lys Gln Thr Gln Arg
            1460                1465                1470

Ser Gly Val Leu Trp Asp Val Pro Ser Pro Pro Glu Thr Gln Lys
            1475                1480                1485

Ala Glu Leu Glu Glu Gly Val Tyr Arg Ile Lys Gln Gln Gly Ile
            1490                1495                1500

Phe Gly Lys Thr Gln Val Gly Val Gly Val Gln Lys Glu Gly Val
            1505                1510                1515

Phe His Thr Met Trp His Val Thr Arg Gly Ala Val Leu Thr His
            1520                1525                1530

Asn Gly Lys Arg Leu Glu Pro Asn Trp Ala Ser Val Lys Lys Asp
            1535                1540                1545

Leu Ile Ser Tyr Gly Gly Gly Trp Lys Leu Ser Ala Gln Trp Gln
            1550                1555                1560

Lys Gly Glu Glu Val Gln Val Ile Ala Val Glu Pro Gly Lys Asn
            1565                1570                1575

Pro Lys Asn Phe Gln Thr Met Pro Gly Ile Phe Gln Thr Thr Thr
            1580                1585                1590

Gly Glu Ile Gly Ala Ile Ala Leu Asp Phe Lys Pro Gly Thr Ser
            1595                1600                1605
```

Gly Ser Pro Ile Ile Asn Arg Glu Gly Lys Val Leu Gly Leu Tyr
1610            1615                1620

Gly Asn Gly Val Val Thr Lys Asn Gly Tyr Val Ser Gly Ile
1625            1630                1635

Ala Gln Thr Asn Ala Glu Pro Asp Gly Pro Thr Pro Glu Leu Glu
1640            1645                1650

Glu Glu Met Phe Lys Lys Arg Asn Leu Thr Ile Met Asp Leu His
1655            1660                1665

Pro Gly Ser Gly Lys Thr Arg Lys Tyr Leu Pro Ala Ile Val Arg
1670            1675                1680

Glu Ala Ile Lys Arg Arg Leu Arg Thr Leu Ile Leu Ala Pro Thr
1685            1690                1695

Arg Val Val Ala Ala Glu Met Glu Glu Ala Leu Lys Gly Leu Pro
1700            1705                1710

Ile Arg Tyr Gln Thr Thr Ala Thr Lys Ser Glu His Thr Gly Arg
1715            1720                1725

Glu Ile Val Asp Leu Met Cys His Ala Thr Phe Thr Met Arg Leu
1730            1735                1740

Leu Ser Pro Val Arg Val Pro Asn Tyr Asn Leu Ile Ile Met Asp
1745            1750                1755

Glu Ala His Phe Thr Asp Pro Ala Ser Ile Ala Ala Arg Gly Tyr
1760            1765                1770

Ile Ser Thr Arg Val Gly Met Gly Glu Ala Ala Ala Ile Phe Met
1775            1780                1785

Thr Ala Thr Pro Pro Gly Thr Ala Asp Ala Phe Pro Gln Ser Asn
1790            1795                1800

Ala Pro Ile Gln Asp Glu Glu Arg Asp Ile Pro Glu Arg Ser Trp
1805            1810                1815

Asn Ser Gly Asn Glu Trp Ile Thr Asp Phe Ala Gly Lys Thr Val
1820            1825                1830

Trp Phe Val Pro Ser Ile Lys Ala Gly Asn Asp Ile Ala Asn Cys
1835            1840                1845

Leu Arg Lys Asn Gly Lys Lys Val Ile Gln Leu Ser Arg Lys Thr
1850            1855                1860

Phe Asp Thr Glu Tyr Gln Lys Thr Lys Leu Asn Asp Trp Asp Phe
1865            1870                1875

Val Val Thr Thr Asp Ile Ser Glu Met Gly Ala Asn Phe Lys Ala
1880            1885                1890

Asp Arg Val Ile Asp Pro Arg Arg Cys Leu Lys Pro Val Ile Leu
1895            1900                1905

Thr Asp Gly Pro Glu Arg Val Ile Leu Ala Gly Pro Met Pro Val
1910            1915                1920

Thr Val Ala Ser Ala Ala Gln Arg Arg Gly Arg Val Gly Arg Asn
1925            1930                1935

Pro Gln Lys Glu Asn Asp Gln Tyr Ile Phe Met Gly Gln Pro Leu
1940            1945                1950

Asn Asn Asp Glu Asp His Ala His Trp Thr Glu Ala Lys Met Leu
1955            1960                1965

Leu Asp Asn Ile Asn Thr Pro Glu Gly Ile Ile Pro Ala Leu Phe
1970            1975                1980

Glu Pro Glu Arg Glu Lys Ser Ala Ala Ile Asp Gly Glu Tyr Arg
1985            1990                1995

```
Leu Lys Gly Glu Ser Arg Lys Thr Phe Val Glu Leu Met Arg Arg
2000                2005                2010

Gly Asp Leu Pro Val Trp Leu Ala His Lys Val Ala Ser Glu Gly
2015                2020                2025

Ile Lys Tyr Thr Asp Arg Lys Trp Cys Phe Asp Gly Glu Arg Asn
2030                2035                2040

Asn Gln Ile Leu Glu Glu Asn Met Asp Val Glu Ile Trp Thr Lys
2045                2050                2055

Glu Gly Glu Lys Lys Lys Leu Arg Pro Arg Trp Leu Asp Ala Arg
2060                2065                2070

Thr Tyr Ser Asp Pro Leu Ala Leu Lys Glu Phe Lys Asp Phe Ala
2075                2080                2085

Ala Gly Arg Lys Ser Ile Ala Leu Asp Leu Val Thr Glu Ile Gly
2090                2095                2100

Arg Val Pro Ser His Leu Ala His Arg Thr Arg Asn Ala Leu Asp
2105                2110                2115

Asn Leu Val Met Leu His Thr Ser Glu His Gly Gly Arg Ala Tyr
2120                2125                2130

Arg His Ala Val Glu Glu Leu Pro Glu Thr Met Glu Thr Leu Leu
2135                2140                2145

Leu Leu Gly Leu Met Ile Leu Leu Thr Gly Gly Ala Met Leu Phe
2150                2155                2160

Leu Ile Ser Gly Lys Gly Ile Gly Lys Thr Ser Ile Gly Leu Ile
2165                2170                2175

Cys Val Ala Ala Ser Ser Gly Met Leu Trp Met Ala Asp Val Pro
2180                2185                2190

Leu Gln Trp Ile Ala Ser Ala Ile Val Leu Glu Phe Phe Met Met
2195                2200                2205

Val Leu Leu Ile Pro Glu Pro Glu Lys Gln Arg Thr Pro Gln Asp
2210                2215                2220

Asn Gln Leu Ala Tyr Val Val Ile Gly Ile Leu Thr Leu Ala Ala
2225                2230                2235

Ile Val Ala Ala Asn Glu Met Gly Leu Leu Glu Thr Thr Lys Arg
2240                2245                2250

Asp Leu Gly Met Ser Lys Glu Pro Gly Val Val Ser Pro Thr Ser
2255                2260                2265

Tyr Leu Asp Val Asp Leu His Pro Ala Ser Ala Trp Thr Leu Tyr
2270                2275                2280

Ala Val Ala Thr Thr Val Ile Thr Pro Met Leu Arg His Thr Ile
2285                2290                2295

Glu Asn Ser Thr Ala Asn Val Ser Leu Ala Ala Ile Ala Asn Gln
2300                2305                2310

Ala Val Val Leu Met Gly Leu Asp Lys Gly Trp Pro Ile Ser Lys
2315                2320                2325

Met Asp Leu Gly Val Pro Leu Leu Ala Leu Gly Cys Tyr Ser Gln
2330                2335                2340

Val Asn Pro Leu Thr Leu Thr Ala Ala Val Leu Leu Leu Val Thr
2345                2350                2355

His Tyr Ala Ile Ile Gly Pro Gly Leu Gln Ala Lys Ala Thr Arg
2360                2365                2370

Glu Ala Gln Lys Arg Thr Ala Ala Gly Ile Met Lys Asn Pro Thr
2375                2380                2385

Val Asp Gly Ile Met Thr Ile Asp Leu Asp Pro Val Ile Tyr Asp
```

```
            2390            2395            2400
Ser Lys Phe Glu Lys Gln Leu Gly Gln Val Met Leu Leu Val Leu
    2405            2410            2415
Cys Ala Val Gln Leu Leu Leu Met Arg Thr Ser Trp Ala Phe Cys
    2420            2425            2430
Glu Ala Leu Thr Leu Ala Thr Gly Pro Ile Thr Thr Leu Trp Glu
    2435            2440            2445
Gly Ser Pro Gly Lys Phe Trp Asn Thr Thr Ile Ala Val Ser Met
    2450            2455            2460
Ala Asn Ile Phe Arg Gly Ser Tyr Leu Ala Gly Gly Leu Ala
    2465            2470            2475
Phe Ser Ile Met Lys Ser Val Gly Thr Gly Lys Arg Gly Thr Gly
    2480            2485            2490
Ser Gln Gly Glu Thr Leu Gly Glu Lys Trp Lys Lys Leu Asn
    2495            2500            2505
Gln Leu Pro Arg Lys Glu Phe Asp Leu Tyr Lys Lys Ser Gly Ile
    2510            2515            2520
Thr Glu Val Asp Arg Thr Glu Ala Lys Glu Gly Leu Lys Arg Gly
    2525            2530            2535
Glu Ile Thr His His Ala Val Ser Arg Gly Ser Ala Lys Leu Gln
    2540            2545            2550
Trp Phe Val Glu Arg Asn Met Val Ile Pro Glu Gly Arg Val Ile
    2555            2560            2565
Asp Leu Gly Cys Gly Arg Gly Gly Trp Ser Tyr Tyr Cys Ala Gly
    2570            2575            2580
Leu Lys Lys Val Thr Glu Val Arg Gly Tyr Thr Lys Gly Gly Pro
    2585            2590            2595
Gly His Glu Glu Pro Val Pro Met Ser Thr Tyr Gly Trp Asn Ile
    2600            2605            2610
Val Lys Leu Met Ser Gly Lys Asp Val Phe Tyr Leu Pro Pro Glu
    2615            2620            2625
Lys Cys Asp Thr Leu Leu Cys Asp Ile Gly Glu Ser Ser Pro Ser
    2630            2635            2640
Pro Thr Val Glu Glu Ser Arg Thr Ile Arg Val Leu Lys Met Val
    2645            2650            2655
Glu Pro Trp Leu Lys Asn Asn Gln Phe Cys Ile Lys Val Leu Asn
    2660            2665            2670
Pro Tyr Met Pro Thr Val Ile Glu His Leu Glu Arg Leu Gln Arg
    2675            2680            2685
Lys His Gly Gly Met Leu Val Arg Asn Pro Leu Ser Arg Asn Ser
    2690            2695            2700
Thr His Glu Met Tyr Trp Ile Ser Asn Gly Thr Gly Asn Ile Val
    2705            2710            2715
Ser Ser Val Asn Met Val Ser Arg Leu Leu Leu Asn Arg Phe Thr
    2720            2725            2730
Met Thr His Arg Arg Pro Thr Ile Glu Lys Asp Val Asp Leu Gly
    2735            2740            2745
Ala Gly Thr Arg His Val Asn Ala Glu Pro Glu Thr Pro Asn Met
    2750            2755            2760
Asp Val Ile Gly Glu Arg Ile Arg Arg Ile Lys Glu Glu His Ser
    2765            2770            2775
Ser Thr Trp His Tyr Asp Asp Glu Asn Pro Tyr Lys Thr Trp Ala
    2780            2785            2790
```

-continued

```
Tyr His Gly Ser Tyr Glu Val Lys Ala Thr Gly Ser Ala Ser Ser
            2795                2800                2805

Met Ile Asn Gly Val Val Lys Leu Leu Thr Lys Pro Trp Asp Val
            2810                2815                2820

Val Pro Met Val Thr Gln Met Ala Met Thr Asp Thr Thr Pro Phe
            2825                2830                2835

Gly Gln Gln Arg Val Phe Lys Glu Lys Val Asp Thr Arg Thr Pro
            2840                2845                2850

Arg Pro Met Pro Gly Thr Arg Lys Val Met Glu Ile Thr Ala Glu
            2855                2860                2865

Trp Leu Trp Arg Thr Leu Gly Arg Asn Lys Arg Pro Arg Leu Cys
            2870                2875                2880

Thr Arg Glu Glu Phe Thr Lys Lys Val Arg Thr Asn Ala Ala Met
            2885                2890                2895

Gly Ala Val Phe Thr Glu Glu Asn Gln Trp Asp Ser Ala Arg Ala
            2900                2905                2910

Ala Val Glu Asp Glu Glu Phe Trp Lys Leu Val Asp Arg Glu Arg
            2915                2920                2925

Glu Leu His Lys Leu Gly Lys Cys Gly Ser Cys Val Tyr Asn Met
            2930                2935                2940

Met Gly Lys Arg Glu Lys Lys Leu Gly Glu Phe Gly Lys Ala Lys
            2945                2950                2955

Gly Ser Arg Ala Ile Trp Tyr Met Trp Leu Gly Ala Arg Tyr Leu
            2960                2965                2970

Glu Phe Glu Ala Leu Gly Phe Leu Asn Glu Asp His Trp Phe Ser
            2975                2980                2985

Arg Glu Asn Ser Tyr Ser Gly Val Glu Gly Glu Gly Leu His Lys
            2990                2995                3000

Leu Gly Tyr Ile Leu Arg Asp Ile Ser Lys Ile Pro Gly Gly Ala
            3005                3010                3015

Met Tyr Ala Asp Asp Thr Ala Gly Trp Asp Thr Arg Ile Thr Glu
            3020                3025                3030

Asp Asp Leu His Asn Glu Glu Lys Ile Thr Gln Gln Met Asp Pro
            3035                3040                3045

Glu His Arg Gln Leu Ala Asn Ala Ile Phe Lys Leu Thr Tyr Gln
            3050                3055                3060

Asn Lys Val Val Lys Val Gln Arg Pro Thr Pro Lys Gly Thr Val
            3065                3070                3075

Met Asp Ile Ile Ser Arg Lys Asp Gln Arg Gly Ser Gly Gln Val
            3080                3085                3090

Gly Thr Tyr Gly Leu Asn Thr Phe Thr Asn Met Glu Ala Gln Leu
            3095                3100                3105

Ile Arg Gln Met Glu Gly Glu Gly Val Leu Ser Lys Ala Asp Leu
            3110                3115                3120

Glu Asn Pro His Leu Leu Glu Lys Lys Val Thr Gln Trp Leu Glu
            3125                3130                3135

Thr Lys Gly Val Glu Arg Leu Lys Arg Met Ala Ile Ser Gly Asp
            3140                3145                3150

Asp Cys Val Val Lys Pro Ile Asp Asp Arg Phe Ala Asn Ala Leu
            3155                3160                3165

Leu Ala Leu Asn Asp Met Gly Lys Val Arg Lys Asp Ile Pro Gln
            3170                3175                3180
```

```
Trp Gln Pro Ser Lys Gly Trp His Asp Trp Gln Gln Val Pro Phe
    3185                3190                3195
Cys Ser His His Phe His Glu Leu Ile Met Lys Asp Gly Arg Lys
    3200                3205                3210
Leu Val Val Pro Cys Arg Pro Gln Asp Glu Leu Ile Gly Arg Ala
    3215                3220                3225
Arg Ile Ser Gln Gly Ala Gly Trp Ser Leu Arg Glu Thr Ala Cys
    3230                3235                3240
Leu Gly Lys Ala Tyr Ala Gln Met Trp Thr Leu Met Tyr Phe His
    3245                3250                3255
Arg Arg Asp Leu Arg Leu Ala Ser Asn Ala Ile Cys Ser Ala Val
    3260                3265                3270
Pro Val His Trp Val Pro Thr Ser Arg Thr Thr Trp Ser Ile His
    3275                3280                3285
Ala His His Gln Trp Met Thr Thr Glu Asp Met Leu Thr Val Trp
    3290                3295                3300
Asn Arg Val Trp Ile Glu Asp Asn Pro Trp Met Glu Asp Lys Thr
    3305                3310                3315
Pro Val Lys Thr Trp Glu Asp Val Pro Tyr Leu Gly Lys Arg Glu
    3320                3325                3330
Asp Gln Trp Cys Gly Ser Leu Ile Gly Leu Thr Ser Arg Ala Thr
    3335                3340                3345
Trp Ala Gln Asn Ile Leu Thr Ala Ile Gln Gln Val Arg Ser Leu
    3350                3355                3360
Ile Gly Asn Glu Glu Phe Leu Asp Tyr Met Pro Ser Met Lys Arg
    3365                3370                3375
Phe Arg Lys Glu Glu Glu Ser Glu Gly Ala Ile Trp
    3380                3385                3390

<210> SEQ ID NO 50
<211> LENGTH: 2426
<212> TYPE: DNA
<213> ORGANISM: Artificial Sequence
<220> FEATURE:
<223> OTHER INFORMATION: Dengue 1 CME chimeric region

<400> SEQUENCE: 50
agttgttagt ctgtgtggac cgacaaggac agttccaaat cggaagcttg cttaacacag    60
ttctaacagt ttgtttgaat agagagcaga tctctggaaa aatgaacaac caacggaaaa   120
agacgggtcg accgtctttc aatatgctga acgcgcgag aaaccgcgtg tcaactggtt    180
cacagttggc gaagagattc tcaaaaggat tgctttcagg ccaaggaccc atgaaattgg    240
tgatggcttt catagcattt ctaagatttc tagccatacc cccaacagca ggaattttgg    300
ctagatggag ctcattcaag aagaatggag cgatcaaagt gttacggggt ttcaaaaaag    360
agatctcaag catgttgaac attatgaaca ggaggaaaaa atctgtgacc atgctcctca    420
tgctgctgcc cacagccctg gcgttccatt tgaccacacg aggggagag ccacacatga    480 tagttagtaa gcaggaaaga ggaaagtcac tgttgtttaa acctctgca ggcatcaata    540 tgtgcactct cattgcgatg gatttggag agttatgcga ggacacaatg acctacaaat    600
gcccccggat cactgaggcg gaaccagatg acgttgactg ctggtgcaat gccacagaca    660
catgggtgac ctatgggacg tgttctcaaa ccggcgaaca ccgacgagac aaacgttccg    720
tggcactggc cccacgtgtg ggacttggtc tagaaacaag aaccgaaaca tggatgtcct    780
ctgaaggtgc ctggaaacaa gtacaaaaag tggagacttg gctttgaga cacccaggat    840
```

```
tcacggtgac agccctttt ttagcacatg ccataggaac atccattact cagaaaggga      900
tcattttcat tctgctgatg ctagtaacac catcaatggc catgcgatgt gtgggaatag      960
gcaacagaga cttcgttgaa ggactgtcag gagcaacgtg ggtggacgtg gtattggagc     1020
atggaagctg cgtcaccacc atggcaaaag ataaaccaac attggacatt gaactcttga     1080
agacggaggt cacaaaccct gccgtcttgc gcaaactgtg cattgaagct aaaatatcaa     1140
acaccaccac cgattcaagg tgtccaacac aaggagaggc tacactggtg gaagaacagg     1200
actcgaactt tgtgtgtcga cgaacgtttg tggacagagg ctggggtaat ggctgcggac     1260
tatttggaaa aggaagccta ctgacgtgtg ctaagttcaa gtgtgtgaca aaactagaag     1320
gaaagatagt tcaatatgaa aacttaaaat attcagtgat agtcactgtc cacactgggg     1380
accagcacca ggtgggaaac gagactacag aacatggaac aattgcaacc ataacacctc     1440
aagctcctac gtcggaaata cagctgactg actacggagc cctcacattg gactgctcgc     1500
ctagaacagg gctggacttt aatgagatgg ttctattgac aatgaaagaa aaatcatggc     1560
ttgtccacaa acaatggttt ctagacttac cactgccttg acttcagga gcttcaacat     1620 ctcaagagac ttggaacaga caagatttgc tggtcacatt caagacagct catgcaaaga     1680
aacaggaagt agtcgtactg ggatcacagg aaggagcaat gcacactgcg ttgactgggg     1740
cgacagaaat ccagacgtca ggaacgacaa caatctttgc aggacacctg aaatgcagac     1800
taaaaatgga taaactgact ttaaaaggga tgtcatatgt aatgtgcaca ggctcattta     1860
agctagagaa ggaagtggct gagacccagc atggaactgt tttagtgcag gttaaatacg     1920
aaggaacaga tgcgccatgc aagatccctt tttcggccca agatgagaaa ggagtgaccc     1980
agaatgggag attgataaca gccaacccca tagtcactga caaagaaaaa ccagtcaaca     2040
ttgagacaga accaccttt ggtgagagct acatcgtggt aggggcaggt gaaaaagctt     2100
tgaaactgag ctggttcaag aagggagca catagggaa atgttcgaa gcaactgccc     2160 gaggagcgcg aaggatggct atcctgggag acaccgcatg ggactttggc tctataggag     2220
gagtgttcac atcagtggga aaattggtac accaggtttt tggagccgca tatgggggttc     2280 tgttcagcgg tgtttcttgg accatgaaaa taggaatagg gattctgctg acatggctag     2340
gattaaactc gaggaacact tcaatggcta tgacgtgcat agctgttgga ggaatcactc     2400
tgtttctggg cttcacagtt caagca                                           2426
```

<210> SEQ ID NO 51
<211> LENGTH: 775
<212> TYPE: PRT
<213> ORGANISM: Artificial Sequence
<220> FEATURE:
<223> OTHER INFORMATION: Dengue 1 CME chimeric region

<400> SEQUENCE: 51

```
Met Asn Asn Gln Arg Lys Lys Thr Gly Arg Pro Ser Phe Asn Met Leu
  1               5                  10                  15

Lys Arg Ala Arg Asn Arg Val Ser Thr Gly Ser Gln Leu Ala Lys Arg
             20                  25                  30

Phe Ser Lys Gly Leu Leu Ser Gly Gln Gly Pro Met Lys Leu Val Met
         35                  40                  45

Ala Phe Ile Ala Phe Leu Arg Phe Leu Ala Ile Pro Pro Thr Ala Gly
     50                  55                  60

Ile Leu Ala Arg Trp Ser Ser Phe Lys Lys Asn Gly Ala Ile Lys Val
 65                  70                  75                  80
```

```
Leu Arg Gly Phe Lys Lys Glu Ile Ser Ser Met Leu Asn Ile Met Asn
                85                  90                  95

Arg Arg Lys Lys Ser Val Thr Met Leu Leu Met Leu Leu Pro Thr Ala
            100                 105                 110

Leu Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Ile Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Thr Glu Thr Trp
    210                 215                 220

Met Ser Glu Gly Ala Trp Lys Gln Val Gln Lys Val Glu Thr Trp
225                 230                 235                 240

Ala Leu Arg His Pro Gly Phe Thr Val Thr Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asp Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ser
        355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Leu Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Ile Ala Thr Ile Thr Pro Gln Ala
        435                 440                 445

Pro Thr Ser Glu Ile Gln Leu Thr Asp Tyr Gly Ala Leu Thr Leu Asp
    450                 455                 460

Cys Ser Pro Arg Thr Gly Leu Asp Phe Asn Glu Met Val Leu Leu Thr
465                 470                 475                 480

Met Lys Glu Lys Ser Trp Leu Val His Lys Gln Trp Phe Leu Asp Leu
                485                 490                 495
```

```
Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560
Gly His Leu Lys Cys Arg Leu Lys Met Asp Lys Leu Thr Leu Lys Gly
                565                 570                 575
Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Ala Gln Asp Glu Lys Gly
    610                 615                 620

Val Thr Gln Asn Gly Arg Leu Ile Thr Ala Asn Pro Ile Val Thr Asp
625                 630                 635                 640
Lys Glu Lys Pro Val Asn Ile Glu Thr Glu Pro Pro Phe Gly Glu Ser
                645                 650                 655
Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Val Gly Lys Leu Val His Gln Val Phe
705                 710                 715                 720
Gly Ala Ala Tyr Gly Val Leu Phe Ser Gly Val Ser Trp Thr Met Lys
                725                 730                 735
Ile Gly Ile Gly Ile Leu Leu Thr Trp Leu Gly Leu Asn Ser Arg Asn
            740                 745                 750

Thr Ser Met Ala Met Thr Cys Ile Ala Val Gly Gly Ile Thr Leu Phe
        755                 760                 765

Leu Gly Phe Thr Val Gln Ala
    770                 775

<210> SEQ ID NO 52
<211> LENGTH: 2423
<212> TYPE: DNA
<213> ORGANISM: Artificial Sequence
<220> FEATURE:
<223> OTHER INFORMATION: Dengue 1 ME chimeric region
<400> SEQUENCE: 52
agttgttagt ctgtgtggac cgacaaggac agttccaaat cggaagcttg cttaacacag      60
ttctaacagt ttgtttgaat agagagcaga tctctggaaa aatgaaccaa cgaaaaaagg     120
tggttagacc acctttcaat atgctgaaac gcgagagaaa ccgcgtatca acccctcaag     180
ggttggtgaa gagattctca accggacttt tttctgggaa aggaccctta cggatggtgc     240
tagcattcat cacgtttttg cgagtccttt ccatcccacc aacagcaggg attctgaaga     300
gatggggaca gttgaagaaa aataaggcca tcaagatact gattggattc aggaaggaga     360
taggccgcat gctgaacatc ttgaacggga gaaaaaggtc tgcagccatg ctcctcatgc     420
tgctgcccac agccctggcg ttccatttga ccacacgagg gggagagcca cacatgatag     480
```

```
ttagtaagca ggaaagagga aagtcactgt tgtttaagac ctctgcaggc atcaatatgt    540
gcactctcat tgcgatggat ttgggagagt tatgcgagga cacaatgacc tacaaatgcc    600
cccggatcac tgaggcggaa ccagatgacg ttgactgctg gtgcaatgcc acagacacat    660
gggtgaccta tgggacgtgt tctcaaaccg gcgaacaccg acgagacaaa cgttccgtgg    720
cactggcccc acacgtggga cttggtctag aaacaagaac cgaaacatgg atgtcctctg    780
aaggtgcctg gaaacaagta caaaaagtgg agacttgggc tttgagacac ccaggattca    840
cggtgacagc cctttttta gcacatgcca taggaacatc cattactcag aaagggatca    900
ttttcattct gctgatgcta gtaacaccat caatggccat gcgatgtgtg ggaataggca    960
acagagactt cgttgaagga ctgtcaggag caacgtgggt ggacgtggta ttggagcatg   1020
gaagctgcgt caccaccatg gcaaaagata aaccaacatt ggacattgaa ctcttgaaga   1080
cggaggtcac aaaccctgcc gtcttgcgca aactgtgcat tgaagctaaa atatcaaaca   1140
ccaccaccga ttcaaggtgt ccaacacaag gagaggctac actggtggaa gaacaggact   1200
cgaactttgt gtgtcgacga acgtttgtgg acagaggctg gggtaatggc tgcggactat   1260
ttggaaaagg aagcctactg acgtgtgcta agttcaagtg tgtgacaaaa ctagaaggaa   1320
agatagttca atatgaaaac ttaaaatatt cagtgatagt cactgtccac actggggacc   1380
agcaccaggt gggaaacgag actacagaac atggaacaat tgcaaccata acacctcaag   1440
ctcctacgtc ggaaatacag ctgactgact acggagccct cacattggac tgctcgccta   1500
gaacagggct ggactttaat gagatggttc tattgacaat gaaagaaaaa tcatggcttg   1560
tccacaaaca atggtttcta gacttaccac tgccttggac ttcaggagct tcaacatctc   1620
aagagacttg gaacagacaa gatttgctgg tcacattcaa gacagctcat gcaaagaaac   1680
aggaagtagt cgtactggga tcacaggaag gagcaatgca cactgcgttg actggggcga   1740
cagaaatcca gacgtcagga acgacaacaa tctttgcagg acacctgaaa tgcagactaa   1800
aaatggataa actgacttta aaagggatgt catatgtaat gtgcacaggc tcatttaagc   1860
tagagaagga agtggctgag acccagcatg gaactgtttt agtgcaggtt aaatacgaag   1920
gaacagatgc gccatgcaag atcccttttt cggcccaaga tgagaaagga gtgacccaga   1980
atgggagatt gataacagcc aaccccatag tcactgacaa agaaaaacca gtcaacattg   2040
agacagaacc accttttggt gagagctaca tcgtggtagg ggcaggtgaa aaagctttga   2100
aactgagctg gttcaagaaa gggagcagca tagggaaaat gttcgaagca actgcccgag   2160
gagcgcgaag gatggctatc ctgggagaca ccgcatggga ctttggctct ataggaggag   2220
tgttcacatc agtgggaaaa ttggtacacc aggtttttgg agccgcatat ggggttctgt   2280
tcagcggtgt ttcttggacc atgaaaatag gaatagggat tctgctgaca tggctaggat   2340
taaactcgag gaacacttca atggctatga cgtgcatagc tgttggagga atcactctgt   2400
ttctgggctt cacagttcaa gca                                           2423
```

```
<210> SEQ ID NO 53
<211> LENGTH: 774
<212> TYPE: PRT
<213> ORGANISM: Artificial Sequence
<220> FEATURE:
<223> OTHER INFORMATION: Dengue 1 ME chimeric region

<400> SEQUENCE: 53

Met Asn Gln Arg Lys Lys Val Val Arg Pro Pro Phe Asn Met Leu Lys
1               5                   10                  15
```

```
Arg Glu Arg Asn Arg Val Ser Thr Pro Gln Gly Leu Val Lys Arg Phe
                20                  25                  30

Ser Thr Gly Leu Phe Ser Gly Lys Gly Pro Leu Arg Met Val Leu Ala
            35                  40                  45

Phe Ile Thr Phe Leu Arg Val Leu Ser Ile Pro Pro Thr Ala Gly Ile
 50                  55                  60

Leu Lys Arg Trp Gly Gln Leu Lys Lys Asn Lys Ala Ile Lys Ile Leu
 65                  70                  75                  80

Ile Gly Phe Arg Lys Glu Ile Gly Arg Met Leu Asn Ile Leu Asn Gly
                85                  90                  95

Arg Lys Arg Ser Ala Ala Met Leu Leu Met Leu Leu Pro Thr Ala Leu
                100                 105                 110

Ala Phe His Leu Thr Thr Arg Gly Gly Glu Pro His Met Ile Val Ser
            115                 120                 125

Lys Gln Glu Arg Gly Lys Ser Leu Leu Phe Lys Thr Ser Ala Gly Ile
130                 135                 140

Asn Met Cys Thr Leu Ile Ala Met Asp Leu Gly Glu Leu Cys Glu Asp
145                 150                 155                 160

Thr Met Thr Tyr Lys Cys Pro Arg Ile Thr Glu Ala Glu Pro Asp Asp
                165                 170                 175

Val Asp Cys Trp Cys Asn Ala Thr Asp Thr Trp Val Thr Tyr Gly Thr
            180                 185                 190

Cys Ser Gln Thr Gly Glu His Arg Arg Asp Lys Arg Ser Val Ala Leu
            195                 200                 205

Ala Pro His Val Gly Leu Gly Leu Glu Thr Arg Thr Glu Thr Trp Met
            210                 215                 220

Ser Ser Glu Gly Ala Trp Lys Gln Val Gln Lys Val Glu Thr Trp Ala
225                 230                 235                 240

Leu Arg His Pro Gly Phe Thr Val Thr Ala Leu Phe Leu Ala His Ala
                245                 250                 255

Ile Gly Thr Ser Ile Thr Gln Lys Gly Ile Ile Phe Ile Leu Leu Met
            260                 265                 270

Leu Val Thr Pro Ser Met Ala Met Arg Cys Val Gly Ile Gly Asn Arg
            275                 280                 285

Asp Phe Val Glu Gly Leu Ser Gly Ala Thr Trp Val Asp Val Val Leu
290                 295                 300

Glu His Gly Ser Cys Val Thr Thr Met Ala Lys Asp Lys Pro Thr Leu
305                 310                 315                 320

Asp Ile Glu Leu Leu Lys Thr Glu Val Thr Asn Pro Ala Val Leu Arg
                325                 330                 335

Lys Leu Cys Ile Glu Ala Lys Ile Ser Asn Thr Thr Thr Asp Ser Arg
            340                 345                 350

Cys Pro Thr Gln Gly Glu Ala Thr Leu Val Glu Glu Gln Asp Ser Asn
            355                 360                 365

Phe Val Cys Arg Arg Thr Phe Val Asp Arg Gly Trp Gly Asn Gly Cys
            370                 375                 380

Gly Leu Phe Gly Lys Gly Ser Leu Leu Thr Cys Ala Lys Phe Lys Cys
385                 390                 395                 400

Val Thr Lys Leu Glu Gly Lys Ile Val Gln Tyr Glu Asn Leu Lys Tyr
                405                 410                 415

Ser Val Ile Val Thr Val His Thr Gly Asp Gln His Gln Val Gly Asn
            420                 425                 430
```

```
Glu Thr Thr Glu His Gly Thr Ile Ala Thr Ile Thr Pro Gln Ala Pro
            435                 440                 445

Thr Ser Glu Ile Gln Leu Thr Asp Tyr Gly Ala Leu Thr Leu Asp Cys
450                 455                 460

Ser Pro Arg Thr Gly Leu Asp Phe Asn Glu Met Val Leu Leu Thr Met
465                 470                 475                 480

Lys Glu Lys Ser Trp Leu Val His Lys Gln Trp Phe Leu Asp Leu Pro
                485                 490                 495

Leu Pro Trp Thr Ser Gly Ala Ser Ser Gln Glu Thr Trp Asn Arg
            500                 505                 510

Gln Asp Leu Leu Val Thr Phe Lys Thr Ala His Ala Lys Lys Gln Glu
                515                 520                 525

Val Val Val Leu Gly Ser Gln Glu Gly Ala Met His Thr Ala Leu Thr
530                 535                 540

Gly Ala Thr Glu Ile Gln Thr Ser Gly Thr Thr Thr Ile Phe Ala Gly
545                 550                 555                 560

His Leu Lys Cys Arg Leu Lys Met Asp Lys Leu Thr Leu Lys Gly Met
                565                 570                 575

Ser Tyr Val Met Cys Thr Gly Ser Phe Lys Leu Glu Lys Glu Val Ala
            580                 585                 590

Glu Thr Gln His Gly Thr Val Leu Val Gln Val Lys Tyr Glu Gly Thr
        595                 600                 605

Asp Ala Pro Cys Lys Ile Pro Phe Ser Ala Gln Asp Glu Lys Gly Val
            610                 615                 620

Thr Gln Asn Gly Arg Leu Ile Thr Ala Asn Pro Ile Val Thr Asp Lys
625                 630                 635                 640

Glu Lys Pro Val Asn Ile Glu Thr Glu Pro Pro Phe Gly Glu Ser Tyr
                645                 650                 655

Ile Val Val Gly Ala Gly Glu Lys Ala Leu Lys Leu Ser Trp Phe Lys
            660                 665                 670

Lys Gly Ser Ser Ile Gly Lys Met Phe Glu Ala Thr Ala Arg Gly Ala
        675                 680                 685

Arg Arg Met Ala Ile Leu Gly Asp Thr Ala Trp Asp Phe Gly Ser Ile
690                 695                 700

Gly Gly Val Phe Thr Ser Val Gly Lys Leu Val His Gln Val Phe Gly
705                 710                 715                 720

Ala Ala Tyr Gly Val Leu Phe Ser Gly Val Ser Trp Thr Met Lys Ile
                725                 730                 735

Gly Ile Gly Ile Leu Leu Thr Trp Leu Gly Leu Asn Ser Arg Asn Thr
            740                 745                 750

Ser Met Ala Met Thr Cys Ile Ala Val Gly Gly Ile Thr Leu Phe Leu
            755                 760                 765

Gly Phe Thr Val Gln Ala
770

<210> SEQ ID NO 54
<211> LENGTH: 60
<212> TYPE: RNA
<213> ORGANISM: Dengue virus

<400> SEQUENCE: 54
ccaacaaccu ugacagcauc cuuagucaug cuuuuagucc auuaugcaau aauaggccca     60

<210> SEQ ID NO 55
<211> LENGTH: 20
```

-continued

<212> TYPE: PRT
<213> ORGANISM: Dengue virus

<400> SEQUENCE: 55

Pro Thr Thr Leu Thr Ala Ser Leu Val Met Leu Leu Val His Thr Ala
1 5 10 15

Ile Ile Gly Pro
20

<210> SEQ ID NO 56
<211> LENGTH: 60
<212> TYPE: RNA
<213> ORGANISM: Dengue virus

<400> SEQUENCE: 56
ccgcugacgc ugacagcggc gguauuuaug cuaguggcuc auuaugccau aauuggaccc 60

<210> SEQ ID NO 57
<211> LENGTH: 20
<212> TYPE: PRT
<213> ORGANISM: Dengue virus

<400> SEQUENCE: 57

Pro Leu Thr Leu Thr Ala Ala Val Pro Met Leu Val Ala His Thr Ala
1 5 10 15

Ile Ile Gly Pro
20

<210> SEQ ID NO 58
<211> LENGTH: 60
<212> TYPE: RNA
<213> ORGANISM: Dengue virus

<400> SEQUENCE: 58
ccuauaaccc ucacagcggc ucuucuuuua uugguagcac auuaugccau cauaggaccg 60

<210> SEQ ID NO 59
<211> LENGTH: 20
<212> TYPE: PRT
<213> ORGANISM: Dengue virus

<400> SEQUENCE: 59

Pro Ile Thr Leu Thr Ala Ala Leu Leu Leu Leu Val Ala His Thr Ala
1 5 10 15

Ile Ile Gly Pro
20

<210> SEQ ID NO 60
<211> LENGTH: 60
<212> TYPE: RNA
<213> ORGANISM: Dengue virus

<400> SEQUENCE: 60
ccacuaacuc ucacagcggc aguucuccug cuagucacgc auuaugcuau uauaggucca 60

<210> SEQ ID NO 61
<211> LENGTH: 20
<212> TYPE: PRT
<213> ORGANISM: Dengue virus

<400> SEQUENCE: 61

Pro Leu Thr Leu Thr Ala Ala Val Leu Leu Leu Val Thr His Thr Ala
1 5 10 15

Ile Ile Gly Pro
        20

<210> SEQ ID NO 62
<211> LENGTH: 47
<212> TYPE: RNA
<213> ORGANISM: Dengue virus

<400> SEQUENCE: 62
ggccgccagg aggaagcugu acuccuggug aaggacuag agguuag                    47

<210> SEQ ID NO 63
<211> LENGTH: 46
<212> TYPE: RNA
<213> ORGANISM: Dengue virus

<400> SEQUENCE: 63
ggggcccaac accaggggaa gcuguacccu ggugguaagg acuaga                    46

<210> SEQ ID NO 64
<211> LENGTH: 16
<212> TYPE: RNA
<213> ORGANISM: Dengue virus

<400> SEQUENCE: 64
ggggcccaag acuaga                                                     16

<210> SEQ ID NO 65
<211> LENGTH: 46
<212> TYPE: RNA
<213> ORGANISM: Dengue virus

<400> SEQUENCE: 65
ggggcccaag gugagaugaa gcuguagucu cacuggaagg acuaga                    46

<210> SEQ ID NO 66
<211> LENGTH: 47
<212> TYPE: RNA
<213> ORGANISM: Dengue virus

<400> SEQUENCE: 66
ggggcccgag cucugaggga agcuguaccu ccuugcaaag gacuaga                   47

<210> SEQ ID NO 67
<211> LENGTH: 47
<212> TYPE: RNA
<213> ORGANISM: Dengue virus

<400> SEQUENCE: 67
ggggcccgaa gccaggagga agcuguacuc cugguggaag gacuaga                   47

<210> SEQ ID NO 68
<211> LENGTH: 84
<212> TYPE: RNA
<213> ORGANISM: Dengue virus

<400> SEQUENCE: 68
gcagcagcgg ggcccaacac caggggaagc uguacccugg ugguaaggac uagagagguu     60
agaggagacc ccccgcaaca acaa                                            84

<210> SEQ ID NO 69
<211> LENGTH: 86

-continued

```
<212> TYPE: RNA
<213> ORGANISM: Dengue virus

<400> SEQUENCE: 69
agcaacaaug ggggcccaag gugagaugaa gcuguagucu cacuggaagg acuagagagg    60
uuagaggaga cccccccaaa acaaaa                                        86

<210> SEQ ID NO 70
<211> LENGTH: 85
<212> TYPE: RNA
<213> ORGANISM: Dengue virus

<400> SEQUENCE: 70
gcagcagcgg ggcccgagcu cugagggaag cuguaccucc uugcaaagga cuagagaggu    60
uagaggagac cccccgcaaa uaaaa                                         85

<210> SEQ ID NO 71
<211> LENGTH: 85
<212> TYPE: RNA
<213> ORGANISM: Dengue virus

<400> SEQUENCE: 71
agcaaaaggg ggcccgaagc caggaggaag cuguacuccu gguggaagga cuagagaggu    60
uagaggagac cccccaaca caaaa                                          85

<210> SEQ ID NO 72
<211> LENGTH: 51
<212> TYPE: DNA
<213> ORGANISM: Dengue virus

<400> SEQUENCE: 72
tggggcccca aggtgagatg aagctgtagt ctcactggaa ggactagagg t             51

<210> SEQ ID NO 73
<211> LENGTH: 21
<212> TYPE: DNA
<213> ORGANISM: dengue virus

<400> SEQUENCE: 73
tggggcccca agactagagg t                                             21

<210> SEQ ID NO 74
<211> LENGTH: 51
<212> TYPE: DNA
<213> ORGANISM: Dengue virus

<400> SEQUENCE: 74
cggggcccga gctctgaggg aagctgtacc tccttgcaaa ggactagagg t             51

<210> SEQ ID NO 75
<211> LENGTH: 20
<212> TYPE: DNA
<213> ORGANISM: Dengue virus

<400> SEQUENCE: 75 ggggcccaa gactagaggt                                                20

<210> SEQ ID NO 76
<211> LENGTH: 51
<212> TYPE: DNA
<213> ORGANISM: Dengue virus
```

<400> SEQUENCE: 76
cagtttgttt gaatagagag cagatctctg atgaataacc aacgaaaaaa g    51

<210> SEQ ID NO 77
<211> LENGTH: 7
<212> TYPE: PRT
<213> ORGANISM: Dengue virus

<400> SEQUENCE: 77

Met Asn Asn Gln Arg Leu Leu
1               5

<210> SEQ ID NO 78
<211> LENGTH: 51
<212> TYPE: DNA
<213> ORGANISM: Dengue virus

<400> SEQUENCE: 78
attatcacat ggataggaat gaactcgagg aacacttcaa tggctatgac g    51

<210> SEQ ID NO 79
<211> LENGTH: 17
<212> TYPE: PRT
<213> ORGANISM: Dengue virus

<400> SEQUENCE: 79

Ile Ile Thr Trp Ile Gly Met Asn Ser Arg Asn Thr Ser Met Ala Met
1               5                   10                  15

Thr

<210> SEQ ID NO 80
<211> LENGTH: 51
<212> TYPE: DNA
<213> ORGANISM: Dengue virus

<400> SEQUENCE: 80
atcttgaacg ggagaaaaag gtctgcaggc atgatcatta tgctgattcc a    51

<210> SEQ ID NO 81
<211> LENGTH: 17
<212> TYPE: PRT
<213> ORGANISM: Dengue virus

<400> SEQUENCE: 81

Ile Leu Asn Gly Arg Leu Arg Ser Ala Gly Met Ile Ile Met Leu Ile
1               5                   10                  15

Pro

<210> SEQ ID NO 82
<211> LENGTH: 50
<212> TYPE: DNA
<213> ORGANISM: Dengue virus

<400> SEQUENCE: 82
cagtttgttt gaatagagag cagatctctg gaaaaatgaa caaccaacgg    50

<210> SEQ ID NO 83
<211> LENGTH: 5
<212> TYPE: PRT
<213> ORGANISM: Dengue virus

<400> SEQUENCE: 83

Met Asn Asn Gln Arg
1               5

<210> SEQ ID NO 84
<211> LENGTH: 51
<212> TYPE: DNA
<213> ORGANISM: Dengue virus

<400> SEQUENCE: 84
cttttaacct ggatagggtt gaactcgagg aacacttcaa tggctatgac g      51

<210> SEQ ID NO 85
<211> LENGTH: 17
<212> TYPE: PRT
<213> ORGANISM: Dengue virus

<400> SEQUENCE: 85

Leu Leu Thr Trp Ile Gly Leu Asn Ser Arg Asn Thr Ser Met Ala Met
1               5                   10                  15

Thr

<210> SEQ ID NO 86
<211> LENGTH: 51
<212> TYPE: DNA
<213> ORGANISM: Dengue virus

<400> SEQUENCE: 86
atcttgaacg ggagaaaaag gtctgcagtc tgtctcatga tgatgttacc a      51

<210> SEQ ID NO 87
<211> LENGTH: 17
<212> TYPE: PRT
<213> ORGANISM: Dengue virus

<400> SEQUENCE: 87

Ile Leu Asn Gly Arg Leu Arg Ser Ala Val Cys Leu Met Met Met Leu
1               5                   10                  15

Pro

<210> SEQ ID NO 88
<211> LENGTH: 50
<212> TYPE: DNA
<213> ORGANISM: Dengue virus

<400> SEQUENCE: 88
cagtttgttt gaatagagag cagatctctg gaaaaatgaa caaccaacgg          50

<210> SEQ ID NO 89
<211> LENGTH: 51
<212> TYPE: DNA
<213> ORGANISM: Dengue virus

<400> SEQUENCE: 89
ctgctgacat ggctaggatt aaactcgagg aacacttcaa tggctatgac g      51

<210> SEQ ID NO 90
<211> LENGTH: 17
<212> TYPE: PRT
<213> ORGANISM: Dengue virus

<400> SEQUENCE: 90

Leu Leu Thr Trp Leu Gly Leu Asn Ser Arg Asn Thr Ser Met Ala Met
1               5                   10                  15

Thr

<210> SEQ ID NO 91
<211> LENGTH: 51
<212> TYPE: DNA
<213> ORGANISM: Dengue virus

<400> SEQUENCE: 91
atcttgaacg ggagaaaaag gtctgcagcc atgctcctca tgctgctgcc c         51

<210> SEQ ID NO 92
<211> LENGTH: 17
<212> TYPE: PRT
<213> ORGANISM: Dengue virus

<400> SEQUENCE: 92

Ile Leu Asn Gly Arg Leu Arg Ser Ala Ala Met Leu Leu Met Leu Leu
1               5                   10                  15
Pro

What is claimed is:

1. An immunogenic composition comprising an attenuated Dengue 1 virus comprising a deletion of about 30 nucleotides from the 3' untranslated region of the dengue 1 genome corresponding to the TL2 stem-loop structure between nucleotides 10562-10591.

2. The composition of claim 1, wherein the attenuated Dengue 1 virus further comprises a mutation generating a mutant having a phenotype comprising temperature sensitivity in Vero cells or the human liver cell line HuH-7, host-cell restriction in mosquito cells or the human liver cell line HuH-7, host-cell adaptation for improved replication in Vero cells, or attenuation in mice or monkeys.

3. A method of inducing an immune response in a human subject comprising administering an effective amount of the composition of claim 1 to the subject.

4. The immunogenic composition of claim 1, further comprising a pharmaceutically acceptable carrier.

5. The immunogenic composition of claim 1, further comprising an adjuvant.

* * * * *